US010588919B2

(12) United States Patent
Baker et al.

(10) Patent No.: US 10,588,919 B2
(45) Date of Patent: Mar. 17, 2020

(54) MATERIALS AND METHODS FOR THE TREATMENT OF VASCULAR DISEASE

(71) Applicant: THE UNIVERSITY COURT OF THE UNIVERSITY OF EDINBURGH, Edinburgh, Midlothian (GB)

(72) Inventors: Andy Baker, Edinburgh (GB); Margaret Dickson Ballantyne, Edinburgh (GB)

(73) Assignee: The University Court of the University of Edinburgh, Edinburgh (GB)

( * ) Notice: Subject to any disclaimer, the term of this patent is extended or adjusted under 35 U.S.C. 154(b) by 41 days.

(21) Appl. No.: 15/557,214

(22) PCT Filed: Mar. 16, 2016

(86) PCT No.: PCT/GB2016/050708
§ 371 (c)(1),
(2) Date: Sep. 11, 2017

(87) PCT Pub. No.: WO2016/146996
PCT Pub. Date: Sep. 22, 2016

(65) Prior Publication Data
US 2019/0046553 A1 Feb. 14, 2019

(30) Foreign Application Priority Data
Mar. 16, 2015 (GB) .................................. 1504387.0

(51) Int. Cl.
C07H 21/02 (2006.01)
C07H 21/04 (2006.01)
(Continued)

(52) U.S. Cl.
CPC ............ *A61K 31/7088* (2013.01); *A61P 9/10* (2018.01); *C12N 15/113* (2013.01); *C12Q 1/6806* (2013.01); *C12Q 1/686* (2013.01); *C12Q 1/6883* (2013.01); *C12N 2310/113* (2013.01); *C12N 2310/20* (2017.05); *C12Q 2600/178* (2013.01)

(58) Field of Classification Search
CPC ..... A61K 31/7088; A61P 9/10; C12Q 1/6806; C12Q 1/686; C12N 15/113; C12N 15/1138
See application file for complete search history.

(56) References Cited

U.S. PATENT DOCUMENTS

2010/0015708 A1* 1/2010 Quay .................... C07H 21/02
435/375

OTHER PUBLICATIONS

Databse EMBL (Online); "TPA:*Homo sapiens* long non-coding RNA OTTHUMT00000382020.1 (RP11-94A24.1 gene), lincRNA", XP002758874, retrieved from EBI accession No. EMBL:HG501622, Oct. 2013.
(Continued)

*Primary Examiner* — Terra C Gibbs
(74) *Attorney, Agent, or Firm* — Kilpatrick Townsend & Stockton LLP

(57) ABSTRACT

The invention provides a method of treating a vascular condition within a subject comprising administering a therapeutic agent to said subject that is capable of modulating the expression levels of a long non-coding RNA (lncRNA) selected from the group consisting of lncRNA2, lncRNA4, lncRNA5, lncRNA6, ncRNA7 and ncRNA8 as defined in FIG. 39.

Figure 1:
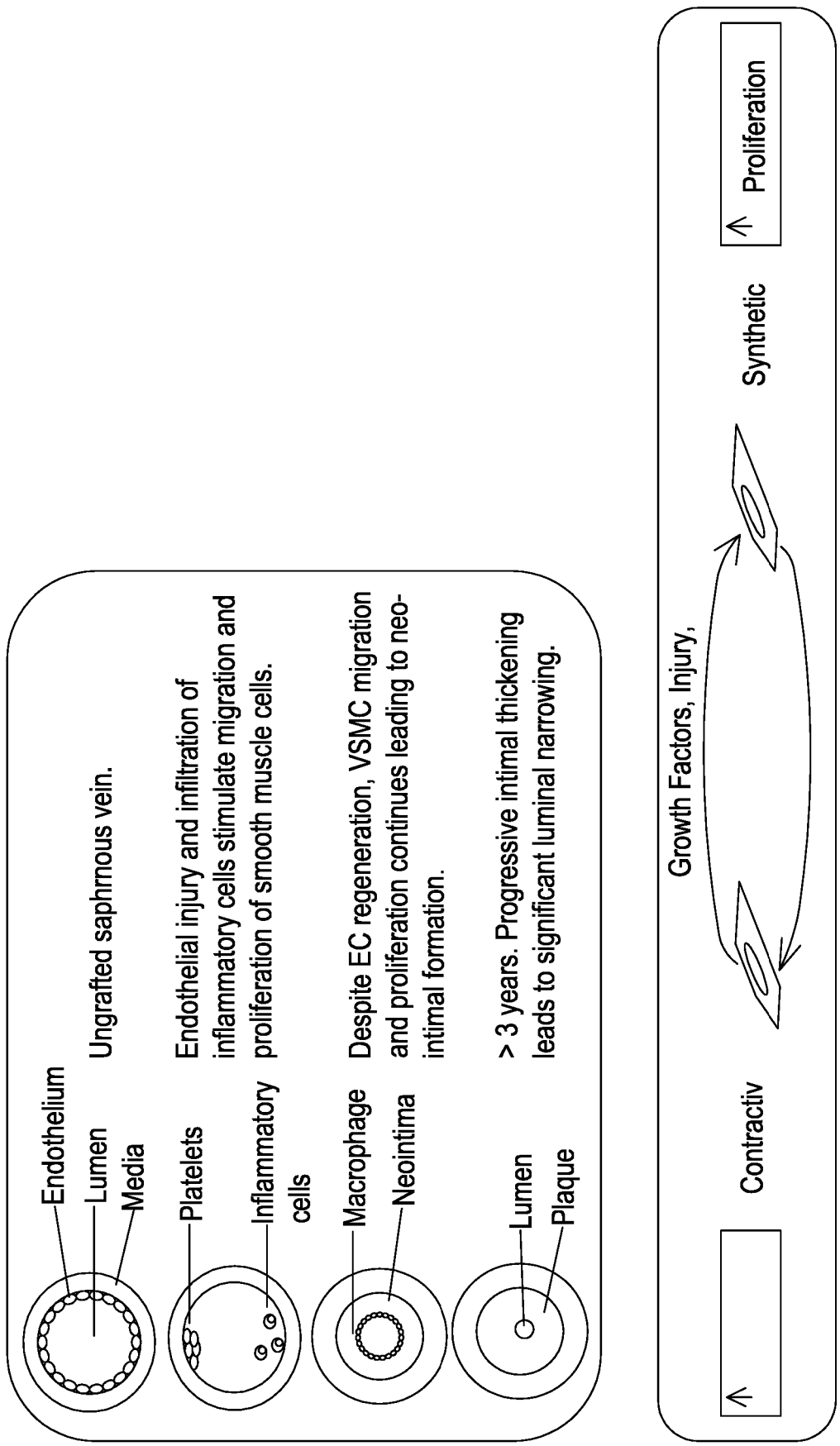

8 Claims, 70 Drawing Sheets
Specification includes a Sequence Listing.

(51) Int. Cl.
| | |
|---|---|
| A61K 48/00 | (2006.01) |
| C12N 15/11 | (2006.01) |
| A61K 31/7088 | (2006.01) |
| C12N 15/113 | (2010.01) |
| C12Q 1/6883 | (2018.01) |
| A61P 9/10 | (2006.01) |
| C12Q 1/6806 | (2018.01) |
| C12Q 1/686 | (2018.01) |

(56) References Cited

OTHER PUBLICATIONS

Ballantyne et al., "lncRNA/MicroRNA interactions in the vasculature", 2016, Clinical Pharmacology & Therapeutics 99(5): 494-501.
Ballantyne et al., "Transcriptional profiling of IL1? and PDGF inducible lncRNA in vascular smooth muscle cells", 2015, Atherosclerosis 241(1): e77.
Ballantyne et al., "Smooth muscle enriched long non-coding RNA (SMILR) regulates cell proliferation—Clinical Perspective", 2016, Circulation, 133(21): 2050-2065.
Bell et al., "Identification and Initial Functional Characterization of a Human Vascular Cell-Enriched Long Noncoding RNA", 2014, Arteriosclerosis, thrombosis, and vascular biology 34(6): 1249-1259.
International Application No. PCT/GB2016/050708, Search Report dated Aug. 29, 2016.
International Application No. PCT/GB2016/050708, Written Opinion dated Aug. 29, 2016.
Liu et al., "Pathogenic role of lncRNA-MALAT1 in endothelial cell dysfunction in diabetes mellitus", 2014, Cell Death & Disease 5(10): e1506.
Uchida et al., "Long noncoding RNAs in cardiovascular diseases", 2015, Circulation research 116(4):737-750.
Vigetti et al., "Natural antisense transcript for hyaluronan synthase 2 (HAS2-AS1) induces transcription of HAS2 via protein O-GlcNAcylation", 2014, Journal of Biological Chemistry 289(42): 28816-28826.
Alexander et al., Epigenetic Control of Smooth Muscle Cell Differentiation and Phenotypic Switching in Vascular Development and Disease, Annu Rev Physiol., vol. 74, 2012, pp. 13-40.
Armand-Labit et al., Identification of a Circulating Microma Profile as a Biomarker of Metastatic Cutaneous Melanoma, Acta Derm Venereol., vol. 96, No. 1, 2016, pp. 29-34.
Billings et al., Comparative Effects of Angiotensin Receptor Blockade and ACE Inhibition on the Fibrinolytic and Inflammatory Responses to Cardiopulmonary Bypass, Clin Pharmacol Ther., vol. 91, No. 6, 2012, pp. 1065-1073.
Bond et al., Synergistic Upregulation of Metalloproteinase-9 By Growth Factors and Inflammatory Cytokines: An Absolute Requirement for Transcription Factor NF-Kappa B, FEBS Lett., vol. 435, No. 1, 1998, pp. 29-34.
Caglayan et al., Disruption of Platelet-Derived Growth Factor-Dependent Phosphatidylinositol 3-Kinase and Phospholipase Cγ 1 Activity Abolishes Vascular Smooth Muscle Cell Proliferation and Migration and Attenuates Neointima Formation in Vivo, J Am Coll Cardiol., vol. 57, No. 25, 2011, pp. 2527-2538.
Chai et al., Overexpression of Hyaluronan in the Tunica Media Promotes the Development of Atherosclerosis, Circulation Research, vol. 96, No. 5, 2005, pp. 583-591.
Climent et al., TGFβ Triggers miR-143/145 Transfer from Smooth Muscle Cells to Endothelial Cells, Thereby Modulating Vessel Stabilization, Circ Res., vol. 116, No. 11, 2015, pp. 1753-1764.
Cui et al., MicroRNA-204 Regulates Vascular Smooth Muscle Cell Calcification in Vitro and in Vivo, Cardiovasc Res., vol. 96, No. 2, 2012, pp. 320-329.
Dardik et al., Shear Stress-stimulated Endothelial Cells Induce Smooth Muscle Cell Chemotaxis via Platelet-derived Growth Factor-BB and Interleukin-1 Alpha, Journal of Vascular Surgery, vol. 41, No. 2, 2005, pp. 321-331.

Davis et al., Evidence of RNAi in Humans from Systemically Administered siRNA via Targeted Nanoparticles, Nature, vol. 464, No. 7291, 2010, pp. 1067-1070.
Deng el al., MicroRNA-143 Activation Regulates Smooth Muscle and Endothelial Cell Crosstalk in Pulmonary Arterial Hypertension, Circ Res., vol. 117, No. 10, 2015, pp. 870-883.
Dodt et al., FLEXBAR—Flexible Barcode and Adapter Processing for Next-Generation Sequencing Platforms, Biology (Basel)., vol. 1, No. 3, 2012, pp. 895-905.
Du et al., Upregulation of a Disintegrin and Metalloproteinase with Thrombospondin Motifs-7 by miR-29 Repression Mediates Vascular Smooth Muscle Calcification., Arterioscler Thromb Vasc Biol., vol. 32, No. 11, 2012, pp. 2580-2588.
Elgar et al., Tuning in to the Signals: Noncoding Sequence Conservation in Vertebrate Genomes, Trends Genet., vol. 24, No. 7, 2008, pp. 344-352.
Elia et al., The Knockout of miR-143 and -145 Alters Smooth Muscle Cell Maintenance and Vascular Homeostasis in Mice: Correlates with Human Disease, Cell Death and Differentiation, vol. 16, 2009. pp. 1590-1598.
Ferns et al., Inhibition of Neointimal Smooth Muscle Accumulation After Angioplasty by an Antibody to PDGF, Science., vol. 253, No. 5024, 1991, pp. 1129-1132.
Gabay et al., IL-1 Pathways in Inflammation and Human Diseases, Nat Rev Rheumnatol., vol. 6, No. 4, 2010, pp. 232-241.
Geisler et al., RNA in Unexpected Places: Long Non-coding RNA Functions in Diverse Cellular Contexts, Nat Rev Mol Cell Biol., vol. 14, No. 11, 2013, pp. 699-712.
Ghouri et al., Lower Cardiorespiratory Fitness Contributes to Increased Insulin Resistance and Fasting Glycaemia in Middle-Aged South Asian Compared with European Men Living in the UK, Diabetologia., vol. 56, No. 10, 2013, pp. 2238-2249.
Glynn et al., Isolation of Secreted microRNAs (miRNAs) From Cell-conditioned Media, Microma., vol. 2, No. 1, 2013, pp. 14-19.
Gomez et al., Smooth Muscle Cell Phenotypic Switching in Atherosclerosis, Cardiovasc Res., vol. 95, No. 2, 2012, pp. 156-164.
Grimm et al., Fatality in Mice Due to Oversaturation of Cellular microRNA/short Hairpin RNA Pathways, Nature, vol. 441, No. 7092, 2006, pp. 537-541.
Guan et al., Nobiletin Inhibits PDGF-BB-Induced Vascular Smooth Muscle Cell Proliferation and Migration and Attenuates Neointimal Hyperplasia in a Rat Carotid Artery Injury Model, Drug Development Research., vol. 75, No. 8, 2014, pp. 489-496.
Hathout et al., Sonographic NASCET Index: A New Doppler Parameter for Assessment of Internal Carotid Artery Stenosis, AJNR Am J Neuroradiol., vol. 26, No. 1, 2005, pp. 68-75.
He et al., Plasma MicroRNAs as Potential Noninvasive Biomarkers for In-Stent Restenosis, PLoS One., vol. 9, No. 11, e112043, 2014, 22 pages.
Hess et al., Saphenous Vein Graft Failure After Coronary Artery Bypass Surgery: Insights from PREVENT IV, Circulation., vol. 130, No. 17, 2014, pp. 1445-1451.
International Application No. PCT/GB2016/050708, International Preliminary Report on Patentability dated Sep. 28, 2017, 11 pages.
Irkle et al., Identifying Active Vascular Microcalcification by (18)F-Sodium Fluoride Positron Emission Tomography. Nat Commun., vol. 6, No. 7495, 2015, 11 pages.
Jaffe et al., Culture of Human Endothelial Cells Derived from Umbilical Veins. Identification by Morphologic and Immunologic Criteria., J Clin Invest., vol. 52, No. 11, 1973, pp. 2745-2756.
Jiang et al., Peripheral Blood miRNAs as a Biomarker for Chronic Cardiovascular Diseases, Scientific Reports., vol. 4, No. 5026, 2014, 6 pages.
Johnson et al., Matrix Metalloproteinase (MMP)-3 Activates MMP-9 Mediated Vascular Smooth Muscle Cell Migration and Neointima Formation in Mice, Arterioscler Thromb Vasc Biol., vol. 31, No. 9, 2011, pp. e35-e44.
Johnson, Matrix metalloproteinases: Influence on Smooth Muscle Cells and Atherosclerotic Plaque Stability, Expert Rev Cardiovasc Ther., vol. 5, No. 2, 2007, pp. 265-282.

(56) References Cited

OTHER PUBLICATIONS

Joshi et al., 18F-fluoride Positron Emission Tomography for Identification of Ruptured and High-risk Coronary Atherosclerotic Plaques: A Prospective Clinical Trial, Lancet., vol. 383, No. 9918, 2014, pp. 705-713.
Karpala et al., Immune Responses to dsRNA: Implications for Gene Silencing Technologies, Immunol Cell Biol., vol. 83, No. 3, 2005, pp. 211-216.
Kashima et al., Crucial Role of Hyaluronan in Neointimal Formation After Vascular Injury, PLoS One., vol. 8, No. 3, e58760, 2013, 12 pages.
Kaushik et al., Dynamic Expression of Long Non-Coding RNAs (lncRNAs) in Adult Zebrafish, Plos One., vol. 8, No. 12, e83616, 2013, 12 pages.
Kim et al., TopHat2: Accurate Alignment of Transcriptomes in the Presence of Insertions, Deletions and Gene Fusions, Genome Biology, vol. 14, No. 4, R36, 2013, 13 pages.
Lemesle et al., Drug-Eluting Stents: Issues of Late Stent Thrombosis, Cardiol Clin. 2010, vol. 28, No. 1, 2010, pp. 97-105.
Li et al., Ras/Rac-Dependent Activation of P38 Mitogen-Activated Protein Kinases in Smooth Muscle Cells Stimulated by Cyclic Strain Stress, Arterioscler Thromb Vasc Biol., vol. 20, No. 3, 2000, 9 pages.
Marx et al., Vascular Smooth Muscle Cell Proliferation in Restenosis, Circ Cardiovasc Interv., vol. 4, No. 1, 2011, pp. 104-111.
Morley-Smith et al., Circulating MicroRNAs for Predicting and Monitoring Response to Mechanical Circulatory Support from a Left Ventricular Assist Device, Eur J Heart Fail., vol. 16, No. 8, 2014, pp. 871-879.
Mortazavi et al., Mapping and Quantifying Mammalian Transcriptomes by RNA-Seq, Nature Methods, vol. 5, No. 7, 2008, pp. 621-628.
Papakonstantinou et al., Platelet-derived Growth Factor Stimulates the Secretion of Hyaluronic Acid by Proliferating Human Vascular Smooth Muscle Cells, Proc Natl Acad Sci U S A., vol. 92, No. 21, 1995, pp. 9881-9885.
Papakonstantinou et al., The Differential Distribution of Hyaluronic Acid in the Layers of Human Atheromatic Aortas is Associated with Vascular Smooth Muscle Cell Proliferation and Migration, Atherosclerosis., vol. 138, No. 1, 1998, pp. 79-89.
Pinel et al., Long-Term in Vivo Imaging of Translated RNAs for Gene Therapy, Gene Ther., vol. 21, No. 4, 2014, pp. 434-439.
Raitoharju et al., miR-21, miR-210, miR-34a, and miR-146a/b are Up-regulated in Human Atherosclerotic Plaques in the Tampere Vascular Study, Atherosclerosis., vol. 219, No. 1, 2011, pp. 211-217.
Rectenwald et al., Direct Evidence for Cytokine Involvement in Neointimal Hyperplasia, Circulation., vol. 102, No. 14, 2000, pp. 1697-1702.
Riessen et al., Distribution of Hyaluronan During Extracellular Matrix Remodeling in Human Restenotic Arteries and Balloon-injured Rat Carotid Arteries, Circulation., vol. 93, No. 6, 1996; pp. 1141-1147.
Rinn et al., Functional Demarcation of Active and Silent Chromatin Domains in Human HOX Loci by Noncoding RNAs, Cell., vol. 129, No. 7, 2007, pp. 1311-1323.
Rudd et al., Imaging Atherosclerotic Plaque inflammation With [18F]-Fluorodeoxyglucose Positron Emission Tomography, Circulation., vol. 105, No. 23, 2002, pp. 2703-2711.
Salic el al., MicroRNAs as Biomarkers for Myocardial Infarction, Current Atherosclerosis Reports., vol. 14, No. 3, 2012, pp. 193-200.
Schermuly et al., Reversal of Experimental Pulmonary Hypertension by PDGF Inhibition, J Clin Invest., vol. 115, No. 10, 2005, pp. 2811-2821.
Soifer et al., MicroRNAs in Disease and Potential Therapeutic Applications, Mol Ther., vol. 15, No. 12, 2007, pp. 2070-2079.
Southgate et al., Involvement of Extracellular-Matrix-Degrading Metalloproteinases in Rabbit Aortic Smooth-Muscle Cell Proliferation, Biochem J., vol. 288, No. (Pt 1), 1992, pp. 93-99.
Taganov et al., NF-kappaB-dependent Induction of microRNA miR-146, an Inhibitor Targeted to Signaling Proteins of Innate Immune Responses, Proc Natl Acad Sci U S A., vol. 103, No. 33, 2006, pp. 12481-12486.
Trapnell et al., Differential Analysis of Gene Regulation at Transcript Resolution With RNA-seq, Nat Biotechnol., vol. 31, No. 1, 2013, pp. 46-53.
Trapnell et al., Transcript Assembly and Quantification by RNA-Seq Reveals Unannotated Transcripts and Isoform Switching During Cell Differentiation, Nature Biotechnology. vol. 28, No. 5, 2010, pp. 511-515.
Upadhyay et al., Cardiovascular and Inflammatory Effects of Intratracheally Instilled Ambient Dust from Augsburg, Germany, in Spontaneously Hypertensive Rats (SHRs), Part Fibre Toxicol., vol. 7, No. 27, 2010, 20 pages.
Van Den Boom et al., Differential Regulation of Hyaluronic Acid Synthase Isoforms in Human Saphenous Vein Smooth Muscle Cells Possible Implications for Vein Graft Stenosis, Circulation Research, vol. 98, No. 1, 2006, pp. 36-44.
Vance et al., The Long Non-coding RNA Paupar Regulates the Expression of Both Local and Distal Genes, EMBO J., vol. 33, No. 4, 2014, pp. 296-311.
Wang et al., Molecular Mechanisms of Long Noncoding RNAs, Mol Cell. 2011, vol. 43, No. 6. 2011, pp. 904-914.

\* cited by examiner

Figure 2:
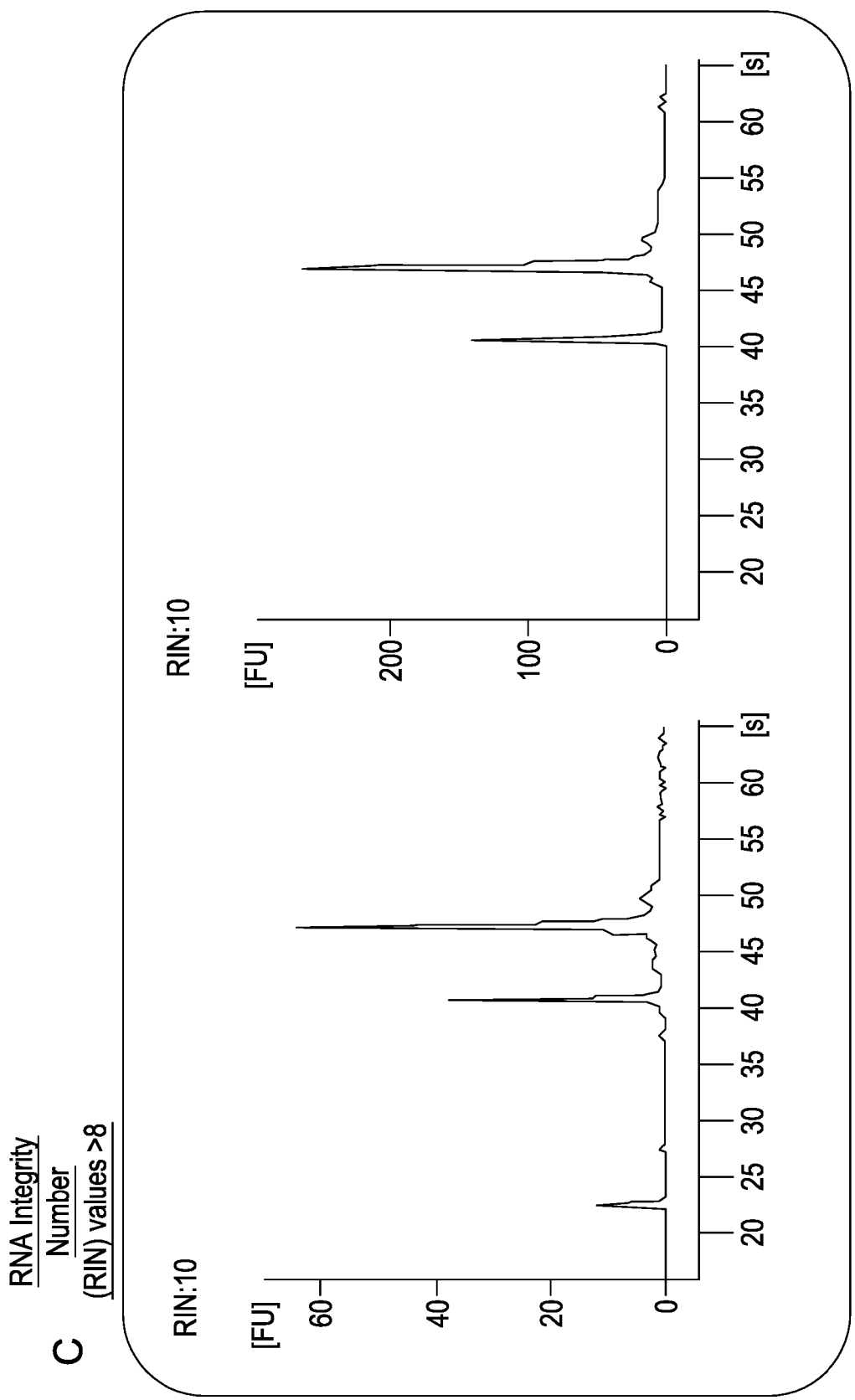

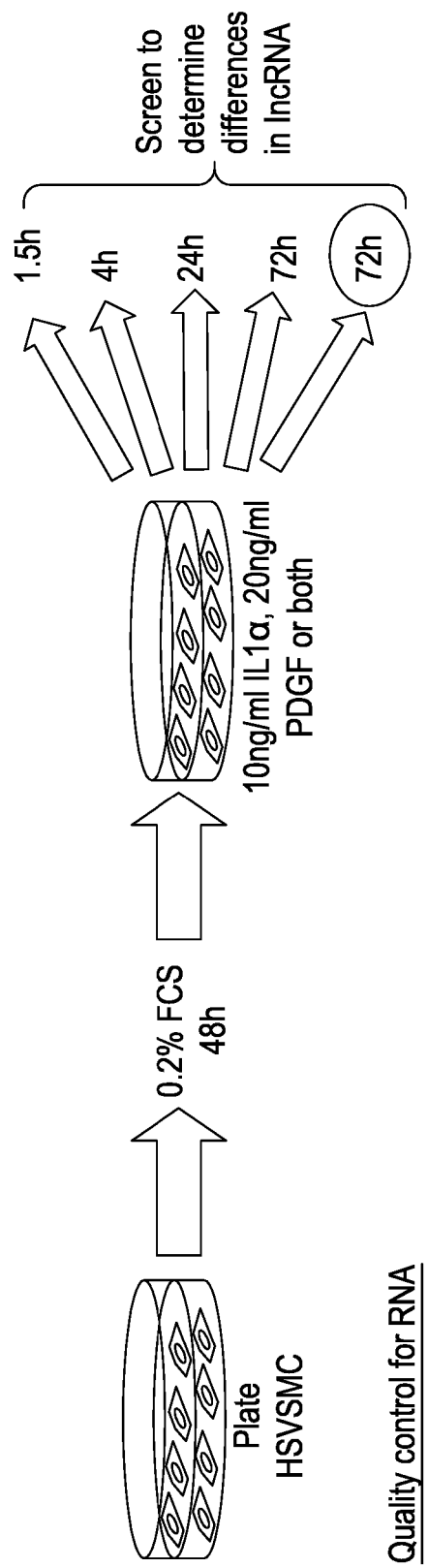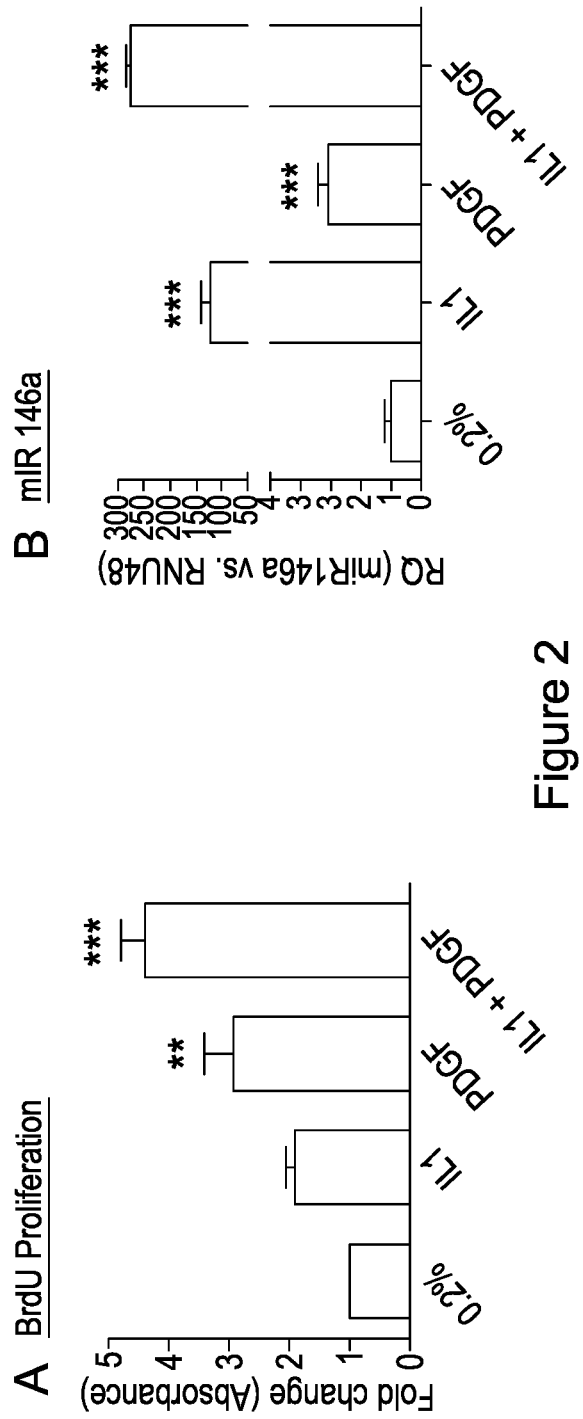
Figure 2

• LncRNA expression levels are related to their function.

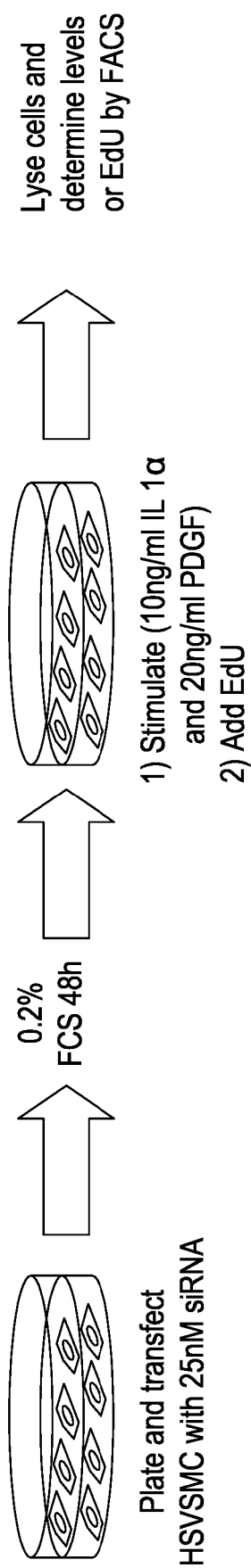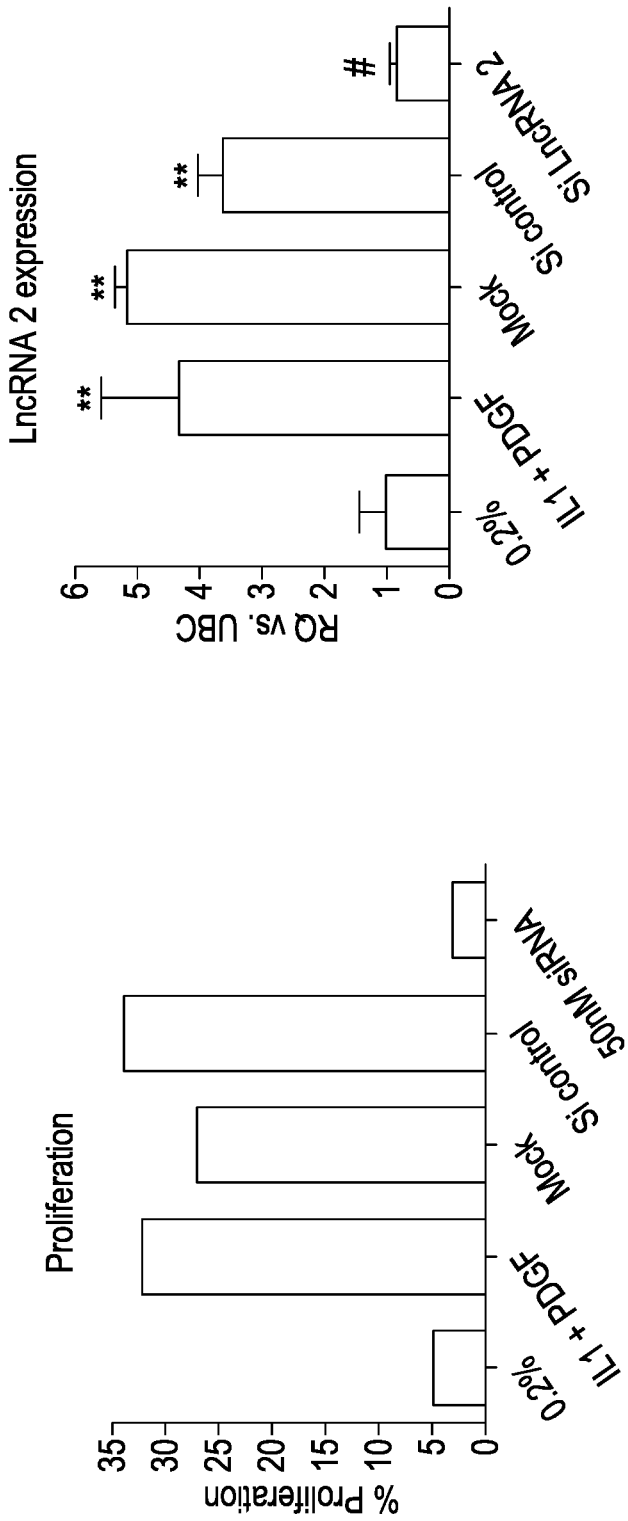
Figure 11

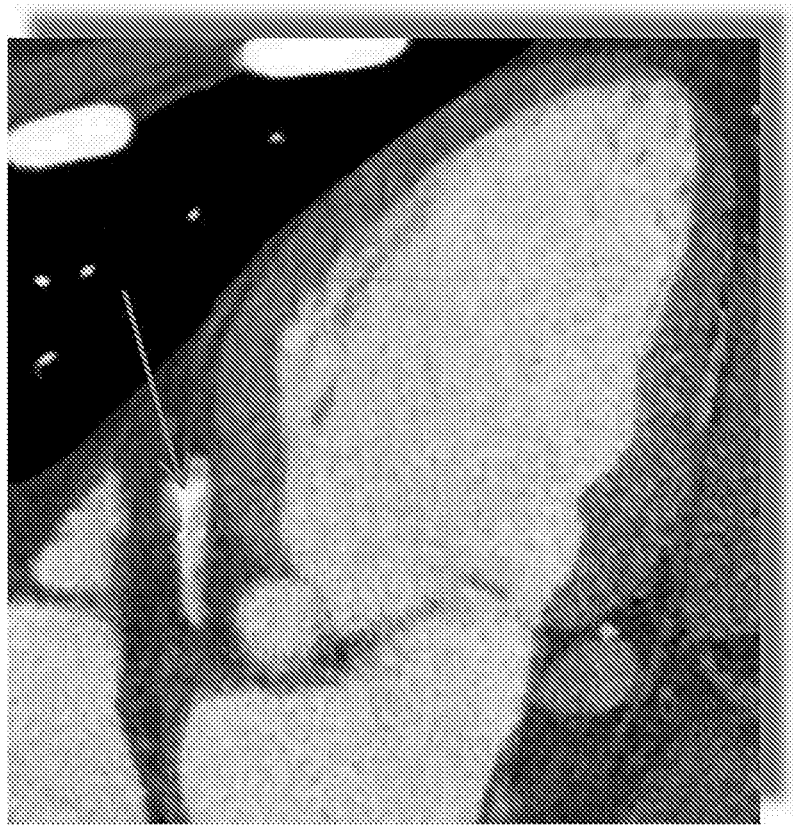
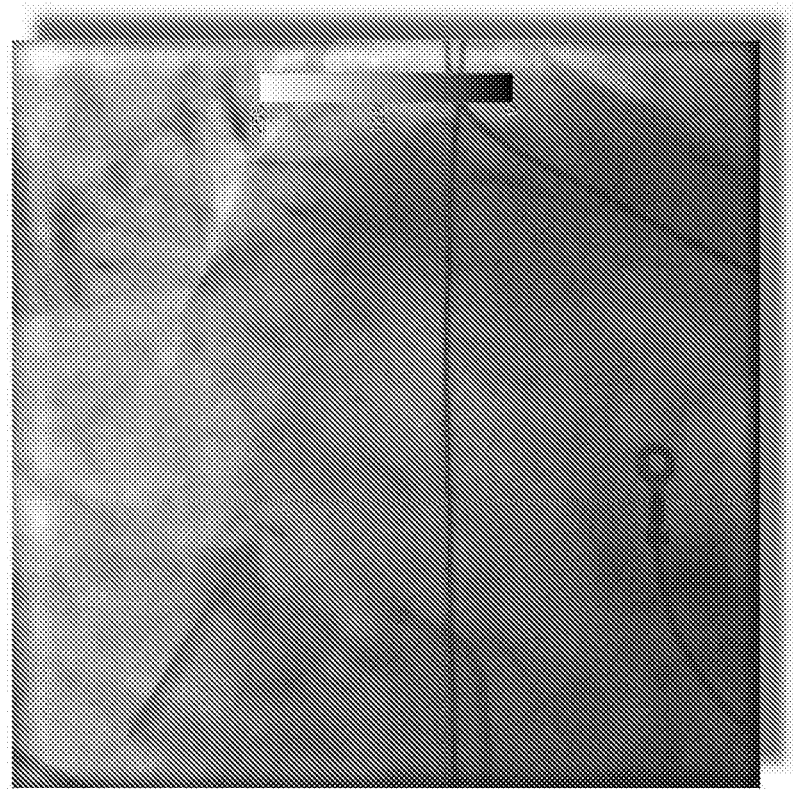
- 40 patients with recent acute myocardial infarction imaged with 18F-Fluoride PET/CT.
- Focal uptake was visible at the site of the angiographic culprit in 37 patients.
Figure 13

LncRNA 2   SEQ ID NO: 18
Gctgcaaacattgggatcagccgtgactatcccataacataatatttctgatttcattcttttcctttctcctaccaatttaatctgcaatc
acttcaagagaagtctgtttaaaggatattcacattctg (intron 1)

Ttcacagagtttgagagaaactgtattcaagttgctgaaaccaagaagctacactcacgagtctcacctaaactcgaatctgattt
agatgacatcatcctggactttgagttgatgaaaccttggaggtcttgggagtaaagcaagtgtgatttgcatatgatggatatgaat
tgtaatggccagagcatg (intron 2)

agatgaaaactcccatttttagggaaccaagactgaattccataatttacatggatgtttggaaggtgtctgcaacttaatctgtgttcg
tttctgagatgttgggcaactccttcttggaagatgtggtaatggtctcttcgaaaagaaaataatcatctgagttttggccaaaatagt
tgatcggattacctatgaaaatgactctcacccaactacaagaatgttatgatgtagaaactctaaatatatgagtaattaactatac
aacactccatccccatgtgaaaatctttaatcttttaagatactgaaattttgtgtatgtctcataatttctgtatatggtcaatgagttttg
ccttagccataagtggtctgtctgaaatcttctctattatttgtgcattttcttcctgatgtaccaagcctagtctgtttgttttttcctaagaga
aaagcagatgattcaactgtgtatttctcagtgttgatattgtggtttgaggtatttcataatcttgagtaaaatcttgtcaa]aaaaaaa
aaaaaa.........

LncRNA 4   SEQ ID NO: 19
GAATGGGGTAACCTGGCTAAATGAGAATTAATGAACCCACACTCATAAGTTTTCATTGA
CTTAGCACCAAGTCGTCCATCAAATATCATCAGATCTGAGAATGCTCTTATGGATATCTG
ATTTTTAGAGGCTGGCATTCATATTTTTAAAAACTGCCACCTGTGACCACACTGCAGGC
CAAACAGAATGTACCTGCTGGTCAGATGCAGCCCAGAGGTCACTGAATTGCAACCTCT
GGACTCTCGGTCAGAGGCAAGCAGCCCTTATTCCAGAACTCCACAGTCCTTCACACCC
TTCCCCAGACCTACACCAAGACCAACTAAGTGGTCAAAAGGTGGACAAACTGAGAGTT
GTATCAAGGCCCTTAGCCTCTCAATTTGTTATCAAGTTTCCCTTTCTGAATCTATTTACC
CTGAAGTATAAATACCCAAGATGAGCCTTAAGAGTGCCTGGTAGAGCAAACAAAGATGC
ATCTTATAGGGAGCAAAGTCTATGCTAACGCAGTGTTTCTCAATCCTGGCTGCACCTTT
GAACCACGGGAGCTTTAAAAGTGACCACTGCAAGGGCCCTACCCACTATGGATCCCAA
TTTCATTGGTTGGGAGAGGGGCCAAGTTTGTTTCCAACTTCCCCAGATGACTCTAATGG
CTGAGAGTTGCAATCAACAGGTAAGTGAATATCCAGGCTGTAAGATGAAGAAAGAGGG
GGTTGTGCCCAAGCCCACTGTGCCTCATAAAGCAGATGATCTCTGCAGCGCTGCGCTT
CTCAAAGAGTGGTCCCAGGACTGCCTCAGTCAGACCACAGACTCCTAAGTTCCTCCTC
AGACTTCATGGATCCAAGCTCTGTGAGGTAATTCTAAGCACATTAAACTTGTAGAACAG
CCATCTGGATTTAATATTACATAATAGCTATAATATTCTGCTATTCTCTAATCTTCAATGT
CAGTTTCTTAAACTGTCAGGCCTGTCTTTAGATGCCCTTCAACTGTGCTGGGGACTATC
TTGATGGCAGCCAGCAAAGAAAATCAGCAAAACCCCAGTGGAGTTTCTGGGTTTTACT
TTTGTTAAGGAAGGTGATGGTTTCTTGACATGACAGGTATCTAGGTGGAAAGGGCAAAG
TGCTAATGCAAACACAATGGAGACACTATGGAATAGCTCTGCCTAGGGACATGTGGAA
GAGCTTCTAGGAGACAGTGTGGACCTTTCCATCCCTAGAGGTCTTCACAAGATAAATTC
CTACCTCCGTCAGTATTCAAAAGGTTTTAGCATCAATACTGTCTGAGAATAAGACATTAG
ACTTGAGTCAGTCCCCTGGCTTCAATCCCAGGATGCCAAGCAGCCTCTAATGGAGACC
GCTGGCTTAATCGTGCTCCTTTCCTGGCATAACAACTCACTGCACCCATGCCTCACCAC
CACGAAGCAGTCTCCTCACCACCCAAATGTGCCTTGGGTGACTTAAATACAGCCATTAG
TATGAATGGTCCCTGTTTTATTCAACACCACCAGTCTTTGCTTTTACCTTCGGCTA
ATGTGGTTCCAGCCTTTTATCCTGCACTCCTTCTTATAATTTAAAAAAAAAAAAACTCCC
CTACTATCTTTATGTTAATATTAACATCAACTAGGTTCTTCTCAAAGGACAGCCAGGCCT
AACTGGCCACGTTAAAATCTGCACAGTGCTTTTGTGTCACTGTCTATTCTATTAGTTTCA
ACATCATGCTAAAATAGGACAGCATGTTCCAAAACTGAAACTGAAACAGGAACGGAGCC
TTGCTGATTTAGCATGAGGAGGGAATTGTAAGCCTTGCACCTGGACACTAAAACTTTTC
AATAAGATGTATGCTAAGCCGTACCTAGCAAACTTACCAGGTCCAAAGTAGAGTACAAG
CAGAAAGTTATTTTTAAAGGATGGGCACTATCCTTGAGGGACTTACCCTTTCTAATCAGC
TTTGCATGGTTTGTTTTGAGACAGTGTCTCACTCTGTTGCCCAGGCTAGAGTGCAGCGG

Figure 15

CACCATCACAGCTCACGGCAGCCTCTGCCTCCCGGGCTCAAGCAATCCCACCTCAGTT
TCCCAAGTAGCTGGGACTACAGGCACACACCACACTCAGCTAATTTTAGTATTTTTGTA
GAGACAGGGTCTCGCCATGTTGCCCAGGCTGGTCTCAAACTCCTGGATTATCTCCCTG
GCCCTGCATTAAAAAAGATGTGCAACAACTTA (no introns)

LncRNA 5  SEQ ID NO: 20
TGTGAGGAGGCCCAGGCCACAAGGAGAGGCCACCTATAAGCATTCAGGCCAGCAGCC
CCAG (intron 1- 5701)
aTCTGCTCCTCCTGCCAAGCTGAACCCAAGACCAGCACCTTCCTCCTTGTGTAAGATGG
TGACATGGATGCCGTCTAATTGCTGCAGAGGAAATACATACATTCAAAAACATTTTACTG
CAAGAGGATGAACAATTTAACATCGGACTGACATCAGACTGATTTGTTATCTCAAACCC
CAGCTTGGCCAGCCTCCAAGTTACATCACCTCCTCAAACCTCAGTTTCCTCATCTGTAA
AGAATGGACCTTCAGGAGTCATGGGAAGCTTAGAAGAAAAAAAAATGTATGTAAAGCA
GCAAGCATAATTATTTTCCTCTCTCATTCACCCTGTCCACAGCCGGGCAGGGGGAGTG
CCATGAAGTCAGCCAGAAATCAGCATATTGGACAGTGTGAGATGAAGTCAGGTTGTAG
GAC

LncRNA 6a  SEQ ID NO: 21
ACATGGATCCTTAAGTCCTCCCTATGCCCCGTTAGAGCACTGATGACATTTACTTTGAAA
TTCCCCTGTTACATGTCTGTTTGCCTAAGTAGACTCTAAGCATCTGCAGAACAGGGGCT
ATGTCTTAGTATCCAGGGTATTTTCTTCACCTGGCACAATTCCTGCCACAGAGTAGTGT
GTCAGCTCTCTATTGTTGTCTAAAAACCCACCTCAAGG (intron1 – 3615)
TGCTGGGATTACAGGTGTGAGCCACTGTGCCTGGCCCCACATTTTTAAAACAATGACT
TTAGGGTTTCAGCTTTTCCTGTCTTTTAAAACAAATTAGCCATTTTTATTCTAAGAAAGG
GTTGTATTATAAAGCTGACCTACTACTAGCTTATCAGAAAAACACGTGGGTCTCATATC
TGATTCTCCTATGTAGCCAAAAGTGCCATTTGTAAGTCTACTAAATGACGGATATTTTCT
GAAGATCTTTTGCCTGGAAAACAAATAGTGCATT

LncRNA 6b  SEQ ID NO: 22
GGGTTGATTCTATTATCTGATGTTTTATTAATCTCTGTGAAATAATTGTGTAAATTAATAT
AGAGACTAGTTGAGAAATGGTGGATAACATGAAGAAGATACCCATTTTGCATAGATTA
GATGTGATCAACCTCACACTATCATATGAAAGTTGGCTGCATTGGAGAGACAGGAATTA
ATATTAAAAATGTTTTCAGTTCAGATTGATATCTTACATTTCCAAATATTATTTTCTTTTGA
ATAT (intron 1 – 1000)
GTGTGAGCCACTGTGCCTGGCCCCACATTTTTAAAACAATGACTTTAGGGTTTCAGCT
TTTCCTGTCTTTTAAAACAAATTAGCCATTTTTATTCTAAGAAAGGGTTGTATTATAAAG
CTGACCTACTACTAGCTTATCAGAAAAACACGTGGGTCTCATATCTGATTCTCCTATGT
AGCCAAAAGTGCCATTTGTAAGTCTACTAAATGACGGATATTTTCTGAAGATCTTTTGCC
TGGAAAACAAATAGTGCATTAAAAAGCTTTTTGGTA

LncRNA 7a  SEQ ID NO: 23
AAAGGTACTTAGACATGTTCCCCACAGGATGTGTTAAGGTGTTGGCCAATCATCAAATA
TTGTCACTCCAAAGAACACATTTAACAGCCGGGAAGAAAATTGTAGGAAAAGAGAGCAC
TTTGGCACGGAAGG (intron 1 – 78610)
GGTCTATCGCCCTGGTTGGAGTGCAGCAGTGTAATCATAGCTCACTGCTGCCATGAAC
TTCTGGGCTCAAGCGATCCTCCCACCTCAGCCTCCCTGTGTGCTGGGATTAAAAGTGT
GAGCCACCGTGCCTCATCGTAAGGGTCTTAAAAGAAACCCTATTTCAT (intron 2 – 787)
ACTTTCTTGATGCACTTGATATGGATTATATAAATCTATGGACAAAATGACATCAGTAC
AATGGAATATTGGAGTTTTCTACCATAATCTCTGCATAGTGCACTGATTTTGACAATCAC
CTATGGATGAAAATACATTTGCCAGAGTCTAGGAGTTAAATGGAAAGTTAACAGCACA
CCGTTGGAGAAAATATCTGGGAGTAGATGCATTCAAGGGAGTAAGAAGAACAATTACC
TGCATCACCTCACCCCAGGGTCCACTTCTTAGTGCCAAGATAGACTCCCTTCAGCAG
GCAATTTCTCCCATGGGGAAAAGGAGAGTATAATGAGTGAGTATCCAGCTTTTCCAGCT Figure 15 (Continued)

GTGTGAGGCACATCCCAAGAAGCCCATCTTTCTTTCACTCAACTCAGAATATTGAGGGT
ATTAGCATGGCTAAGTGGCTGGGACAGGGCAGTAGCAGGAAAGAAAGGAGAGGACTC
ACAGCAACCAGGACTTGAAACTCAGTACAGGGTACATATCCTTTGAAGCATTTCACAGA
GCCCATCAGGAGGCCCACCCATGAACCACTTGGGACACCATATCTGTAGCATCTCCCT
GCAACTGGCCCATAGGAGCCCCGATGTTTGTGCATATTCCCCTTCCCTTTCTCCTAT
AGTCAGTTGCCTGCACATGCACTCCAGATGGTGAGTGTGAGCATTTACCTACAGCTTTT
GAGTACATGCAGTCAGCAGGCTCAACTTTGAAGGATTGGGAGGAATACAAAATTGAGC
ATTTCAGGGCACTGTCCTAGAGGAAACAAACAGAAAGCTTTCAGGACCCAGTTTGGTTT
TGTGGATTTAAGAAGACACACAATCATCAGAATTTCTTCTCCACCCATCCAAGAAGT
GTGGATTGGGTGAATCCATAGAAAGATCTGAGAGAGCCTCAGATTCCCTATAGGCTCA
CTGTTGAAGATATTTCTCTCAAATCCAGTCAGTAAAGACTAGAGAAAGTGACTCTTTCTT
CAAATGTGAAGACAGCAGTGCAAGACTTGAGGAACATGAAAAATCAAGGACACCTAGT
ACCACCAAAGGAACATAATTTTCTGGTACCCAACCACAAAGAAATGGAGATACACAAAT
TGTCTGACAAAGAATTCACAACAATTGTTTTAAGGAAGTCAGTAAGCTACAAGAGAACAC
AGAGAACTTAATGATATTAAGAAAGCGACACATGAACAAAATAAGATGTTCAACAAAAAG
ATAGAAATTATTAAAAACAACCATGATTTTCGAGCTGAGAATACAATGAATGAAATGGAA
AACACAATAGAGTTTCAATAGCAGACTTGATCAAGCAGAAGAAAGGGTCTGTCAACTCA
AATACTAGTCATTTGAAATTATTCAGTAAAAGAAATAAAAAGGAATGAAAATGCTTATGC
GATTGATGCAACACCATGAAGAGTAGTCATATATGCACTATGGGAGTCTCAGAAAAAGA
AAGAGATAAAGGGGAAGAAAACTAACTTAAAGAACTAGATCAGTCTCTCCTTATCTGTA
GTTTTGCTTTCCTTGGTTTCAGGTACAGTACAATGATATGTTTTAAGAGACAGACAATGA
AAGAGAACATGCAAATATTGACATAATTTTATTACAGTATATTGTCATAGTTTTCTATTT
TGTTATTAGTTGTTATTCTCTTACTGTGCCTAATTTATACATTAAACTTTATCATAGGAATA
GTGGTGGTGGCCTGTCTGGAGTGGCCACTGCCAGGATGCCAGCTGCAGCAGGGGAG
GTGTAGCTGGGGCTGTGCACTCCGCAGAGCTGGGGGGGGCCAGGAACAGGTGATCCT
AGTGGGAGCCCTATATGCTACTGAGTTAGTGGGGTGGGAGCCTGTGCTCCCAGGCATA
GCTGCAGCTGCCCAGCCATGGCTCCAGCCCTAGGCATACCTGTGCTCTCAGGGGCCC
TGGAAGTCCCTGCCCTTACAGGCTTGGAAGTGCCTGCTCCCATTCCCTGGCCTCTTT
CCACTGCTGGCACCTGCTCTGTGGCAGAGCAAAGTTGTGGATGTGTTGTGATAGCTGA
GCCTGGGAGCTGTTGTGACGTGGTCAGGTGTGTGTGTTCAGGGCAGTTCTGATACACC
AGACTCCCCACTGCCTTTGCCCCCTCTGGAAACTGCTTCTGAGGCTGAAACTTTGGATA
TTAATGAGCAAGGATGGTGGGGGAGGCCAGGACGGCTGAGGGCAGCTAGGTGTGGG
CCTGTGGACACCCCTTAGTGCGGACAGTCTGGGTGCTGTGGATGGCATGTTGATGGCA
GCGAGAGGCAGACATGTTCCTAGGTGGGAACGGGTGGGTCCCTGGTGAAACCTCACC
TTCAAGCCAGGGACAGCTTGAAGCATGGGGCCTGGCTGCCAGTTCCGGTTGCAGTCT
GTGACCTGGAGTGAAAACTTCATTGATGTCTTTCAGCCAATTGGATGGTGCTTTTTCCA
GACCCACAAATGGCTGCCCATGGACCAAGCAGTATGTACTTCCTCCATTCTGAGCCCAT
GAAAACCCCAGACTCAGTCAGACTCTGACACTCATCAGGATGACAAGCCTGCAAATAG
GATCTACCCATTTTGGGTATGCACTCCACTGAGAGCTATTCTGTCACTCAATAAAGCTC
CTTTCTGCCTTGCTC
LncRNA 7b SEQ ID NO: 24
ACAAAGTTTATATTAGAGCGTCATCCATTAATGCTTTGGCTAGGAGGG (intron 1 –
76782)
GGTCTATCGCCCTGGTTGGAGTGCAGCAGTGTAATCATAGCTCACTGCTGCCATGAAC
TTCTGGGCTCAAGCGATCCTCCCACCTCAGCCTCCCTGTGTGCTGGGATTAAAAGTGT
GAGCCACCGTGCCTCATCGTAAGGGTCTTAAAAGAAACCCTATTTCAT (intron 2 – 767)
ACTTTCTTGATGCACTTGATATGGATTATATAAATCTATGGACAAAAATGACATCAGTAC
AATGGAATATTGGAGTTTTCTACCATAATCTCTGCATAGTGCACTGATTTTGACAATCAC
CTATGGATGAAAATACATTTGCCAGAGTCTAGGAGTTAAATGGAAAAGTTAACAGCACA Figure 15 (Continued)

CCGTTGGAGAAAAATATCTGGGAGTAGATGCATTCAAGGGAGTAAGAAGAACAATTACC
TGCATCACCTCACCCCCAGGGTCCACTTCTTAGTGCCAAGATAGACTCCCTTCAGCAG
GCAATTTCTCCCATGGGGAAAAGGAGAGTATAATGAGTGAGTATCCAGCTTTTCCAGCT
GTGTGAGGCACATC

LncRNA 8a  SEQ ID NO: 25
CTGAACAACAAGTTAACTGCTGTTCCCAGTTATATCTGGTCTTTCCCACCCCCAAACATA
CACAAAGATTTTTGTCATTCTTGGCACTGGACAACAGAAGTGATAAGACATGCCAGCA
GAACTCTAAAGGCAGAATGTCCTTCCACCTGTTTTATGCTGTAAGACAAACTTCCAAGT
GCGAGGCAGTGTGGAGGGCTGTTGCCTTGAATGGCAGCTGAATGCACCAGCGGGATC
CTTGGCAGCAATGCCCAGGCACTGAAGTCGGGCATTCAGGAGAGCTAAATGGAGAAAA
GAAACTTGAGCAAACTGCTTCCTGGAACACTGAGAACCTGAATGGGAATTAAGAAGAA
CCAGATTCTTTCTATTCTTCCACCAGCCAAGGTCAGATTTCCAAACTTCTATTGATTCTA
ATCTTTCCCAAACAGTGCTGTGGCAATGTATGAAAGTAATAAAATAATCCTTTTCTGTT
AAAAAAAAAATTGCTGTTACTTGCTGTTTTGTTATGCTTTTGCTGGAGATTTTCCCACCC
ATCTTAAAGCAGCAACTTCAGGATGGGGGAATCAAGCAAAACCATGGTGAAGAGATTCA
TTTAAAGAGGACAAGTGATTTATTCTACATCTCAGGAGACAGTTCCTTAAG (intron 1-1941)
GTGATGAGCACAAAAGGATCCATCTTATACAGTGCTTGCCAGCTTCCATAATACTACTC
ACCACGATGTTGAAATCACCTGTTCCAGAACCAGTCCTGTCCTTTGACAAGAAGGATTT
AATTATCAGTAGTGGTGGGGACTGGCTGGAGAGAGGAAAAACACTTCAAGGACTCTGC
CACCTTTCGTAGATGGAGAGTGCAAAGTTTGTACCATGGAACTCCTTCTCTAACAGTTA
CTCTGTGGCAGTGCCTATTTCAAACCTCCTTAACTTCTGATTGTATAGATGTTTGTTTC
ATTTGTTCATCTGTTTGTTCACTTAGTCAGAGATGTTTAAGCCTTAAGAGAAATAGTGG
ACTAGAAAATGCCTTGGAAAAGTACAAAGTTCAATCCAAGTAAACTGTTTTTAAACTAGG
AATTTATGAAGCCTAAAATATAAAATGTATATACATGGATATGCTCTGAAGTGAGGTAGA
GGGGTAGAAATCAACATTGTGATATTGTACTATAGTTTTGCAAGATGTTACCATTGGGG
GAAAATGTTTGAAGGGTATACGGGATATCTCTGCCTTATTTCTTACAACTGCATGTGAAT
CTACAGTTATCTCAAAATAAAAATTTAATTAACAATTGATTACAATTAA

LncRNA 8b  SEQ ID NO: 26
ACAACAAGTTAACTGCTGTTCCCAGTTATATCTGGTCTTTCCCACCCCCAAACATACACA
AAGATTTTTGTCATTCTTGGCACTGGACAACAGAAGTGATAAGACATGCCAGCAGAAC
TCTAAAGGCAGAATGTCCTTCCACCTGTTTTATGCTGTAAGACAAACTTCCAAGTGCGA
GGCAGTGTGGAGGGCTGTTGCCTTGAATGGCAGCTGAATGCACCAGCGGGATCCTTG
GCAGCAATGCCCAGGCACTGAAGTCGGGCATTCAGGAGAGCTAAATGGAGAAAAGAAA
CTTGAGCAAACTGCTTCCTGGAACACTGAGAACCTGAATGGGAATTAAGAAGAACCAG
ATTCTTTCTATTCTTCCACCAGCCAAG (intron 1- 2201)
GTGATGAGCACAAAAGGATCCATCTTATACAGTGCTTGCCAGCTTCCATAATACTACTC
ACCACGATGTTGAAATCACCTGTTCCAGAACCAGTCCTGTCCTTTGACAAGAAGGATTT
AATTATCAGTAGTGGTGGGGACTGGCTGGAGAGAGGAAAAACACTTCAAGGACTCTGC
CACCTTTCGTAGATGGAGAGTGCAAAGTTTGTACCATGGAACTCCTTCTCTAACAGTTA
CTCTGTGGCAGTGCCTATTTCAAACCTCCTTAACTTCTGATTGTATAGATGTTTGTTTC
ATTTGTTCATCTGTTTGTTCACTTAGTCAGAGATGTTTAAGCCTTAAGAGAAATAGTGG
ACTAGAAAATGCCTTGGAAAAGTACAAAGTTCAATCCAAGTAAACTGTTTTTAAACTAGG
AATTTATGAAGCCTAAAATATAAAATGTATATACATGGATATGCTCTGAA Figure 15 (Continued)

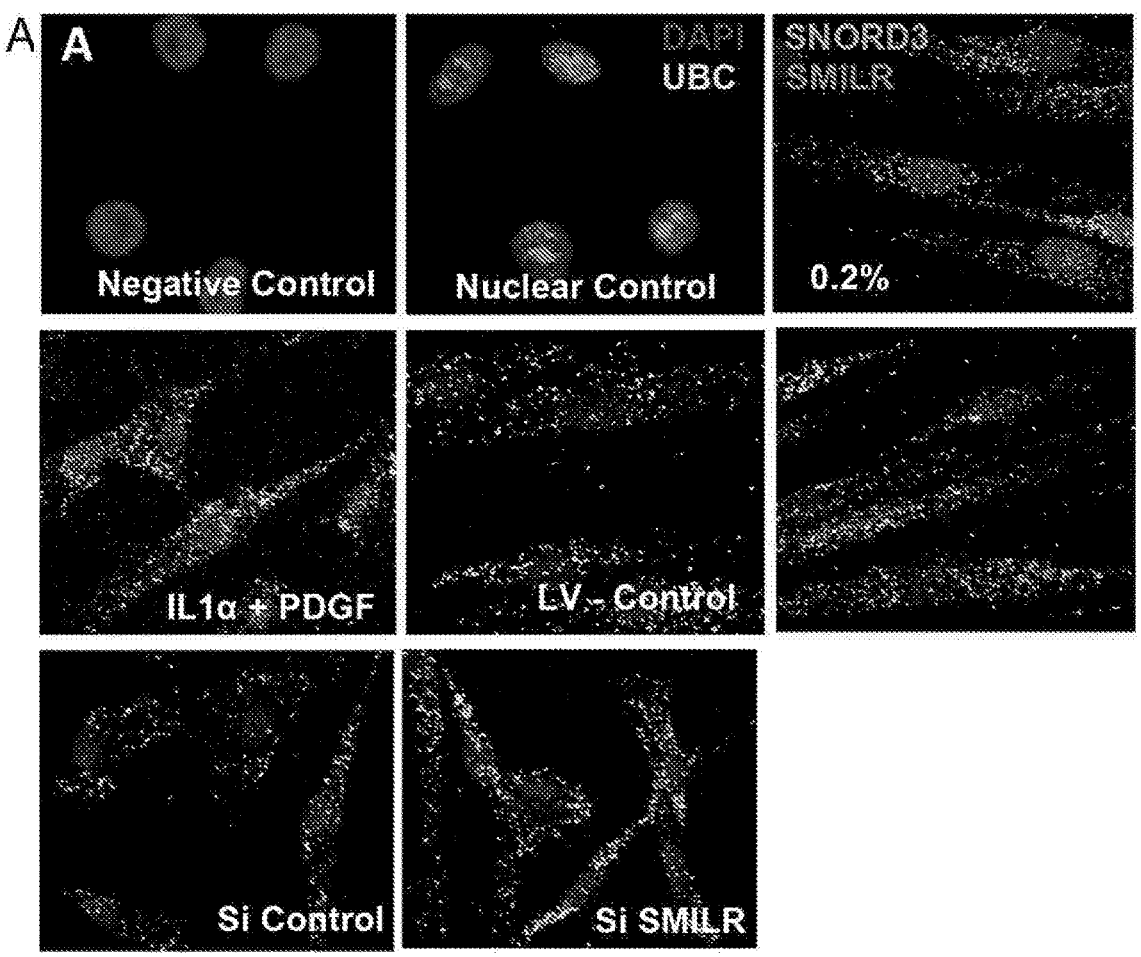
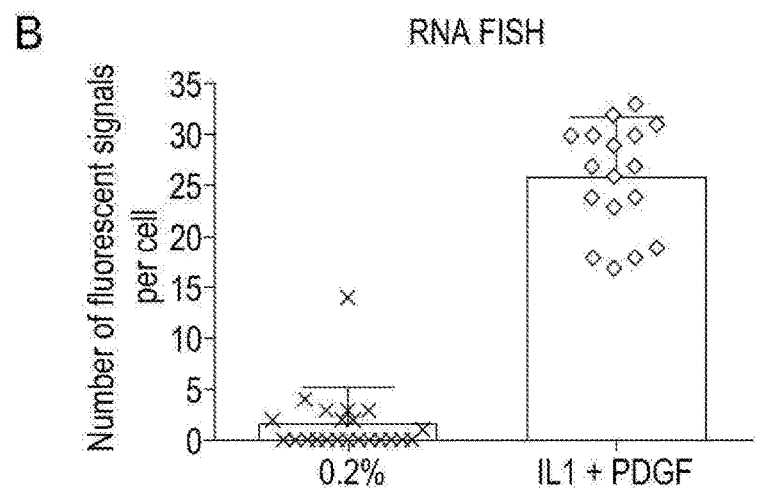
Figure 18

Figure 23:
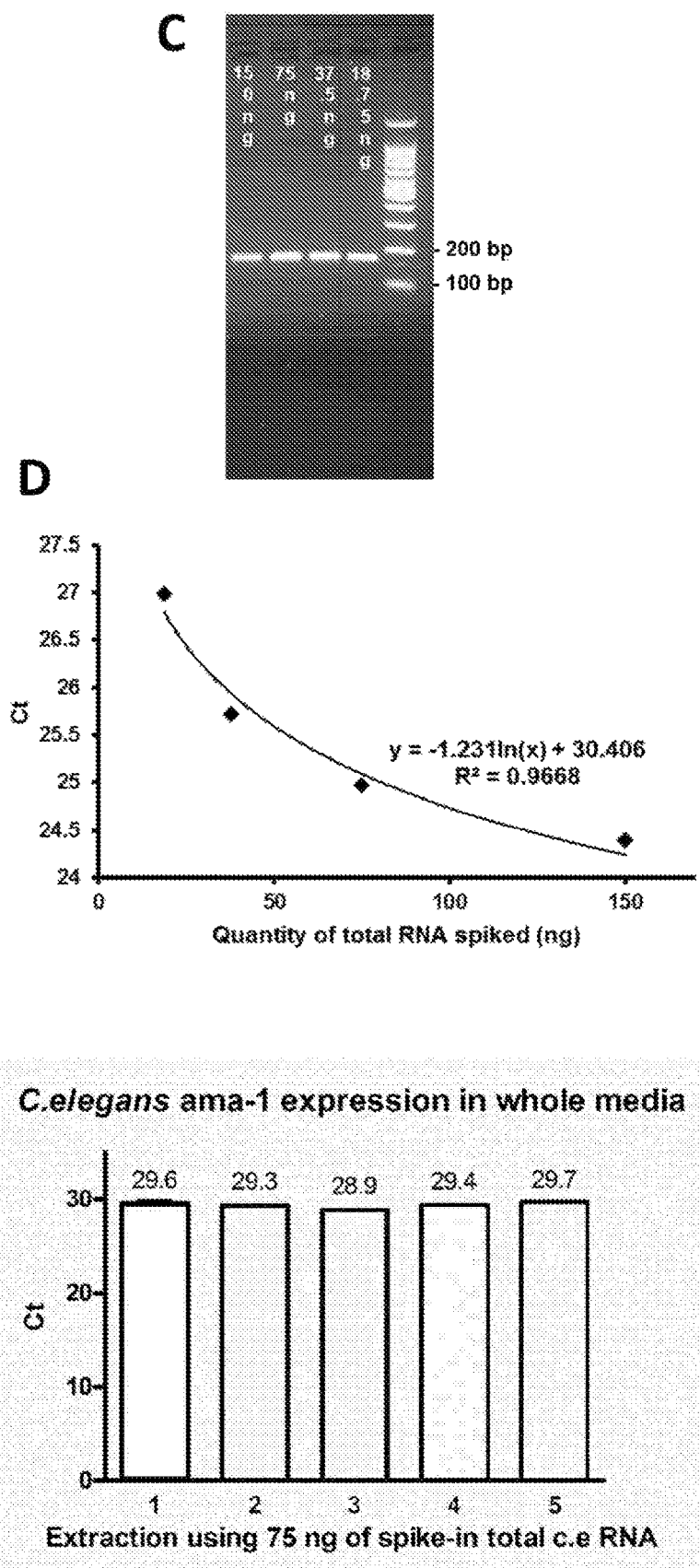

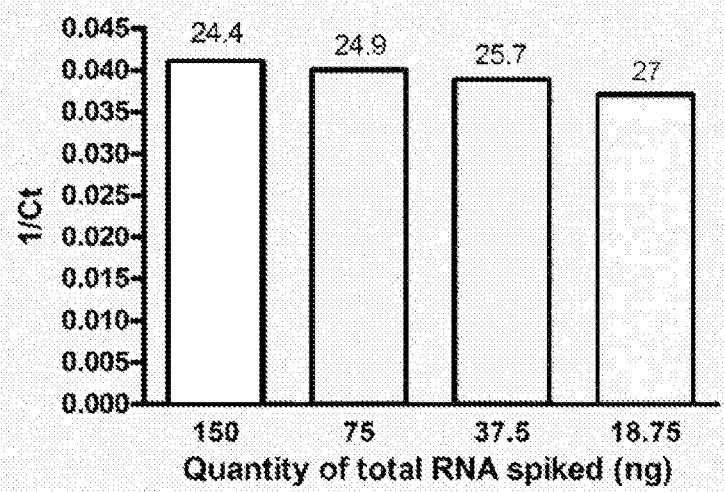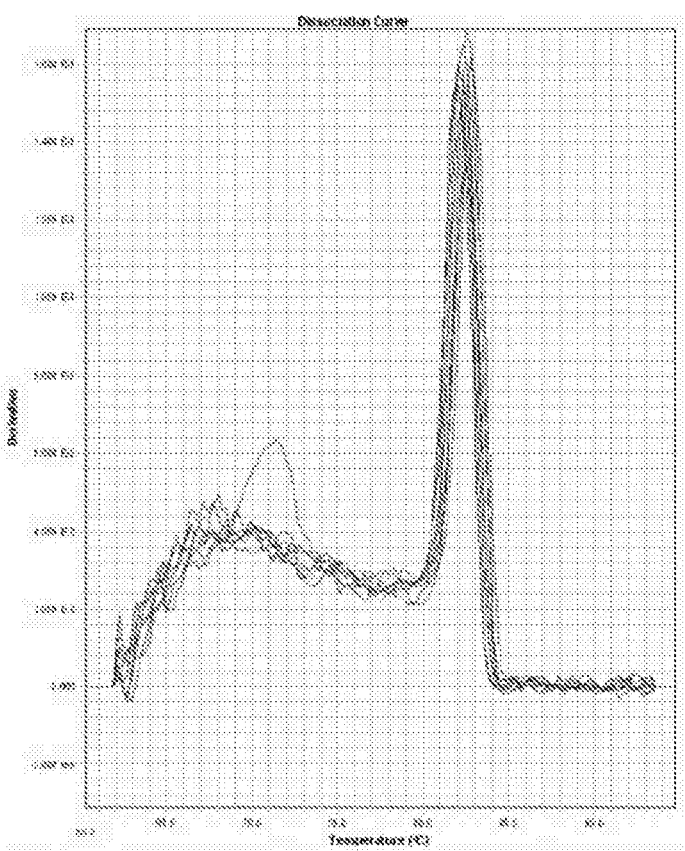
Figure 23

A

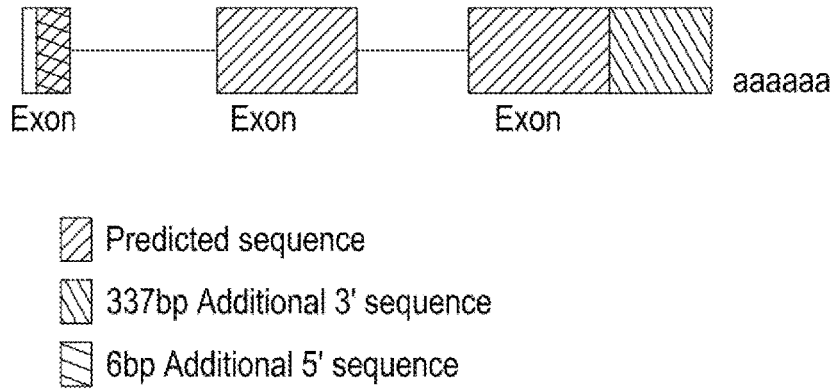

Exon    Exon    Exon    aaaaaa

⬚ Predicted sequence
⬚ 337bp Additional 3' sequence
⬚ 6bp Additional 5' sequence

B

RP1194A24.1LncRNA2 SEQ ID NO: 27
GCTGCAAACATTGGGATCAGCCGTGACTATCCCATAACATAATATTTCTGATTTCATTCTTTT
CCTTTCTCCTACCAATTTAATCTGCAATCACTTCAAGAGAAGTCTGTTTAAAGGATATTCACA
TTCTG (intron1-11,398)
TTCACAGAGTTTGAGAGAAACTGTATTCAAGTTGCTGAAACCAAGAAGCTACACTCACGAGT
CTCACCTAAACTCGAATCTGATTTAGATGACATCATCCTGGACTTTGAGTTGATGAAACCTTG
GAGGTCTTGGGAGTAAAGCAAGTGTGATTTGCATATGATGGATATGAATTGTAATGGCCAGA
GCATGGCTGTG (intron 2- 2,269)
AGATGAAAACTCCCATTTTAGGGAACCAAGACTGAATTCCATAATTTACATGGATGTTTGGAA
GGTGTCTGCAACTTAATCTGTGTTCGTTTCTGAGATGTTGGGCAACTCCTTCTTGGAAGATG
TGGTAATGGTCTCTTCGAAAAGAAAATAATCATCTGAGTTTTGGCCAAAATAGTTGATCGGAT
TACCTATGAAAATGACTCTCACCCAACTACAAGAATGTTATGATGTAGAAACTCTAAATATAT
GAGTAATTAACTATACAACACTCCATCCCCATGTGAAAATCTTTAATCTTTTAAGATACTGAAA
TTTTGTGTATGTCTCATAATTTTCTGTATATGGTCAATGAGTTTTGCCTTAGCCATAAGTGGT
CTGTCTGAAATCTTCTCTATTATTTGTGCATTTTCTTCCTGATGTACCAAGCCTAGTCTGTTTG
TTTTTTCCTAAGAGAAAAGCAGATGATTCAACTGTGTATTTCTCAGTGTTGATATTGTGGTTT
GAGGTATTTCATAATCTTGAGTAAAATCTTGTCATAAAAAAAAAAAAAAAAAAAAAA

Figure 30

A The Pearson correlation:

|  | crp dct | trans dct |
|---|---|---|
| Crp | 1.0000 | |
| Transdct | 0.5719<br>0.0001 | 1.0000 |

So  $r=0.5719$,  $r2=0.327$,  $p<0.001$

B If we take out the two outliers (the two highest dCts):

pwcorr crp transdct, sig

|  | crp dct | trans dct |
|---|---|---|
| Crp | 1.0000 | |
| Transdct | 0.389<br>0.0144 | 1.0000 |

$r=0.389$, $r^2=0.151$, $p=0.014$

Figure 37

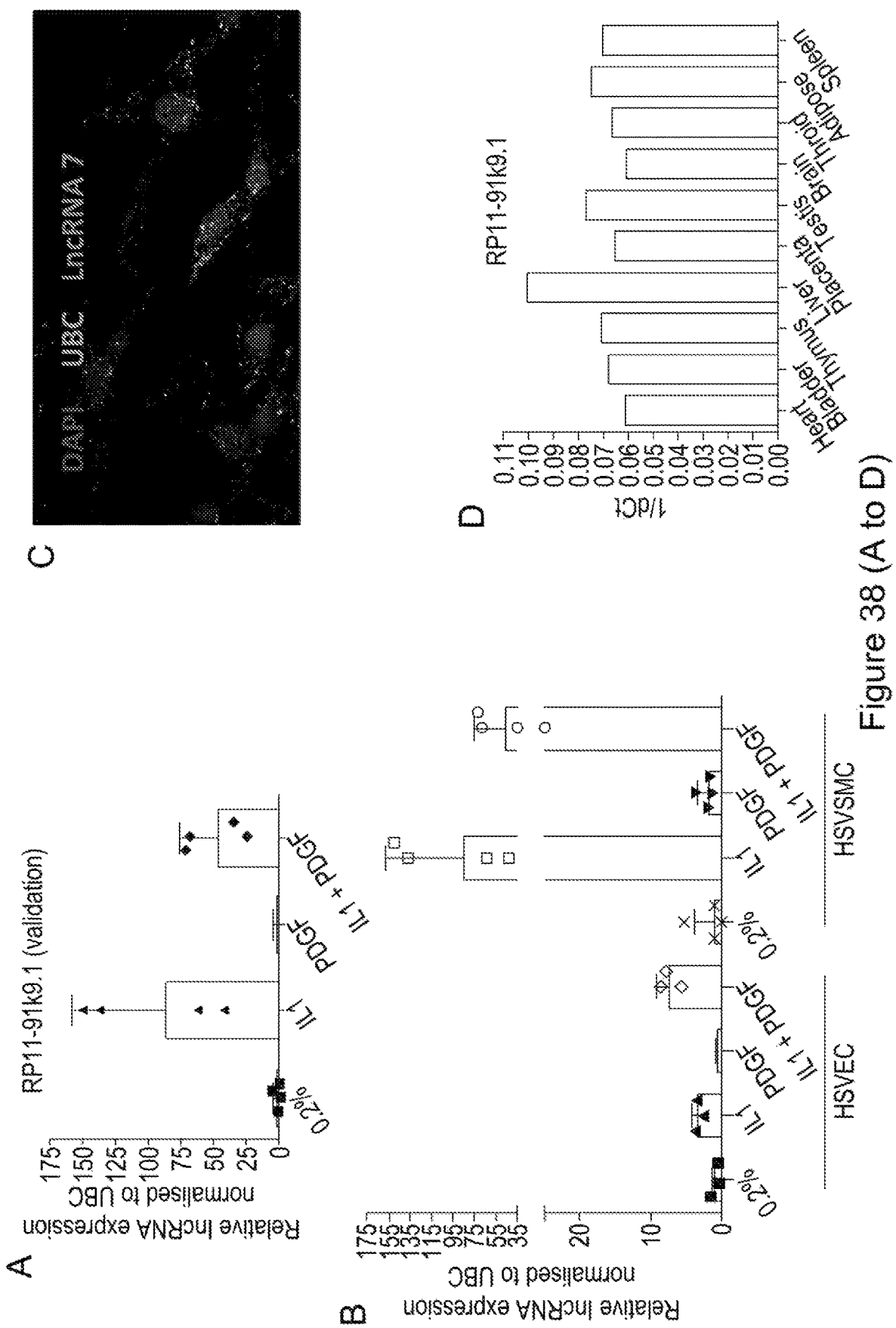
Figure 38 (A to D)

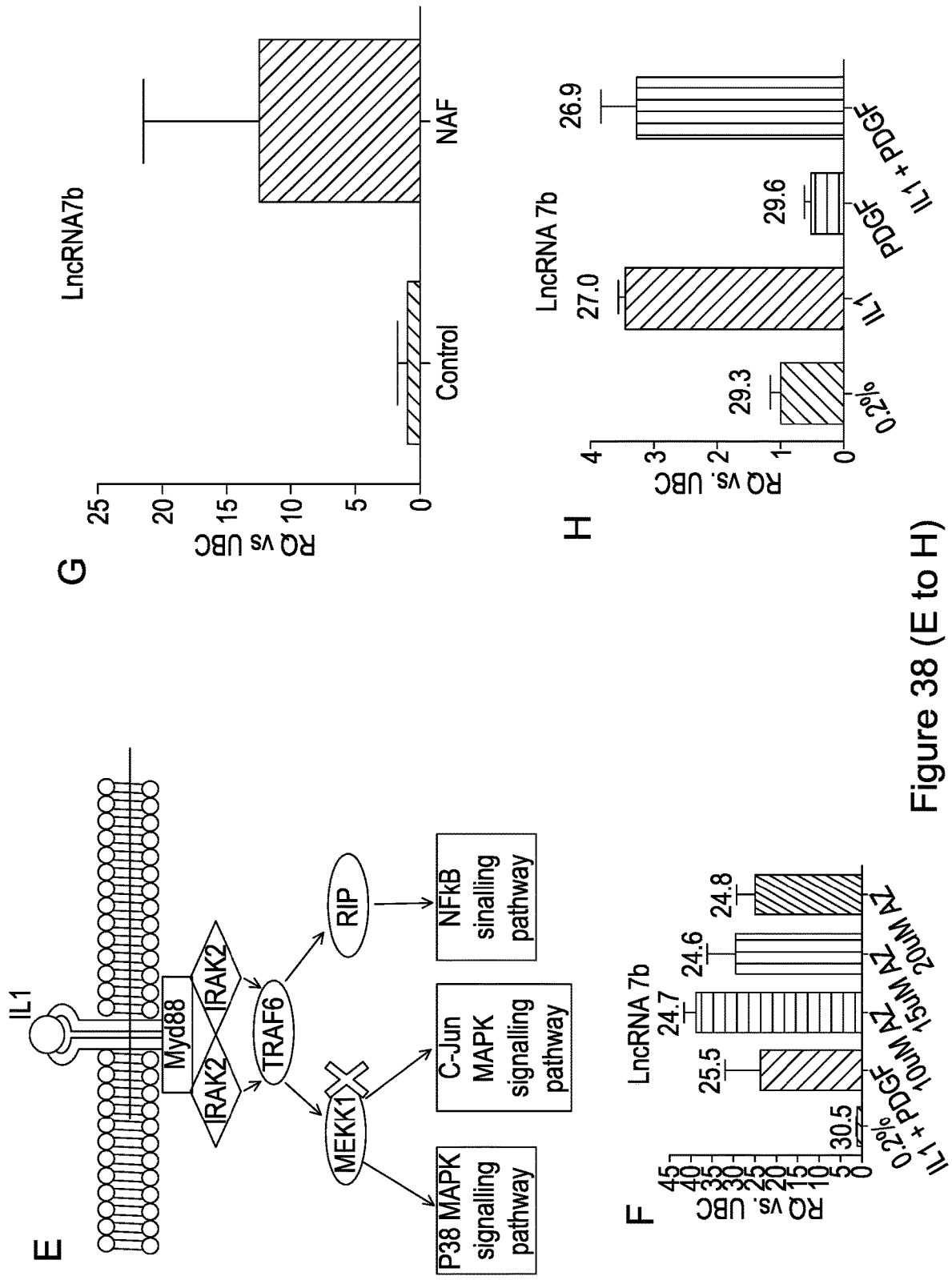
Figure 38 (E to H)

SMILR (LncRNA2) DNA sequence SEQ ID NO: 28
GCTGCAAACATTGGGATCAGCCGTGACTATCCCATAACATAATATTTCTGATTTCATTCTTTTCCTTT
CTCCTACCAATTTAATCTGCAATCACTTCAAGAGAAGTCTGTTTAAAGGATATTCACATTCTGTTCAC
AGAGTTTGAGAGAAACTGTATTCAAGTTGCTGAAACCAAGAAGCTACACTCACGAGTCTCACCTAAAC
TCGAATCTGATTTAGATGACATCATCCTGGACTTTGAGTTGATGAAACCTTGGAGGTCTTGGGAGTAA
AGCAAGTGTGATTTGCATATGATGGATATGAATTGTAATGGCCAGAGCATGGCTGTGAGATGAAAACT
CCCATTTTAGGGAACCAAGACTGAATTCCATAATTTACATGGATGTTTGGAAGGTGTCTGCAACTTAA
TCTGTGTTCGTTTCTGAGATGTTGGGCAACTCCTTCTTGGAAGATGTGGTAATGGTCTCTTCGAAAAG
AAAATAATCATCTGAGTTTTGGCCAAAATAGTTGATCGGATTACCTATGAAAATGACTCTCACCCAAC
TACAAGAATGTTATGATGTAGAAACTCTAAATATATGAGTAATTAACTATACAACACTCCATCCCCAT
GTGAAAATCTTTAATCTTTTAAGATACTGAAATTTTGTGTATGTCTCATAATTTTCTGTATATGGTCA
ATGAGTTTTGCCTTAGCCATAAGTGGTCTGTCTGAAATCTTCTCTATTATTTGTGCATTTTCTTCCTG
ATGTACCAAGCCTAGTCTGTTTGTTTTTCCTAAGAGAAAAGCAGATGATTCAACTGTGTATTTCTCA
GTGTTGATATTGTGGTTTGAGGTATTTCATAATCTTGAGTAAAATCTTGTCATAAAAAAAAAAAAAA
AAAAAA

SMILR (LncRNA 2) RNA sequence SEQ ID NO: 29
CGACGUUUGU AACCCUAGUC GGCACUGAUA GGGUAUUGUA UUAUAAAGAC UAAAGUAAGA
AAAGGAAAGA GGAUGGUUAA AUUAGACGUU AGUGAAGUUC UCUUCAGACA AAUUUCCUAU
AAGUGUAAGA CAAGUGUCUC AAACUCUCUU UGACAUAAGU UCAACGACUU UGGUUCUUCG
AUGUGAGUGC UCAGAGUGGA UUUGAGCUUA GACUAAAUCU ACUGUAGUAG GACCUGAAAC
UCAACUACUU UGGAACCUCC AGAACCCUCA UUUCGUUCAC ACUAAACGUA UACUACCUAU
ACUUAACAUU ACCGGUCUCG UACCGACACU CUACUUUUGA GGGUAAAAUC CCUUGGUUCU
GACUUAAGGU AUUAAAUGUA CCUACAAACC UUCCACAGAC GUUGAAUUAG ACACAAGCAA
AGACUCUACA ACCCGUUGAG GAAGAACCUU CUACACCAUU ACCAGAGAAG CUUUUCUUUU
AUUAGUAGAC UCAAAACCGG UUUUAUCAAC UAGCCUAAUG GAUACUUUUA CUGAGAGUGG
GUUGAUGUUC UUACAAUACU ACAUCUUUGA GAUUUAUAUA CUCAUUAAUU GAUAUGUUGU
GAGGUAGGGG UACACUUUUA GAAAUUAGAA AAUUCUAUGA CUUUAAAACA CAUACAGAGU
AUUAAAAGAC AUAUACCAGU UACUCAAAAC GGAAUCGGUA UUCACCAGAC AGACUUUAGA
AGAGAUAAUA AACACGUAAA AGAAGGACUA CAUGGUUCGG AUCAGACAAA CAAAAAAGGA
UUCUCUUUUC GUCUACUAAG UUGACACAUA AAGAGUCACA ACUAUAACAC CAAACUCCAU
AAAGUAUUAG AACUCAUUUU AGAACAGUAU UUUUUUUUUU UUUUUUUUUU

LncRNA 4 DNA sequence SEQ ID NO: 30
GAATGGGGTAACCTGGCTAAATGAGAATTAATGAACCCACACTCATAAGTTTTCATTGACTTAGCACC
AAGTCGTCCATCAAATATCATCAGATCTGAGAATGCTCTTATGGATATCTGATTTTTAGAGGCTGGCA
TTCATATTTTTAAAAACTGCCACCTGTGACCACACTGCAGGCCAAACAGAATGTACCTGCTGGTCAGA
TGCAGCCCAGAGGTCACTGAATTGCAACCTCTGGACTCTCGGTCAGAGGCAAGCAGCCCTTATTCCAG
AACTCCACAGTCCTTCACACCCTTCCCCAGACCTACACCAAGACCAACTAAGTGGTCAAAAGGTGGAC
AAACTGAGAGTTGTATCAAGGCCCTTAGCCTCTCAATTTGTTATCAAGTTTCCCTTTCTGAATCTATT
TACCCTGAAGTATAAATACCCAAGATGAGCCTTAAGAGTGCCTGGTAGAGCAAACAAAGATGCATCTT
ATAGGGAGCAAAGTCTATGCTAACGCAGTGTTTCTCAATCCTGGCTGCACCTTTGAACCACGGGAGCT
TTAAAAGTGACCACTGCAAGGGCCCTACCCACTATGGATCCCAATTTCATTGGTTGGGAGAGGGCCA
AGTTTGTTTCCAACTTCCCCAGATGACTCTAATGGCTGAGAGTTGCAATCAACAGGTAAGTGAATATC
CAGGCTGTAAGATGAAGAAAGAGGGGGTTGTGCCCAAGCCCACTGTGCCTCATAAAGCAGATGATCTC
TGCAGCGCTGCGCTTCTCAAAGAGTGGTCCCAGGACTGCCTCAGTCAGACCACAGACTCCTAAGTTCC
TCCTCAGACTTCATGGATCCAAGCTCTGTGAGGTAATTCTAAGCACATTAAACTTGTAGAACAGCCAT
CTGGATTTAATATTACATAATAGCTATAATATTCTGCTATTCTCTAATCTTCAATGTCAGTTTCTTAA
ACTGTCAGGCCTGTCTTTAGATGCCCTTCAACTGTGCTGGGGACTATCTTGATGGCAGCCAGCAAGA
AAATCAGCAAAACCCCAGTGGAGTTTCTGGGTTTTACTTTTGTTAAGGAAGGTGATGGTTTCTTGAC
ATGACAGGTATCTA

Figure 39

GGTGGAAAGGGCAAAGTGCTAATGCAAACACAATGGAGACACTATGGAATAGCTCTGCCTAGGGACAT
GTGGAAGAGCTTCTAGGAGACAGTGTGGACCTTTCCATCCCTAGAGGTCTTCACAAGATAAATTCCTA
CCTCCGTCA
GTATTCAAAAGGTTTTAGCATCAATACTGTCTGAGAATAAGACATTAGACTTGAGTCAGTCCCCTGGC
TTCAATCCCAGGATGCCAAGCAGCCTCTAATGGAGACCGCTGGCTTAATCGTGCTCCTTTCCTGGCAT
AACAACTCACTGCACCCATGCCTCACCACCACGAAGCAGTCTCCTCACCACCCAAATGTGCCTTGGGT
GACTTAAATACAGCCATTAGTATGAATGGTCCCTGTTTTTATTCAACACCACACCAGTCTTTGCTTT
TACCTTCGGCTAATGTGGTTCCAGCCTTTTATCCTGCACTCCTTCTTATAATTTAAAAAAAAAAAAA
CTCCCCTACTATCTTTATGTTAATATTAACATCAACTAGGTTCTTCTCAAAGGACAGCCAGGCCTAAC
TGGCCACGTTAAAATCTGCACAGTGCTTTTGTGTCACTGTCTATTCTATTAGTTTCAACATCATGCTA
AAATAGGACAGCATGTTCCAAAACTGAAACTGAAACAGGAACGGAGCCTTGCTGATTTAGCATGAGGA
GGGAATTGTAAGCCTTGCACCTGGACACTAAAACTTTTCAATAAGATGTATGCTAAGCCGTACCTAGC
AAACTTACCAGGTCCAAAGTAGAGTACAAGCAGAAAGTTATTTTTAAAGGATGGGCACTATCCTTGAG
GGACTTACCCTTTCTAATCAGCTTTGCATGGTTTGTTTTGAGACAGTGTCTCACTCTGTTGCCCAGGC
TAGAGTGCAGCGGCACCATCACAGCTCACGGCAGCCTCTGCCTCCGGGCTCAAGCAATCCCACCTCA
GTTTCCCAAGTAGCTGGGACTACAGGCACACACCACACTCAGCTAATTTTAGTATTTTTGTAGAGAC
AGGGTCTCGCCATGTTGCCCAGGCTGGTCTCAAACTCCTGGATTATCTCCCTGGCCCTGCATTAAAAA
AGATGTGCAACAACTTA

LncRNA 4 RNA sequence SEQ ID NO: 31

CUUACCCCAU UGGACCGAUU UACUCUUAAU UACUUGGGUG UGAGUAUUCA AAAGUAACUG
AAUCGUGGUU CAGCAGGUAG UUUAUAGUAG UCUAGACUCU UACGAGAAUA CCAUAGACU
AAAAAUCUCC GACCGUAAGU AUAAAAAUUU UUGACGGUGG ACACUGGUGU GACGUCCGGU
UUGUCUUACA UGGACGACCA GUCUACGUCG GGUCUCCAGU GACUUAACGU UGGAGACCUG
AGAGCCAGUC UCCGUUCGUC GGGAAUAAGG UCUUGAGGUG UCAGGAAGUG UGGGAAGGGG
UCUGGAUGUG GUUCUGGUUG AUUCACCAGU UUUCCACCUG UUUGACUCUC AACAUAGUUC
CGGGAAUCGG AGAGUUAAAC AAUAGUUCAA AGGGAAAGAC UUAGAUAAAU GGGACUUCAU
AUUUAUGGGU UCUACUCGGA AUUCUCACGG ACCAUCUCGU UUGUUUCUAC GUAGAAUAUC
CCUCGUUUCA GAUACGAUUG CGUCACAAAG AGUUAGGACC GACGUGGAAA CUUGGUGCCC
UCGAAAUUUU CACUGGUGAC GUUCCCGGGA UGGGUGAUAC CUAGGGUUAA AGUAACCAAC
CCUCUCCCCG GUUCAAACAA AGGUUGAAGG GGUCUACUGA GAUUACCGAC UCUCAACGUU
AGUUGUCCAU UCACUUAUAG GUCCGACAUU CUACUUCUUU CUCCCCCAAC ACGGGUUCGG
GUGACACGGA GUAUUUCGUC UACUAGAGAC GUCGCGACGC GAAGAGUUUC UCACCAGGGU
CCUGACGGAG UCAGUCUGGU GUCUGAGGAU UCAAGGAGGA GUCUGAAGUA CCUAGGUUCG
AGACACUCCA UUAAGAUUCG UGUAAUUUGA ACAUCUUGUC GGUAGACCUA AAUUAUAAUG
UAUUAUCGAU AUUAUAAGAC GAUAAGAGAU UAGAAGUUAC AGUCAAAGAA UUUGACAGUC
CGGACAGAAA UCUACGGGAA GUUGACACGA CCCCUGAUAG AACUACCGUC GGUCGUUUCU
UUUAGUCGUU UUUGGGGUCA CCUCAAAGAC CCAAAAUGAA AACAAUUCCU UCCACUACCA
AAGAACUGUA CUGUCCAUAG AUCCACCUUU CCCGUUUCAC GAUUACGUUU GUGUUACCUC
UGUGAUACCU UAUCGAGACG GAUCCCUGUA CACCUUCUCG AAGAUCCUCU GUCACACCUG
GAAAGGUAGG GAUCUCCAGA AGUGUUCUAU UUAAGGAUGG AGGCAGUCAU AAGUUUCCA
AAAUCGUAGU UAUGACAGAC UCUUAUUCUG UAAUCUGAAC UCAGUCAGGG GACCGAAGUU
AGGGUCCUAC GGUUCGUCGG AGAUUACCUC UGGCGACCGA AUUAGCACGA GGAAAGGACC
GUAUUGUUGA GUGACGUGGG UACGGAGUGG UGGUGCUUCG UCAGAGGAGU GGUGGGUUUA
CACGGAACCC ACUGAAUUUA UGUCGGUAAU CAUACUUACC AGGGGACAAA AAUAAGUUGU
GGUGUGGUCA GAAACGAAAA UGGAAGCCGA UUACACCAAG GUCGGAAAAU AGGACGUGAG
GAAGAAUAUU AAAUUUUUUU UUUUUUUGAG GGGAUGAUAG AAAUACAAUU AUAAUUGUAG
UUGAUCCAAG AAGAGUUUCC UGUCGGUCCG GAUUGACCGG UGCAAUUUUA GACGUGUCAC
GAAAACACAG UGACAGAUAA GAUAAUCAAA GUUGUAGUAC GAUUUUAUCC UGUCGUACAA
GGUUUUGACU UUGACUUUGU CCUUGCCUCG GAACGACUAA AUCGUACUCC UCCCUUAACA

Figure 39 Continued

```
UUCGGAACGU GGACCUGUGA UUUUGAAAAG UUAUUCUACA UACGAUUCGG CAUGGAUCGU
UUGAAUGGUC CAGGUUUCAU CUCAUGUUCG UCUUUCAAUA AAAAUUUCCU ACCCGUGAUA
GGAACUCCCU GAAUGGGAAA GAUUAGUCGA AACGUACCAA ACAAACUCU GUCACAGAGU
GAGACAACGG GUCCGAUCUC ACGUCGCCGU GGUAGUGUCG AGUGCCGUCG GAGACGGAGG
GCCCGAGUUC GUUAGGGUGG AGUCAAGGG UUCAUCGACC CUGAUGUCCG UGUGUGGUGU
GAGUCGAUUA AAAUCAUAAA AAACAUCUCU GUCCAGAGC GGUACAACGG GUCCGACCAG
AGUUUGAGGA CCUAAUAGAG GGACCGGGAC GUAAUUUUUU CUACACGUUG UUGAAU
```

LncRNA 5 DNA sequence SEQ ID NO: 32
```
TGTGAGGAGGCCCAGGCCACAAGGAGAGGCCACCTATAAGCATTCAGGCCAGCAGCCCCAGaTCTGCT
CCTCCTGCCAAGCTGAACCCAAGACCAGCACCTTCCTCCTTGTGTAAGATGGTGACATGGATGCCGTC
TAATTGCTGCAGAGGAAATACATACATTCAAAACATTTTACTGCAAGAGGATGAACAATTTAACATC
GGACTGACATCAGACTGATTTGTTATCTCAAACCCCAGCTTGGCCAGCCTCCAAGTTACATCACCTCC
TCAAACCTCAGTTTCCTCATCTGTAAAGAATGGACCTTCAGGAGTCATGGGAAGCTTAGAAGAAAAAA
AAAATGTATGTAAAGCAGCAAGCATAATTATTTTCCTCTCTCATTCACCCTGTCCACAGCCGGGCAGG
GGGAGTGCCATGAAGTCAGCCAGAAATCAGCATATTGGACAGTGTGAGATGAAGTCAGGTTGTAGGAC
```

LncRNA 5 RNA sequence SEQ ID NO: 33
```
ACACUCCUCC GGGUCCGGUG UUCCUCUCCG GUGGAUAUUC GUAAGUCCGG UCGUCGGGGU
CUAGACGAGG AGGACGGUUC GACUUGGGUU CUGGUCGUGG AAGGAGGAAC ACAUUCUACC
ACUGUACCUA CGGCAGAUUA ACGACGUCUC CUUUAUGUAU GUAAGUUUUU GUAAAAUGAC
GUUCUCCUAC UUGUUAAAUU GUAGCCUGAC UGUAGUCUGA CUAAACAAUA GAGUUGGGG
UCGAACCGGU CGGAGGUUCA AUGUAGUGGA GGAGUUUGGA GUCAAGGAG UAGACAUUUC
UUACCUGGAA GUCCUCAGUA CCCUUCGAAU CUUCUUUUUU UUUUACAUAC AUUUCGUCGU
UCGUAUUAAU AAAAGGAGAG AGUAAGUGGG ACAGGUGUCG GCCCGUCCCC CUCACGGUAC
UUCAGUCGGU CUUUAGUCGU AUAACCUGUC ACACUCUACU UCAGUCCAAC AUCCUG
```

LncRNA 6a DNA sequence SEQ ID NO: 34
```
ACATGGATCCTTAAGTCCTCCCTATGCCCGTTAGAGCACTGATGACATTTACTTTGAAATTCCCCTG
TTACATGTCTGTTTGCCTAAGTAGACTCTAAGCATCTGCAGAACAGGGGCTATGTCTTAGTATCCAGG
GTATTTTCTTCACCTGGCACAATTCCTGCCACAGAGTAGTGTGTCAGCTCTCTATTGTTGTCTAAAAA
CCCACCTCAAGGTGCTGGGATTACAGGTGTGAGCCACTGTGCCTGGCCCCACATTTTTTAAAACAATG
ACTTTAGGGTTTCAGCTTTTCCTGTCTTTTAAAACAAATTAGCCATTTTTTATTCTAAGAAAGGGTTG
TATTATAAAGCTGACCTACTACTAGCTTATCAGAAAAAACACGTGGGTCTCATATCTGATTCTCCTAT
GTAGCCAAAAGTGCCATTTGTAAGTCTACTAAATGACGGATATTTTCTGAAGATCTTTTGCCTGGAAA
ACAAATAGTGCATT
```

LncRNA 6a RNA sequence SEQ ID NO: 35
```
UGUACCUAGG AAUUCAGGAG GGAUACGGGG CAAUCUCGUG ACUACUGUAA AUGAAACUUU
AAGGGGACAA UGUACAGACA AACGGAUUCA UCUGAGAUUC GUAGACGUCU UGUCCCCGAU
ACAGAAUCAU AGGUCCCAUA AAAGAAGUGG ACCGUGUUAA GGACGGUGUC UCAUCACACA
GUCGAGAGAU AACAACAGAU UUUUGGGUGG AGUUCCACGA CCCUAAUGUC CACACUCGGU
GACACGGACC GGGGUGUAAA AAAUUUUGUU ACUGAAAUCC CAAAGUCGAA AAGGACAGAA
AAUUUUGUUU AAUCGGUAAA AAAUAAGAUU CUUUCCCAAC AUAAUAUUUC GACUGGAUGA
UGAUCGAAUA GUCUUUUUUG UGCACCCAGA GUAUAGACUA AGAGGAUACA UCGGUUUUCA
CGGUAAACAU UCAGAUGAUU UACUGCCUAU AAAAGACUUC UAGAAACGG ACCUUUUGUU
UAUCACGUAA
```

Figure 39 Continued

LncRNA 6b DNA sequence SEQ ID NO: 36
GGGTTGATTCTATTATCTGATGTTTTATTAATCTCTGTGAAATAATTGTGTAAATTAATATAGAGACT
AGTTGAGAAATGGTGGATAACATGAAGAAGATACCCATTTTTGCATAGATTAGATGTGATCAACCTCA
CACTATCATATGAAAGTTGGCTGCATTGGAGAGACAGGAATTAATATTAAAAATGTTTTCAGTTCAGA
TTGATATCTTACATTTCCAAATATTATTTTCTTTTGAATATGTGTGAGCCACTGTGCCTGGCCCCACA
TTTTTTAAAACAATGACTTTAGGGTTTCAGCTTTTCCTGTCTTTTAAAACAAATTAGCCATTTTTTAT
TCTAAGAAAGGGTTGTATTATAAAGCTGACCTACTACTAGCTTATCAGAAAAAACACGTGGGTCTCAT
ATCTGATTCTCCTATGTAGCCAAAAGTGCCATTTGTAAGTCTACTAAATGACGGATATTTTCTGAAGA
TCTTTTGCCTGGAAAACAAATAGTGCATTAAAAAGCTTTTTTGGTA

LncRNA 6b RNA sequence SEQ ID NO: 37
CCCAACUAAG AUAAUAGACU ACAAAAUAAU UAGAGACACU UUAUUAACAC AUUUAAUUAU
AUCUCUGAUC AACUCUUUAC CACCUAUUGU ACUUCUUCUA UGGGUAAAAA CGUAUCUAAU
CUACACUAGU UGGAGUGUGA UAGUAUACUU UCAACCGACG UAACCUCUCU GUCCUUAAUU
AUAAUUUUUA CAAAAGUCAA GUCUAACUAU AGAAUGUAAA GGUUUAUAAU AAAAGAAAAC
UUAUACACAC UCGGUGACAC GGACCGGGGU GUAAAAAAUU UUGUUACUGA AAUCCCAAAG
UCGAAAAGGA CAGAAAAUUU UGUUUAAUCG GUAAAAAAUA AGAUUCUUUC CCAACAUAAU
AUUUCGACUG GAUGAUGAUC GAAUAGUCUU UUUUGUGCAC CCAGAGUAUA GACUAAGAGG
AUACAUCGGU UUUCACGGUA AACAUUCAGA UGAUUUACUG CCUAUAAAAG ACUUCUAGAA
AACGGACCUU UUGUUUAUCA CGUAAUUUUU CGAAAAAACC AU

LncRNA 7a DNA sequence SEQ ID NO: 38
AAAGGTACTTAGACATGTTCCCCACAGGATGTGTTAAGGTGTTGGCCAATCATCAAATATTGTCACTC
CAAAGAACACATTTAACAGCCGGGAAGAAAATTGTAGGAAAAGAGAGCACTTTGGCACGGAAGGGGTC
TATCGCCCTGGTTGGAGTGCAGCAGTGTAATCATAGCTCACTGCTGCCATGAACTTCTGGGCTCAAGC
GATCCTCCCACCTCAGCCTCCCTGTGTGCTGGGATTAAAAGTGTGAGCCACCGTGCCTCATCGTAAGG
GTCTTAAAAGAAACCCTATTTCATACTTTCTTGATGCACTTGATATGGATTATATAAATCTATGGACA
AAAATGACATCAGTACAATGGAATATTGGAGTTTTCTACCATAATCTCTGCATAGTGCACTGATTTTG
ACAATCACCTATGGATGAAAATACATTTGCCAGAGTCTAGGAGTTAAATGGAAAAGTTAACAGCACAC
CGTTGGAGAAAATATCTGGGAGTAGATGCATTCAAGGGAGTAAGAAGAACAATTACCTGCATCACCT
CACCCCCAGGGTCCACTTCTTAGTGCCAAGATAGACTCCCTTCAGCAGGCAATTTCTCCCATGGGAA
AAGGAGAGTATAATGAGTGAGTATCCAGCTTTTCCAGCTGTGTGAGGCACATCCCAAGAAGCCCATCT
TTCTTTCACTCAACTCAGAATATTGAGGGTATTAGCATGGCTAAGTGGCTGGGACAGGGCAGTAGCAG
GAAAGAAAGGAGAGGACTCACAGCAACCAGGACTTGAAACTCAGTACAGGGTACATATCCTTTGAAGC
ATTTCACAGAGCCCATCAGGAGGCCCACCCATGAACCACTTGGGACACCATATCTGTAGCATCTCCCT
GCAACTGGCCCATAGGAGCCCCCGATGTTTTGTGCATATTCCCCTTCCCTTTCTCCTATAGTCAGTTG
CCTGCACATGCACTCCAGATGGTGAGTGTGAGCATTTACCTACAGCTTTTGAGTACATGCAGTCAGCA
GGCTCAACTTTGAAGGATTGGGAGGAATACAAAATTGAGCATTTCAGGGCACTGTCCTAGAGGAAACA
AACAGAAAGCTTTCAGGACCCAGTTTGGTTTTGTGGATTTAAGAGAAGACACACAATCATCAGAATTT
CTTCTCCACCCATCCAAGAAGTGTGGATTGGGTGAATCCATAGAAAAGATCTGAGAGAGCCTCAGATT
CCCTATAGGCTCACTGTTGAAGATATTTCTCTCAAATCCAGTCAGTAAAGACTAGAGAAAGTGACTCT
TTCTTCAAATGTGAAGACAGCAGTGCAAGACTTTGAGGAACATGAAAAATCAAGGACACCTAGTACCA
CCAAAGGAACATAATTTTCTGGTACCCAACCACAAAGAAATGGAGATACACAAATTGTCTGACAAAGA
ATTCACAACAATTGTTTTAAGGAAGTCAGTAAGCTACAAGAGAACACAGAGAACTTAATGATATTAAG
AAAGCGACACATGAACAAAATAAGATGTTCAACAAAAAGATAGAAATTATTAAAAACAACCATGATTT
TCGAGCTGAGAATACAATGAATGAAATGGAAAACACAATAGAGTTTCAATAGCAGACTTGATCAAGCA
GAAGAAAGGGTCTGTCAACTCAAATACTAGTCATTTGAAATTATTCAGTAAAAGAAATAAAAAGGAAT
GAAAAATGCTTATGCGATTGATGCAACACCATGAAGAGTAGTCATATATGCACTATGGGAGTCTCAGA
AAAAGAAAGAGATAAAGGGGAAGAAAACTAACTTAAAGAACTAGATCAGTCTCT

Figure 39 Continued

```
CCTTATCTGTAGTTTTGCTTTCCTTGGTTTCAGGTACAGTACAATGATATGTTTTAAGAGACAGACAA
TGAAAGAGAACATGCAAATATTGACATAATTTTTATTACAGTATATTGTCATAGTTTTTCTATTTTGT
TATTAGTTGTTATTCTCTTACTGTGCCTAATTTATACATTAAACTTTATCATAGGAATAGTGGTGGTG
GCCTGTCTGGAGTGGCCACTGCCAGGATGCCAGCTGCAGCAGGGGAGGTGTAGCTGGGGCTGTGCACT
CCGCAGAGCTGGGGGGGCCAGGAACAGGTGATCCTAGTGGGAGCCCTATATGCTACTGAGTTAGTGG
GGTGGGAGCCTGTGCTCCCAGGCATAGCTGCAGCTGCCCAGCCATGGCTCCAGCCCTAGGCATACCTG
TGCTCTCAGGGGCCCTGGAAGTCCCCTGCCCTTACAGGCTTGGAAGTGCCTGCTCCCATTCCCTGGCC
TCTTTCCACTGCTGGCACCTGCTCTGTGGCAGAGCAAAGTTGTGGATGTGTTGTGATAGCTGAGCCTG
GGAGCTGTTGTGACGTGGTCAGGTGTGTGTGTTCAGGGCAGTTCTGATACACCAGACTCCCCACTGCC
TTTGCCCCCTCTGGAAACTGCTTCTGAGGCTGAAACTTTGGATATTAATGAGCAAGGATGGTGGGGGA
GGCCAGGACGGCTGAGGGCAGCTAGGTGTGGGCCTGTGGACACCCCTTAGTGCGGACAGTCTGGGTGC
TGTGGATGGCATGTTGATGGCAGCGAGAGGCAGACATGTTCCTAGGTGGGAACGGGTGGGTCCCTGGT
GAAACCTCACCTTCAAGCCAGGGACAGCTTGAAGCATGGGGCCTGGCTGCCAGTTCCGGTTGCAGTC
TGTGACCTGGAGTGAAAACTTCATTGATGTCTTTCAGCCAATTGGATGGTGCTTTTTCCAGACCCACA
AATGGCTGCCCATGGACCAAGCAGTATGTACTTCCTCCATTCTGAGCCCATGAAAACCCCAGACTCAG
TCAGACTCTGACACTCATCAGGATGACAAGCCTGCAAATAGGATCTACCCATTTTGGGTATGCACTCC
ACTGAGAGCTATTCTGTCACTCAATAAAGCTCCTTTCTGCCTTGCTC
```

LncRNA 7a RNA sequence SEQ ID NO: 39

```
UUUCCAUGAA UCUGUACAAG GGGUGUCCUA CACAAUUCCA CAACCGGUUA GUAGUUUAUA
ACAGUGAGGU UUCUUGUGUA AAUUGUCGGC CCUUCUUUUA ACAUCCUUUU CUCUCGUGAA
ACCGUGCCUU CCCCAGAUAG CGGGACCAAC CUCACGUCGU CACAUUAGUA UCGAGUGACG
ACGGUACUUG AAGACCCGAG UUCGCUAGGA GGGUGGAGUC GGAGGGACAC ACGACCCUAA
UUUUCACACU CGGUGGCACG GAGUAGCAUU CCCAGAAUUU UCUUUGGGAU AAAGUAUGAA
AGAACUACGU GAACUAUACC UAAUAUAUUU AGAUACCUGU UUUUACUGUA GUCAUGUUAC
CUUAUAACCU CAAAAGAUGG UAUUAGAGAC GUAUCACGUG ACUAAAACUG UUAGUGGAUA
CCUACUUUUA UGUAAACGGU CUCAGAUCCU CAAUUUACCU UUUCAAUUGU CGUGUGGCAA
CCUCUUUUUA UAGACCCUCA UCUACGUAAG UUCCUCAUU CUUCUUGUUA AUGGACGUAG
UGGAGUGGGG GUCCCAGGUG AAGAAUCACG GUUCUAUCUG AGGGAAGUCG UCCGUUAAAG
AGGGUACCCC UUUUCCUCUC AUAUUACUCA CUCAUAGGUC GAAAAGGUCG ACACACUCCG
UGUAGGGUUC UUCGGGUAGA AAGAAAGUGA GUUGAGUCUU AUAACUCCCA UAAUCGUACC
GAUUCACCGA CCCUGUCCCG UCAUCGUCCU UUCUUUCCUC UCCUGAGUGU CGUUGGUCCU
GAACUUUGAG UCAUGUCCCA UGUAUAGGAA ACUUCGUAAA GUGUCUCGGG UAGUCCUCCG
GGUGGGUACU UGGUGAACCC UGUGGUAUAG ACAUCGUAGA GGGACGUUGA CCGGGUAUCC
UCGGGGGCUA CAAAACACGU AUAAGGGGAA GGGAAAGAGG AUAUCAGUCA ACGGACGUGU
ACGUGAGGUC UACCACUCAC ACUCGUAAAU GGAUGUCGAA AACUCAUGUA CGUCAGUCGU
CCGAGUUGAA ACUUCCUAAC CCUCCUUAUG UUUUAACUCG UAAAGUCCCG UGACAGGAUC
UCCUUUGUUU GUCUUUCGAA AGUCCUGGGU CAAACCAAAA CACCUAAAUU CUCUUCUGUG
UGUUAGUAGU CUUAAAGAAG AGGUGGGUAG GUUCUUCACA CCUAACCCAC UUAGGUAUCU
UUUCUAGACU CUCUCGGAGU CUAAGGGAUA UCCGAGUGAC AACUUCUAUA AAGAGAGUUU
AGGUCAGUCA UUUCUGAUCU CUUUCACUGA GAAAGAAGUU UACACUUCUG UCGUCACGUU
CUGAAACUCC UUGUACUUUU UAGUUCCUGU GGAUCAUGGU GGUUUCCUUG UAUUAAAAGA
CCAUGGGUUG GUGUUUCUUU ACCUCUAUGU GUUUAACAGA CUGUUUCUUA AGUGUUGUUA
ACAAAAUUCC UUCAGUCAUU CGAUGUUCUC UUGUGUCUCU UGAAUUACUA UAAUUCUUUC
GCUGUGUACU UGUUUUAUUC UACAAGUUGU UUUUCUAUCU UUAAUAAUUU UUGUUGGUAC
UAAAAGCUCG ACUCUUAUGU UACUUACUUU ACCUUUUGUG UUAUCUCAAA GUUAUCGUCU
GAACUAGUUC GUCUUCUUUC CCAGACAGUU GAGUUUAUGA UCAGUAAACU UUAAUAAGUC
AUUUUCUUUA UUUUUCCUUA CUUUUUACGA AUACGCUAAC UACGUUGUGG UACUUCUCAU
CAGUAUAUAC GUGAUACCCU CAGAGUCUUU UUCUUUCUCU AUUUCCCCUU CUUUUGAUUG
AAUUUCUUGA UCUAGUCAGA GAGGAAUAGA CAUCAAAACG AAAGGAACCA AAGUCCAUGU
```

Figure 39 Continued

CAUGUUACUA UACAAAAUUC UCUGUCUGUU ACUUUCUCUU GUACGUUUAU AACUGUAUUA
AAAAUAAUGU CAUAUAACAG UAUCAAAAAG AUAAAACAAU AAUCAACAAU AAGAGAAUGA
CACGGAUUAA AUAUGUAAUU UGAAAUAGUA UCCUUAUCAC CACCACCGGA CAGACCUCAC
CGGUGACGGU CCUACGGUCG ACGUCGUCCC CUCCACAUCG ACCCCGACAC GUGAGGCGUC
UCGACCCCCC CCGGUCCUUG UCCACUAGGA UCACCUCGG GAUAUACGAU GACUCAAUCA
CCCCACCCUC GGACACGAGG GUCCGUAUCG ACGUCGACGG GUCGGUACCG AGGUCGGGAU
CCGUAUGGAC ACGAGAGUCC CCGGGACCUU CAGGGGACGG GAAUGUCCGA ACCUUCACGG
ACGAGGGUAA GGGACCGGAG AAAGGUGACG ACCGUGGACG AGACACCGUC UCGUUUCAAC
ACCUACACAA CACUAUCGAC UCGGACCCUC GACAACACUG CACCAGUCCA CACACACAAG
UCCCGUCAAG ACUAUGUGGU CUGAGGGGUG ACGGAAACGG GGGAGACCUU UGACGAAGAC
UCCGACUUUG AAACCUAUAA UUACUCGUUC CUACCACCCC CUCCGGUCCU GCCGACUCCC
GUCGAUCCAC ACCCGGACAC CUGUGGGGAA UCACGCCUGU CAGACCCACG ACACCUACCG
UACAACUACC GUCGCUCUCC GUCUGUACAA GGAUCCACCC UUGCCCACCC AGGGACCACU
UUGGAGUGGA AGUUCGGUCC CUGUCGAACU UCGUACCCCC GGACCGACGG UCAAGGCCAA
CGUCAGACAC UGGACCUCAC UUUUGAAGUA ACUACAGAAA GUCGGUUAAC CUACCACGAA
AAAGGUCUGG GUGUUUACCG ACGGGUACCU GGUUCGUCAU ACAUGAAGGA GGUAAGACUC
GGGUACUUUU GGGGUCUGAG UCAGUCUGAG ACUGUGAGUA GUCCUACUGU UCGGACGUUU
AUCCUAGAUG GGUAAAACCC AUACGUGAGG UGACUCUCGA UAAGACAGUG AGUUAUUUCG
AGGAAAGACG GAACGAG

LncRNA 7b DNA sequence SEQ ID NO: 40
ACAAAGTTTATATTAGAGCGTCATCCATTAATGCTTTGGCTAGGAGGGGGTCTATCGCCCTGGTTGGA
GTGCAGCAGTGTAATCATAGCTCACTGCTGCCATGAACTTCTGGGCTCAAGCGATCCTCCCACCTCAG
CCTCCCTGTGTGCTGGGATTAAAAGTGTGAGCCACCGTGCCTCATCGTAAGGGTCTTAAAAGAAACCC
TATTTCATACTTTCTTGATGCACTTGATATGGATTATATAAATCTATGGACAAAAATGACATCAGTAC
AATGGAATATTGGAGTTTTCTACCATAATCTCTGCATAGTGCACTGATTTTGACAATCACCTATGGAT
GAAAATACATTTGCCAGAGTCTAGGAGTTAAATGGAAAAGTTAACAGCACACCGTTGGAGAAAAATAT
CTGGGAGTAGATGCATTCAAGGGAGTAAGAAGAACAATTACCTGCATCACCTCACCCCCAGGGTCCAC
TTCTTAGTGCCAAGATAGACTCCCTTCAGCAGGCAATTTCTCCCATGGGAAAAGGAGAGTATAATGA
GTGAGTATCCAGCTTTTCCAGCTGTGTGAGGCACATC

LncRNA 7b RNA sequence SEQ ID NO: 41
UGUUUCAAAU AUAAUCUCGC AGUAGGUAAU UACGAAACCG AUCCUCCCCC AGAUAGCGGG
ACCAACCUCA CGUCGUCACA UUAGUAUCGA GUGACGACGG UACUUGAAGA CCCGAGUUCG
CUAGGAGGGU GGAGUCGGAG GGACACACGA CCCUAAUUUU CACACUCGGU GGCACGGAGU
AGCAUUCCCA GAAUUUUCUU UGGGAUAAAG UAUGAAAGAA CUACGUGAAC UAUACCUAAU
AUAUUUAGAU ACCUGUUUUU ACUGUAGUCA UGUUACCUUA UAACCUCAAA AGAUGGUAUU
AGAGACGUAU CACGUGACUA AAACUGUUAG UGGAUACCUA CUUUUAUGUA AACGGUCUCA
GAUCCUCAAU UUACCUUUUC AAUUGUCGUG UGGCAACCUC UUUUUAUAGA CCCUCAUCUA
CGUAAGUUCC CUCAUUCUUC UUGUUAAUGG ACGUAGUGGA GUGGGGUCC CAGGUGAAGA
AUCACGGUUC UAUCUGAGGG AAGUCGUCCG UUAAAGAGGG UACCCCUUUU CCUCUCAUAU
UACUCACUCA UAGGUCGAAA AGGUCGACAC ACUCCGUGUA G

LncRNA 8a DNA sequence SEQ ID NO: 42
CTGAACAACAAGTTAACTGCTGTTCCCAGTTATATCTGGTCTTTCCCACCCCCAAACATACACAAAAG
ATTTTTGTCATTCTTGGCACTGGACAACAGAAGTGATAAGACATGCCAGCAGAACTCTAAAGGCAGAA
TGTCCTTCCACCTGTTTTATGCTGTAAGACAAACTTCCAAGTGCGAGGCAGTGTGGAGGGCTGTTGCC
TTGAATGGCAGCTGAATGCACCAGCGGGATCCTTGGCAGCAATGCCCAGGCACTGAAGTCGGGCATTC
AGGAGAGCTAAATGGAGAAA

Figure 39 Continued

AGAAACTTGAGCAAACTGCTTCCTGGAACACTGAGAACCTGAATGGGAAATTAAGAAGAACCAGATTC
TTTCTATTCTTCCACCAGCCAAGGTCAGATTTCCAAACTTCTATTGATTCTAATCTTTCCCAAACAGT
GCTGTGGCAATGTATGAAAGTAATAAAAATAATCCTTTTTCTGTTAAAAAAAAATTGCTGTTACTTG
CTGTTTTGTTATGCTTTTGCTGGAGATTTTCCCACCCATCTTAAAGCAGCAACTTCAGGATGGGGGAA
TCAAGCAAACCATGGTGAAGAGATTCATTTAAAGAGGACAAGTGATTTATTCTACATCTCAGGAGAC
AGTTCCTTAAGGTGATGAGCACAAAAGGATCCATCTTATACAGTGCTTGCCAGCTTCCATAATACTAC
TCACCACGATGTTGAAATCACCTGTTCCAGAACCAGTCCTGTCCTTTGACAAGAAGGATTTAATTATC
AGTAGTGGTGGGGACTGGCTGGAGAGAGGAAAAACACTTCAAGGACTCTGCCACCTTTCGTAGATGGA
GAGTGCAAAGTTTGTACCATGGAACTCCTTCTCTAACAGTTACTCTGTGGCAGTGCCTATTTCAAACC
TCCCTTAACTTCTGATTGTATAGATGTTTGTTTCATTTGTTCATCTGTTTGTTCACTTAGTCAGAGAT
GTTTTAAGCCTTAAGAGAAATAGTGGACTAGAAAATGCCTTGGAAAAGTACAAAGTTCAATCCAAGTA
AACTGTTTTTAAACTAGGAATTTATGAAGCCTAAAATATAAAATGTATATACATGGATATGCTCTGAA
GTGAGGTAGAGGGGTAGAAATCAACATTGTGATATTGTACTATAGTTTTGCAAGATGTTACCATTGGG
GGAAAATGTTTGAAGGGTATACGGGATATCTCTGCCTTATTTCTTACAACTGCATGTGAATCTACAGT
TATCTCAAAATAAAAATTTAATTAACAATTGATTACAATTAA

LncRNA 8a RNA sequence  SEQ ID NO: 43

GACUUGUUGU UCAAUUGACG ACAAGGGUCA AUAUAGACCA GAAAGGGUGG GGGUUUGUAU
GUGUUUUCUA AAAACAGUAA GAACCGUGAC CUGUUGUCUU CACUAUUCUG UACGGUCGUC
UUGAGAUUUC CGUCUUACAG GAAGGUGGAC AAAAUACGAC AUUCUGUUUG AAGGUUCACG
CUCCGUCACA CCUCCCGACA ACGGAACUUA CCGUCGACUU ACGUGGUCGC CUAGGAACC
GUCGUUACGG GUCCGUGACU UCAGCCCGUA AGUCCUCUCG AUUUACCUCU UUUCUUUGAA
CUCGUUUGAC GAAGGACCUU GUGACUCUUG GACUUACCCU UUAAUUCUUC UUGGUCUAAG
AAAGAUAAGA AGGUGGUCGG UUCCAGUCUA AAGGUUUGAA GAUAACUAAG AUUAGAAAGG
GUUUGUCACG ACACCGUUAC AUACUUUCAU UAUUUUUAUU AGGAAAAAGA CAAUUUUUUU
UUUAACGACA AUGAACGACA AAACAAUACG AAAACGACCU CUAAAAGGGU GGGUAGAAUU
UCGUCGUUGA AGUCCUACCC CCUUAGUUCG UUUUGGUACC ACUUCUCUAA GUAAAUUUCU
CCUGUUCACU AAAUAAGAUG UAGAGUCCUC UGUCAAGGAA UUCCACUACU CGUGUUUUCC
UAGGUAGAAU AUGUCACGAA CGGUCGAAGG UAUUAUGAUG AGUGGUGCUA CAACUUUAGU
GGACAAGGUC UUGGUCAGGA CAGGAAACUG UUCUUCCUAA AUUAAUAGUC AUCACCACCC
CUGACCGACC UCUCUCCUUU UUGUGAAGUU CCUGAGACGG UGGAAAGCAU CUACCUCUCA
CGUUUCAAAC AUGGUACCUU GAGGAAGAGA UUGUCAAUGA GACACCGUCA CGGAUAAAGU
UUGGAGGGAA UUGAAGACUA ACAUAUCUAC AAACAAAGUA AACAAGUAGA CAAACAAGUG
AAUCAGUCUC UACAAAAUUC GGAAUUCUCU UUAUCACCUG AUCUUUUACG GAACCUUUUC
AUGUUUCAAG UUAGGUUCAU UUGACAAAAA UUUGAUCCUU AAAUACUUCG GAUUUUAUAU
UUUACAUAUA UGUACCUAUA CGAGACUUCA CUCCAUCUCC CCAUCUUUAG UUGUAACACU
AUAACAUGAU AUCAAAACGU UCUACAAUGG UAACCCCCUU UUACAAACUU CCCAUAUGCC
CUAUAGAGAC GGAAUAAAGA AUGUUGACGU ACACUUAGAU GUCAAUAGAG UUUUAUUUUU
AAAUUAAUUG UUAACUAAUG UUAAUU

LncRNA 8b DNA sequence  SEQ ID NO: 44

ACAACAAGTTAACTGCTGTTCCCAGTTATATCTGGTCTTTCCCACCCCCAAACATACACAAAAGATTT
TTGTCATTCTTGGCACTGGACAACAGAAGTGATAAGACATGCCAGCAGAACTCTAAAGGCAGAATGTC
CTTCCACCTGTTTTATGCTGTAAGACAAACTTCCAAGTGCGAGGCAGTGTGGAGGGCTGTTGCCTTGA
ATGGCAGCTGAATGCACCAGCGGGATCCTTGGCAGCAATGCCCAGGCACTGAAGTCGGGCATTCAGGA
GAGCTAAATGGAGAAAGAAACTTGAGCAAACTGCTTCCTGGAACACTGAGAACCTGAATGGGAAATT
AAGAAGAACCAGATTCTTTCTATTCTTCCACCAGCCAAGGTGATGAGCACAAAAGGATCCATCTTATA
CAGTGCTTGCCAGCTTCCATAATACTACTCACCACGATGTTGAAATCACCTGTTCCAGAACCAGTCCT
GTCCTTTGACAAGAAGGATTTAATTATCAGTAGTGG

Figure 39 Continued

```
TGGGGACTGGCTGGAGAGAGGAAAAACACTTCAAGGACTCTGCCACCTTTCGTAGATGGAGAGTGCAA
AGTTTGTACCATGGAACTCCTTCTCTAACAGTTACTCTGTGGCAGTGCCTATTTCAAACCTCCCTTAA
CTTCTGATTGTATAGATGTTTGTTTCATTTGTTCATCTGTTTGTTCACTTAGTCAGAGATGTTTTAAG
CCTTAAGAGAAATAGTGGACTAGAAAATGCCTTGGAAAAGTACAAAGTTCAATCCAAGTAAACTGTTT
     TTAAACTAGGAATTTATGAAGCCTAAAATATAAAATGTATATACATGGATATGCTCTGAA
```

LncRNA 8b RNA sequence SEQ ID NO: 45
```
AAGUCUCGUA UAGGUACAUA UAUGUAAAAU AUAAAAUCCG AAGUAUUUAA GGAUCAAAUU
UUUGUCAAAU GAACCUAACU UGAAACAUGA AAAGGUUCCG UAAAAGAUCA GGUGAUAAAG
AGAAUUCCGA AUUUUGUAGA GACUGAUUCA CUUGUUUGUC UACUUGUUUA CUUUGUUUGU
AGAUAUGUUA GUCUUCAAUU CCCUCCAAAC UUUAUCCGUG ACGGUGUCUC AUUGACAAUC
UCUUCCUCAA GGUACCAUGU UUGAAACGUG AGAGGUAGAU GCUUCCACC GUCUCAGGAA
CUUCACAAAA AGGAGAGAGG UCGGUCAGGG GUGGUGAUGA CUAUUAAUUU AGGAAGAACA
GUUUCCUGUC CUGACCAAGA CCUUGUCCAC UAAAGUUGUA GCACCACUCA UCAUAAUACC
UUCGACCGUU CGUGACAUAU UCUACCUAGG AAAACACGAG UAGUGGAACC GACCACCUUC
UUAUCUUUCU UAGACCAAGA AGAAUUAAAG GGUAAGUCCA AGAGUCACAA GGUCCUUCGU
CAAACGAGUU CAAAGAAAAG AGGUAAAUCG AGAGGACUUA CGGGCUGAAG UCACGGACCC
GUAACGACGG UUCCUAGGGC GACCACGUAA GUCGACGGUA AGUUCGUUG UCGGGAGGUG
UGACGGAGCG UGAACCUUCA AACAGAAUGU CGUAUUUUGU CCACCUUCCU GUAAGACGGA
AAUCUCAAGA CGACCGUACA GAAUAGUGAA GACAACAGGU CACGGUUCUU ACUGUUUUUA
GAAAACACAU ACAAACCCCC ACCCUUUCUG GUCUAUAUUG ACCCUUGUCG UCAAUUGAAC
AACA
```

LncRNA2 (SMILR) Pig DNA sequence SEQ ID NO: 46

Exon 1
```
TGACTATCCCACAATATCCTAGTTCTGATTTCATTCCTTCTCATCCTACTAACTCAGCTTCCAGTCAT
TCTAAGAGAATTCTCTTTGAAGGAGAGTCA
```

Exon 2
```
AGACAGAATTCCACAATTTACATAGATGATTGGTTGGTAACTGTACCTTAATCTGTGTTAGTCTCTGA
GATACTGGGTAAGAATTTCTGGAAAAACATAGTAAATGTCTTTTTTTTTTTCATAATCATCTGATTT
CTGGTCAAAAGGATTAACTAGATTACCTAAGAAAATGACTCTCATGCAACTCAAAGAAT
```

LncRNA2 (SMILR) Pig RNA sequence SEQ ID NO: 47
```
ACUGAUAGGG UGUUAUAGGA UCAAGACUAA AGUAAGGAAG AGUAGGAUGA UUGAGUCGAA

GGUCAGUAAG AUUCUCUUAA GAGAAACUUC CUCUCAGUUC UGUCUUAAGG UGUUAAAUGU

AUCUACUAAC CAACCAUUGA CAUGGAAUUA GACACAAUCA GAGACUCUAU GACCCAUUCU

UAAAGACCUU UUUGUAUCAU UUACAGAAAA AAAAAAAAGU AUUAGUAGAC UAAAGACCAG

UUUUCCUAAU UGAUCUAAUG GAUUCUUUUA CUGAGAGUAC GUUGAGUUUC UUA
```

Figure 39 Continued

SEQUENCE LISTING

```
<160> NUMBER OF SEQ ID NOS: 47

<210> SEQ ID NO 1
<211> LENGTH: 20
<212> TYPE: RNA
<213> ORGANISM: Artificial Sequence
<220> FEATURE:
<223> OTHER INFORMATION: siRNA

<400> SEQUENCE: 1
ccauaauuua cauggauguu                                               20

<210> SEQ ID NO 2
<211> LENGTH: 27
<212> TYPE: RNA
<213> ORGANISM: Artificial Sequence
<220> FEATURE:
<223> OTHER INFORMATION: siRNA

<400> SEQUENCE: 2
uuccaaacau ccauguaaau uauggaa                                       27

<210> SEQ ID NO 3
<211> LENGTH: 20
<212> TYPE: DNA
<213> ORGANISM: Artificial Sequence
<220> FEATURE:
<223> OTHER INFORMATION: Forward primer sequence

<400> SEQUENCE: 3
accttggagg tcttgggagt                                               20
```

```
<210> SEQ ID NO 4
<211> LENGTH: 20
<212> TYPE: DNA
<213> ORGANISM: Artificial Sequence
<220> FEATURE:
<223> OTHER INFORMATION: Forward primer sequence

<400> SEQUENCE: 4
aaaaactgcc acctgtgacc                                                   20

<210> SEQ ID NO 5
<211> LENGTH: 21
<212> TYPE: DNA
<213> ORGANISM: Artificial Sequence
<220> FEATURE:
<223> OTHER INFORMATION: Forward primer sequence

<400> SEQUENCE: 5
ctgcattgga gagacaggaa t                                                 21

<210> SEQ ID NO 6
<211> LENGTH: 20
<212> TYPE: DNA
<213> ORGANISM: Artificial Sequence
<220> FEATURE:
<223> OTHER INFORMATION: Forward primer sequence

<400> SEQUENCE: 6
tggctaggag ggggtctatc                                                   20

<210> SEQ ID NO 7
<211> LENGTH: 20
<212> TYPE: DNA
<213> ORGANISM: Artificial Sequence
<220> FEATURE:
<223> OTHER INFORMATION: Forward primer sequence

<400> SEQUENCE: 7
ccaaggtgat gagcacaaaa                                                   20

<210> SEQ ID NO 8
<211> LENGTH: 39
<212> TYPE: DNA
<213> ORGANISM: Artificial Sequence
<220> FEATURE:
<223> OTHER INFORMATION: Forward primer sequence

<400> SEQUENCE: 8
gattacgcca agctttgcaa acattgggat cagccgtga                              39

<210> SEQ ID NO 9
<211> LENGTH: 20
<212> TYPE: DNA
<213> ORGANISM: Artificial Sequence
<220> FEATURE:
<223> OTHER INFORMATION: Reverse primer sequence

<400> SEQUENCE: 9
ttgcagacac cttccaaaca                                                   20

<210> SEQ ID NO 10
<211> LENGTH: 20
<212> TYPE: DNA
<213> ORGANISM: Artificial Sequence
<220> FEATURE:
<223> OTHER INFORMATION: Reverse primer sequence
```

```
<400> SEQUENCE: 10
ttggtgtagg tctggggaag                                          20

<210> SEQ ID NO 11
<211> LENGTH: 24
<212> TYPE: DNA
<213> ORGANISM: Artificial Sequence
<220> FEATURE:
<223> OTHER INFORMATION: Reverse primer sequence

<400> SEQUENCE: 11
aaagctgaaa ccctaaagtc attg                                     24

<210> SEQ ID NO 12
<211> LENGTH: 20
<212> TYPE: DNA
<213> ORGANISM: Artificial Sequence
<220> FEATURE:
<223> OTHER INFORMATION: Reverse primer sequence

<400> SEQUENCE: 12
cacggtggct cacactttta                                          20

<210> SEQ ID NO 13
<211> LENGTH: 20
<212> TYPE: DNA
<213> ORGANISM: Artificial Sequence
<220> FEATURE:
<223> OTHER INFORMATION: Reverse primer sequence

<400> SEQUENCE: 13
aaaggtggca gagtccttga                                          20

<210> SEQ ID NO 14
<211> LENGTH: 39
<212> TYPE: DNA
<213> ORGANISM: Artificial Sequence
<220> FEATURE:
<223> OTHER INFORMATION: Reverse primer sequence

<400> SEQUENCE: 14
gattacgcca agctttctca cagccatgct ctggccatt                     39

<210> SEQ ID NO 15
<211> LENGTH: 20
<212> TYPE: DNA
<213> ORGANISM: Artificial Sequence
<220> FEATURE:
<223> OTHER INFORMATION: Forward

<400> SEQUENCE: 15
tgtgtgcccg tctgttgtgt                                          20

<210> SEQ ID NO 16
<211> LENGTH: 20
<212> TYPE: DNA
<213> ORGANISM: Artificial Sequence
<220> FEATURE:
<223> OTHER INFORMATION: Reverse

<400> SEQUENCE: 16
gagtcctgcg tcgagagagc                                          20

<210> SEQ ID NO 17
```

```
<211> LENGTH: 20
<212> TYPE: DNA
<213> ORGANISM: Artificial Sequence
<220> FEATURE:
<223> OTHER INFORMATION: Probe

<400> SEQUENCE: 17
cagtggcgcc cgaacaggga                                                       20

<210> SEQ ID NO 18
<211> LENGTH: 877
<212> TYPE: DNA
<213> ORGANISM: Homo sapiens

<400> SEQUENCE: 18
gctgcaaaca ttgggatcag ccgtgactat cccataacat aatatttctg atttcattct           60
tttcctttct cctaccaatt taatctgcaa tcacttcaag agaagtctgt ttaaaggata          120
ttcacattct gttcacagag tttgagagaa actgtattca agttgctgaa accaagaagc          180
tacactcacg agtctcacct aaactcgaat ctgatttaga tgacatcatc ctggactttg          240
agttgatgaa accttggagg tcttgggagt aaagcaagtg tgatttgcat atgatggata          300
tgaattgtaa tggccagagc atgagatgaa aactcccatt ttagggaacc aagactgaat          360
tccataattt acatggatgt ttggaaggtg tctgcaactt aatctgtgtt cgtttctgag          420
atgttgggca actccttctt ggaagatgtg gtaatggtct cttcgaaaag aaaataatca          480
tctgagtttt ggccaaaata gttgatcgga ttacctatga aaatgactct cacccaacta          540
caagaatgtt atgatgtaga aactctaaat atatgagtaa ttaactatac aacactccat          600
ccccatgtga aaatctttaa tcttttaaga tactgaaatt ttgtgtatgt ctcataattt          660
tctgtatatg gtcaatgagt tttgccttag ccataagtgg tctgtctgaa atcttctcta          720
ttatttgtgc attttcttcc tgatgtacca agcctagtct gtttgttttt tcctaagaga          780
aaagcagatg attcaactgt gtatttctca gtgttgatat tgtggtttga ggtatttcat          840
aatcttgagt aaaatcttgt caaaaaaaaa aaaaaaa                                   877

<210> SEQ ID NO 19
<211> LENGTH: 2216
<212> TYPE: DNA
<213> ORGANISM: Homo sapiens

<400> SEQUENCE: 19
gaatggggta acctggctaa atgagaatta atgaacccac actcataagt tttcattgac           60
ttagcaccaa gtcgtccatc aaatatcatc agatctgaga atgctcttat ggatatctga          120
tttttagagg ctggcattca tattttaaa aactgccacc tgtgaccaca ctgcaggcca           180
aacagaatgt acctgctggt cagatgcagc ccagaggtca ctgaattgca acctctggac          240
tctcggtcag aggcaagcag cccttattcc agaactccac agtccttcac acccttcccc          300
agacctacac caagaccaac taagtggtca aaaggtggac aaactgagag ttgtatcaag          360
gcccttagcc tctcaatttg ttatcaagtt tccctttctg aatctattta ccctgaagta          420 taaatacccca agatgagcct taagagtgcc tggtagagca acaaagatg catcttatag          480 ggagcaaagt ctatgctaac gcagtgtttc tcaatcctgg ctgcacctt gaaccacggg           540 agcttttaaaa gtgaccactg caagggccct acccactatg gatcccaatt tcattggttg        600 ggagagggggc caagtttgtt tccaacttcc ccagatgact ctaatggctg agagttgcaa          660
tcaacaggta agtgaatatc caggctgtaa gatgaagaaa gaggggggttg tgcccaagcc        720
```

```
cactgtgcct cataaagcag atgatctctg cagcgctgcg cttctcaaag agtggtccca      780
ggactgcctc agtcagacca cagactccta agttcctcct cagacttcat ggatccaagc      840
tctgtgaggt aattctaagc acattaaact tgtagaacag ccatctggat ttaatattac      900
ataatagcta taatattctg ctattctcta atcttcaatg tcagtttctt aaactgtcag      960
gcctgtcttt agatgccctt caactgtgct ggggactatc ttgatggcag ccagcaaaga     1020
aaatcagcaa aaaccccagt ggagtttctg ggttttactt tgttaaggaa ggtgatggt      1080 ttcttgacat gacaggtatc taggtggaaa gggcaaagtg ctaatgcaaa cacaatggag     1140
acactatgga atagctctgc ctagggacat gtggaagagc ttctaggaga cagtgtggac     1200
ctttccatcc ctagaggtct tcacaagata aattcctacc tccgtcagta ttcaaaaggt     1260
tttagcatca atactgtctg agaataagac attagacttg agtcagtccc ctggcttcaa     1320
tcccaggatg ccaagcagcc tctaatggag accgctggct taatcgtgct cctttcctgg     1380
cataacaact cactgcaccc atgcctcacc accacgaagc agtctcctca ccacccaaat     1440
gtgccttggg tgacttaaat acagccatta gtatgaatgg tcccctgttt ttattcaaca     1500
ccacaccagt ctttgctttt accttcggct aatgtggttc cagccttta tcctgcactc      1560 cttcttataa tttaaaaaaa aaaaaactc ccctactatc tttatgttaa tattaacatc      1620
aactaggttc ttctcaaagg acagccaggc taactggcc acgttaaaat ctgcacagtg       1680
cttttgtgtc actgtctatt ctattagttt caacatcatg ctaaaatagg acagcatgtt     1740
ccaaaactga aactgaaaca ggaacggagc cttgctgatt tagcatgagg agggaattgt     1800
aagccttgca cctggacact aaaacttttc aataagatgt atgctaagcc gtacctagca     1860
aacttaccag gtccaaagta gagtacaagc agaaagttat ttttaaagga tgggcactat     1920
ccttgaggga cttaccctt ctaatcagct ttgcatggtt tgttttgaga cagtgtctca     1980
ctctgttgcc caggctagag tgcagcggca ccatcacagc tcacggcagc ctctgcctcc     2040
cgggctcaag caatcccacc tcagtttccc aagtagctgg gactacaggc acacaccaca     2100
ctcagctaat tttagtattt tttgtagaga cagggtctcg ccatgttgcc caggctggtc     2160
tcaaactcct ggattatctc cctggccctg cattaaaaaa gatgtgcaac aactta          2216

<210> SEQ ID NO 20
<211> LENGTH: 476
<212> TYPE: DNA
<213> ORGANISM: Homo sapiens

<400> SEQUENCE: 20
tgtgaggagg cccaggccac aaggagaggc cacctataag cattcaggcc agcagcccca       60
gatctgctcc tcctgccaag ctgaacccaa gaccagcacc ttcctccttg tgtaagatgg      120
tgacatggat gccgtctaat tgctgcagag gaaatacata cattcaaaaa cattttactg      180
caagaggatg aacaatttaa catcggactg acatcagact gatttgttat ctcaaacccc      240
agcttggcca gcctccaagt tacatcacct cctcaaacct cagtttcctc atctgtaaag      300 aatggaccctt caggagtcat gggaagctta gaagaaaaaa aaaatgtatg taaagcagca     360
agcataatta ttttcctctc tcattcaccc tgtccacagc cgggcagggg gagtgccatg     420
aagtcagcca gaaatcagca tattggacag tgtgagatga agtcaggttg taggac         476

<210> SEQ ID NO 21
<211> LENGTH: 490
<212> TYPE: DNA
```

<213> ORGANISM: Homo sapiens

<400> SEQUENCE: 21

| acatggatcc ttaagtcctc cctatgcccc gttagagcac tgatgacatt tactttgaaa | 60 |
| ttcccctgtt acatgtctgt ttgcctaagt agactctaag catctgcaga acaggggcta | 120 |
| tgtcttagta tccagggtat tttcttcacc tggcacaatt cctgccacag agtagtgtgt | 180 |
| cagctctcta ttgttgtcta aaacccacc tcaaggtgct gggattacag gtgtgagcca | 240 |
| ctgtgcctgg ccccacattt tttaaaacaa tgactttagg gtttcagctt ttcctgtctt | 300 |
| ttaaaacaaa ttagccattt tttattctaa gaaagggttg tattataaag ctgacctact | 360 |
| actagcttat cagaaaaaac acgtgggtct catatctgat tctcctatgt agccaaaagt | 420 |
| gccatttgta agtctactaa atgacggata ttttctgaag atcttttgcc tggaaaacaa | 480 |
| atagtgcatt | 490 |

<210> SEQ ID NO 22
<211> LENGTH: 522
<212> TYPE: DNA
<213> ORGANISM: Homo sapiens

<400> SEQUENCE: 22

| gggttgattc tattatctga tgttttatta atctctgtga aataattgtg taaattaata | 60 |
| tagagactag ttgagaaatg gtggataaca tgaagaagat acccattttt gcatagatta | 120 |
| gatgtgatca acctcacact atcatatgaa agttggctgc attggagaga caggaattaa | 180 |
| tattaaaaat gttttcagtt cagattgata tcttacattt ccaaatatta ttttcttttg | 240 |
| aatatgtgtg agccactgtg cctggcccca cattttttaa acaatgact ttagggtttc | 300 |
| agcttttcct gtctttaaa acaaattagc cattttttat tctaagaaag ggttgtatta | 360 |
| taaagctgac ctactactag cttatcagaa aaaacacgtg gtctcatat ctgattctcc | 420 |
| tatgtagcca aaagtgccat ttgtaagtct actaaatgac ggatatttc tgaagatctt | 480 |
| ttgcctggaa aacaaatagt gcattaaaaa gcttttttgg ta | 522 |

<210> SEQ ID NO 23
<211> LENGTH: 2957
<212> TYPE: DNA
<213> ORGANISM: Homo sapiens

<400> SEQUENCE: 23

| aaaggtactt agacatgttc cccacaggat gtgttaaggt gttggccaat catcaaatat | 60 |
| tgtcactcca agaacacat ttaacagccg ggaagaaaat tgtaggaaaa gagagcactt | 120 |
| tggcacggaa ggggtctatc gccctggttg gagtgcagca gtgtaatcat agctcactgc | 180 |
| tgccatgaac ttctgggctc aagcgatcct cccacctcag cctccctgtg tgctgggatt | 240 |
| aaaagtgtga gccaccgtgc ctcatcgtaa gggtcttaaa agaaacccta tttcatactt | 300 |
| tcttgatgca cttgatatgg attatataaa tctatggaca aaaatgacat cagtacaatg | 360 |
| gaatattgga gttttctacc ataatctctg catagtgcac tgattttgac aatcacctat | 420 |
| ggatgaaaat acatttgcca gagtctagga gttaaatgga aaagttaaca gcacaccgtt | 480 |
| ggagaaaaat atctgggagt agatgcattc aagggagtaa aagaacaat tacctgcatc | 540 |
| acctcacccc cagggtccac ttcttagtgc caagatagac tccttcagc aggcaatttc | 600 |
| tcccatgggg aaaaggagag tataatgagt gagtatccag cttttccagc tgtgtgaggc | 660 |
| acatcccaag aagcccatct ttctttcact caactcagaa tattgagggt attagcatgg | 720 |

```
ctaagtggct gggacagggc agtagcagga aagaaaggag aggactcaca gcaaccagga      780
cttgaaactc agtacagggt acatatcctt tgaagcattt cacagagccc atcaggaggc      840
ccacccatga accacttggg acaccatatc tgtagcatct ccctgcaact ggcccatagg      900 agccccgat gttttgtgca tattccccctt cccctttctcc tatagtcagt tgcctgcaca     960
tgcactccag atggtgagtg tgagcattta cctacagctt ttgagtacat gcagtcagca     1020
ggctcaactt tgaaggattg ggaggaatac aaaattgagc atttcagggc actgtcctag    1080
aggaaacaaa cagaaagctt tcaggaccca gtttggtttt gtggatttaa gagaagacac    1140
acaatcatca gaatttcttc tccacccatc caagaagtgt ggattgggtg aatccataga    1200
aaagatctga gagagcctca gattccctat aggctcactg ttgaagatat ttctctcaaa    1260
tccagtcagt aaagactaga gaaagtgact cttttcttcaa atgtgaagac agcagtgcaa    1320
gactttgagg aacatgaaaa atcaaggaca cctagtacca ccaaaggaac ataattttct    1380
ggtacccaac cacaaagaaa tggagataca caaattgtct gacaaagaat tcacaacaat    1440
tgttttaagg aagtcagtaa gctacaagag aacacagaga acttaatgat attaagaaag    1500
cgacacatga acaaaataag atgttcaaca aaaagataga aattattaaa aacaaccatg    1560
attttcgagc tgagaataca atgaatgaaa tggaaaacac aatagagttt caatagcaga    1620
cttgatcaag cagaagaaag ggtctgtcaa ctcaaatact agtcatttga aattattcag    1680
taaaagaaat aaaaaggaat gaaaaatgct tatgcgattg atgcaacacc atgaagagta    1740
gtcatatatg cactatggga gtctcagaaa aagaaagaga taaggggaa gaaaactaac     1800 ttaaagaact agatcagtct ctccttatct gtagttttgc tttccttggt ttcaggtaca    1860
gtacaatgat atgttttaag agacagacaa tgaaagagaa catgcaaata ttgacataat    1920
ttttattaca gtatattgtc atagtttttc tattttgtta ttagttgtta ttctcttact    1980
gtgcctaatt tatacattaa actttatcat aggaatagtg gtggtggcct gtctggagtg    2040
gccactgcca ggatgccagc tgcagcaggg gaggtgtagc tggggctgtg cactccgcag    2100
agctgggggg ggccaggaac aggtgatcct agtgggagcc ctatatgcta ctgagttagt    2160
ggggtgggag cctgtgctcc caggcatagc tgcagctgcc cagccatggc tccagcccta    2220
ggcatacctg tgctctcagg ggccctggaa gtccctgcc cttacaggct tggaagtgcc     2280
tgctcccatt ccctggcctc tttccactgc tggcacctgc tctgtggcag agcaaagttg    2340
tggatgtgtt gtgatagctg agcctgggag ctgttgtgac gtggtcaggt gtgtgtgttc    2400
agggcagttc tgatacacca gactccccac tgccttttgcc ccctctggaa actgcttctg    2460
aggctgaaac tttggatatt aatgagcaag gatggtgggg gaggccagga cggctgaggg    2520
cagctaggtg tgggcctgtg gacacccctt agtgcggaca gtctgggtgc tgtggatggc    2580
atgttgatgg cagcgagagg cagacatgtt cctaggtggg aacgggtggg tccctggtga    2640
aacctcacct tcaagccagg gacagcttga agcatggggg cctggctgcc agttccggtt    2700
gcagtctgtg acctggagtg aaaacttcat tgatgtcttt cagccaattg gatggtgctt    2760
tttccagacc cacaaatggc tgcccatgga ccaagcagta tgtacttcct ccattctgag    2820
cccatgaaaa cccagactc agtcagactc tgacactcat caggatgaca agcctgcaaa    2880
taggatctac ccattttggg tatgcactcc actgagagct attctgtcac tcaataaagc    2940
tcctttctgc cttgctc                                                    2957
```

<210> SEQ ID NO 24

```
<211> LENGTH: 581
<212> TYPE: DNA
<213> ORGANISM: Homo sapiens

<400> SEQUENCE: 24
acaaagttta tattagagcg tcatccatta atgctttggc taggaggggg tctatcgccc      60
tggttggagt gcagcagtgt aatcatagct cactgctgcc atgaacttct gggctcaagc     120
gatcctccca cctcagcctc cctgtgtgct gggattaaaa gtgtgagcca ccgtgcctca     180
tcgtaagggt cttaaaagaa accctatttc atactttctt gatgcacttg atatggatta     240
tataaatcta tggacaaaaa tgacatcagt acaatggaat attggagttt tctaccataa     300
tctctgcata gtgcactgat tttgacaatc acctatggat gaaaatacat ttgccagagt     360
ctaggagtta aatggaaaag ttaacagcac accgttggag aaaaatatct gggagtagat     420
gcattcaagg gagtaagaag aacaattacc tgcatcacct cacccccagg gtccacttct     480
tagtgccaag atagactccc ttcagcaggc aatttctccc atggggaaaa ggagagtata     540
atgagtgagt atccagcttt tccagctgtg tgaggcacat c                         581

<210> SEQ ID NO 25
<211> LENGTH: 1286
<212> TYPE: DNA
<213> ORGANISM: Homo sapiens

<400> SEQUENCE: 25
ctgaacaaca agttaactgc tgttcccagt tatatctggt ctttcccacc cccaaacata      60
cacaaaagat ttttgtcatt cttggcactg gacaacagaa gtgataagac atgccagcag     120
aactctaaag gcagaatgtc cttccacctg ttttatgctg taagacaaac ttccaagtgc     180
gaggcagtgt ggagggctgt tgccttgaat ggcagctgaa tgcaccagcg ggatccttgg     240
cagcaatgcc caggcactga agtcgggcat tcaggagagc taaatggaga aaagaaactt     300
gagcaaactg cttcctggaa cactgagaac ctgaatggga aattaagaag aaccagattc     360
tttctattct tccaccagcc aaggtcagat ttccaaactt ctattgattc taatctttcc     420
caaacagtgc tgtggcaatg tatgaaagta ataaaaataa tccttttttct gttaaaaaaa     480
aaattgctgt tacttgctgt tttgttatgc ttttgctgga gattttccca cccatcttaa     540
agcagcaact tcaggatggg ggaatcaagc aaaaccatgg tgaagagatt catttaaaga     600
ggacaagtga tttattctac atctcaggag acagttcctt aaggtgatga gcacaaaagg     660
atccatctta tacagtgctt gccagcttcc ataatactac tcaccacgat gttgaaatca     720
cctgttccag aaccagtcct gtcctttgac aagaaggatt taattatcag tagtggtggg     780
gactggctgg agagaggaaa aacacttcaa ggactctgcc acctttcgta gatggagagt     840
gcaaagtttg taccatggaa ctccttctct aacagttact ctgtggcagt gcctatttca     900
aacctccctt aacttctgat tgtatagatg tttgtttcat ttgttcatct gtttgttcac     960
ttagtcagag atgttttaag ccttaagaga atagtggac tagaaaatgc cttggaaaag    1020
tacaaagttc aatccaagta aactgttttt aaactaggaa tttatgaagc ctaaaatata    1080
aaatgtatat acatggatat gctctgaagt gaggtagagg ggtagaaatc aacattgtga    1140
tattgtacta tagttttgca agatgttacc attgggggaa aatgtttgaa gggtatacgg    1200
gatatctctg ccttatttct tacaactgca tgtgaatcta cagttatctc aaaataaaaa    1260
tttaattaac aattgattac aattaa                                         1286
```

```
<210> SEQ ID NO 26
<211> LENGTH: 844
<212> TYPE: DNA
<213> ORGANISM: Homo sapiens

<400> SEQUENCE: 26
acaacaagtt aactgctgtt cccagttata tctggtcttt cccacccccca aacatacaca      60
aaagattttt gtcattcttg gcactggaca acagaagtga taagacatgc cagcagaact     120
ctaaaggcag aatgtccttc cacctgtttt atgctgtaag acaaacttcc aagtgcgagg     180
cagtgtggag ggctgttgcc ttgaatggca gctgaatgca ccagcgggat ccttggcagc     240
aatgcccagg cactgaagtc gggcattcag gagagctaaa tggagaaaag aaacttgagc     300
aaactgcttc ctggaacact gagaacctga atgggaaatt aagaagaacc agattctttc     360
tattcttcca ccagccaagg tgatgagcac aaaaggatcc atcttataca gtgcttgcca     420
gcttccataa tactactcac cacgatgttg aaatcacctg ttccagaacc agtcctgtcc     480
tttgacaaga aggatttaat tatcagtagt ggtggggact ggctggagag aggaaaaaca     540
cttcaaggac tctgccacct ttcgtagatg gagagtgcaa agtttgtacc atggaactcc     600
ttctctaaca gttactctgt ggcagtgcct atttcaaacc tcccttaact tctgattgta     660
tagatgtttg tttcatttgt tcatctgttt gttcacttag tcagagatgt tttaagcctt     720
aagagaaata gtggactaga aaatgccttg gaaaagtaca agttcaatc caagtaaact     780
gttttttaaac taggaattta tgaagcctaa aatataaaat gtatatacat ggatatgctc     840
tgaa                                                                   844

<210> SEQ ID NO 27
<211> LENGTH: 890
<212> TYPE: DNA
<213> ORGANISM: Homo sapiens

<400> SEQUENCE: 27
gctgcaaaca ttgggatcag ccgtgactat cccataacat aatatttctg atttcattct      60
tttcctttct cctaccaatt taatctgcaa tcacttcaag agaagtctgt ttaaaggata     120
ttcacattct gttcacagag tttgagagaa actgtattca agttgctgaa accaagaagc     180
tacactcacg agtctcacct aaactcgaat ctgatttaga tgacatcatc ctggactttg     240
agttgatgaa accttggagg tcttgggagt aaagcaagtg tgatttgcat atgatggata     300
tgaattgtaa tggccagagc atggctgtga gatgaaaact cccatttag ggaaccaaga     360
ctgaattcca taatttacat ggatgtttgg aaggtgtctg caacttaatc tgtgttcgtt     420
tctgagatgt tgggcaactc cttcttggaa gatgtggtaa tggtctcttc gaaaagaaaa     480
taatcatctg agttttggcc aaaatagttg atcggattac ctatgaaaat gactctcacc     540
caactacaag aatgttatga tgtagaaact ctaaatatat gagtaattaa ctatacaaca     600
ctccatcccc atgtgaaaat ctttaatctt ttaagtactt gaaatttgt gtatgtctca     660
taattttctg tatatggtca atgagttttg ccttagccat aagtggtctg tctgaaatct     720
tctctattat ttgtgcattt tcttcctgat gtaccaagcc tagtctgttt gtttttttcct     780
aagagaaaag cagatgattc aactgtgtat ttctcagtgt tgatattgtg gtttgaggta     840
tttcataatc ttgagtaaaa tcttgtcata aaaaaaaaaa aaaaaaaaa                  890

<210> SEQ ID NO 28
<211> LENGTH: 890
<212> TYPE: DNA
```

<213> ORGANISM: Homo sapiens

<400> SEQUENCE: 28

| gctgcaaaca | ttgggatcag | ccgtgactat | cccataacat | aatatttctg | atttcattct | 60 |
| tttcctttct | cctaccaatt | taatctgcaa | tcacttcaag | agaagtctgt | ttaaaggata | 120 |
| ttcacattct | gttcacagag | tttgagagaa | actgtattca | agttgctgaa | accaagaagc | 180 |
| tacactcacg | agtctcacct | aaactcgaat | ctgatttaga | tgacatcatc | ctggactttg | 240 |
| agttgatgaa | accttggagg | tcttgggagt | aaagcaagtg | tgatttgcat | atgatggata | 300 |
| tgaattgtaa | tggccagagc | atggctgtga | gatgaaaact | cccatttag | ggaaccaaga | 360 |
| ctgaattcca | taatttacat | ggatgtttgg | aaggtgtctg | caacttaatc | tgtgttcgtt | 420 |
| tctgagatgt | tgggcaactc | cttcttggaa | gatgtggtaa | tggtctcttc | gaaagaaaa | 480 |
| taatcatctg | agttttggcc | aaaatagttg | atcggattac | ctatgaaaat | gactctcacc | 540 |
| caactacaag | aatgttatga | tgtagaaact | ctaaatatat | gagtaattaa | ctatacaaca | 600 |
| ctccatcccc | atgtgaaaat | ctttaatctt | ttaagatact | gaaattttgt | gtatgtctca | 660 |
| taattttctg | tatatggtca | atgagttttg | ccttagccat | aagtggtctg | tctgaaatct | 720 |
| tctctattat | ttgtgcattt | tcttcctgat | gtaccaagcc | tagtctgttt | gttttttcct | 780 |
| aagagaaaag | cagatgattc | aactgtgtat | ttctcagtgt | tgatattgtg | gtttgaggta | 840 |
| tttcataatc | ttgagtaaaa | tcttgtcata | aaaaaaaaa | aaaaaaaaaa | | 890 |

<210> SEQ ID NO 29
<211> LENGTH: 890
<212> TYPE: RNA
<213> ORGANISM: Homo sapiens

<400> SEQUENCE: 29

| cgacguuugu | aacccuaguc | ggcacugaua | ggguauugua | uuauaaagac | uaaaguaaga | 60 |
| aaaggaaaga | ggaugguuaa | auuagacguu | agugaaguuc | ucuucagaca | aauuccuau | 120 |
| aaguguaaga | caagugucuc | aaacucucuu | ugacauaagu | ucaacgacuu | ugguucuucg | 180 |
| augugagugc | ucagagugga | uuugagcuua | gacuaaaucu | acuguaguag | gaccugaaac | 240 |
| ucaacuacuu | uggaaccucc | agaacccuca | uuucguucac | acuaaacgua | uacuaccuau | 300 |
| acuuaacauu | accggucucg | uaccgacacu | cuacuuuuga | ggguaaaauc | ccuugguucu | 360 |
| gacuuaaggu | auuaaaugua | ccuacaaacc | uuccacagac | guugaauuag | acacaagcaa | 420 |
| agacucuaca | acccguugag | gaagaaccuu | cuacaccauu | accagagaag | cuuucuuuu | 480 |
| auuaguagac | ucaaaaccgg | uuuuaucaac | uagccuaaug | gauacuuuua | cugagagugg | 540 |
| guugauguuc | uuacaauacu | acaucuuuga | gauuuauaua | cucauuaauu | gauauguugu | 600 |
| gagguagggg | uacacuuuua | gaauuagaa | aauucuauga | cuuuaaaaca | cauacagagu | 660 |
| auuaaaagac | auauaccagu | uacucaaaac | ggaaucggua | ucaccagac | agacuuuaga | 720 |
| agagauaaua | aacacguaaa | agaaggacua | cauggguucgg | aucagacaaa | caaaaaagga | 780 |
| uucucuuuuc | gucuacuaag | uugacacaua | aagagucaca | acuauaacac | caaacuccau | 840 |
| aaaguauuag | aacucauuuu | agaacaguau | uuuuuuuuu | uuuuuuuuu | | 890 |

<210> SEQ ID NO 30
<211> LENGTH: 2216
<212> TYPE: DNA
<213> ORGANISM: Homo sapiens

<400> SEQUENCE: 30

```
gaatggggta acctggctaa atgagaatta atgaacccac actcataagt tttcattgac    60
ttagcaccaa gtcgtccatc aaatatcatc agatctgaga atgctcttat ggatatctga   120
tttttagagg ctggcattca tatttttaaa aactgccacc tgtgaccaca ctgcaggcca   180
aacagaatgt acctgctggt cagatgcagc ccagaggtca ctgaattgca acctctggac   240
tctcggtcag aggcaagcag cccttattcc agaactccac agtccttcac acccttcccc   300
agacctacac caagaccaac taagtggtca aaggtggac aaactgagag ttgtatcaag    360
gcccttagcc tctcaatttg ttatcaagtt tccctttctg aatctattta ccctgaagta   420
taaataccca agatgagcct taagagtgcc tggtagagca acaaagatg catcttatag    480
ggagcaaagt ctatgctaac gcagtgtttc tcaatcctgg ctgcaccttt gaaccacggg   540
agctttaaaa gtgaccactg caagggccct acccactatg gatcccaatt tcattggttg   600
ggagagggc caagtttgtt tccaacttcc ccagatgact ctaatggctg agagttgcaa    660
tcaacaggta agtgaatatc caggctgtaa gatgaagaaa gagggggttg tgcccaagcc   720
cactgtgcct cataaagcag atgatctctg cagcgctgcg cttctcaaag agtggtccca   780
ggactgcctc agtcagacca cagactccta agttcctcct cagacttcat ggatccaagc   840
tctgtgaggt aattctaagc acattaaact tgtagaacag ccatctggat ttaatattac   900
ataatagcta taatattctg ctattctcta atcttcaatg tcagtttctt aaactgtcag   960
gcctgtcttt agatgccctt caactgtgct ggggactatc ttgatggcag ccagcaaaga  1020
aaatcagcaa aaaccccagt ggagtttctg ggttttactt ttgttaagga aggtgatggt  1080
ttcttgacat gacaggtatc taggtggaaa gggcaaagtg ctaatgcaaa cacaatggag  1140
acactatgga atagctctgc ctagggacat gtggaagagc ttctaggaga cagtgtggac  1200
cttttccatcc ctagaggtct tcacaagata aattcctacc tccgtcagta ttcaaaaggt  1260
tttagcatca atactgtctg agaataagac attagacttg agtcagtccc ctggcttcaa  1320
tcccaggatg ccaagcagcc tctaatggag accgctggct taatcgtgct cctttcctgg  1380
cataacaact cactgcaccc atgcctcacc accacgaagc agtctcctca ccacccaaat  1440
gtgccttggg tgacttaaat acagccatta gtatgaatgg tcccctgttt ttattcaaca  1500
ccacaccagt ctttgctttt accttcggct aatgtggttc cagccttta tcctgcactc  1560
cttcttataa tttaaaaaaa aaaaaactc ccctactatc tttatgttaa tattaacatc  1620
aactaggttc ttctcaaagg acagccaggc ctaactggcc acgttaaaat ctgcacagtg  1680
cttttgtgtc actgtctatt ctattagttt caacatcatg ctaaaatagg acagcatgtt  1740
ccaaaactga aactgaaaca ggaacggagc cttgctgatt tagcatgagg agggaattgt  1800
aagccttgca cctggacact aaaactttt aataagatgt atgctaagcc gtacctagca  1860
aacttaccag gtccaaagta gagtacaagc agaaagttat ttttaaagga tgggcactat  1920
ccttgaggga cttacccttt ctaatcagct ttgcatggtt tgttttgaga cagtgtctca  1980
ctctgttgcc caggctagag tgcagcggca ccatcacagc tcacggcagc ctctgcctcc  2040
cgggctcaag caatcccacc tcagtttccc aagtagctgg gactacaggc acacaccaca  2100
ctcagctaat tttagtattt tttgtagaga cagggtctcg ccatgttgcc caggctggtc  2160
tcaaactcct ggattatctc cctggccctg cattaaaaaa gatgtgcaac aactta       2216
```

<210> SEQ ID NO 31
<211> LENGTH: 2216
<212> TYPE: RNA

<213> ORGANISM: Homo sapiens

<400> SEQUENCE: 31

| | | | | | |
|---|---|---|---|---|---|
| cuuaccccau | uggaccgauu | uacucuuaau | uacuuggguc | ugaguauuca | aaaguaacug 60 |
| aaucgugguu | cagcaggua | uuuauaguag | ucuagacucu | uacgagaaua | ccuauagacu 120 |
| aaaaaucucc | gaccguaagu | auaaaaauuu | uugacggugg | acacuggugu | gacguccggu 180 |
| uugucuuaca | uggacgacca | gucuacgucg | ggucuccagu | gacuuaacgu | uggagaccug 240 |
| agagccaguc | uccguucguc | gggaauaagg | ucuugaggug | ucaggaagug | ugggaagggg 300 |
| ucuggaugug | guucgguug | auucaccagu | uuuccaccug | uuugacucuc | aacauaguuc 360 |
| cgggaaucgg | agaguuaaac | aauaguucaa | agggaaagac | uuagauaaau | gggacuucau 420 |
| auuuauggu | ucuacucgga | auucucacgg | accaucucgu | uuguuucuac | guagaauauc 480 |
| ccucguuuca | gauacgauug | cgucacaaag | aguuaggacc | gacguggaaa | cuuggugccc 540 |
| ucgaaauuuu | cacuggugac | guucccggga | ugggugauac | cuagggguuaa | aguaaccaac 600 |
| ccucucccg | guucaaacaa | agguugaagg | ggucuacuga | gauuaccgac | ucucaacguu 660 |
| aguuguccau | ucacuauag | guccgacauu | cuacuucuuu | ucccccaac | acggguucgg 720 |
| gugacacgga | guauuucguc | uacuagagac | gucgcgacgc | gaagaguuuc | ucaccagggu 780 |
| ccugacggag | ucagucuggu | gucgaggau | ucaaggagga | gucugaagua | ccuaggucg 840 |
| agacacucca | uuaagauucg | uguaauuuga | acaucuuguc | gguagaccua | aauuauaaug 900 |
| uauuaucgau | auuauaagac | gauaagagau | uagaaguuac | agucaaagaa | uuugacaguc 960 |
| cggacagaaa | ucuacgggaa | guugacacga | ccccugauag | aacuaccguc | ggucguuucu 1020 |
| uuuagucguu | uuuggggua | ccucaaagac | ccaaaaugaa | aacaauuccu | uccacuacca 1080 |
| aagaacugua | cuguccauag | auccaccuuu | cccguucac | gauuacguuu | uguuuaccuc 1140 |
| ugugauaccu | uaucgagacg | gaucccugua | caccuucucg | aagauccucu | gucacaccug 1200 |
| gaaaggugg | gaucuccaga | aguguucuau | uuaaggaugg | aggcagucau | aaguuuucca 1260 |
| aaaucguagu | uaugacagac | ucuuauucug | uaaucugaac | ucagucaggg | gaccgaaguu 1320 |
| aggguccuac | gguucgucgg | agauuaccuc | uggcgaccga | auuagcacga | ggaaaggacc 1380 |
| guauuguuga | gugacguggg | uacggagugg | uggugcuucg | ucagaggagu | ggugguuua 1440 |
| cacggaaccc | acugauuuua | ugucgguaau | cauacuuacc | aggggacaaa | auaaguugu 1500 |
| ggugugguca | gaaacgaaaa | uggaagccga | uuacaccaag | gucggaaaau | aggacgugag 1560 |
| gaagaauauu | aaauuuuuuu | uuuuuugag | gggaugauag | aaauacaauu | auaauuguag 1620 |
| uugauccaag | aagaguuucc | ugucgguccg | gauugaccgg | ugcaauuuua | gacgugucac 1680 |
| gaaaacacag | ugacagauaa | gauaaucaaa | guuguaguac | gauuuuaucc | ugucguacaa 1740 |
| gguuuugacu | uugacuuugu | ccuugccucg | gaacgacuaa | aucguacucc | ucccuuaaca 1800 |
| uucggaacgu | ggaccuguga | uuugaaaag | uuauucuaca | uacgauucgg | cauggaucgu 1860 |
| uugaauggguc | cagguuucau | cucauguucg | ucuuucaaua | aaaauuuccu | acccgugaua 1920 |
| ggaacucccu | gaaugggaaa | gauuagucga | acguaccaa | acaaaacucu | gucacagagu 1980 |
| gagacaacgg | guccgaucuc | acgucgccgu | gguagugucg | agugccgucg | gagacggagg 2040 |
| gcccgaguuc | guuagggugg | agucaaaggg | uucaucgacc | cugaugucg | uguggugu 2100 |
| gagucgauua | aaaucauaaa | aaacaucucu | gucccagagc | gguacaacgg | guccgaccag 2160 |
| aguuugagga | ccuaauagag | ggaccgggac | guaauuuuuu | cuacacguug | uugaau 2216 |

<210> SEQ ID NO 32
<211> LENGTH: 476
<212> TYPE: DNA
<213> ORGANISM: Homo sapiens

<400> SEQUENCE: 32

```
tgtgaggagg cccaggccac aaggagaggc cacctataag cattcaggcc agcagcccca      60
gatctgctcc tcctgccaag ctgaacccaa gaccagcacc ttcctccttg tgtaagatgg     120
tgacatggat gccgtctaat tgctgcagag gaaatacata cattcaaaaa cattttactg     180
caagaggatg aacaatttaa catcggactg acatcagact gatttgttat ctcaaacccc     240
agcttggcca gcctccaagt tacatcacct cctcaaacct cagtttcctc atctgtaaag     300
aatggacctt caggagtcat gggaagctta aagaaaaaaa aaatgtatg taaagcagca      360
agcataatta ttttcctctc tcattcaccc tgtccacagc cgggcagggg gagtgccatg     420
aagtcagcca gaaatcagca tattggacag tgtgagatga agtcaggttg taggac         476
```

<210> SEQ ID NO 33
<211> LENGTH: 476
<212> TYPE: RNA
<213> ORGANISM: Homo sapiens

<400> SEQUENCE: 33

```
acacuccucc ggguccggug uuccucuccg guggauauuc guaaguccgg ucgucggggu      60
cuagacgagg aggacgguuc gacuuggguu cuggucgugg aaggaggaac acauucuacc     120
acuguaccua cggcagauua acgacgucuc cuuuauguau guaaguuuuu guaaaaugac     180
guucuccuac uuguuaaauu guagccugac uguagucuga cuaaacaaua gaguuugggg     240
ucgaaccggu cggagguuca auguaguggu ggaguuugga gucaaaggag uagacauuuc     300
uuaccuggaa guccucagua cccuucgaau cuucuuuuuu uuuuacauac auuucgucgu     360
ucguauuaau aaaaggagag aguaaguggg acaggugucg gcccguccccc cucacgguac    420
uucagucggu cuuuagucgu auaaccuguc acacucuacu ucaguccaac auccug          476
```

<210> SEQ ID NO 34
<211> LENGTH: 490
<212> TYPE: DNA
<213> ORGANISM: Homo sapiens

<400> SEQUENCE: 34

```
acatggatcc ttaagtcctc cctatgcccc gttagagcac tgatgacatt tactttgaaa      60
ttcccctgtt acatgtctgt ttgcctaagt agactctaag catctgcaga acaggggcta     120
tgtcttagta tccagggtat tttcttcacc tggcacaatt cctgccacag agtagtgtgt     180
cagctctcta ttgttgtcta aaaacccacc tcaaggtgct gggattacag gtgtgagcca     240
ctgtgcctgg ccccacattt tttaaaacaa tgactttagg gtttcagctt ttcctgtctt     300
ttaaaacaaa ttagccattt tttattctaa gaaaggttg tattataaag ctgacctact      360
actagcttat cagaaaaaac acgtgggtct catatctgat tctcctatgt agccaaaagt     420
gccatttgta agtctactaa atgacggata ttttctgaag atcttttgcc tggaaaacaa     480
atagtgcatt                                                             490
```

<210> SEQ ID NO 35
<211> LENGTH: 490
<212> TYPE: RNA
<213> ORGANISM: Homo sapiens

<400> SEQUENCE: 35

```
uguaccuagg aauucaggag ggauacgggg caaucucgug acuacuguaa augaaacuuu        60
aaggggacaa uguacagaca aacggauuca ucugagauuc guagacgucu uguccccgau       120
acagaaucau agguccccaua aaagaagugg accguguuaa ggacgggguc ucaucacaca      180
gucgagagau aacaacagau uuuggguggu aguuccacga cccuaaugu cacacucggu        240
gacacggacc gggguguaaa aaauuuuguu acugaaaucc caaagucgaa aaggacagaa      300
aauuuuguuu aaucgguaaa aaauaagauu cuuucccaac auaauauuuc gacuggauga      360
ugaucgaaua gucuuuuuug ugcacccaga guauagacua agaggauaca ucgguuuuca      420
cgguaaacau ucagaugauu uacugccuau aaaagacuuc uagaaaacgg accuuuuguu      480
uaucacguaa                                                              490
```

<210> SEQ ID NO 36
<211> LENGTH: 522
<212> TYPE: DNA
<213> ORGANISM: Homo sapiens

<400> SEQUENCE: 36

```
gggttgattc tattatctga tgttttatta atctctgtga ataattgtg taaattaata         60
tagagactag ttgagaaatg gtggataaca tgaagaagat acccattttt gcatagatta      120
gatgtgatca acctcacact atcatatgaa agttggctgc attggagaga caggaattaa      180
tattaaaaat gttttcagtt cagattgata tcttacattt ccaatatta ttttcttttg       240
aatatgtgtg agccactgtg cctggcccca cattttttaa aacaatgact ttagggtttc     300
agcttttcct gtctttttaaa acaaattagc cattttttat tctaagaaag ggttgtatta    360
taaagctgac ctactactag cttatcgaaa aaaacacgtg ggtctcatat ctgattctcc      420
tatgtagcca aaagtgccat ttgtaagtct actaatgac ggatatttc tgaagatctt       480
ttgcctggaa acaaatagt gcattaaaaa gcttttttgg ta                         522
```

<210> SEQ ID NO 37
<211> LENGTH: 522
<212> TYPE: RNA
<213> ORGANISM: Homo sapiens

<400> SEQUENCE: 37

```
cccaacuaag auaauagacu acaaaauaau uagagacacu uuauuaacac auuuaauuau       60
aucucugauc aacucuuuac caccuauugu acuucuucua uggguaaaaa cguaucuaau     120
cuacacuagu uggaguguga uaguauacuu ucaaccgacg uaaccucucu guccuuaauu     180
auaauuuuua caaagucaa gucuaacuau agaauguaaa gguuuauaau aaaagaaaac      240
uuauacacac ucggugacac ggaccggggu guaaaaaauu uuguuacuga aaucccaaag    300
ucgaaaagga cagaaaauuu uguuuaaucg guaaaaaaua agauucuuuc ccaacauaau      360
auuucgacug gaugaugauc gaauagucuu uuugugcac ccagaguaua dacuaagagg      420
auacaucggu uuucacggua acauucaga ugauuacug ccuauaaaag acuucuagaa      480
aacggaccuu uuguuuauca cguauuuuuu cgaaaaaacc au                        522
```

<210> SEQ ID NO 38
<211> LENGTH: 2957
<212> TYPE: DNA
<213> ORGANISM: Homo sapiens

<400> SEQUENCE: 38

-continued

```
aaaggtactt agacatgttc cccacaggat gtgttaaggt gttggccaat catcaaatat        60
tgtcactcca aagaacacat ttaacagccg ggaagaaaat tgtaggaaaa gagagcactt       120
tggcacggaa ggggtctatc gccctggttg gagtgcagca gtgtaatcat agctcactgc       180
tgccatgaac ttctgggctc aagcgatcct cccacctcag cctccctgtg tgctgggatt       240
aaaagtgtga gccaccgtgc ctcatcgtaa gggtcttaaa agaacccta tttcatactt        300 tcttgatgca cttgatatgg attatataaa tctatggaca aaaatgacat cagtacaatg       360
gaatattgga gttttctacc ataatctctg catagtgcac tgattttgac aatcacctat       420
ggatgaaaat acatttgcca gagtctagga gttaaatgga aaagttaaca gcacaccgtt       480
ggagaaaaat atctgggagt agatgcattc aagggagtaa aagaacaat tacctgcatc        540 acctcacccc cagggtccac ttcttagtgc aagatagac tcccttcagc aggcaatttc        600
tcccatgggg aaaaggagag tataatgagt gagtatccag ctttttccagc tgtgtgaggc      660 acatcccaag aagcccatct ttctttcact caactcagaa tattgagggt attagcatgg       720
ctaagtggct gggacagggc agtagcagga aagaaggag aggactcaca gcaaccagga       780
cttgaaactc agtacagggt acatatcctt tgaagcattt cacagagccc atcaggaggc      840
ccacccatga accacttggg acaccatatc tgtagcatct ccctgcaact ggcccatagg       900 agccccgat gttttgtgca tattcccctt ccctttctcc tatagtcagt tgcctgcaca       960
tgcactccag atggtgagtg tgagcattta cctacagctt ttgagtacat gcagtcagca     1020
ggctcaactt tgaaggattg ggaggaatac aaaattgagc atttcagggc actgtcctag    1080
aggaaacaaa cagaaagctt tcaggaccca gtttggtttt gtggatttaa gagaagacac    1140
acaatcatca gaatttcttc tccacccatc caagaagtgt ggattgggtg aatccataga    1200
aaagatctga gagagcctca gattccctat aggctcactg ttgaagatat ttctctcaaa    1260
tccagtcagt aaagactaga gaaagtgact ctttcttcaa atgtgaagac agcagtgcaa    1320
gactttgagg aacatgaaaa atcaaggaca cctagtacca ccaaaggaac ataatttct    1380 ggtacccaac cacaaagaaa tggagataca caaattgtct gacaaagaat tcacaacaat    1440
tgttttaagg aagtcagtaa gctacaagag aacacagaga acttaatgat attaagaaag    1500
cgacacatga acaaaataag atgttcaaca aaaagataga aattattaaa acaaccatg     1560 attttcgagc tgagaataca atgaatgaaa tggaaaacac aatagagttt caatagcaga    1620
cttgatcaag cagaagaaag ggtctgtcaa ctcaaatact agtcatttga aattattcag    1680
taaaagaaat aaaaaggaat gaaaaatgct tatgcgattg atgcaacacc atgaagagta    1740
gtcatatatg cactatggga gtctcagaaa aagaaagaga taagggggaa gaaaactaac    1800
ttaaagaact agatcagtct ctccttatct gtagttttgc tttccttggt ttcaggtaca    1860
gtacaatgat atgttttaag agacagacaa tgaaagagaa catgcaaata ttgacataat    1920
ttttattaca gtatattgtc atagttttc tattttgtta ttagttgtta ttctcttact     1980
gtgcctaatt tatacattaa actttatcat aggaatagtg gtggtggcct gtctggagtg    2040
gccactgcca ggatgccagc tgcagcaggg gaggtgtagc tggggctgtg cactccgcag    2100
agctgggggg ggccaggaac aggtgatcct agtgggagcc ctatatgcta ctgagttagt    2160
ggggtgggag cctgtgctcc caggcatagc tgcagctgcc cagccatggc tccagcccta    2220
ggcatacctg tgctctcagg ggccctggaa gtccctgcc cttacaggct tggaagtgcc    2280
tgctcccatt ccctggcctc tttccactgc tggcacctgc tctgtggcag agcaaagttg    2340
```

-continued

| | |
|---|---|
| tggatgtgtt gtgatagctg agcctgggag ctgttgtgac gtggtcaggt gtgtgtgttc | 2400 |
| agggcagttc tgatacacca gactccccac tgcctttgcc ccctctgaaa actgcttctg | 2460 |
| aggctgaaac tttggatatt aatgagcaag gatggtgggg gaggccagga cggctgaggg | 2520 |
| cagctaggtg tgggcctgtg gacacccctt agtgcggaca gtctgggtgc tgtggatggc | 2580 |
| atgttgatgg cagcgagagg cagacatgtt cctaggtggg aacgggtggg tccctggtga | 2640 |
| aacctcacct tcaagccagg gacagcttga agcatggggg cctggctgcc agttccggtt | 2700 |
| gcagtctgtg acctggagtg aaaacttcat tgatgtcttt cagccaattg gatggtgctt | 2760 |
| tttccagacc cacaaatggc tgcccatgga ccaagcagta tgtacttcct ccattctgag | 2820 |
| cccatgaaaa ccccagactc agtcagactc tgacactcat caggatgaca agcctgcaaa | 2880 |
| taggatctac ccattttggg tatgcactcc actgagagct attctgtcac tcaataaagc | 2940 |
| tcctttctgc cttgctc | 2957 |

<210> SEQ ID NO 39
<211> LENGTH: 2957
<212> TYPE: RNA
<213> ORGANISM: Homo sapiens

<400> SEQUENCE: 39

| | |
|---|---|
| uuuccaugaa ucuguacaag ggguguccua cacaauucca caaccgguua guaguuuaua | 60 |
| acagugaggu uucuugugua aauugucggc ccuucuuuua acauccuuuu cucucgugaa | 120 |
| accgugccuu ccccagauag cgggaccaac cucacgucgu cacauuagua ucgagugacg | 180 |
| acgguacuug aagacccgag uucgcuagga ggugggaguc ggaggacac acgacccuaa | 240 |
| uuuucacacu cgguggcacg gaguagcauu cccagaauuu ucuuugggau aaaguaugaa | 300 |
| agaacuacgu gaacuauacc uaauauauuu agauaccugu uuuuacugua gucauguuac | 360 |
| cuuauaaccu caaaagaugg uauuagagac guaucacgug acuaaaacug uuagggauua | 420 |
| ccuacuuuua uguaaacggu ucagauccu caauuuaccu uuucaauugu cguguggcaa | 480 |
| ccucuuuuua uagacccuca ucuacguaag uucccucauu cuucuguuua auggacguag | 540 |
| uggaguggggg gucccaggug aagaaucacg guucuaucug agggaagucg uccguuaaag | 600 |
| agggugacccc uuuccucuc auauuacuca cucauaagguc gaaaaggucg acacacuccg | 660 |
| uguagggguuc uucggguaga agaaaaguga guugagucuu auaacuccca uaaucguacc | 720 |
| gauucaccga cccugucccg ucaucguccu ucuuuccuc uccugagugu cguuggucuu | 780 |
| gaacuuugag ucaugucccca guauaggaa acuucguaaa gugucucggg uaguccuccg | 840 |
| ggugggguacu uggugaaccc uguggauaug acaucguaga gggacguuga ccgggguaucc | 900 |
| ucggggggcua caaaacacgu auaaggggaa gggaagagg auaucaguca acggacgugu | 960 |
| acgugaggguc uaccacucac acucguaaau ggaugucgaa aacucaugua cgucagucgu | 1020 |
| ccgaguugaa acuuccuaac ccuccuuaug uuuuaacucg uaaaguccccg ugacaggauc | 1080 |
| uccuuuguuu gucuuucgaa aguccugggu caaaccaaaa caccuaaaauu ucuucugug | 1140 |
| uguuaguagu cuuaaagaag aggugggguag guucuucaca ccuaacccac uuagguaucu | 1200 |
| uuucuagacu cucucggagu cuaagggaua uccgagugac aacuucuaua aagagaguuu | 1260 |
| aggucagucca uuucugaucu cuuucacuga gaaagaaguu uacacuucug ucgucacguu | 1320 |
| cugaaacucc uuguacuuuu uagucccugu ggaucaugggu gguuuccuug uauuaaaaga | 1380 |
| ccauggguug uguuucuuuu accucuaugu guuuaacaga cuguuucuua agucuuguua | 1440 |
| acaaaauucc uucagucauu cgauguucuc uugugucucu ugaauuacua uaauucuuuc | 1500 |

```
gcugugguacu uguuuuauuc uacaaguugu uuuucuaucu uuaauaauuu uuguugguac    1560
uaaaagcucg acucuuaugu uacuuacuuu accuuuugug uuaucucaaa guuaucgucu    1620
gaacuaguuc gucuucuuuc ccagacaguu gaguuuauga ucaguaaacu uuaauaaguc    1680
auuuucuuua uuuuuccuua cuuuuuacga auacgcuaac uacguugugg uacuucucau    1740
caguauauac gugauacccu cagagucuuu uucuuucucu auuccccuu cuuuugauug      1800 aauuucuuga ucuagucaga gaggaauaga caucaaaacg aaaggaacca aagccaugu     1860 cauguuacua uacaaaauuc ucugucuguu acuuucucuu guacguuuau aacuguauua    1920
aaaauaaugu cauauaacag uaucaaaaag auaaaacaau aaucaacaau aagagaauga    1980
cacggauuaa auauguaauu ugaauaguaa uccuuaucac caccaccgga cagaccucac    2040
cggugacggu ccuacggucg acgucguccc cuccacaucg accccgacac gugaggcguc    2100 ucgaccccccc ccgguccuug uccacuagga ucacccucgg gauauacgau gacucaauca    2160
ccccacccuc ggacacgagg guccguaucg acgucgacgg gucgguaccg aggucgggau    2220
ccguauggac acgagagucc ccgggaccuu caggggacgg gaauguccga accuucacgg    2280
acgaggguaa gggaccggag aaaggugacg accguggacg agacaccguc ucguuucaac    2340
accuacacaa cacuaucgac ucggacccuc gacaacacug caccagucca cacacacaag    2400
ucccgucaag acuaugggu cugagggggug acggaaacgg gggagaccuu ugacgaagac    2460
uccgacuuug aaaccuauaa uuacucguuc cuaccacccc cuccggguccu gccgacuccc    2520 gucgauccac acccggacac cuguggggaa ucacgccugu cagacccacg acaccuaccg    2580
uacaacuacc gucgcucucc gucuguacaa ggauccaccc uugcccaccc agggaccacu    2640
uuggagugga aguucgguccc cugucgaacu ucgucacccc ggaccgacgg ucaaggccaa    2700
cgucagacac uggaccucac uuuugaaguaa acuacagaaa gucgguuaac cuaccacgaa    2760
aaaggucugg guguuuaccg acggguaccu gguucgucau acaugaagga gguaagacuc    2820
ggguacuuuu ggggucugag ucagucugag acugugagua guccuacugu ucggacguuu    2880
auccuagaug gguaaaaccc auacgugagg ugacucucga uaagacagug aguuauuucg    2940
aggaaagacg gaacgag                                                    2957
```

<210> SEQ ID NO 40
<211> LENGTH: 581
<212> TYPE: DNA
<213> ORGANISM: Homo sapiens

<400> SEQUENCE: 40

```
acaaagttta tattagagcg tcatccatta atgctttggc taggagggg tctatcgccc      60 tggttggagt gcagcagtgt aatcatagct cactgctgcc atgaacttct gggctcaagc    120
gatcctccca cctcagcctc cctgtgtgct gggattaaaa gtgtgagcca ccgtgcctca    180
tcgtaagggt cttaaaagaa accctatttc atactttctt gatgcacttg atatggatta    240
tataaatcta tggacaaaaa tgacatcagt acaatggaat attggagttt ctaccataa    300 tctctgcata gtgcactgat tttgacaatc acctatggat gaaatacat ttgccagagt     360 ctaggagtta aatggaaaag ttaacagcac accgttggag aaaaatatct gggagtagat    420
gcattcaagg gagtaagaag aacaattacc tgcatcacct caccccagg gtccacttct     480 tagtgccaag atagactccc ttcagcaggc aatttctccc atggggaaaa ggagagtata    540
atgagtgagt atccagcttt tccagctgtg tgaggcacat c                        581
```

<210> SEQ ID NO 41
<211> LENGTH: 581
<212> TYPE: RNA
<213> ORGANISM: Homo sapiens

<400> SEQUENCE: 41

```
uguuucaaau auaaucucgc aguagguaau uacgaaaccg auccucccccc agauagcggg      60 accaaccuca cgucgucaca uuaguaucga gugacgacgg uacuugaaga cccgaguucg     120
cuaggagggu ggagucggag ggacacacga cccuauuuuu cacacucggu ggcacggagu     180
agcauucccu gaauuuucuu ugggauaaag uaugaaagaa cuacgugaac uauaccuaau     240
auauuuagau accuguuuuu acuguaguca uguuaccuua uaaccucaaa agaugguauu     300
agagacguau cacgugacua aaacuguuag uggauaccua cuuuuaugua aacggcucua     360
gauccucaau uuaccuuuuc aauugucgug uggcaaccuc uuuuuauaga cccucaucua     420
cguaaguucc cucauucuuc uuguuaaugg acguagugga gugggggucc caggugaaga     480
aucacgguuc uaucugaggg aagucguccg uuaaagaggg uaccccuuuu ccucucauau     540
uacucacuca uaggucgaaa aggucgacac acuccgugua g                         581
```

<210> SEQ ID NO 42
<211> LENGTH: 1286
<212> TYPE: DNA
<213> ORGANISM: Homo sapiens

<400> SEQUENCE: 42

```
ctgaacaaca agttaactgc tgttcccagt tatatctggt ctttcccacc cccaaacata      60
cacaaaagat ttttgtcatt cttggcactg acaacagaa gtgataagac atgccagcag     120
aactctaaag gcagaatgtc cttccacctg ttttatgctg taagacaaac ttccaagtgc     180
gaggcagtgt ggagggctgt tgccttgaat ggcagctgaa tgcaccagcg ggatccttgg     240
cagcaatgcc caggcactga agtcgggcat tcaggagagc taaatggaga aaagaaactt     300
gagcaaactg cttcctggaa cactgagaac ctgaatggga aattaagaag aaccagattc     360
tttctattct tccaccagcc aaggtcagat ttccaaactt ctattgattc taatcttttcc     420 caaacagtgc tgtggcaatg tatgaaagta ataaaaataa tcctttttct gttaaaaaaa     480
aaattgctgt tacttgctgt tttgttatgc ttttgctgga gattttccca cccatcttaa     540
agcagcaact tcaggatggg ggaatcaagc aaaaccatgg tgaagagatt catttaaaga     600
ggacaagtga tttattctac atctcaggag acagttcctt aaggtgatga gcacaaaagg     660
atccatctta tacagtgctt gccagcttcc ataatactac tcaccacgat gttgaaatca     720
cctgttccag aaccagtcct gtcctttgac aagaaggatt taattatcag tagtggtggg     780
gactggctgg agagaggaaa aacacttcaa ggactctgcc acctttcgta gatggagagt     840
gcaaagtttg taccatggaa ctccttctct aacagttact ctgtggcagt gcctatttca     900 aacctcccctt aacttctgat tgtatagatg tttgtttcat ttgttcatct gtttgttcac     960
ttagtcagag atgttttaag ccttaagaga aatagtggac tagaaaatgc cttggaaaag    1020
tacaaagttc aatccaagta aactgttttt aaactaggaa tttatgaagc ctaaaatata    1080
aaatgtatat acatggatat gctctgaagt gaggtagagg ggtagaaatc aacattgtga    1140
tattgtacta tagttttgca agatgttacc attgggggaa aatgtttgaa gggtatacgg    1200
gatatctctg cctttattct tacaactgca tgtgaatcta cagttatctc aaaataaaaa    1260
tttaattaac aattgattac aattaa                                         1286
```

<210> SEQ ID NO 43
<211> LENGTH: 1286
<212> TYPE: RNA
<213> ORGANISM: Homo sapiens

<400> SEQUENCE: 43

| | | | | | |
|---|---|---|---|---|---|
| gacuuguugu | ucaauugacg | acaaggguca | auauagacca | gaaagggugg | ggguuuguau | 60 |
| guguuucua | aaaacaguaa | gaaccgugac | cuguugucuu | cacuauucug | uacggucguc | 120 |
| uugagauuuc | cgucuuacag | gaaggugac | aaaauacgac | auucguuug | aagguucacg | 180 |
| cuccgucaca | ccucccgaca | acggaacuua | ccgucgacuu | acgggucgc | ccuaggaacc | 240 |
| gucguuacgg | guccgugacu | ucagcccgua | agccucucg | auuuaccucu | uuucuuugaa | 300 |
| cucguuugac | gaaggaccuu | ugacucuug | gacuuacccu | uuaauucuuc | uuggucuaag | 360 |
| aaagauaaga | aggggucgg | uuccagucua | aagguugaa | gauaacuaag | auuagaaagg | 420 |
| guuugucacg | acaccguuac | auacuuucau | uauuuuauu | aggaaaaaga | caauuuuuu | 480 |
| uuuaacgaca | augaacgaca | aaacaauacg | aaaacgaccu | cuaaaagggu | ggguagaauu | 540 |
| ucgucguuga | aguccuaccc | ccuuaguucg | uuuuggucgu | acuucucuaa | guaaauuucu | 600 |
| ccuguucacu | aaauaagaug | uagagccuc | ugucaaggaa | uuccacuacu | cguguuuucc | 660 |
| uagguagaau | augucacgaa | cggucgaagg | uauuagauag | aguggugcua | caacuuuagu | 720 |
| ggacaagguc | uuggucagga | caggaaacug | uucuuccuaa | auuaauaguc | aucaccaccc | 780 |
| cugaccgacc | ucucuccuuu | uugugaaguu | ccugagacgg | uggaaagcau | cuaccucuca | 840 |
| cguuucaaac | augguaccuu | gaggaagaga | uugucaauga | gacaccguca | cggauaaagu | 900 |
| uuggagggaa | uugaagacua | acauaucuac | aaacaaagua | aacaaguaga | caaacaagug | 960 |
| aaucagucuc | uacaaaauuc | ggaauucucu | uuaucaccug | aucuuuuacg | gaaccuuuuc | 1020 |
| auguuucaag | uuagguucau | uugacaaaaa | uuugauccuu | aaauacuucg | gauuuuauau | 1080 |
| uuuacauaua | uguaccuaua | cgagacuuca | cuccaucucc | ccaucuuuag | uuguaacacu | 1140 |
| auaacaugau | aucaaaacgu | ucuacaaugg | uaacccccuu | uuacaaacuu | cccaugcc | 1200 |
| cuauagagac | ggaauaaaga | auguugacgu | acacuuagau | gucaauagag | uuuuauuuu | 1260 |
| aaauuaauug | uuaacuaaug | uuaauu | | | | 1286 |

<210> SEQ ID NO 44
<211> LENGTH: 844
<212> TYPE: DNA
<213> ORGANISM: Homo sapiens

<400> SEQUENCE: 44

| | | | | | |
|---|---|---|---|---|---|
| acaacaagtt | aactgctgtt | cccagttata | tctggtcttt | cccaccccca | aacatacaca | 60 |
| aaagattttt | gtcattcttg | gcactggaca | acagaagtga | taagacatgc | cagcagaact | 120 |
| ctaaaggcag | aatgtccttc | cacctgtttt | atgctgtaag | acaaacttcc | aagtgcgagg | 180 |
| cagtgtggag | ggctgttgcc | ttgaatggca | gctgaatgca | ccagcgggat | ccttggcagc | 240 |
| aatgcccagg | cactgaagtc | gggcattcag | gagagctaaa | tggagaaaag | aaacttgagc | 300 |
| aaactgcttc | ctggaacact | gagaacctga | atgggaaatt | aagaagaacc | agattctttc | 360 |
| tattcttcca | ccagccaagg | tgatgagcac | aaaaggatcc | atcttataca | gtgcttgcca | 420 |
| gcttccataa | tactactcac | cacgatgttg | aaatcacctg | ttccagaacc | agtcctgtcc | 480 |
| tttgacaaga | aggattaat | tatcagtagt | ggtgggact | ggctggagag | aggaaaaaca | 540 |

| | | |
|---|---|---|
| cttcaaggac tctgccacct ttcgtagatg gagagtgcaa agtttgtacc atggaactcc | | 600 |
| ttctctaaca gttactctgt ggcagtgcct atttcaaacc tcccttaact tctgattgta | | 660 |
| tagatgtttg tttcatttgt tcatctgttt gttcacttag tcagagatgt tttaagcctt | | 720 |
| aagagaaata gtggactaga aaatgccttg gaaaagtaca aagttcaatc caagtaaact | | 780 |
| gtttttaaac taggaattta tgaagcctaa aatataaaat gtatatacat ggatatgctc | | 840 |
| tgaa | | 844 |

<210> SEQ ID NO 45
<211> LENGTH: 844
<212> TYPE: RNA
<213> ORGANISM: Homo sapiens

<400> SEQUENCE: 45

| | | |
|---|---|---|
| aagucucgua uagguacaua uauguaaaau auaaaauccg aaguauuuaa ggaucaaauu | | 60 |
| uuugucaaau gaaccuaacu ugaaacauga aaagguuccg uaaagauca ggugauaaag | | 120 |
| agaauuccga auuuguaga gacugauuca cuuguuguc uacuuguuua cuuguuugu | | 180 |
| agauauguua gucuucaauu cccuccaaac uuuauccgug acggugucuc auugacaauc | | 240 |
| ucuuccucaa gguaccaugu uugaaacgug agagguagau gcuuccacc gucucaggaa | | 300 |
| cuucacaaaa aggagagagg ucggucaggg guggugauga cuauuaauuu aggaagaaca | | 360 |
| guuccuguc cugaccaaga ccuugccac uaaagugua gcaccacuca ucauaauacc | | 420 |
| uucgaccguu cgugacauau ucuaccuagg aaaacacgag uaguggaacc gaccaccuuc | | 480 |
| uuaucuuucu uagaccaaga agaauuaaag gguaagucca agagucacaa gguccuucgu | | 540 |
| caaacgaguu caaagaaaag agguaaaucg agaggacuua cgggcugaag ucacggaccc | | 600 |
| guaacgacgg uuccuaggc gaccacguaa gucgacggua aguuccguug ucgggaggug | | 660 |
| ugacggagcg ugaaccuuca aacagaaugu cguauuugu ccaccuuccu guaagacgga | | 720 |
| aaucucaaga cgaccguaca gaauagugaa gacaacaggu cacgguucuu acuguuuua | | 780 |
| gaaaacacau acaaaccccc acccuuucug gucuauauug acccuugucg ucaauugaac | | 840 |
| aaca | | 844 |

<210> SEQ ID NO 46
<211> LENGTH: 293
<212> TYPE: DNA
<213> ORGANISM: Sus domesticus

<400> SEQUENCE: 46

| | | |
|---|---|---|
| tgactatccc acaatatcct agttctgatt tcattccttc tcatcctact aactcagctt | | 60 |
| ccagtcattc taagagaatt ctctttgaag gagagtcaag acagaattcc acaatttaca | | 120 |
| tagatgattg gttggtaact gtaccttaat ctgtgttagt ctctgagata ctgggtaaga | | 180 |
| atttctggaa aaacatagta aatgtctttt ttttttttca taatcatctg atttctggtc | | 240 |
| aaaaggatta actagattac ctaagaaaat gactctcatg caactcaaag aat | | 293 |

<210> SEQ ID NO 47
<211> LENGTH: 293
<212> TYPE: RNA
<213> ORGANISM: Sus domesticus

<400> SEQUENCE: 47

| | | |
|---|---|---|
| acugauaggg uguuauagga ucaagacuaa aguaaggaag aguaggauga uugagucgaa | | 60 |
| ggucaguaag auucucuuaa gagaaacuuc cucucaguuc ugucuuaagg uguuaaaugu | | 120 |

```
aucuacuaac caaccauuga cauggaauua gacacaauca gagacucuau gacccauucu      180
uaaagaccuu uuuguaucau uuacagaaaa aaaaaaaagu auuaguagac uaaagaccag      240
uuuuccuaau ugaucuaaug gauucuuuua cugagaguac guugaguuuc uua             293
```

MATERIALS AND METHODS FOR THE TREATMENT OF VASCULAR DISEASE

CROSS REFERENCE TO RELATED APPLICATIONS

This application is a national stage application under 35 U.S.C. § 371 of PCT/GB2016/050708 filed Mar. 16, 2016, which claims priority to GB Application No. 1504387.0 filed Mar. 16, 2015, the disclosures of which are hereby incorporated by reference herein in their entireties.

FIELD OF THE INVENTION

The present invention relates to materials and methods for the treatment of vascular disease. Particularly, but not exclusively, the invention provides materials and methods for inhibiting smooth muscle cell proliferation. The invention also relates to biomarkers of vascular conditions and related methods.

BACKGROUND OF THE INVENTION

Vascular disease is caused by factors such as the inflammation and weakness of the veins and arteries and by the build-up of fatty deposits in blood vessels. Cardiovascular disease is the leading global cause of death, accounting for over 17 million deaths per year and growing. Cardiovascular and related diseases claims more deaths each year than all forms of cancers combined. Accordingly, there is a great deal of interest in trying to understand the mechanism behind vascular disease with an aim to developing materials and methods for treating the disease or preventing its onset. FIG. 1 provides an illustration of vascular pathology and shows how physical injury including endothelial damage and infiltration of inflammatory cells stimulate migration and proliferation of smooth muscle cells (SMCs).

Smooth muscle cell proliferation and migration is a necessary function during vascular development and in response to vascular injury. However, pathological proliferation and migration is a major factor in atherogenesis and restenosis. The distinction between physiological and pathological proliferation and migration is thought to be driven by modulation of vascular smooth muscle cell (VSMC) phenotypes. VSMCs exist in a wide range of phenotypes. In normal blood vessels the predominant phenotype is the contractile phenotype which regulates blood vessel diameter and blood flow. However, in response to injury, the contractile phenotype switches to the synthetic, migratory and proliferative phenotype. The response to injury is multicellular and involves a number of growth factors including platelet derived growth factor (PDGF). Where the migrating and proliferating VSMC fail to switch back to contractile phenotype, they instead induce pathogenic vascular remodelling and generate intimal vascular lesions.

Neointimal formation caused by SMC migration and proliferation is a hallmark in vascular pathology. Local cytokine (e.g. IL1α) and growth factor (e.g. PDGF) networks are known to regulate SMC phenotype in vascular disease[B,C], for example via synergistic activation of the protein complex $NF_{\kappa}B^{[D]}$. However, to date no therapeutic intervention has proved successful in targeting vascular remodelling.

Coronary artery bypass grafting (CABG) is the preferred treatment for patients with multi-vessel disease. However, 30 to 50% of grafted vessels fail due to stenotic occlusion within 5 to 10 years of treatment.

There is therefore a need for novel interventions that will permit vascular adaptation to insult but will prevent neointimal thickening. Success depends on a much deeper understanding of mechanisms responsible for the switch from migration mode to invasion mode.

High throughput RNA sequencing technologies have shown that non-coding RNA makes up the majority of transcribed RNA in the genome. Long non-coding RNAs (lncRNA) are a large and diverse class of transcribed RNA molecules with a length of more than 200 nucleotides that do not encode proteins. Their expression is believed to be developmentally regulated and lncRNA can be tissue- and cell-type specific.

LncRNA are thought to exert their function either by binding to DNA or RNA in a sequence specific manner or by binding to proteins. Some lncRNAs can modulate smaller regulatory RNAs such as microRNAs. LncRNAs are not defined by a specific function as they can apparently regulate gene expression and protein synthesis in a number of different ways. Post-transcriptional functions of lncRNA include regulating RNA processing events such as splicing, editing, localisation, translation and degradation.

With such wide ranging functions, it is not surprising that lncRNAs play a role in the development and pathology of disease. LncRNAs have been found to be differentially expressed in various types of cancers and have been found to be dysregulated in diseases such as cardiovascular disease, neurological disorders and immune mediated diseases.

Phenotypic switching of vascular smooth muscle cells (VSMCs) from a contractile to a synthetic state is implicated in diverse vascular pathologies including atherogenesis, plaque stabilisation, and neointimal hyperplasia. However, very little is known as to the role of long non coding RNA (lncRNA) during this process. The inventors have investigated a role for long non-coding (lnc)RNAs in VSMC biology and pathology.

SUMMARY OF THE INVENTION

The present inventors hypothesised that lncRNAs may be dysregulated in the setting of vascular pathology and associated neo-intimal formation owing to their ability to modulate gene expression at the epigenetic level amongst other potentially relevant mechanisms of action. In support of this hypothesis, the inventors have surprisingly found lncRNAs that show specific SMC expression. This specific expression may be induced by factors such as IL1α and PDGF treatment in SMC alone or SMC and endothelial cells (EC) respectively. The inventors have additionally found that certain lncRNA expression can be significantly inhibited using factors such as MEKK1 and p38 inhibitors indicating a role in cell cycle, inflammation and apoptosis. Advantageously, the inventors have also found that certain lncRNAs may be used as biomarkers of vascular conditions, particularly inflammatory vascular conditions.

Accordingly, and at its most general, the invention provides materials and methods for modulating selected lncRNAs thereby providing exciting new therapies for the treatment of vascular disease such as atherosclerosis, late stage vein graft failure and other vascular proliferative disorders. Furthermore, the invention provides materials and methods for diagnosing a vascular condition in a subject.

The inventors have identified 97 lncRNA from sequence analysis of human saphenous vein smooth muscle cells (HSVSMC) that were significantly different with a logFC>2 and FDR<0.01. They focused on 6 of the most differently expressed lncRNA, 4 of which were down-regulated greater than 20 fold and two which were up-regulated greater than 40 fold (20.8+5.7 and 43.7+11.7, respectively, n=4). The effects were validated by qRT-PCR.

The inventors surprisingly found that LncRNAs showed distinct tissue distribution possibly owing to their distinct cellular functions. Two lncRNAs, named LncRNA 2 and 7, showed specific SMC expression and were expressed by IL1α and PDGF treatment in SMC alone or SMC and EC (respectively). Due to its specific localisation in SMC and not EC, LncRNA 2 demonstrates particular potential as a new therapeutic target for the treatment of vascular disease, and in particular late stage vein graft failure, as its modulation will effect SMC, but not EC. In the treatment of neointimal formation it is preferable to target smooth muscle cell proliferation and migration whilst having no detrimental effect on re-endothelialisation of the vessel wall.

The inventors therefore focused on the novel lncRNA, lncRNA2, which they termed smooth muscle induced lncRNA enhances replication (SMILR). As used herein, the term "SMILR" is used interchangeably with the term "lncRNA2". In one embodiment, the term "lncRNA2" encompasses the lncRNA2 RNA sequence shown in FIG. 39 ("lncRNA2.1") and the RNA sequence obtainable from the cDNA sequence shown in FIG. 15 ("lncRNA2"). The lncRNA2.1 sequence shown in FIG. 39 is obtainable from the DNA sequence with Ensembl ID: RP11-94A24.1. Accordingly, in one embodiment, the terms SMILR, lncRNA2.1 (or lncRNA2) and RP11-94A24.1 are used interchangeably.

In one aspect, "SMILR" (or "lncRNA2") refers to the lncRNA2 RNA sequence of FIG. 39 ("lncRNA2.1").

The inventors have interestingly found that following stimulation, SMILR expression was increased and that this expression is associated with localisation in both the nucleus and cytoplasm, and was also, surprisingly, detected in conditioned media. Furthermore, knockdown of SMILR markedly reduced cell proliferation. Mechanistically, it was noted that expression of genes proximal to SMILR were also altered by IL1α/PDGF treatment, and HAS2 expression was reduced by SMILR knockdown. In human samples, the inventors observed increased expression of SMILR in unstable atherosclerotic plaques compared to adjacent tissue within the same patient ("stable" region) and detected increased levels in plasma from patients with high plasma C-reactive protein.

These results identify SMILR as a driver of VSMC proliferation and suggest that modulation of SMILR may be a novel therapeutic strategy to reduce vascular pathologies.

Accordingly, in a first aspect there is provided a method of treating vascular conditions within a subject comprising administering a therapeutic agent to said subject that is capable of modulating the expression levels of a lncRNA selected from the group consisting of lncRNA2, lncRNA4, lncRNA5, lncRNA6, lncRNA7 and lncRNA8. Preferably the lncRNA is selected from lncRNA2 and lncRNA7 and the agent is capable of down-regulating said lncRNA in SMC. More preferably the lncRNA is lncRNA2.The vascular condition may be a vascular disease or it may be a condition arising from injury or trauma of the vascular tissue. Examples of vascular disease include, but are not limited to, cardiovascular disease, atherosclerosis, ischemia, stroke, aneurysm, Buerger's disease, peripheral venous disease, peripheral artery disease (PAD) and carotid artery disease. Other conditions may include vascular grafts, such as late stage vein graft failure or in-stent restenosis.

As used herein, the term "lncRNA4" encompasses (e.g. refers to) the lncRNA4 RNA sequence shown in FIG. 39 (the lncRNA4 RNA sequence is also obtainable from the DNA sequence shown in FIGS. 15 and 39). The lncRNA4 RNA sequence shown in FIG. 39 can be obtained from the cDNA sequence with Ensembl ID: RP11-709B3.2. Accordingly, in one embodiment, the terms lncRNA4 and RP11-709B3.2 are used interchangeably.

As used herein, the term "lncRNA5" encompasses (e.g. refers to) the lncRNA5 RNA sequence shown in FIG. 39 (the lncRNA5 RNA sequence is also obtainable from the cDNA sequence shown in FIGS. 15 and 39). The lncRNA5 RNA sequence shown in FIG. 39 can be obtained from the DNA sequence with Ensembl ID: RP11-76114.4. Accordingly, in one embodiment, the terms lncRNA5 and RP11-76114.4 are used interchangeably.

As used herein, the term "lncRNA6" encompasses (e.g. refers to) the lncRNA6a and lncRNA6b RNA sequences shown in FIG. 39 (the lncRNA6a and lncRNA6b RNA sequences are also obtainable from the cDNA sequences shown in FIGS. 15 and 39). The lncRNA6a and lncRNA6b RNA sequences shown in FIG. 39 can be obtained from the DNA sequence with Ensembl ID: RP11-760H22.2. Accordingly, in one embodiment, the terms lncRNA6 and RP11-760H22.2 are used interchangeably.

As used herein, the term "lncRNA7" encompasses (e.g. refers to) the lncRNA7a and lncRNA7b RNA sequences shown in FIG. 39 (the lncRNA7a and lncRNA7b RNA sequences are also obtainable from the cDNA sequences shown in FIGS. 15 and 39). The lncRNA7a and lncRNA7b RNA sequences shown in FIG. 39 can be obtained from the DNA sequence with Ensembl ID: RP11-91k9.1. Accordingly, in one embodiment, the terms lncRNA7 and RP11-91k9.1 are used interchangeably.

As used herein, the term "lncRNA8" encompasses (e.g. refers to) the lncRNA8a and lncRNA8b RNA sequences shown in FIG. 39 (the lncRNA8a and lncRNA8b RNA sequences are also obtainable from the cDNA sequences shown in FIGS. 15 and 39). The lncRNA8a and lncRNA8b RNA sequences shown in FIG. 39 can be obtained from the DNA sequence with Ensembl ID: AC018647.3. Accordingly, in one embodiment, the terms lncRNA7 and AC018647.3 are used interchangeably.

The subject can include a non-human mammal, e.g. mouse, rat, guinea pig, pig. It is a preferred embodiment that the subject is a human.

Accordingly, the invention encompasses lncRNA homologues of lncRNAs selected from the group consisting of lncRNA2, lncRNA4, lncRNA5, lncRNA6, lncRNA7 and lncRNA8 in species other than humans. An example of the RNA sequence for pig lncRNA2 is provided in FIG. 39.

In accordance with the first aspect, the agent may be any therapeutic compound which is capable of modulating the level of lncRNA in SMCs. In a preferred embodiment, the agent is capable of down-regulating lncRNA 2 or lncRNA7. Still more preferred is an agent which is capable of down-regulating lncRNA2.

Many agents capable of down-regulating lncRNA will be known to the skilled person. The agent may target the lncRNA directly, e.g. a complementary nucleic acid sequence which binds directly to the lncRNA or at least a portion of it; or it may target the lncRNA indirectly, e.g. by blocking the lncRNA interaction with a downstream or upstream member of the lncRNA signalling pathway.

As a non-limiting example, SMILR has been shown herein to interact with Has2 (hyaluronan synthase 2). Accordingly, SMILR activity may be targeted (e.g. down-regulated/reduced) by at least partially blocking the interaction between SMILR and Has2. Accordingly, an (therapeutic) agent of the invention may include an agent that blocks the interaction between SMILR and Has2.

As a further non-limiting example, IcnRNA7 has been shown to be capable of binding Hur (also known as Hur antigen R; and ELAVL1), a nuclear binding protein known to play a role in smooth muscle proliferation. Accordingly, IcnRNA7 activity may be targeted (e.g. down-regulated/ reduced) by at least partially blocking the interaction between lncRNA7 and Hur. Accordingly, an (therapeutic) agent of the invention may include an agent that blocks the interaction between lncRNA7 and Hur. lncRNA interacts with Hur at the protein level. As an example, the human protein sequence for HuR can be found at: UniProtKB-Q15717 (ELAV1_HUMAN).

When targeting the lncRNA directly, it is preferable to use a complementary targeting oligonucleotide. The targeting oligonucleotide may be single stranded oligonucleotide, an antisense oligonucleotide, siRNA, shRNA, miRNA, or an anti-microRNA antisense oligonucleotide. In some embodiments, the targeting oligonucleotide binds specifically to at least a portion of the lncRNA in a cell and causes degradation of the target lncRNA. However, it is also possible that the degradation is brought about by RNAseH. Alternatively, the degradation is caused by an RNAi pathway. In some embodiments, viral vectors containing shRNAs may be used to target the lncRNA. Each of these embodiments is described in more detail below.

Inhibition of lncRNAs, e.g. to upregulate gene expression by blocking interactions with epigenetic complexes, is known in the art. For example, lncRNAs bind to the PRC2 complex and guide the complex to target gene promoters to repress expression. This repressive action of the lncRNA may be inhibited in a number of ways, each of which forms an embodiment of the present invention. For example, small molecules may be used to inhibit the interaction with the PRC2 complex at the lncRNA binding site to de-repress transcription. Alternatively, naked or liposome-encapsulated oligonucleotides (RNA or DNA) may target lncRNAs to form DNA/RNA-lncRNA duplexes that recruit RNase H. Further, viral particles containing lncRNA-targeting shRNAs may be used to deliver shRNAs that generate siRNAs (targeting the RISC complex to the lncRNA in the cell. In summary, the small molecule approach prevents the formation of a functional PRC2-lncRNA complex; the RNase H results in lncRNA cleavage and decay; and the RISC complex cleaves and degrades the lncRNA.

Accordingly, in some embodiments, the targeting oligonucleotide binds specifically with the target lncRNA and down-regulates the function of the lncRNA by blocking its interaction with downstream proteins.

The knockdown of target lncRNA in vitro is preferably achieved using siRNA. However, as these molecules can be unstable in vivo and sometimes non-penetrating of the cell, in may be preferable to use modified antisense oligonucleotides that are stable and nuclease resistant. They may be short oligonucleotides (between 12 and 30 or 15 and 25 nucleotides in length), single stranded oligonucleotides (e.g. DNA) which are complementary to the lncRNA of interest. Modified oligonucleotides of the invention targeting the lncRNA may contain a mixture of 2'-O-methyl RNA and Locked Nucleic Acid (LNA) and/or modifications at their 5' and 3' ends to protect against nuclease cleavage and phosphothioate backbone to enhance cellular uptake.

In some embodiments, RNA interference (RNAi) may be used to down-regulate expression of lncRNAs. In vivo, RNAi-based agents may require a delivery vehicle such as liposomes, nanoparticles or viruses to protect the siRNA or shRNA vectors from nuclease degradation, prevent non-site accumulation and to enhance cellular uptake.

Viral vectors have been used successfully in the art to deliver RNAi oligonucleotides to the cell of interest and achieve successful knockdown of lncRNA. In some embodiments, the viral vector is a lentiviral vector.

An alternative approach to down-regulating lncRNA in accordance with the invention is to use chromatin-modifying enzymes. These interact with the lncRNA and form complexes thereby inhibiting their function. Targeting lncRNAs at their site of interaction with chromatin modifying enzymes is a well-defined indirect approach to inhibiting the biological activity of the lncRNA and provides an alternative method to the direct approach of targeting the lncRNA alone.

In some embodiments, the therapeutic agent targets lncRNA-protein interactions or complexes as this increases the specificity of the agents and reduces off-target effects.

Where the agent is a targeting oligonucleotide (RNA or DNA), it is preferable that it has at least a region which is complementary to a region of the target lncRNA. The RNA sequence of lncRNA2 is provided in FIG. 39 and can also be obtained from the cDNA sequence shown in FIG. 15. More preferably, the targeting oligonucleotide is substantially complementary to a region on the target lncRNA. The targeting oligonucleotide preferably has at least 5, 7, 9, 10, 12, 14, 15, 17, 20, 25, 30, 40, 50, 60, 70, 80, 90 or 100 nucleotides complementary to a region on the target lncRNA.

The target oligonucleotides of the invention are preferably at least 10, 12, 14, 15, 17, 20, 25, 30, 40, 50, 60, 70, 80, 90 or 100 nucleotides in length. More preferably that are between 10 and 100 nucleotides, 10 and 70, 10 and 60, 20 and 40, 15 and 30, 10 and 30 or 12 and 25 nucleotides in length.

In accordance with this first aspect of the invention, multiple targeting oligonucleotides may be used. These may be different and target different regions of the target lncRNA, or they may be the same. The multiple targeting oligonucleotides may be separate or connected to each other via a cleavable linker (e.g. an endonuclease-sensitive linker).

As mentioned above, the targeting oligonucleotide may by RNA or DNA. The oligonucleotide may be modified by methods known to the skilled person to increase activity and/or increase stability. For example the targeting oligonucleotide may be modified to resist nuclease digestion. Specific examples of modified oligonucleotides include those which comprise modified backbones e.g. phosphorothioates, phosphotriesters, methyl phosphonates, short chain alkyl or cycloalkyl intersugar linkages.

The targeting oligonucleotide may be conjugated to a label, e.g. cholesterol, biotin moiety, Vitamin A, folate, sigma receptor ligands, aptamers, peptides such as CPP, or hydrophobic molecules such as lipids. In some embodiments, the targeting oligonucleotide is chemically linked to one or more moieties or conjugates that enhance the oligonucleotide's activity, cellular distribution or cellular uptake. Such moieties may include lipids, e.g. cholesterol, or a phospholipid.

In some embodiments, the targeting oligonucleotide is a double stranded siRNA molecule comprising or consisting of the following sequence

```
The sense strand sequence is SEQ ID NO: 1:
rCrCrArUrArArUrUrUrArCrArUrGrGrArUrGrUrU The antisense strand is:
                                      SEQ ID NO: 2
rUrUrCrCrArArArCrArUrCrCrArUrGrUrArArArUrUrArUrGr
GrArA.
``` wherein the target lncRNA is lncRNA2.

The invention also provides an agent as described above for use in a method of treating a vascular condition in a subject.

In a second aspect of the invention, there is provided a pharmaceutical composition comprising an agent capable of modulating lncRNA selected from the group consisting of lncRNA2, lncRNA4, lncRNA5, lncRNA6, lncRNA7 and lncRNA8. Preferably the lncRNA is selected from lncRNA2 and lncRNA7 and the agent is capable of down-regulating said lncRNA in SMC. More preferably the lncRNA is lncRNA2.

Preferably, the agent is capable of modulating the function and/or effect degradation of the target lncRNA in a SMC.

More preferably, the pharmaceutical composition comprises a therapeutic agent as described above; preferably a targeting oligonucleotide as described above in respect of the first aspect of the invention.

In some embodiments, the agent is an siRNA molecule comprising or consisting of the following sequence

```
The sense strand sequence is SEQ ID NO: 1:
rCrCrArUrArArUrUrUrArCrArUrGrGrArUrGrUrU The antisense strand is:
                                      SEQ ID NO: 2
rUrUrCrCrArArArCrArUrCrCrArUrGrUrArArArUrUrArUrGr
GrArA.
```

The pharmaceutical composition of the invention may be in solid or liquid form, such as tablets, capsules, powders, syrups, aerosols, solutions, formulations, suspensions or emulsions. Formulation for oral administration may be in solid form or aqueous solution or suspension. The aqueous solution or suspension may be made up from powder or granular forms. The therapeutic agents of the invention may be mixed with adjuvants well known in the art such as water, polyethylene glycol, propylene glycol, ethanol, various oils and/or various buffers.

In some embodiments, the therapeutic agents are mixed with carriers which will prevent the agent from rapid elimination or degradation in vivo. Such carriers include controlled release formulations including various biocompatible polymers.

The pharmaceutical composition of the invention is formulated depending on its route of administration, e.g. parenteral (intravenous, intradermal, subcutaneous, oral (inhalation), transdermal, transmucosal and rectal administration). The composition therefore may be prepared by admixing one or more of the following components: a diluent (e.g water), saline solutions, fixed oils, polyethylene glycols, synthetic solvents, chelating agents, and buffers. Other ingredients may be included to alter pH (such as acids or bases) or for the adjustment or tonicity (such as salts or sugars).

Pharmaceutical compositions of the invention may be prepared in a dosage unit form for ease of administration and uniformity of dose. Each unit preferably contains a predetermined quantity of the therapeutic agent calculated to produce the desired therapeutic effect in combination with a suitable carrier and optionally a delivery system.

The invention further provides a method of preparing a pharmaceutical composition as described above comprising the step of admixing the therapeutic agent with a pharmaceutical carrier.

In a third aspect of the invention there is provided a method of screening for therapeutic agents useful in the treatment of vascular conditions (such as those described above) in a subject. The screening method may comprise the steps of contacting a lncRNA selected from the group lncRNA2, lncRNA4, lncRNA5, lncRNA6, lncRNA7 and lncRNA8 (preferably the lncRNA is selected from lncRNA2 and lncRNA7; more preferably the lncRNA is lncRNA2) with a test compound and determining whether the biological activity of the lncRNA is altered in the presence of said compound as compared to its biological activity in the absence of said compound. The biological activity of the lncRNA may be its expression, i.e. the test compound may result in less or more lncRNA being present in the cell, or the biological activity may be a change in the downstream pathway, e.g. the test compound may prevent or reduce binding of the lncRNA to its binding target and as a result the downstream signalling pathway is altered. For example, the inventors have found that inhibition of MEKK1 and/or p38 lead to a decrease in lncRNA2 in SMCs.

It is further believed that the actual location of the lncRNA within the cell may influence its biological function. For example the lncRNA may be nuclear or cytoplasmic, or even secreted. Accordingly, it may be possible to alter the function of the lncRNA by changing the way it is localised in the cell. This would be particularly important if the lncRNA had more than one function where each function is associated with the lncRNA location. Wth this in mind, the screen may be used to determine compound which alter the cellular location of the lncRNA. The determination of a change in cellular location can be carried out using standard techniques known to the skilled person, for example using labelled targets.

The test compound is preferably determined to up-regulate (increase) or down-regulate (inhibit) the lncRNA. By way of example, if the lncRNA is lncRNA 2 or 7, it is preferably that the test compound down regulates, i.e. inhibits the lncRNA activity in the cell. In some embodiments the cell is a SMC.

Accordingly, the screening method may comprise determining alterations in downstream events in the lncRNA signalling pathway. Alternatively, the screening method may comprises determining alterations upstream in the lncRNA pathway, e.g. an alteration in events which leads to reduced expression of the lncRNA. For example, the test compound may modulate the MEKK1 and p38 cellular pathways.

Preferably the screening method is carried out in vivo and the test compound is contacted with a cell such as an SMC or HSVSMC.

In some embodiments the test compound and/or lncRNA is coupled to a detectable label. The method may further use a known compound or ligand of lncRNA (or a ligand of a known component of the lncRNA signalling pathway) where alteration in the biological activity of the lncRNA is determined by displacement of the ligand to the lncRNA (or component) in the presence of the test compound.

Screening methods are well known in the art. Assays may be designed where the lncRNA or the text compound is fixed to a solid support.

The test compound may be a small molecule, preferably selected from polypeptide, peptide, nucleic acid molecule or other small molecule such as organic or inorganic compounds, salts, esters and other pharmaceutically acceptable forms thereof.

The method of the third aspect may further comprise selecting the test compound, determining its structure and providing said compound for use in treating a vascular condition in a subject. The method may further comprise optimising the structure of the selected compound for use as a pharmaceutical and/or testing the compound for optimal pharmaceutical activity.

A test compound identified by the screening method of the invention may be formulated into a pharmaceutical composition for use in the treatment of a vascular condition in a subject.

The data presented herein demonstrate for the first time that lncRNA2 (also known as SMILR herein) is found located in the conditioned media from stimulated HSVSMC (see FIG. 19D and the corresponding description thereof below), suggesting that it is actively secreted or released from the cells, in response to particular stimuli. Furthermore, data are provided demonstrating that SMILR (lncRNA2) expression is dysregulated in unstable human carotid (atherosclerotic) plaques (see FIG. 21 and the corresponding description thereof below). Notably, a 3.9±2.3 fold increase in SMILR (lncRNA2) expression was observed in high-risk plaques compared to adjacent stable regions of the carotid artery. Intriguingly, the inventors also observed an increase in HAS2 but not HAS2-AS1.

Accordingly, in a further general aspect, the invention provides the use of lncRNA2 as a biomarker for a vascular condition, and/or use of lncRNA2 as a biomarker for susceptibility to a vascular condition. The vascular condition may be any of the vascular diseases or conditions discussed herein in the context of other aspects of the invention.

In one embodiment, lncRNA2 is used as a biomarker for atherosclerosis (e.g. unstable atherosclerotic plaques). As used herein, unstable atherosclerotic plaques are atherosclerotic plaques that are at risk of rupture, a clinical event leading to myocardial infarction.

In one embodiment, lncRNA2 is used as a biomarker for a vascular condition (and/or susceptibility to a vascular condition) in conjunction with HAS2.

In one embodiment, lncRNA2 has the RNA sequence shown in FIG. 39.

Although the description explains the biomarker aspects of the invention in the context of lncRNA2, the invention is also directed to the use of lncRNA7 as a biomarker for a vascular condition, and/or use of lncRNA7 as a biomarker for susceptibility to a vascular condition. Accordingly, any of the aspects described in the context of the use of lncRNA2 as a biomarker may (and/or methods of diagnosis or identifying susceptibility to a vascular condition) equally be applied to lncRNA7.

In a further general aspect, the invention provides a method of diagnosing or identifying susceptibility to a vascular condition in a patient comprising:

(i) determining the level of lncRNA2 in a sample isolated from the patient; and (ii) comparing the level of lncRNA2 in the patient sample with the level of lncRNA2 in a control sample or with a predetermined reference level of lncRNA2, wherein an increased level of lncRNA2 in the patient sample compared to the control sample or compared to the predetermined reference level identifies the patient as having or being susceptible to having a vascular condition. The vascular condition may be any of the vascular/inflammatory diseases or conditions discussed herein in the context of other aspects of the invention.

In one embodiment, the vascular condition is atherosclerosis. By way of example, the method may be used to diagnose or identify patients that have or are at risk of having with unstable atherosclerotic plaques (e.g. the method identifies atherosclerotic plaques (and/or patients) that are unstable and/or are at risk of plaque rupture).

In one embodiment, lncRNA2 has the RNA sequence shown in FIG. 39.

In one embodiment, the predetermined reference level is the average level of lncRNA2 in a control patient. Alternatively, the predetermined reference level may be the average level of lncRNA2 in a control sample derived from the same (test) patient.

As used herein, the term "biological sample" and "sample isolated from a patient" are used interchangeably to refer to tissues, cells and biological fluids isolated from a patient, as well as tissues, cells and fluids present within a patient. The sample may be any suitable sample such as a blood sample, a serum sample, a plasma sample, a sputum sample, a faecal sample, a biopsy of body tissues, for example a biopsy of vascular tissue. A preferred sample is plasma.

As used herein "patient" refers to an individual, e.g., a human, having or at risk of having (i.e. susceptible to) a vascular condition. The terms "patient" and "test patient" are used interchangeably herein.

The level of lncRNA2 can be measured in a number of ways, including: measuring the amount of the RNA molecule present in a sample (e.g. lncRNA2 expression levels); or measuring the activity of lncRNA2 in the sample.

Any known RNA detection methods may be used to detect the level of lncRNA2 in a sample. For example, the level of lncRNA2 in a sample can be determined both by in situ and by in vitro formats. lncRNA2 RNA may be detected using Southern or Northern blot analysis, polymerase chain reaction or probe arrays. In one embodiment a sample may be contacted with a nucleic acid molecule (i.e. a probe, such as a labeled probe) that can hybridize to the lncRNA2 RNA. Such techniques are well known in the art.

Alternatively, the level of lncRNA2 RNA in a sample may be evaluated with nucleic acid amplification, for example by rtPCR, ligase chain reaction, self sustained sequence replication, transcriptional amplification or any other nucleic acid amplification method, followed by the detection of the amplified molecules using techniques known in the art.

The level of lncRNA2 in a sample may also be determined by determining the level of SMILR activity in a sample. By way of example, SMILR activity may be assessed by measuring its effect on HAS2.

Methods of the invention further comprise comparing the level or expression of lncRNA2 in the patient sample with the level or expression of lncRNA2 in a control sample or with a predetermined reference level for lncRNA2.

In one embodiment, methods of the invention include contacting a control sample with a compound or agent capable of detecting lncRNA2 and comparing the level of the lncRNA2 in the control sample with the level of lncRNA2 in the patient sample.

As used herein "reference level" or "control", refers to a sample having a normal level of lncRNA2 expression, for example a sample from a healthy subject not having or suspected of having a vascular condition or alternatively a sample from the same subject that the biological test sample is obtained from, for example a sample obtained from an equivalent (vascular) area that is devoid of vascular disease. Alternatively, the reference level may be comprised of an lncRNA2 expression level from a reference database, which may be used to generate a pre-determined cut off value, i.e. a diagnostic score that is statistically predictive of a symptom or disease or lack thereof or may be a pre-determined reference level based on a standard population sample, or alternatively, a pre-determined reference level based on a subject's base line level of expression, i.e. from an equivalent (vascular) area that is devoid of vascular disease.

Alternatively, predictions may be based on the normalized expression level of lncRNA2. Expression levels are normalized by correcting the absolute expression level of lncRNA2 in a sample by comparing its expression to the expression of a reference nucleic acid that is not a marker, e.g., an mRNA, such as an mRNA that is constitutively expressed. This normalization allows the comparison of the expression level in one sample to another sample, or between samples from different sources. This normalized expression can then optionally be compared to a reference level or control.

In one embodiment the diagnostic or predictive methods involve determining the level of lncRNA2 in a sample and determining the level of at least one further biomarker, for example HAS2 in a biological test sample. Preferably, the level of the at least one further biomarker is determined using any one of the above mentioned methods. The level of at least one further biomarker may be determined in the same biological sample or a different biological sample to the level of lncRNA2.

The inventors have also surprisingly found that lncRNA2 levels are increased in plasma from patients with high plasma C-reactive protein (CRP) (patients with varying levels of metabolic dysfunction). Accordingly, in one aspect, the invention provides lncRNA2 as a biomarker for vascular inflammatory conditions, such as those described elsewhere herein (for example atherosclerosis). Of note, there are a number of vascular conditions with an inflammatory angle (such as bypass grafts, in stent restenosis, hypertension), all of which are well known in the art (and encompassed by the invention)

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

Aspects and embodiments of the present invention will now be illustrated, by way of example, with reference to the accompanying figures. Further aspects and embodiments will be apparent to the person skilled in the art. All documents mentioned in this text are incorporated herein by reference.

FIGURES

FIG. 1. Pathological process of vein graft failure.

FIG. 2—RNA-seq quality control. Proliferation and NFKB synergistic effect were confirmed via A: BrdU (thymidine analgoue) incorporation (Graph shows variation of quadruplicate results, mean±SEM, n=4. *P<0.001 or P<0.01 vs. 0.2% control).and B: analysis of the inflammation-associated miRNA miR146α (Representative graph showing variation of triplicate results normalised to UBC n=3 repeated independently. Significance compared to 0.2% control) C: RIN integrity assessed by agilent was >8 in all RNA-seq samples.

Figure 3:
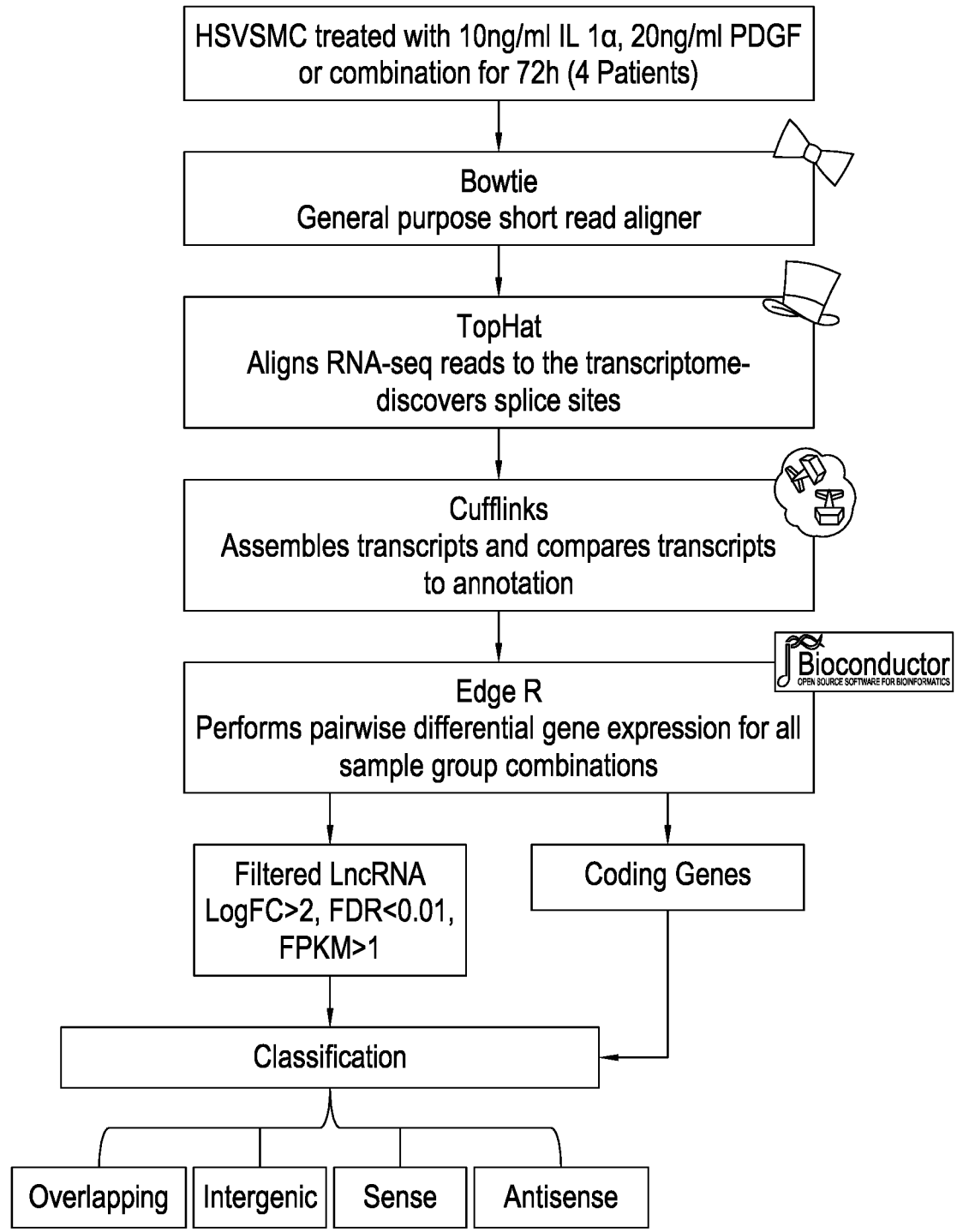
Figure 4A:
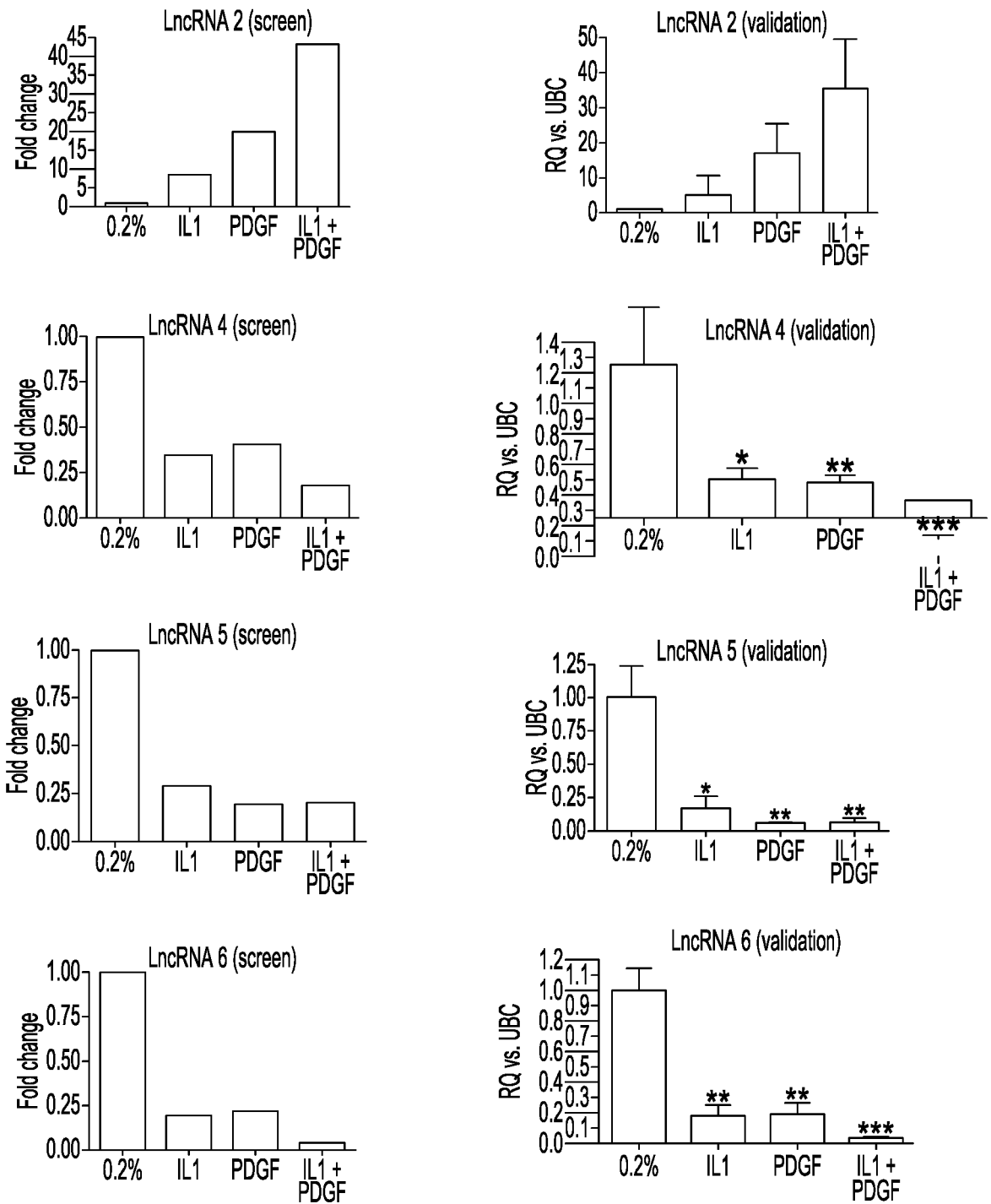
Figure 4A:
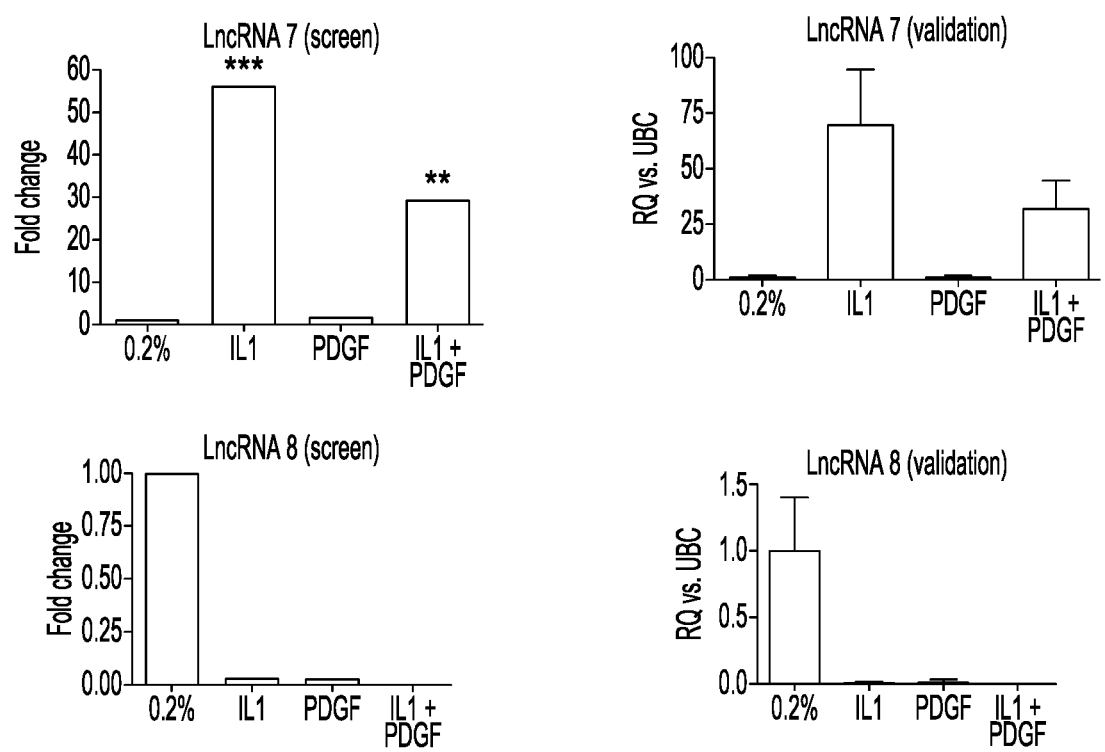
Figure 4B:
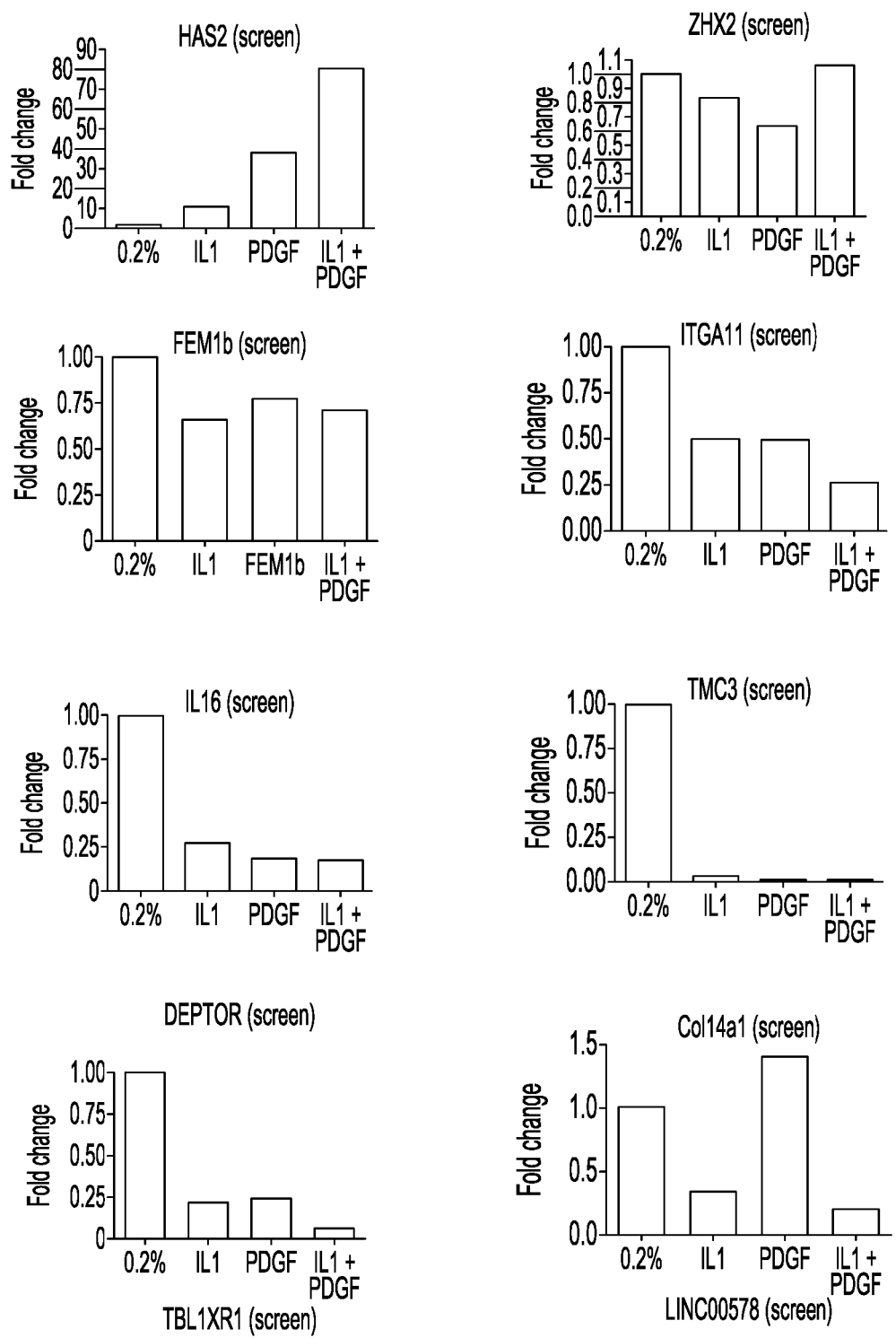
Figure 4B:
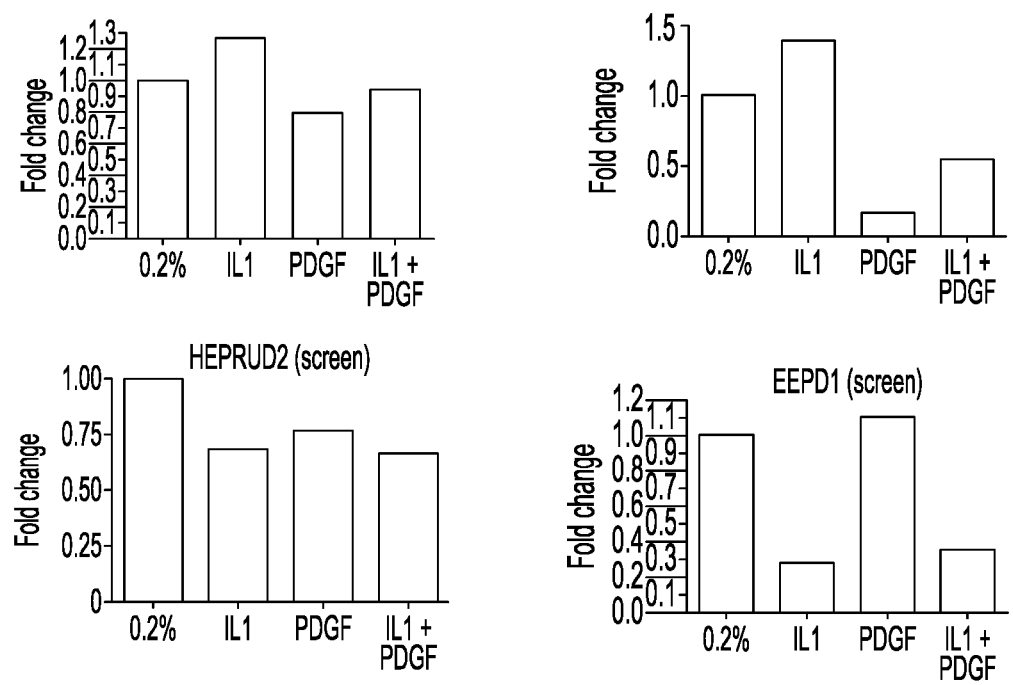

FIG. 3. Work-flow overview of lncRNA-seq screen.

FIG. 4—Validation of LncRNA expression. A: Expression of LncRNA after 72 h from screen (left) and subsequent validation via SYBR green qRT-PCR (right) n=4, * P<0.05,  P<0.01, * P<0.001 vs. 0.2% media (1 way anova, Tukeys post hoc). B: Expression of nearest protein coding genes (from screen).

FIG. 5: Analysis of vascular cell specific patterns. A: LncRNA expression was assessed in a select tissue panel via quantitive real time PCR. Data shows 1/ΔCT normalised to UBC. B: LncRNA 2 and 7 showed up-regulation in HSVSMC when treated with IL1α/PDGF for 48 h. Treatment for 48 h of HSV endothelial cells (HSVEC) showed significant up-regulation of LncRNA 7 with treatment but no effect on LncRNA 2.

Figure 6:
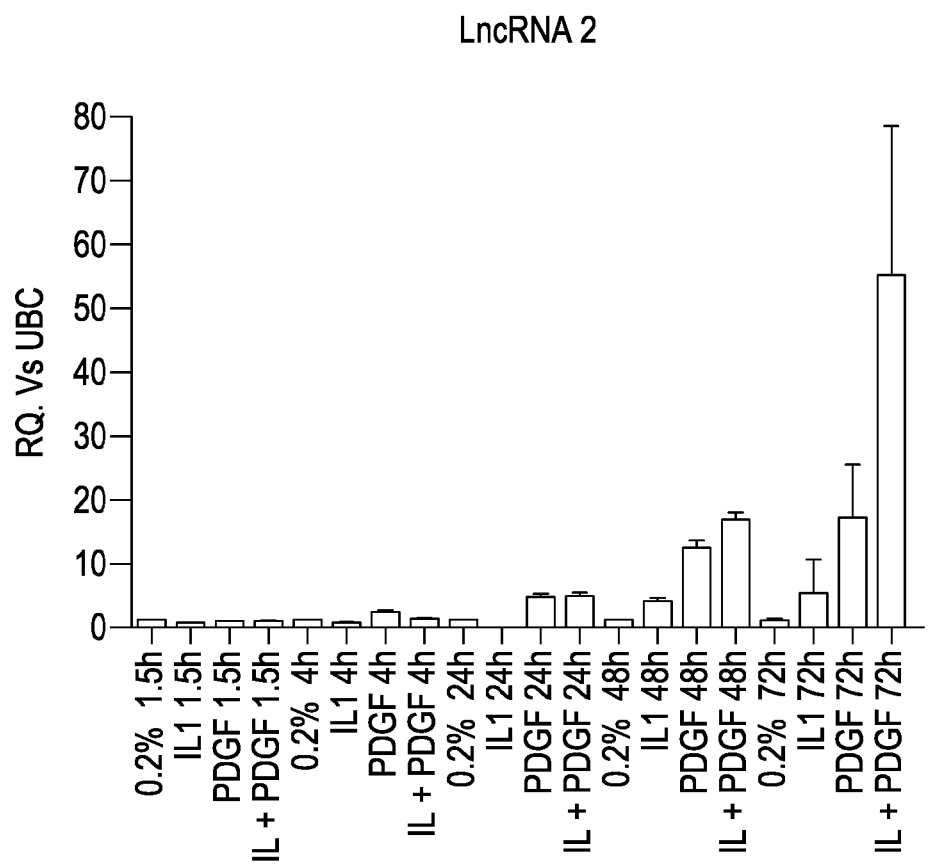

FIG. 6: Treatment with IL1α and PDGF significantly altered lncRNA 2 expression profiles at 4, 24, 48 and 72 h. HSVSMC were treated with 0.2% media or media containing 10 ng/ml IL1α, 20 ng/ml PDGF or a combination of both stimulants at varying time points. Samples were analysed for lncRNA expression via real time analysis. Representative graph showing variation of triplicate results normalised to UBC.

Figure 7:
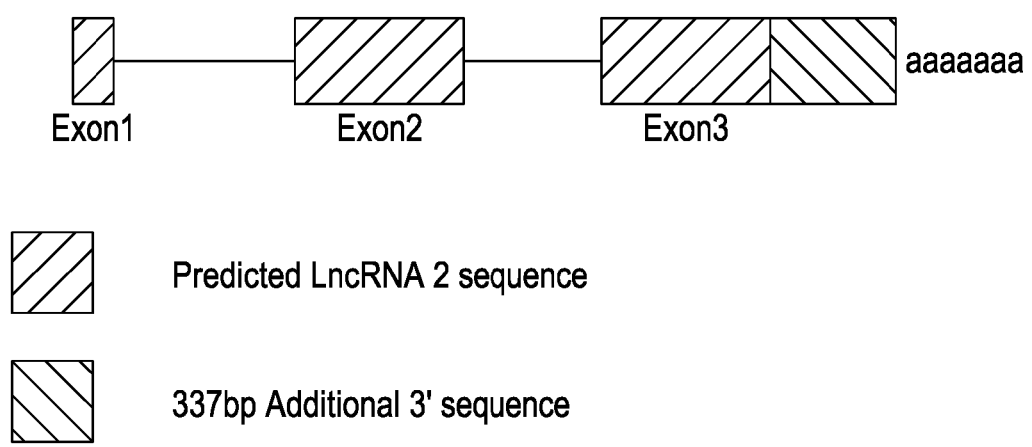

FIG. 7: Identification of additional 337 bp sequence at the 3' end of LncRNA 2 via 5', 3' RACE.

Figure 8:
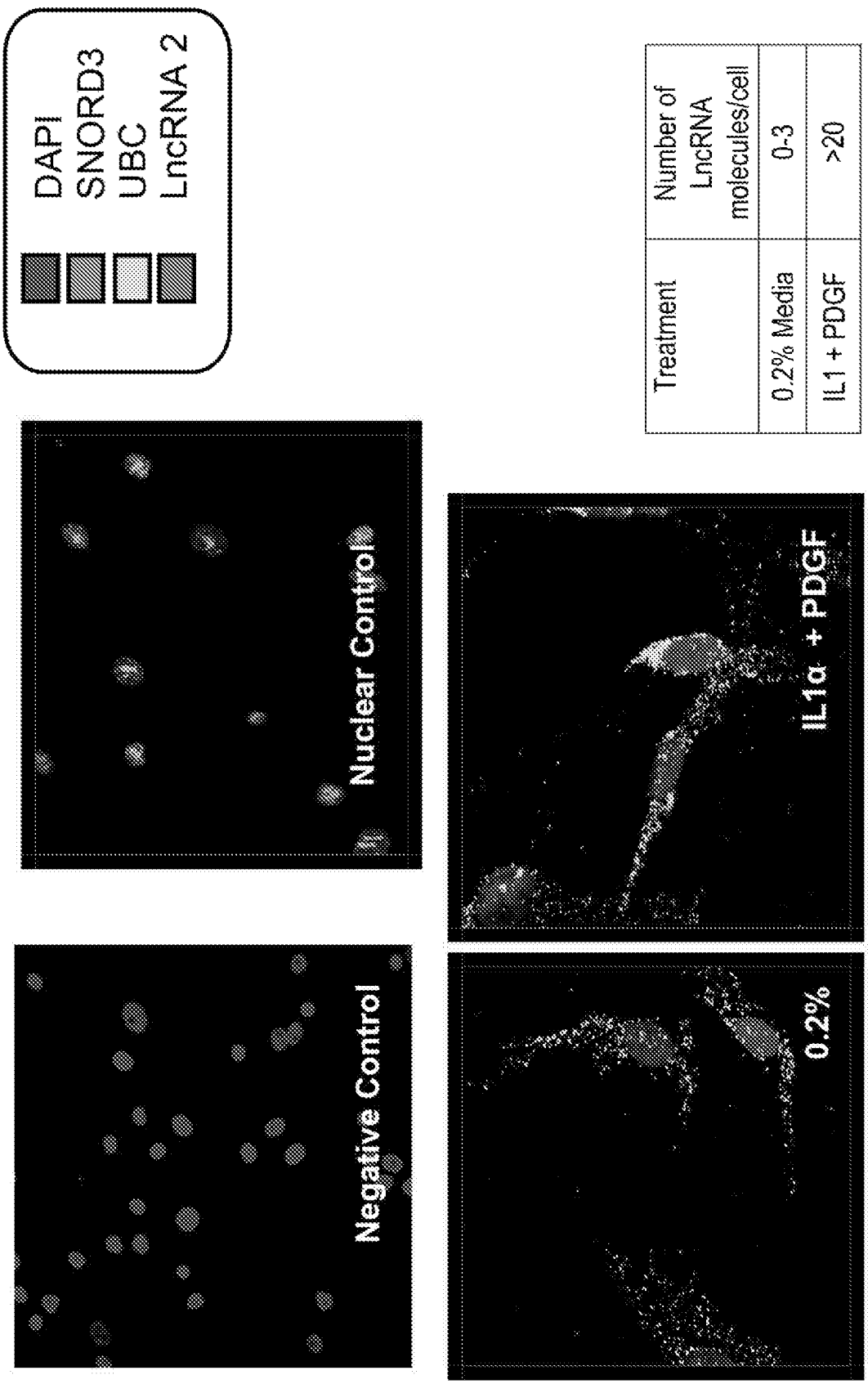

FIG. 8: RNA FISH to determine localisation of LncRNAs 2. LncRNAs 2 showed specific expression within the nucleus and cytoplasm of HSVSMC. UBC used as marker of cell border. SNORD3 used as a marker of nuclear permeabilization.

Figure 9:
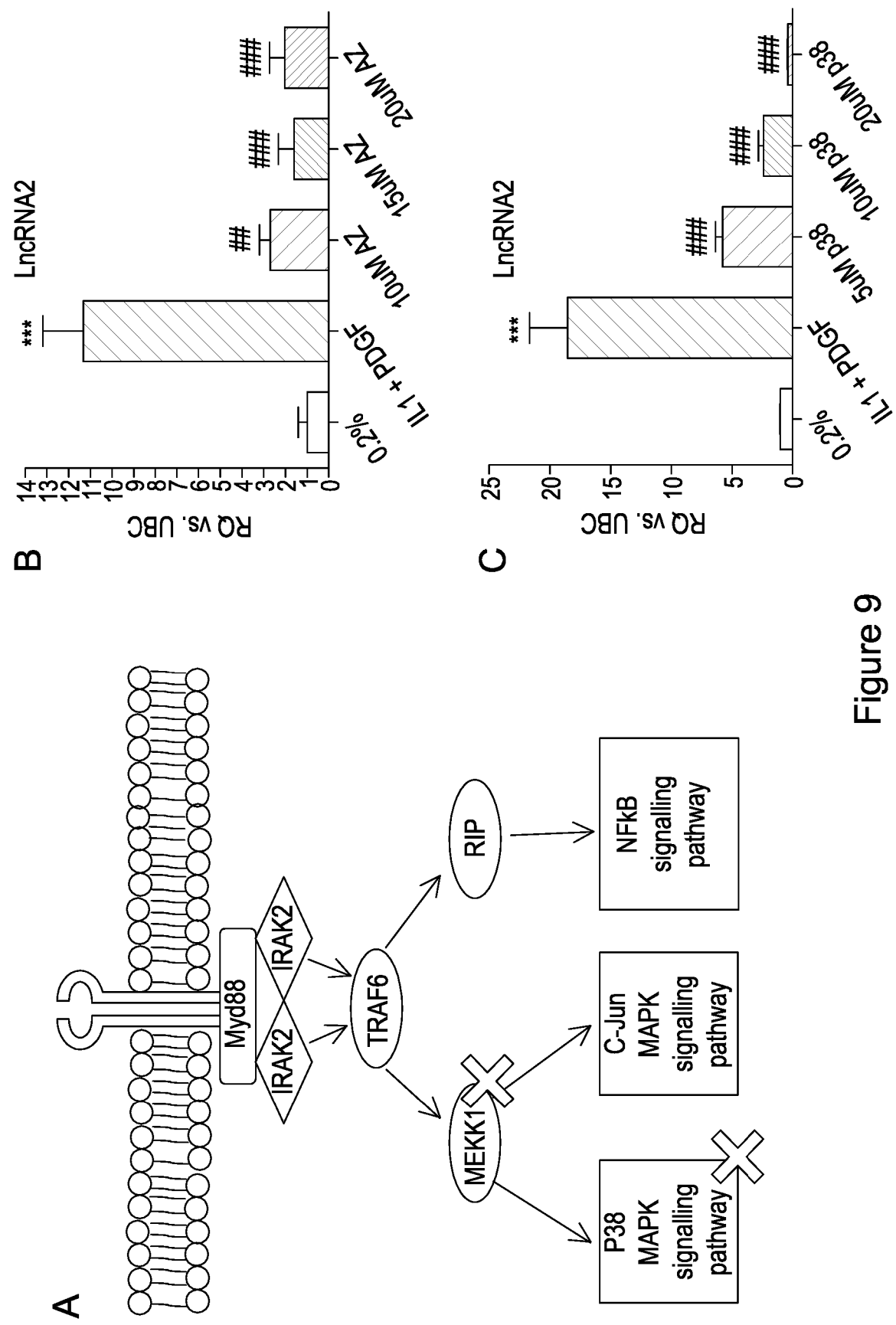

FIG. 9: Effect of inhibitors of MEKK1 and p38 upon IL-1 and PDGF induced LncRNA 2 expression. A: Schematic diagram showing specific sites of inhibition. HSVSMC were pre-treated for 60 minutes with the indicated concentration of the MEKK1 inhibitor AZD6244 or the p38 inhibitor SB203580. Following exposure to 0.2% FCS or 10 ng/ml IL1α/20 nM PDGF for 48 h, expression of LncRNA 2 was determined by qRT-PCR. B: LncRNA 2 expression following MEKK1 inhibition. C: LncRNA 2 following p38 inhibition.

Figure 10:
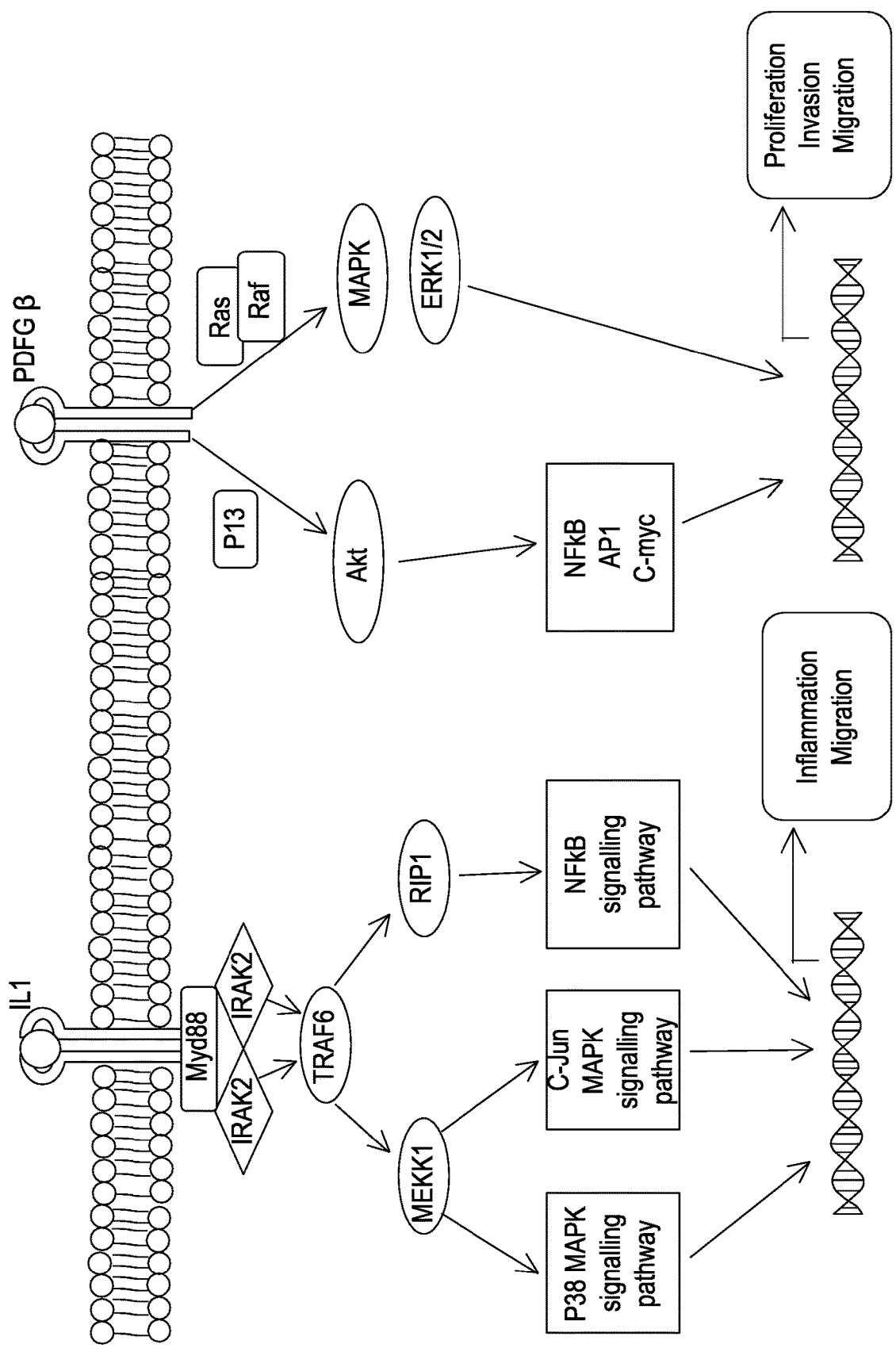

FIG. 10. PDGF and IL1a signalling pathways

FIG. 11. SiRNA mediated knock down of lncRNA inhibits SMC proliferation.

Figure 12:
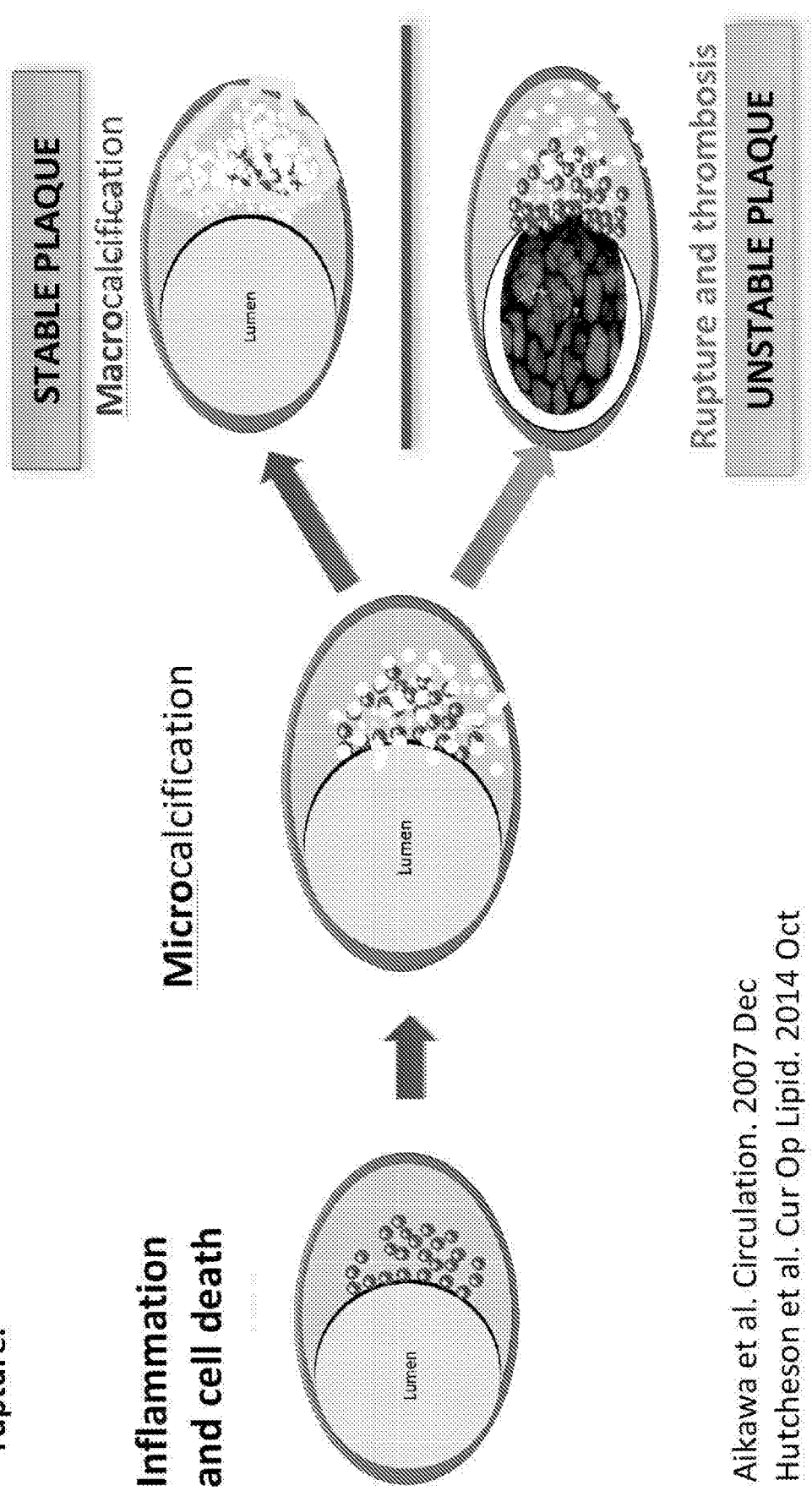

FIG. 12. LncRNA2 patterns correlate with areas of high fluoride uptake imaging in carotid arteries.

FIG. 13. Non-coding RNA patterns correlate with areas of high fluoride uptake imaging in carotid arteries. 40 patients with recent acute myocardial infarction imaged with 18F-Fluoride PET/CT. Focal uptake was visible at the site of the angiographic culprit in 37 patients.

Figure 14:
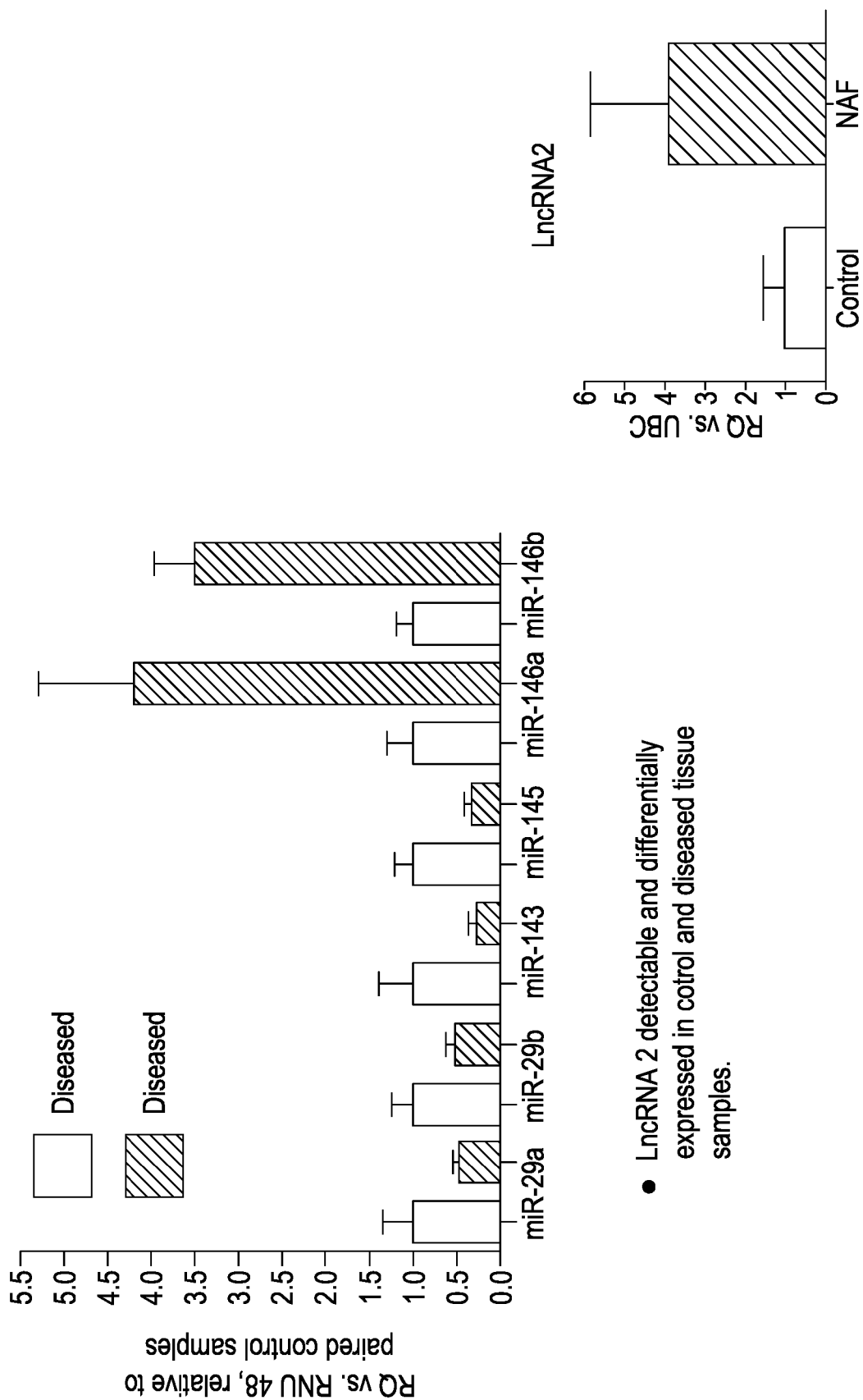

FIG. 14. LncRNA 2 correlates with areas of high FDG uptake imaging. LncRNA2 detectable and differentially expressed in control and disease tissue samples.

FIG. 15. cDNA sequences for lncRNA2, lncRNA4, lncRNA5, lncRNA6, lncRNA7, and lncRNA8. cDNA sequences for lncRNA 4-8 were obtained from Ensembl. cDNA for lncRNA2 was obtained from Ensembl and additional sequence derived from 5', 3' RACE.

Figure 16:
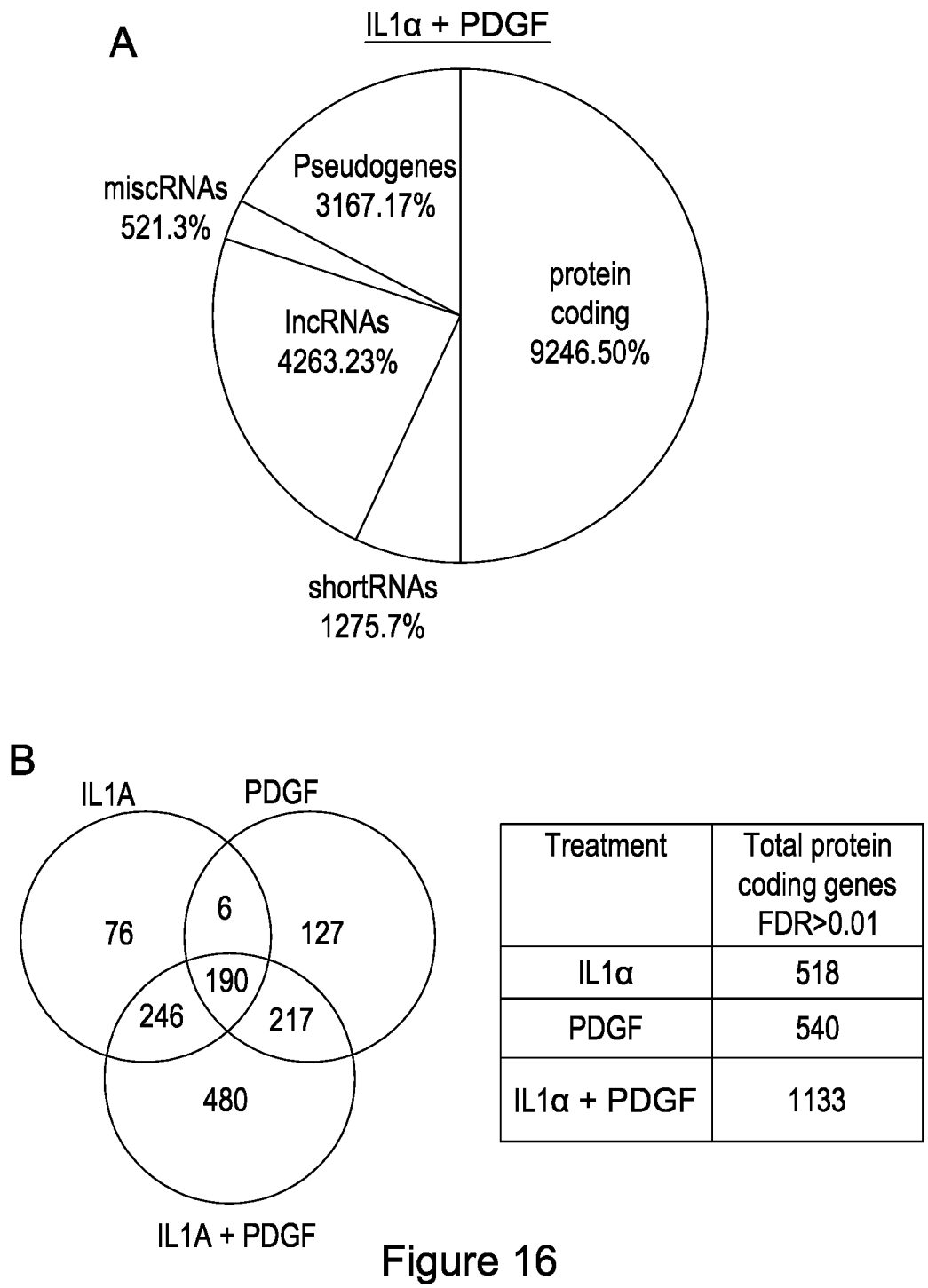

FIG. 16. (A): Biotype distribution of all transcripts identified by RNA-seq analysis generated from HSVSM cells treated with IL1α and PDGF, cutoff at FPKM>0.1 (B): Venn diagram indicating overlap of protein coding genes with altered expression (analysed using EdgeR, FDR<0.01) across each treatment.

Figure 17A:
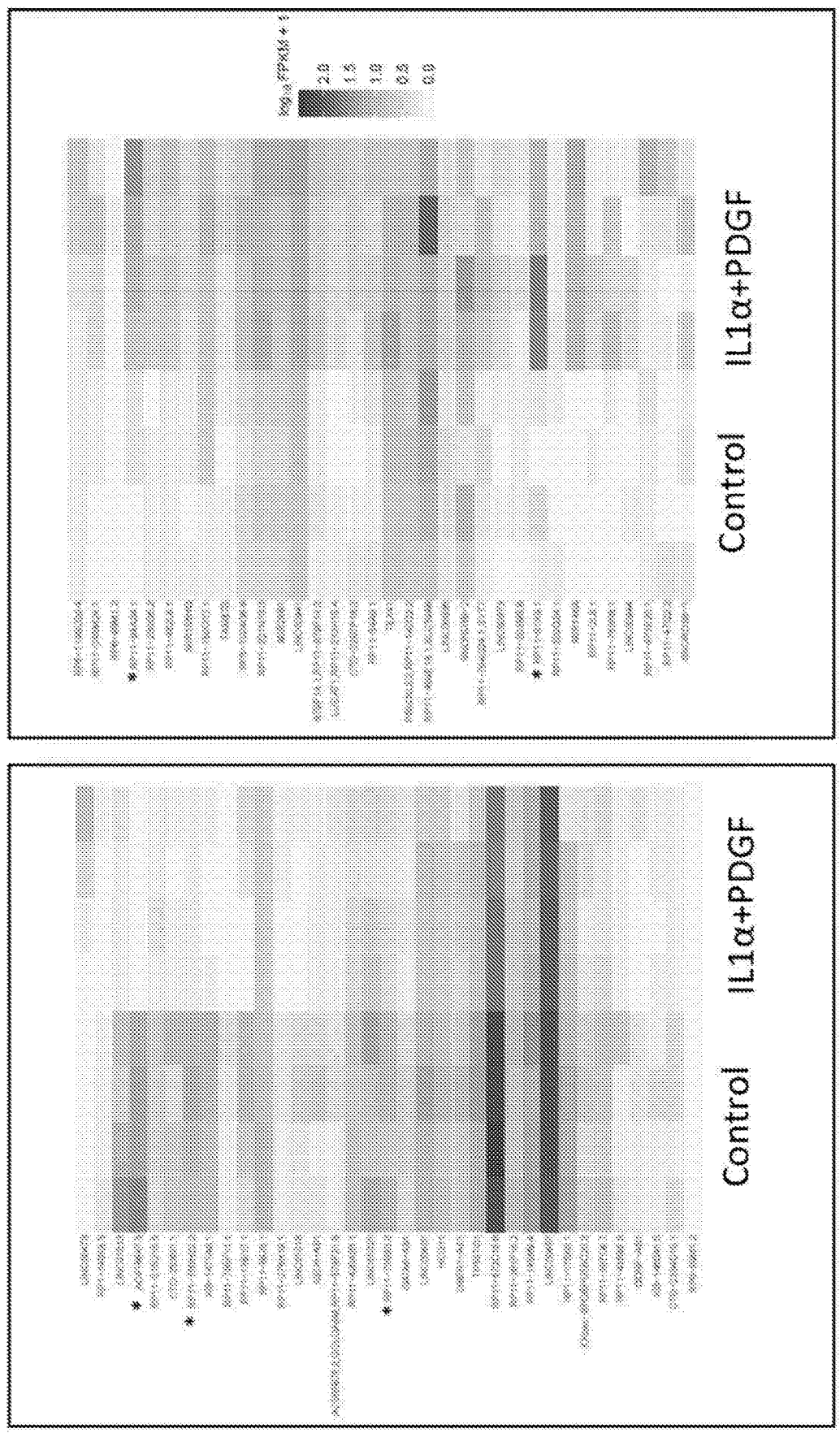

FIG. 17. Identification of differentially expressed LncRNAs in HSVSMC treated with IL1a and PDGF. (A): Heatmaps showing order of differentially expressed transcripts within the 4 patient samples before and after IL1α/PDGF treatment. LncRNA selected for validation marked by * (B): Heatmap representing the fold change of the 5 lncRNAs selected for validation. Heatmaps represent data from RNA-seq pipeline.

FIG. 18. Localisation of SMILER. (A): RNA FISH analysis of SMILR, cytoplasmic UBC mRNA and nuclear SNORD3 RNA in HSVSMC, Magnification ×630 for all panels. UBC and SNORD3 used for confirmation of cellular compartments (B): Quantification of LncRNA molecules per cell in indicated conditions. Greater than 5 images were selected at random from each condition and at least 5 cells counted in each image.

Figure 19:
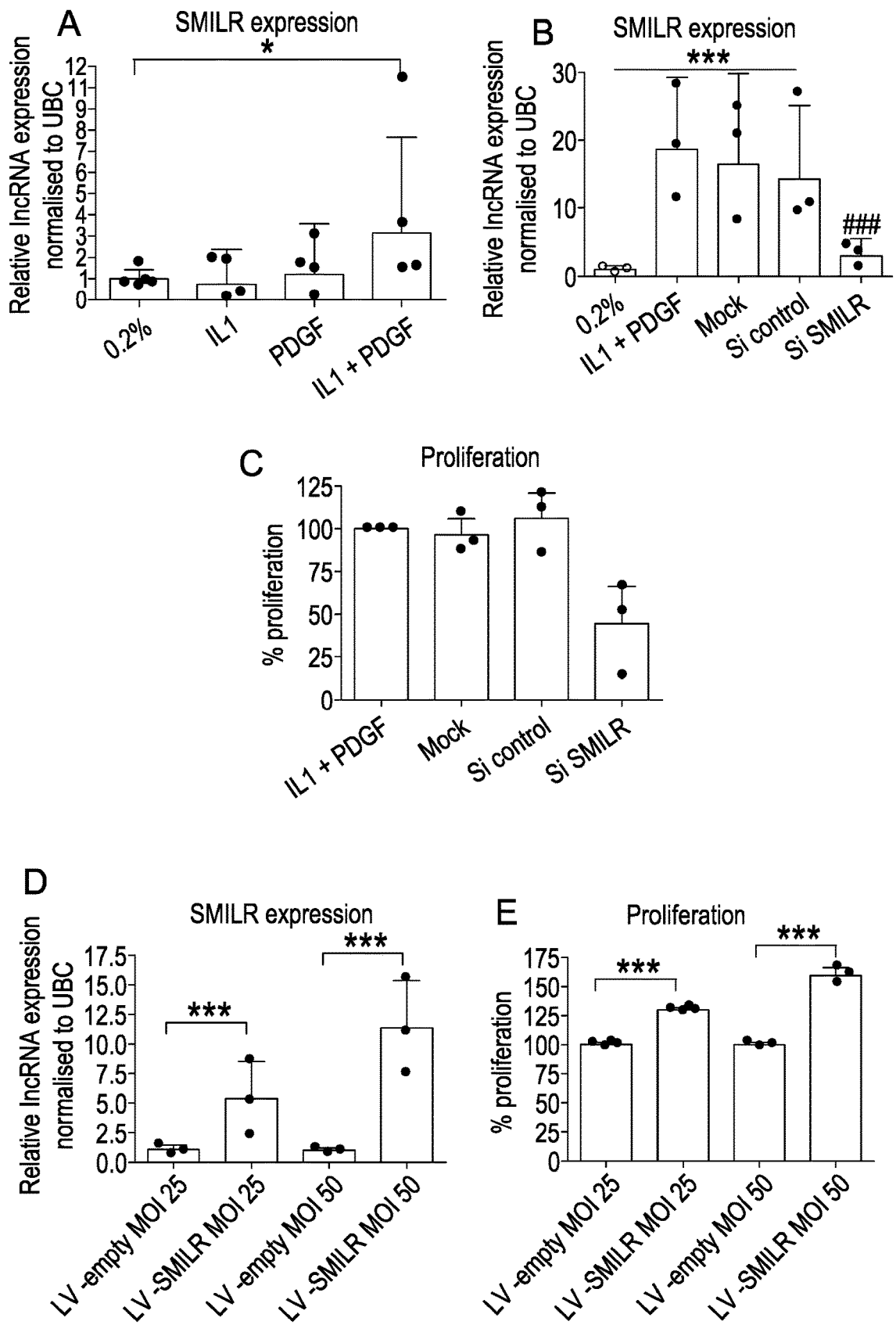

FIG. 19. Functional regulation of SMILR. (A): SMILR expression in conditioned media from HSVSMC cultured in 0.2%, IL1 or PDGF conditions. Unpaired t test * P<0.05 vs. 0.2% (n=4). (B): Confirmation of the effect of siRNA targeting SMILR in HSVSMC using qRT-PCR, representative image of technical triplicates (n=3) (C): IL1/PDGF induced proliferation classed as 100% for analysis across patient samples, knockdown of SMILR inhibits EdU incorporation in HSVSMC (n=3) 1 way ANOVA vs Si Control. (D): qRT-PCR analysis of SMILR expression following infection with either an empty lentivirus (LV-E) or lentivirus containing SMILR sequence (LV-S) at an MOI of 25 (n=3) and MOI 50 (n=3) ***P<0.001 vs. relevant empty control assessed via multiple comparison ANOVA.

Figure 20:
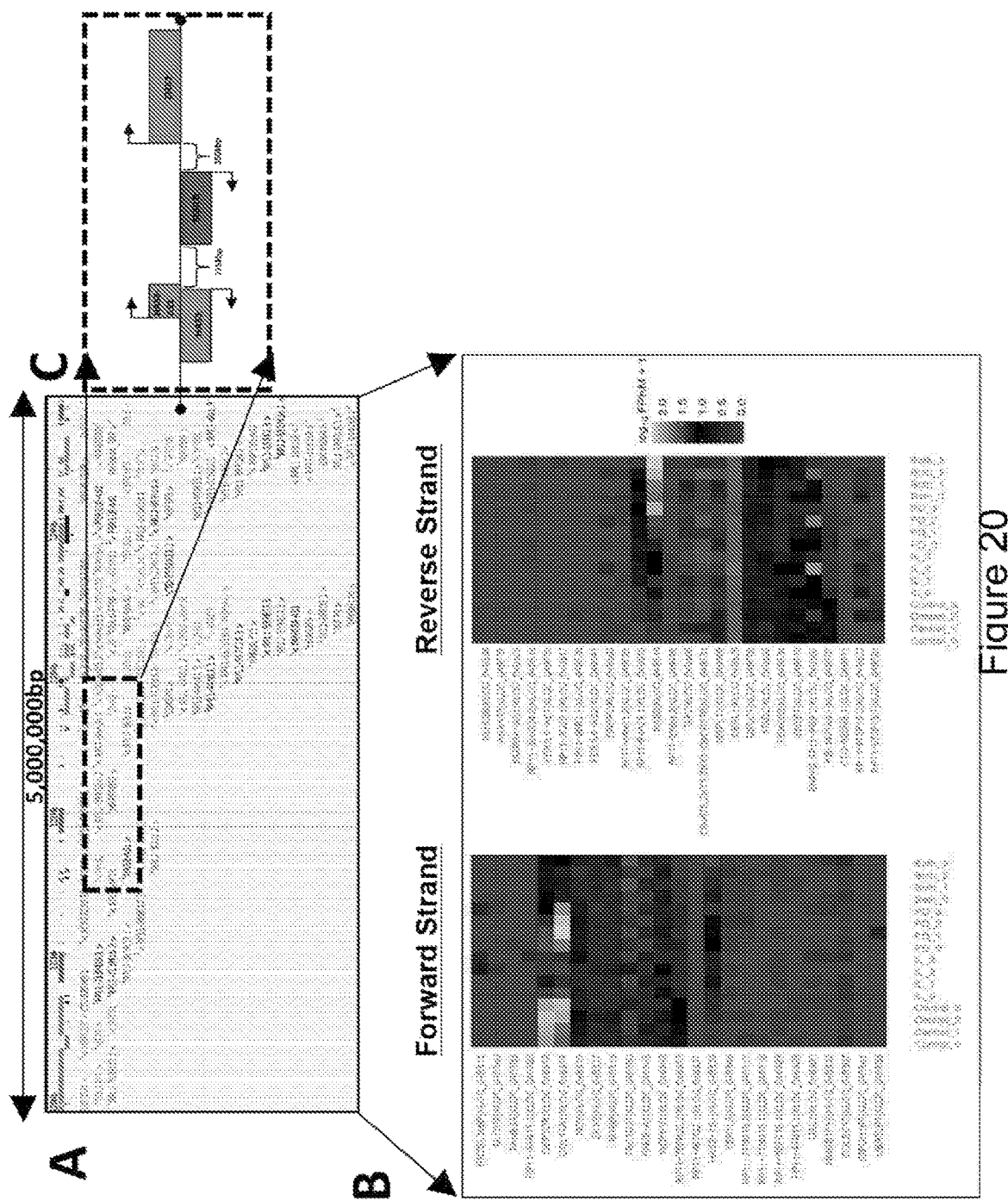
Figure 20:
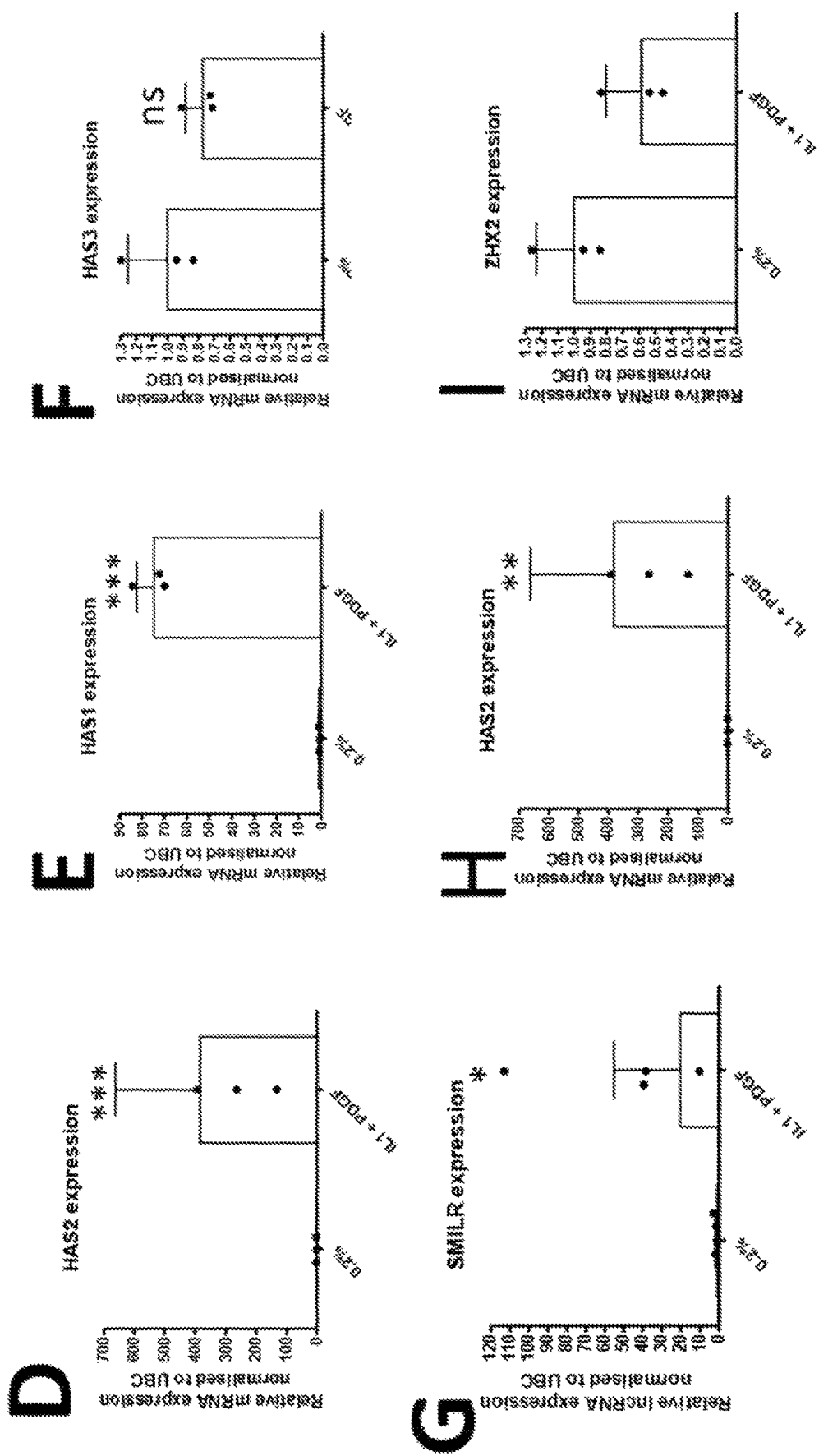
Figure 20:
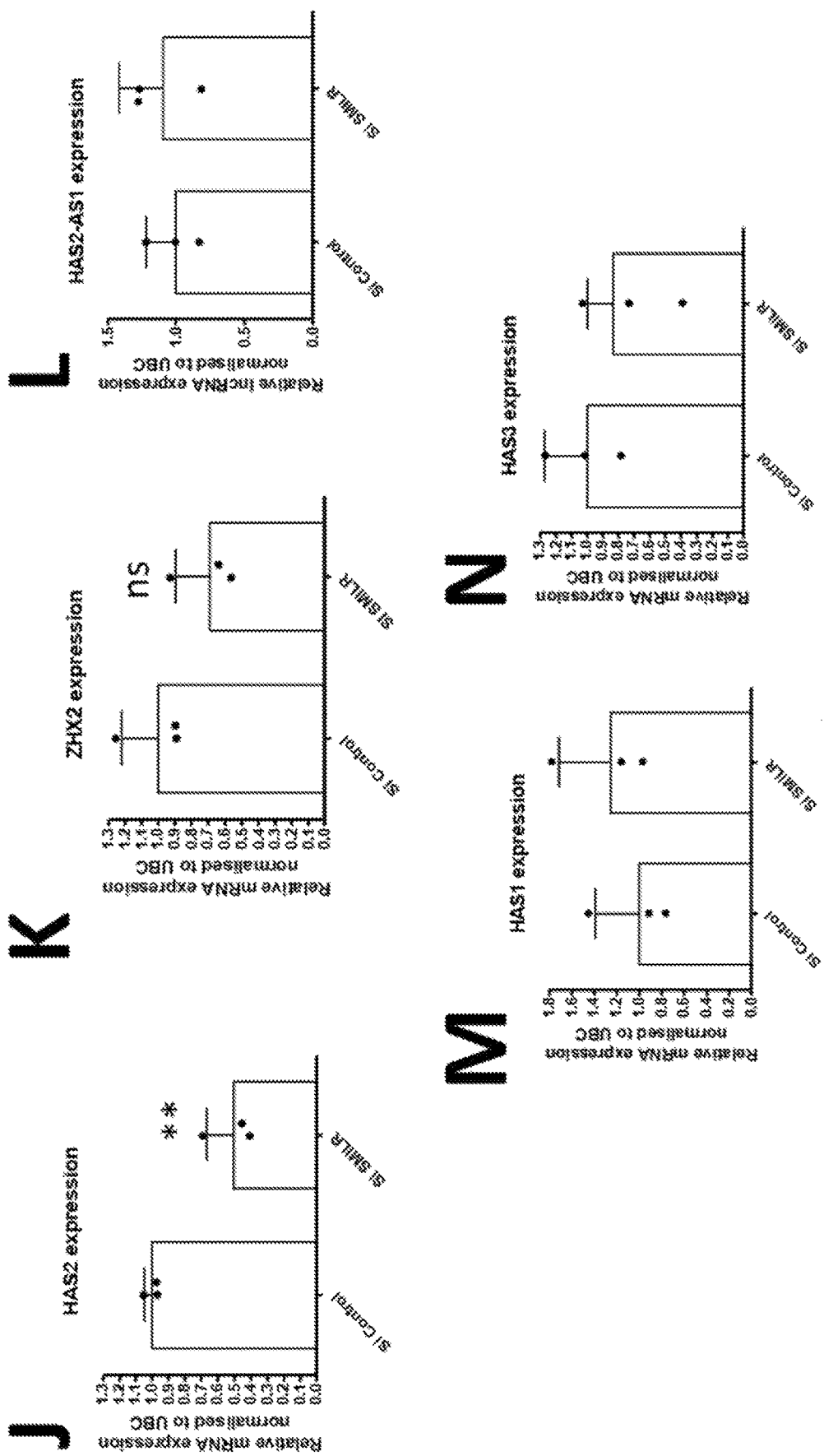

FIG. 20. SMILR regulates proximal gene HAS2 in chromosome 8. (A): Schematic view of the 8q24.1 region showing lncRNAs and protein coding genes over the 5,000,000 bp region from Ensemble. (B): Regulation of protein coding and non-coding genes within the selected region following IL1α and PDGF treatment, heatmap depicts expression of genes found with RNA-seq in 4 patient samples. (C): Dotted line marks region containing SMILR lincRNA and closest protein coding genes HAS2 and ZHX2. (D): Expression of proximal gene HAS2-modulated in the same manner as SMILR with IL1α and PDGF treatment (n=3). (E-F): Additional HAS isoforms are differentially modulated by IL1 and PDGF (n=3). (G-I): Validation of RNA seq data for lncRNAs SMILR and HAS2-AS1 by qRT-PCR (n=3). (J): Inhibition of SMILR expression via dsiRNA treatment significantly inhibits HAS2 expression determined by qRT-PCR **P<0.005 vs. Si Control. One way-ANOVA (n=3). (K-N): SMILR inhibition had no effect on proximal genes ZHX2 of HAS2-AS1 nor additional HAS isoforms, HAS1 or HAS3 (n=3). All graphs D-N assessed by unpaired student t-test.

Figure 21:
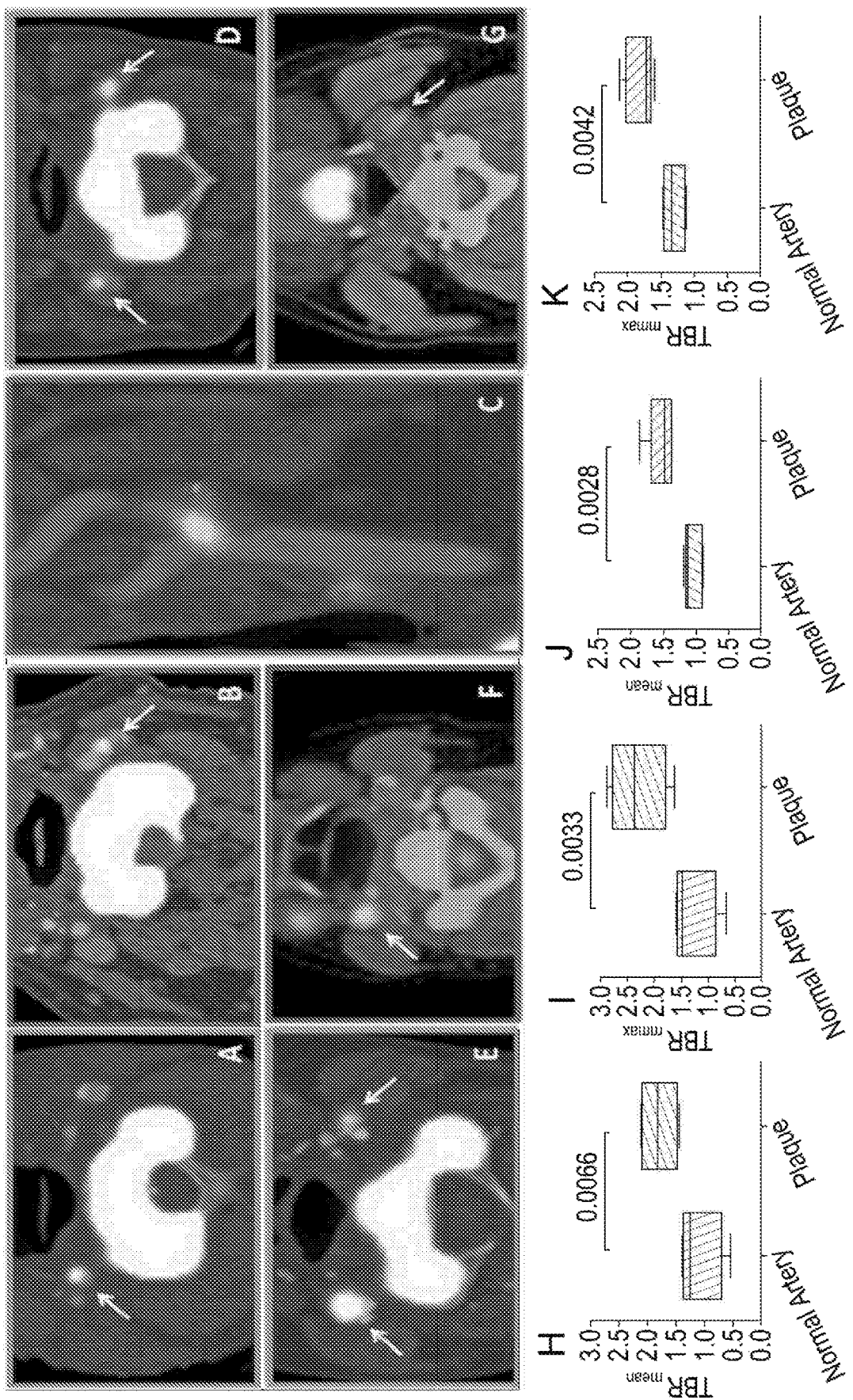
Figure 21:
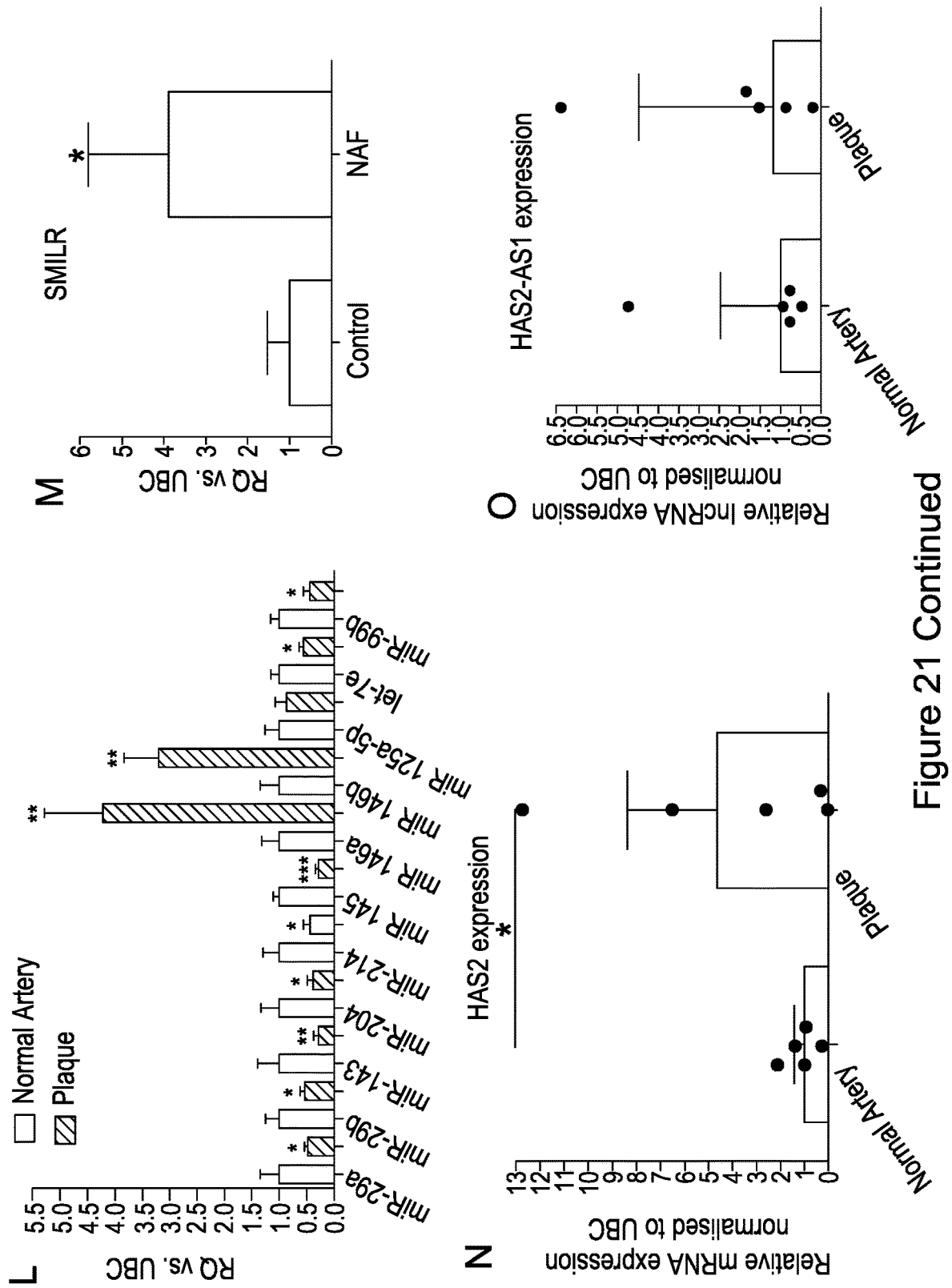

FIG. 21. Uptake [18F]-Fluoride and [18F]-FDG within plaque and normal artery and changes in non-coding RNA expression within carotid plaques. Axial images demonstrating unilateral (A, B) or bilateral [18F]-Fluoride carotid uptake (D, E). Image C is a multi-planar reformat of B. Axial images demonstrating [18F]-FDG carotid uptake (F, G). H shows the Siemens Biograph Clinical PET/CT system used for imaging. White arrows indicate carotid radio-ligand uptake. (H-K): (L): MicroRNA profile of atherosclerotic plaque and paired healthy carotid controls (n=6) assessed by qRT-PCR (paired students t test). Expression of SMILR (M), HAS2 (N) and HAS2-AS1(0) within atherosclerotic plaque (n=6). analysed via qRT-PCR analysis, * P<0.001,  P<0.01 and * P<0.05 assessed by paired students t test.

Figure 22:
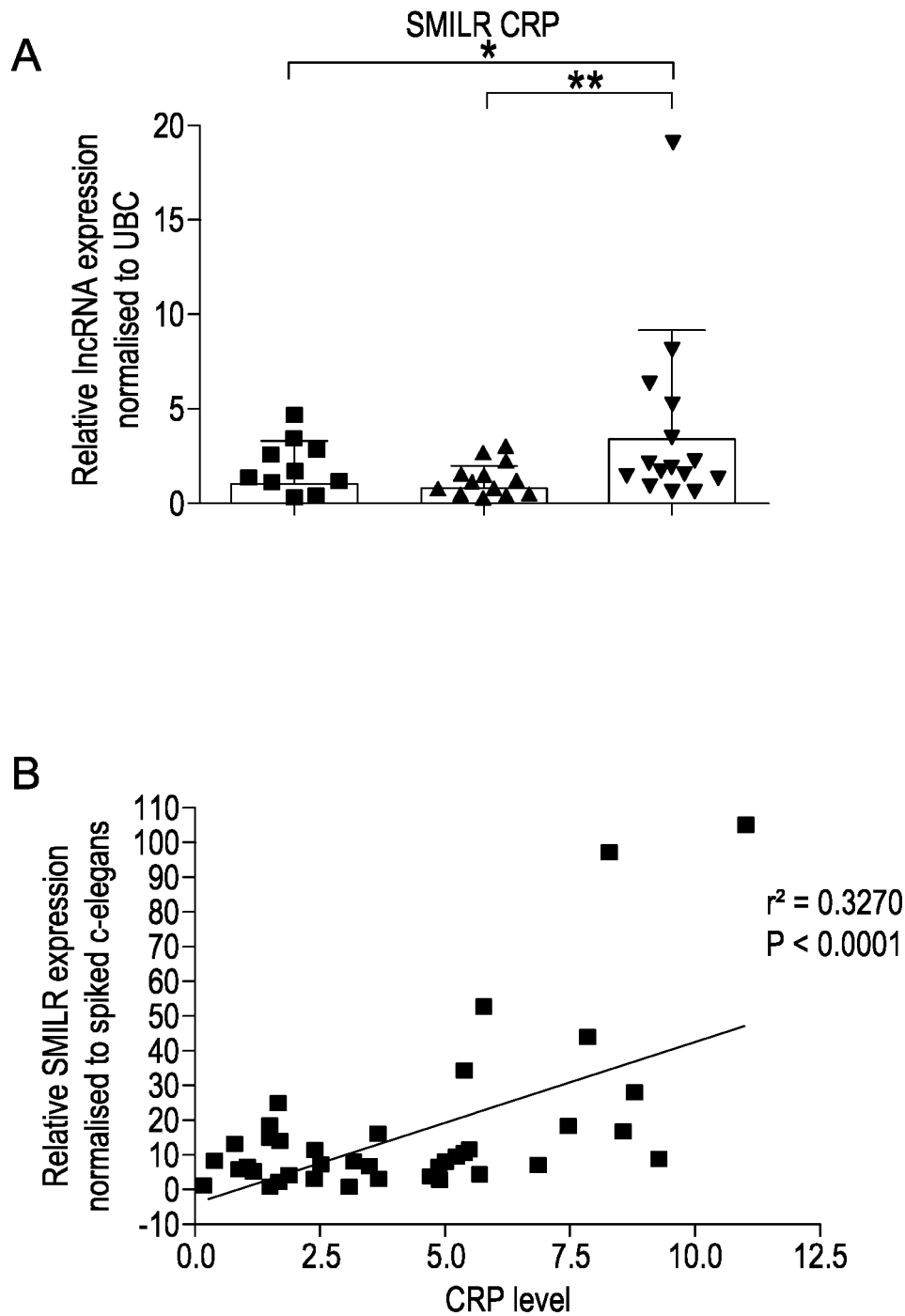

FIG. 22. SMILR is detectable within plasma samples and correlates with patient CRP levels. (A): SMILR expression is increased in patients with higher CRP levels (n=13 CRP<2, n=13 CRP2-5 and n=15 CRP>5, *P<0.05, **P<0.01 via 1-way ANOVA). (B): Correlation between SMILR expression and CRP levels (linear regression P<0.0001).

FIG. 23. Spike-in method of C. elegans total RNA in whole HSVSMC media. (A): Dose response effect of C. elegans ama-1 expression. Expression determined by qRT-PCR and results displayed as 1/Ct. Number at the top of each histogram corresponds to Ct values. (B): Specificity of products analysis by melting curve. (C): Specificity of products analysed using agarose gel. The cDNA amplicon size has been resolved by migration on a 2% agarose gel using 100 bp ladder. (D): Correlation between quantity spike-in and ama-1 expression. C. elegans ama-1 expression follow a logarithmic function: y=-1.231ln(x)+30.406 with a coefficient of correlation $r^2$=0.9668. (E): Reproducibility of the technique. Following RNA extraction after 75 ng of spike-in total C. elegans RNA, ama-1 expression was determined by qRT-PCR and the results have been displayed as Ct.

Figure 24:
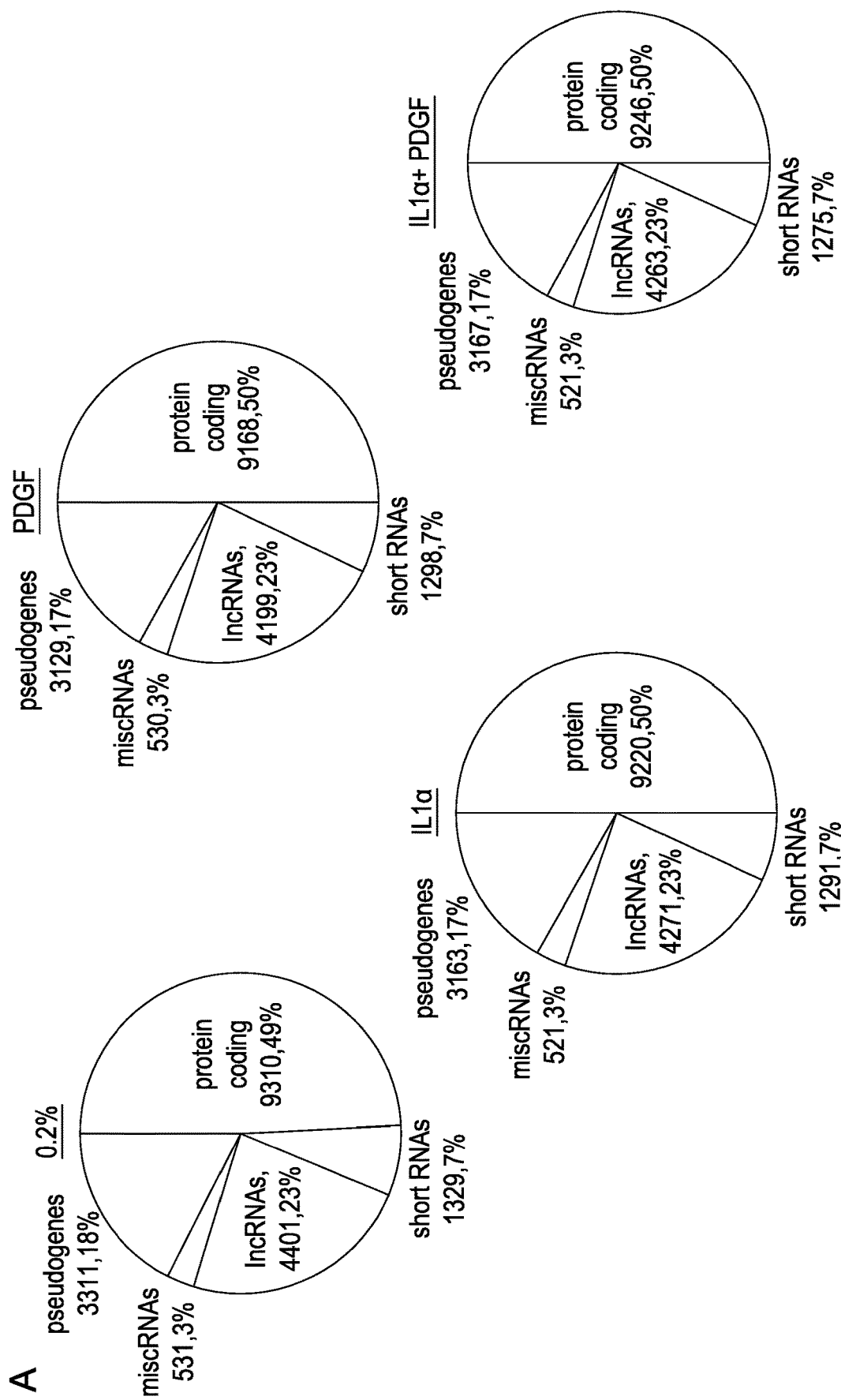
Figure 24:
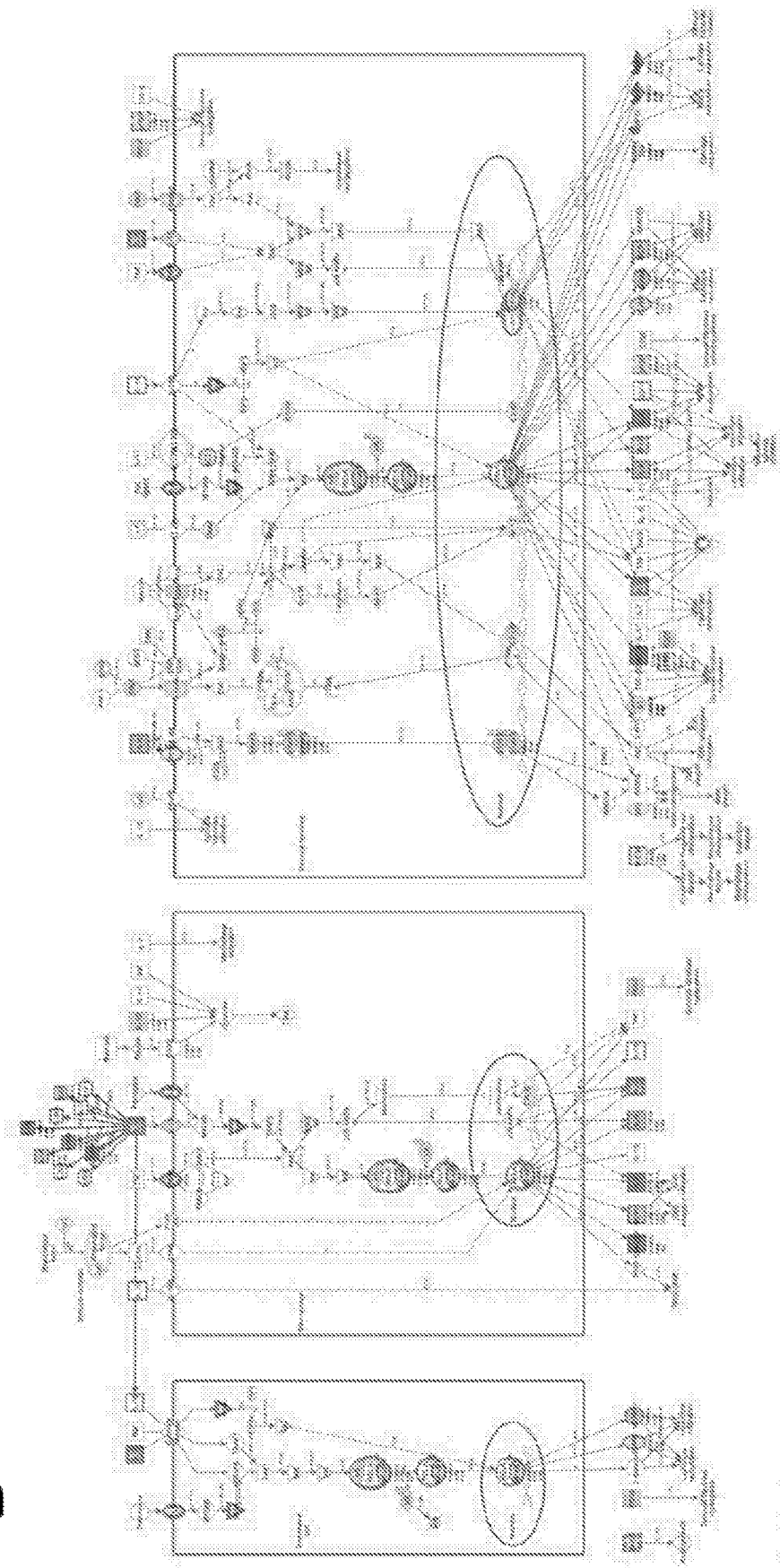

FIG. 24. Assessment of RNA-seq data. (A): Biotype distribution of all transcripts identified by RNA-seq analysis generated from HSVSM cells treated with IL1α and PDGF, cutoff at FPKM>0.1 (B): IPA analysis of top protein coding genes following IL1α and PDGF treatment.

Figure 25:
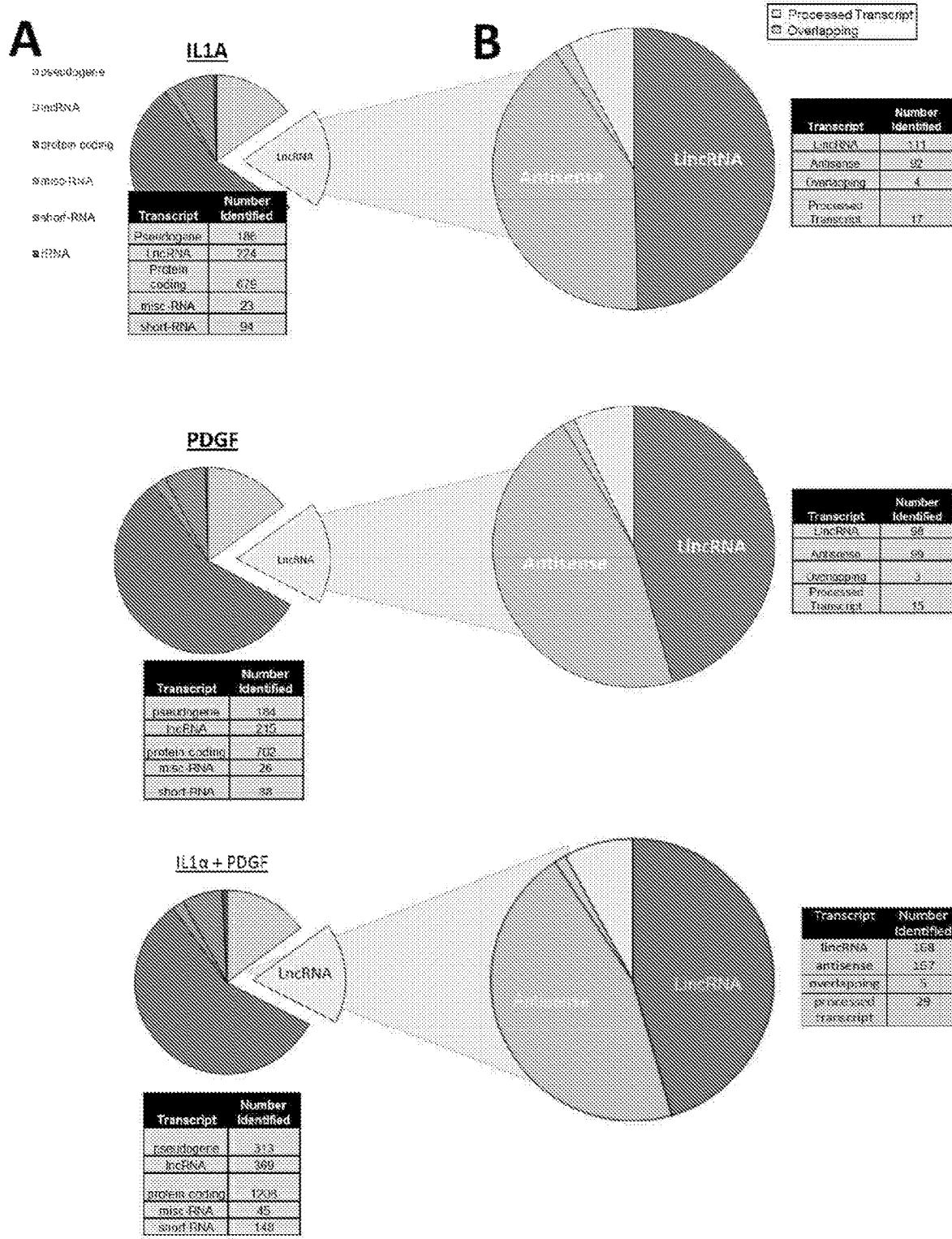

FIG. 25. Identification of differentially expressed LncRNAs in HSVSMC treated with IL1α and PDGF. Transcripts differentially expressed between 0.2% and stated treatment (p<0.01), pie chart indicates the relative percentage, and tables present numbers, of each biotype differentially expressed. LncRNAs differentially expressed between 0.2% vs IL1α/PDGF can be subdivided based on lncRNA biotype. Groups include intervening lncRNA (lincRNA), antisense, overlapping and processed transcripts.

Figure 26:
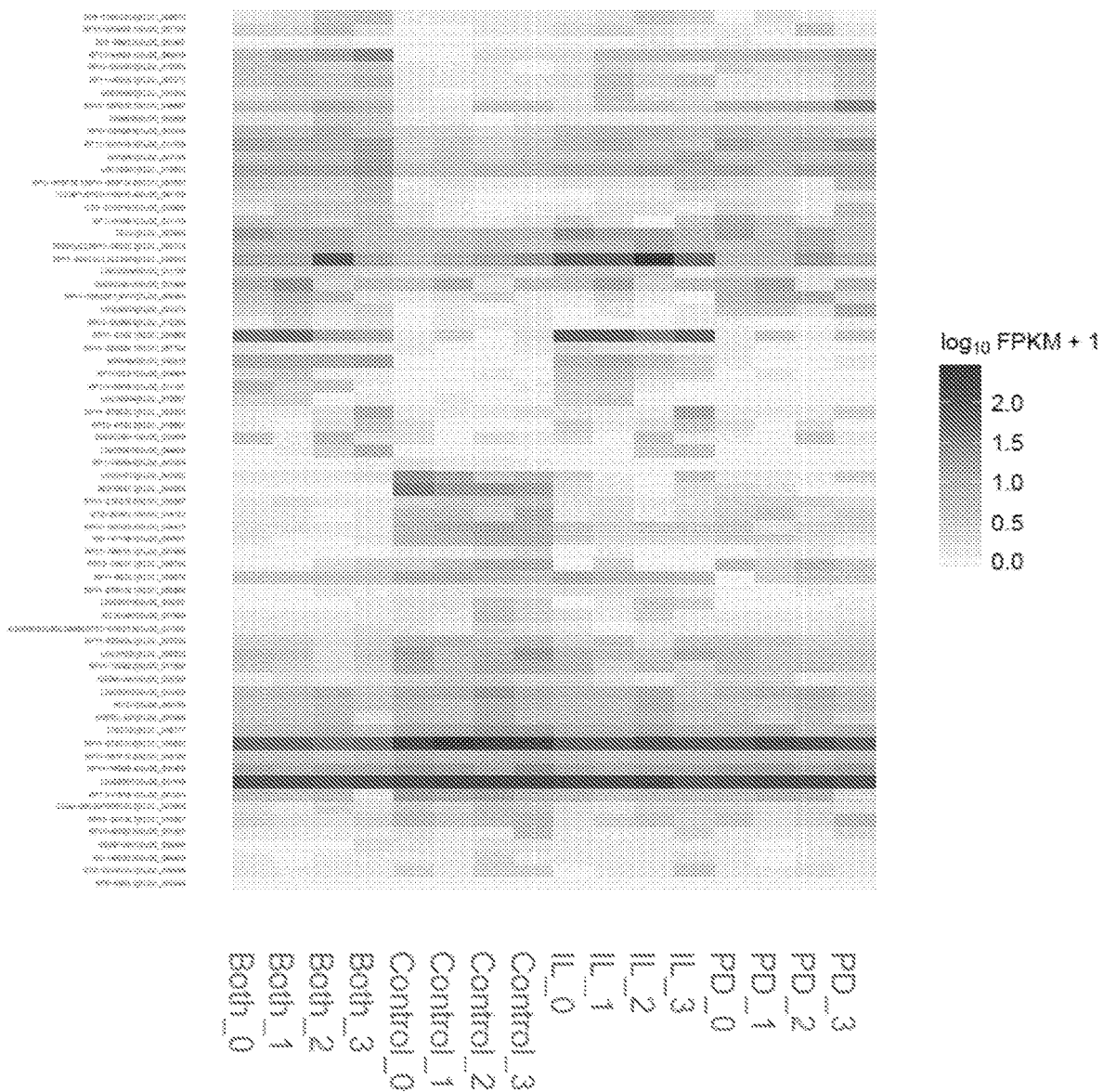

FIG. 26. Heat map of most significantly dysregulated intervening lncRNAs across all treatment groups. Heat map shows most significant changes in intervening lncRNA 0.2% vs IL1+PDGF treatment. LincRNA cut off using FDR<0.01, FPKM>1.

Figure 27:
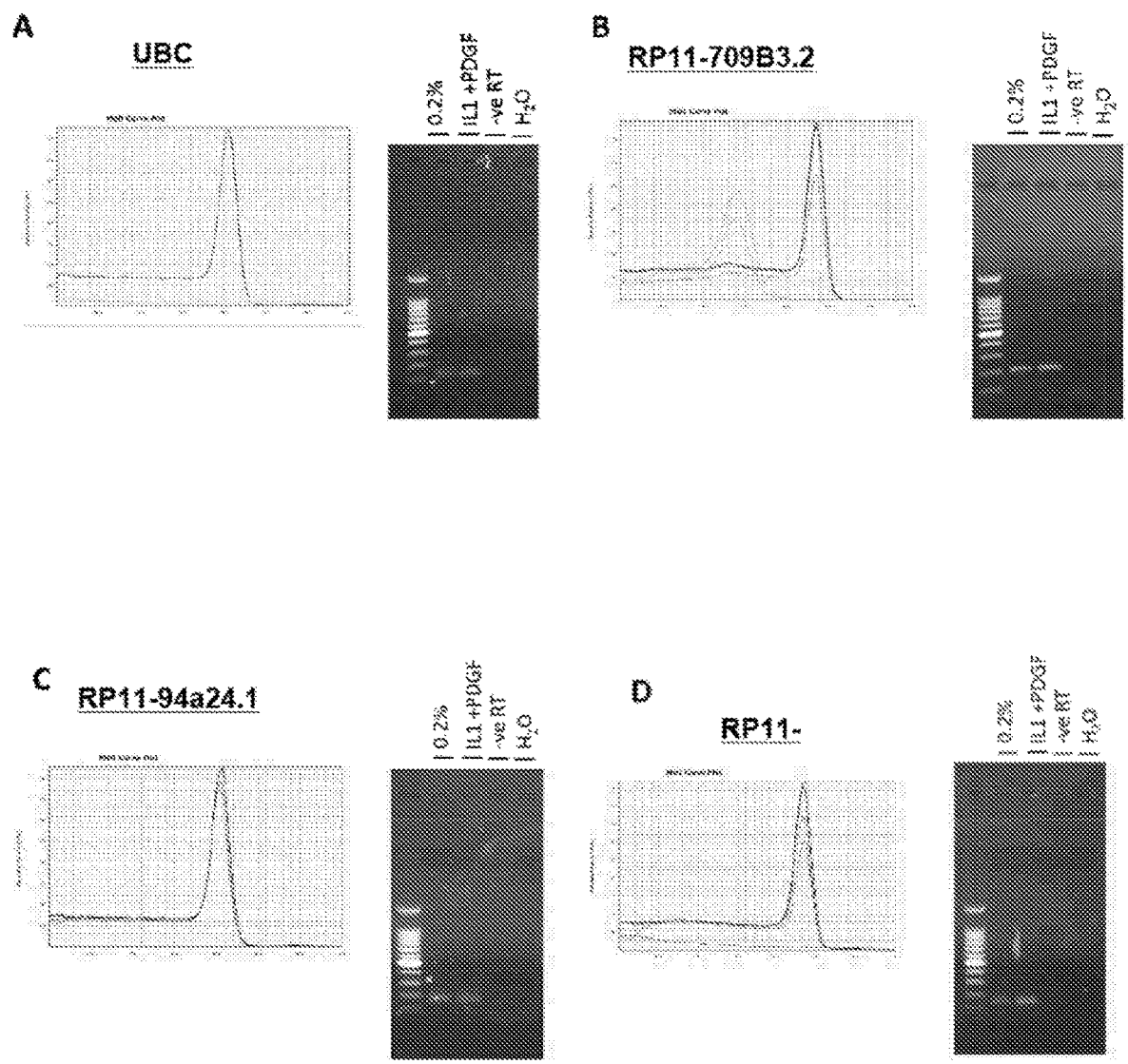
Figure 27:
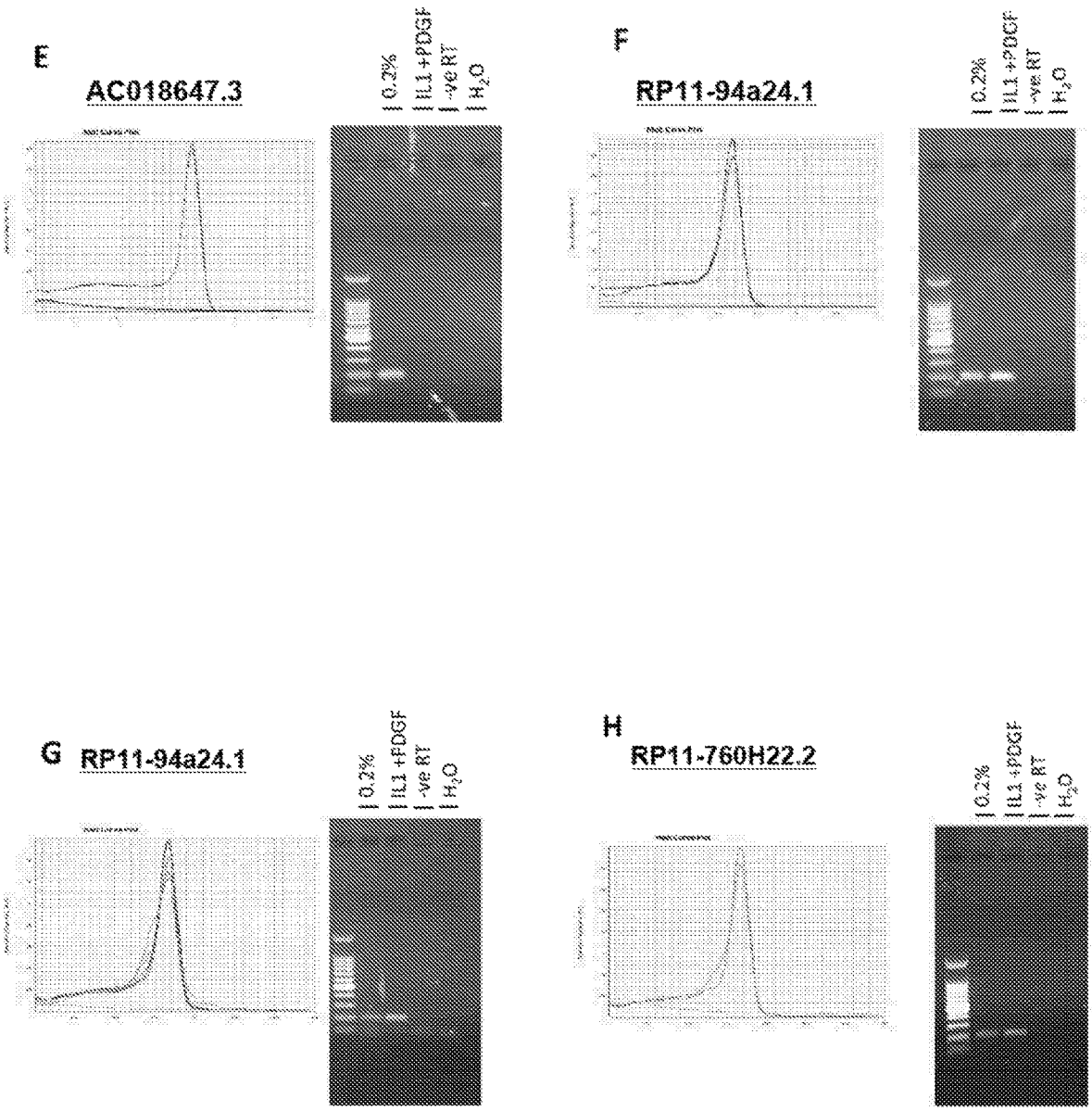

FIG. 27. Dissociation curves and gel products of PCR reactions indicating single PCR products. (A-H) Dissociation curves and gels for each lncRNA primer set. Primers were tested under 0.2% and IL1+PDGFconditions. Each gel also contains lanes containing—ve RT and $H_2O$ samples.

Figure 28:
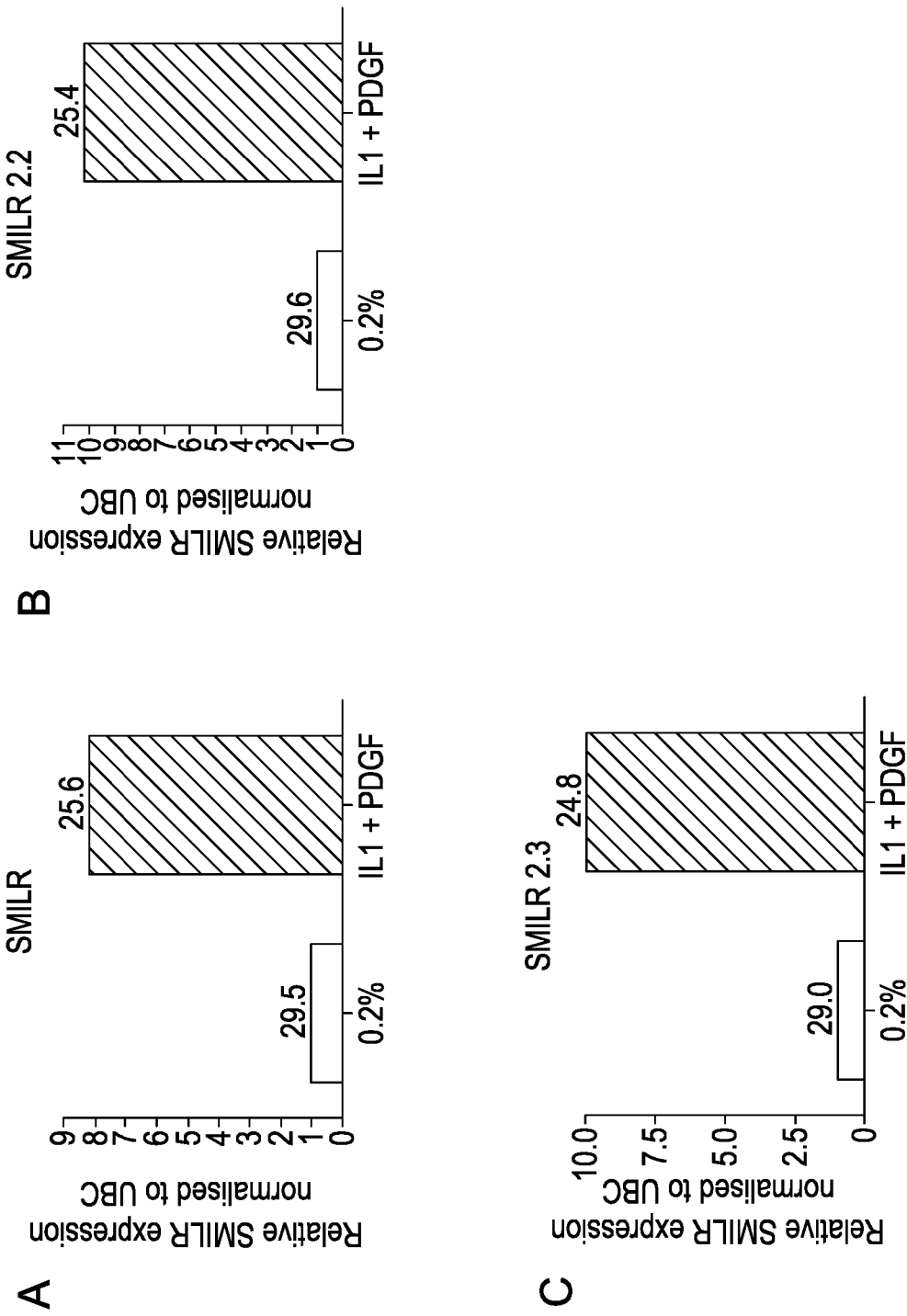

FIG. 28. Validation of additional SMILR primers. (A-C): Assessment of SMILR via qRT-PCR expression via 3 independent primer sets. The number on top of graphs represent Ct values obtained under 0.2% and dual stimulated conditions.

Figure 29:
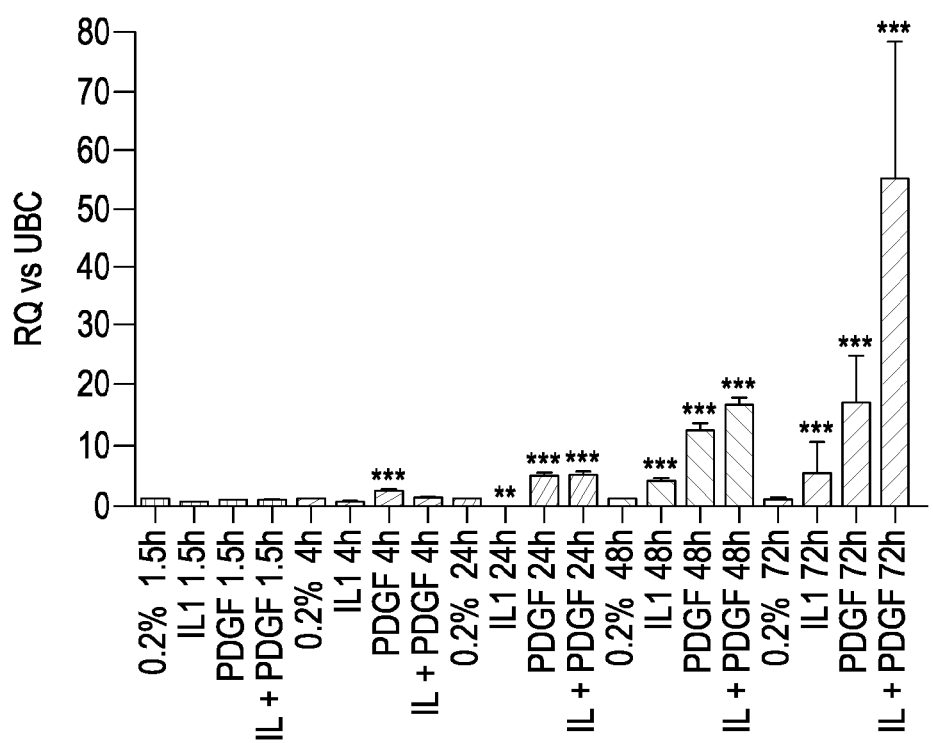
Figure 31A:
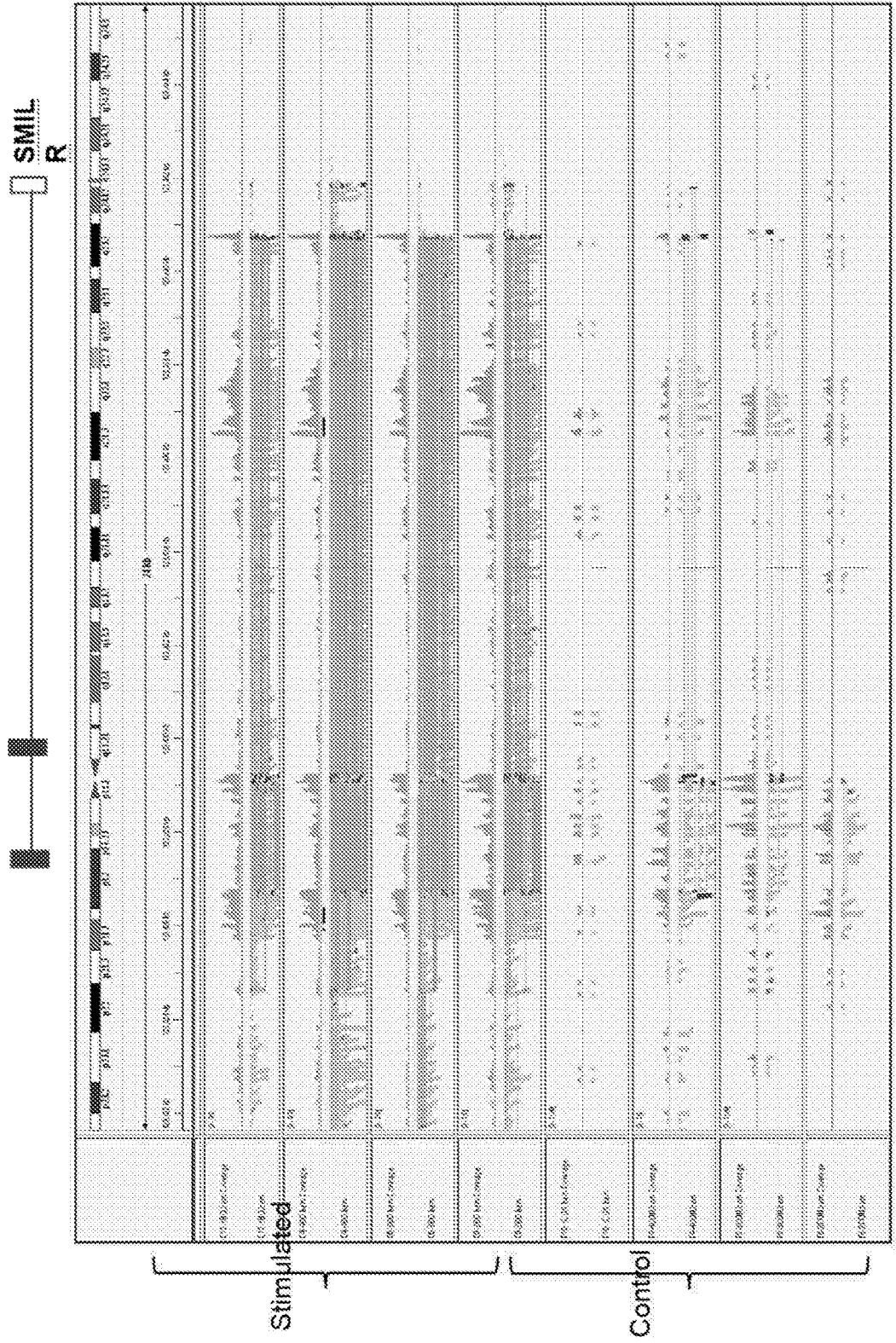
Figure 31B:
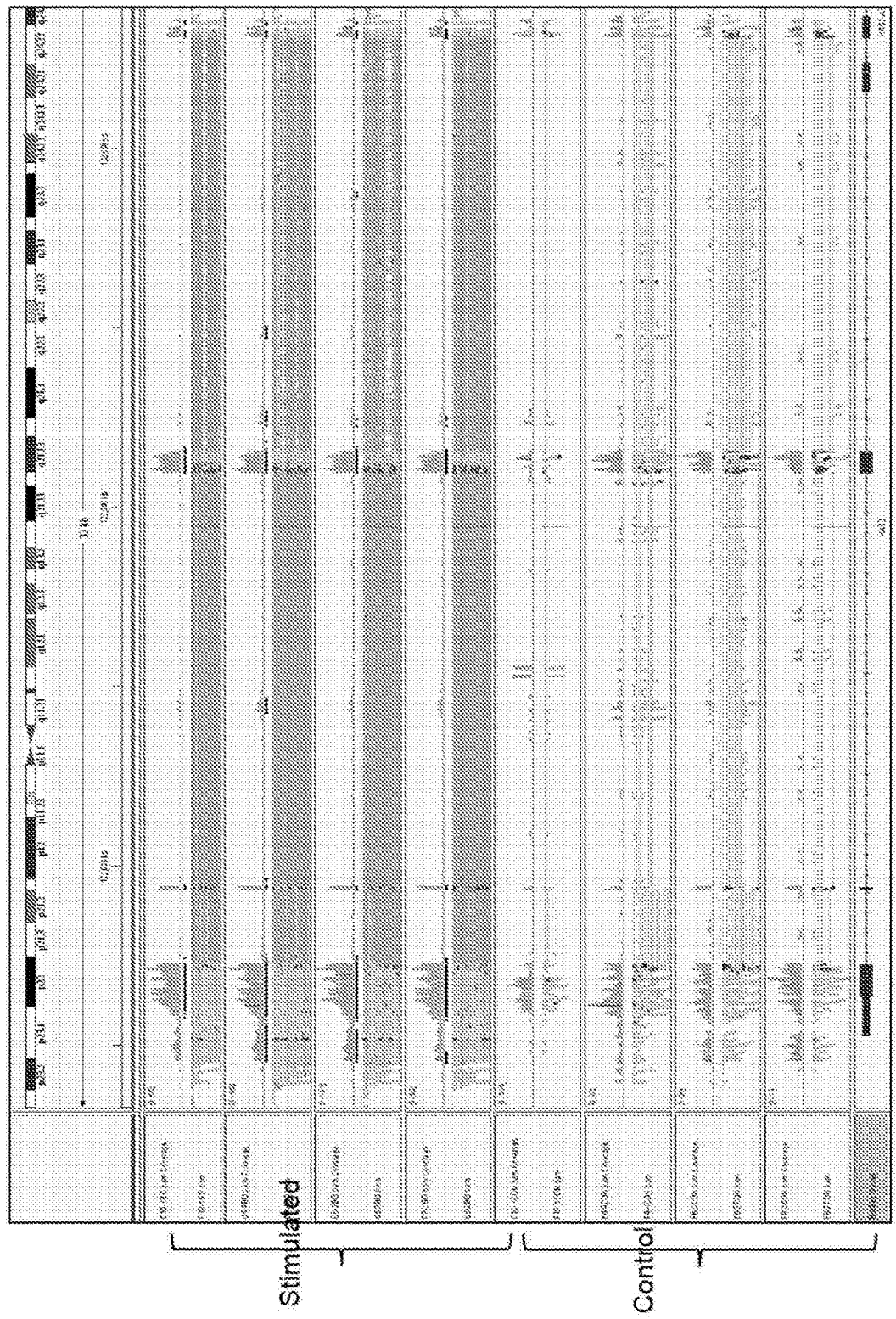
Figure 31C:
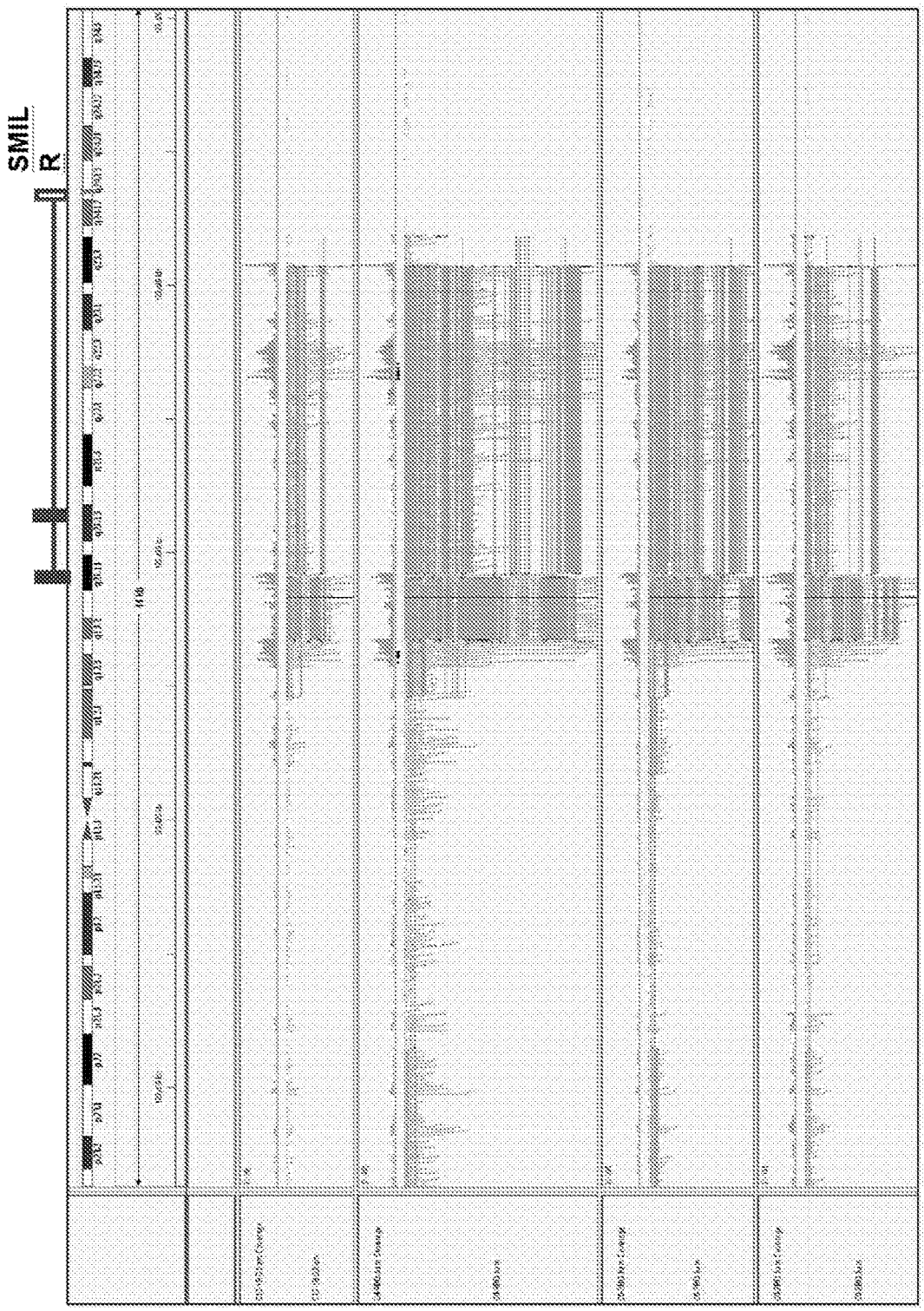
Figure 31D:
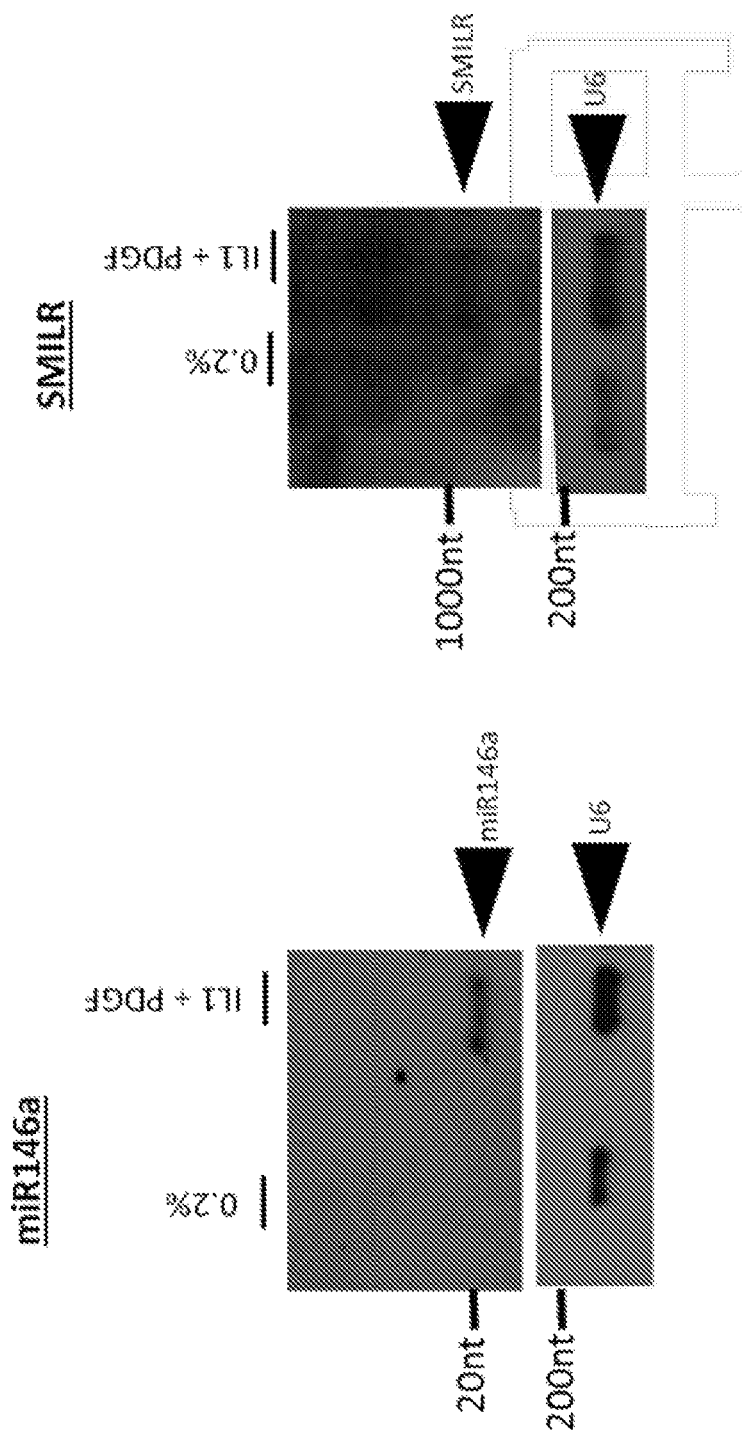

FIG. 29. Temporal regulation of lncRNA 2 assessed by qRT-PCR. HSVSMC were stimulated with IL1α, PDGF of a combination for the stated time points. RNA was extracted and expression determined by qRT-PCR.

FIG. 30. Visual representation of full SMILR transcript. (A):Grey boxes indicate the predicted SMILR sequence obtained from UCSC genome browser (RP11-94A24.1). Black boxes represent additional 316 basepair sequence obtained via 3' RACE of SMILR transcript. *$P<0.001$,  $P<0.01$ and * $P<0.05$ vs 0.2% in each time point (1 way ANOVA). (B): Full length sequence of lncRNA 2.

FIG. 31. Raw sequencing profiles generated utilising tophat files, constructed on integrative genome viewer (IGV). (A): Raw sequencing reads of SMILR under both basal and dual stimulated (IL1+PDGF) conditions n=4. (B): Raw sequencing reads of HAS2 indicating a similar expression pattern following stimulation. (C): Raw sequencing reads of SMILR under stimulated conditions—expanded (D): Northern analysis of miR146a and SMILR RNA. U6 shown as loading control.

Figure 32:
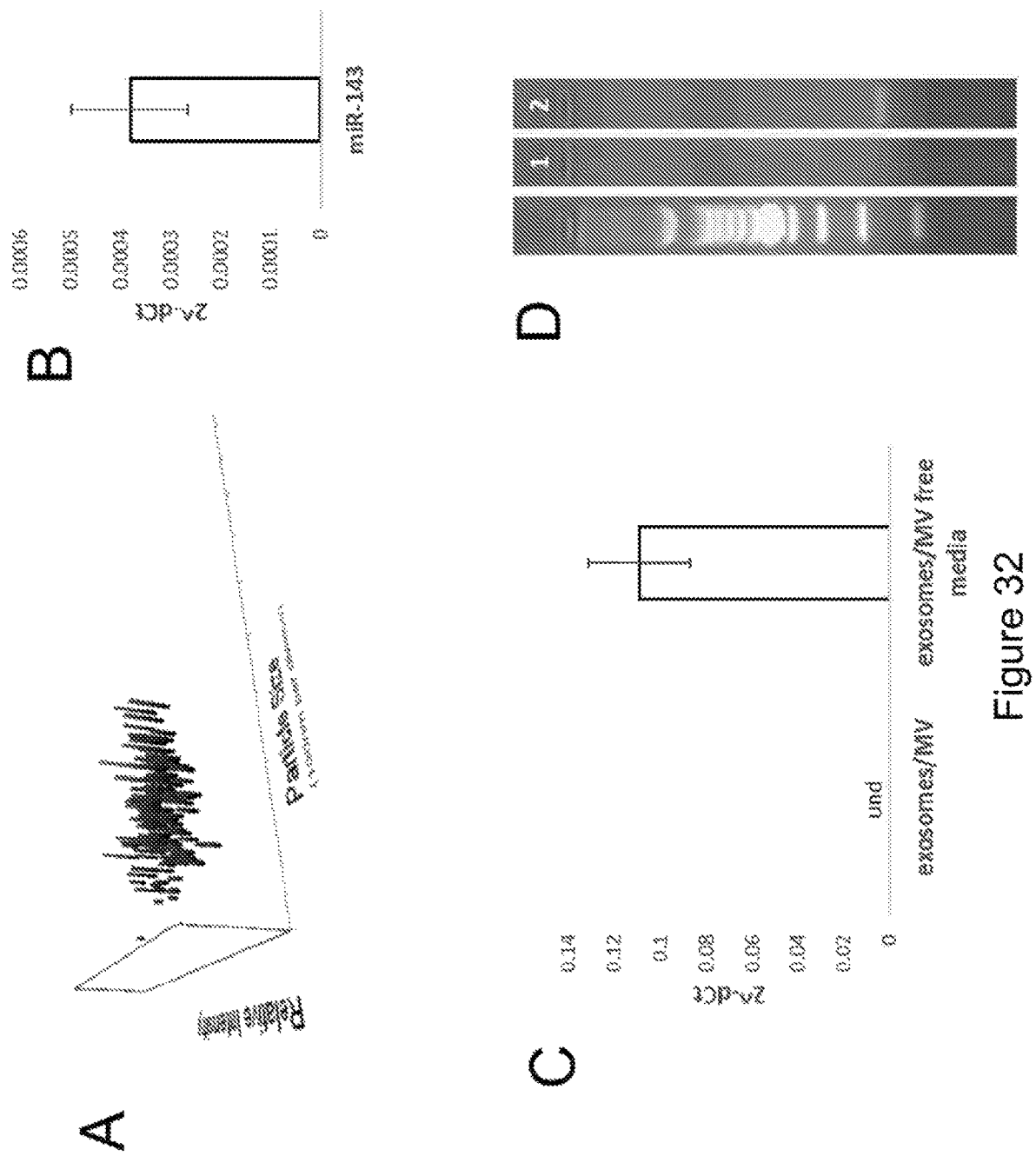
Figure 32:
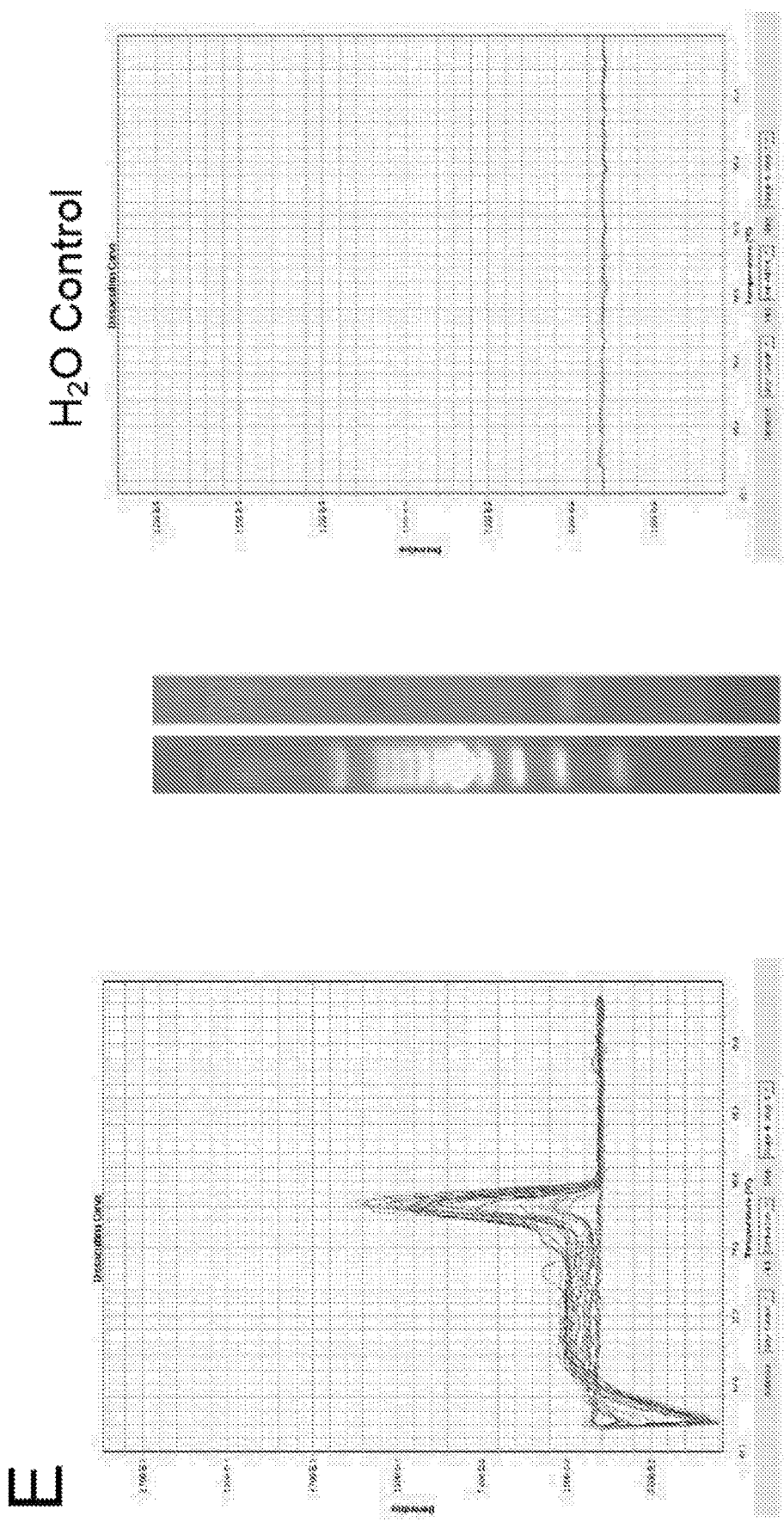
Figure 32:
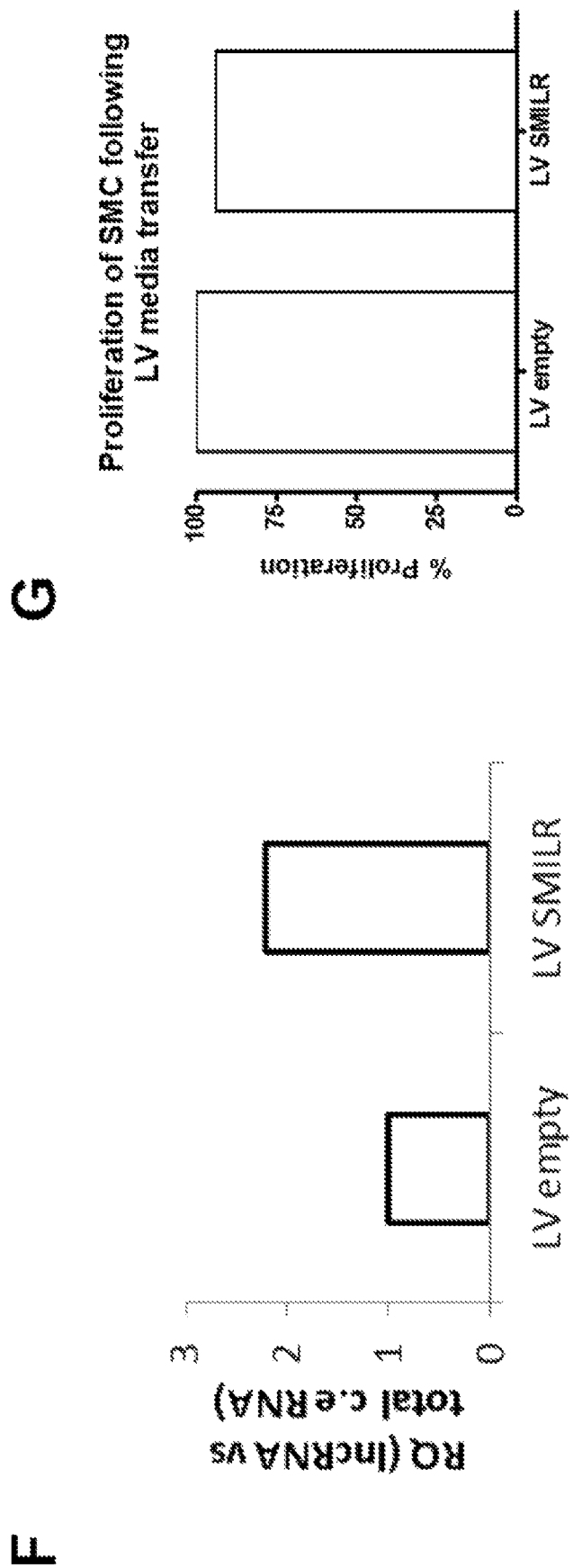

FIG. 32. Exosome isolation from HSVSMC conditioned media. (A): Size evaluation using the Nanosight of exosomes and MV isolated using the Total exosome isolation kit from 0.2% conditioned media. Sizes obtained between 70 and 600 nm. (B): Quantification of miR-143 in exosomes/MV isolated using the Total exosome isolation kit from 0.2% conditioned media. (C): SMILR expression analysed by qRT-PCR in exosomes/MV and exosomes/MV free media compartment from IL-1α+PDGF conditioned media. (D): Agarose gel of qRT-PCR products obtained in C; 1: exosomes/MV compartment, 2: exosomes/MV free media. (E): melting curves and gel electrophoresis of SMILR primer set in conditioned media. (F): SMILR expression from conditioned media following control lentivirus or SMILR lentivirus infection of cells. (G): Subsequent proliferation of quiesced cells following 48 h incubation with lentivirus conditioned media.

Figure 33:
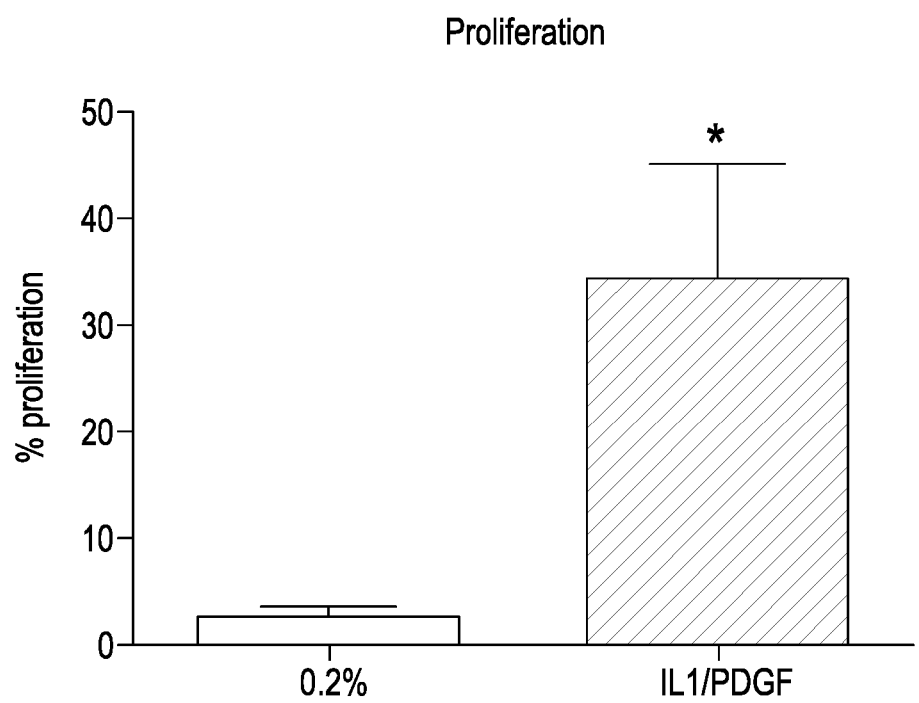

FIG. 33. Proliferation of HSVSMC 0.2% vs IL1+PDGF treatment. $P<0.05$ students t test.

Figure 34:
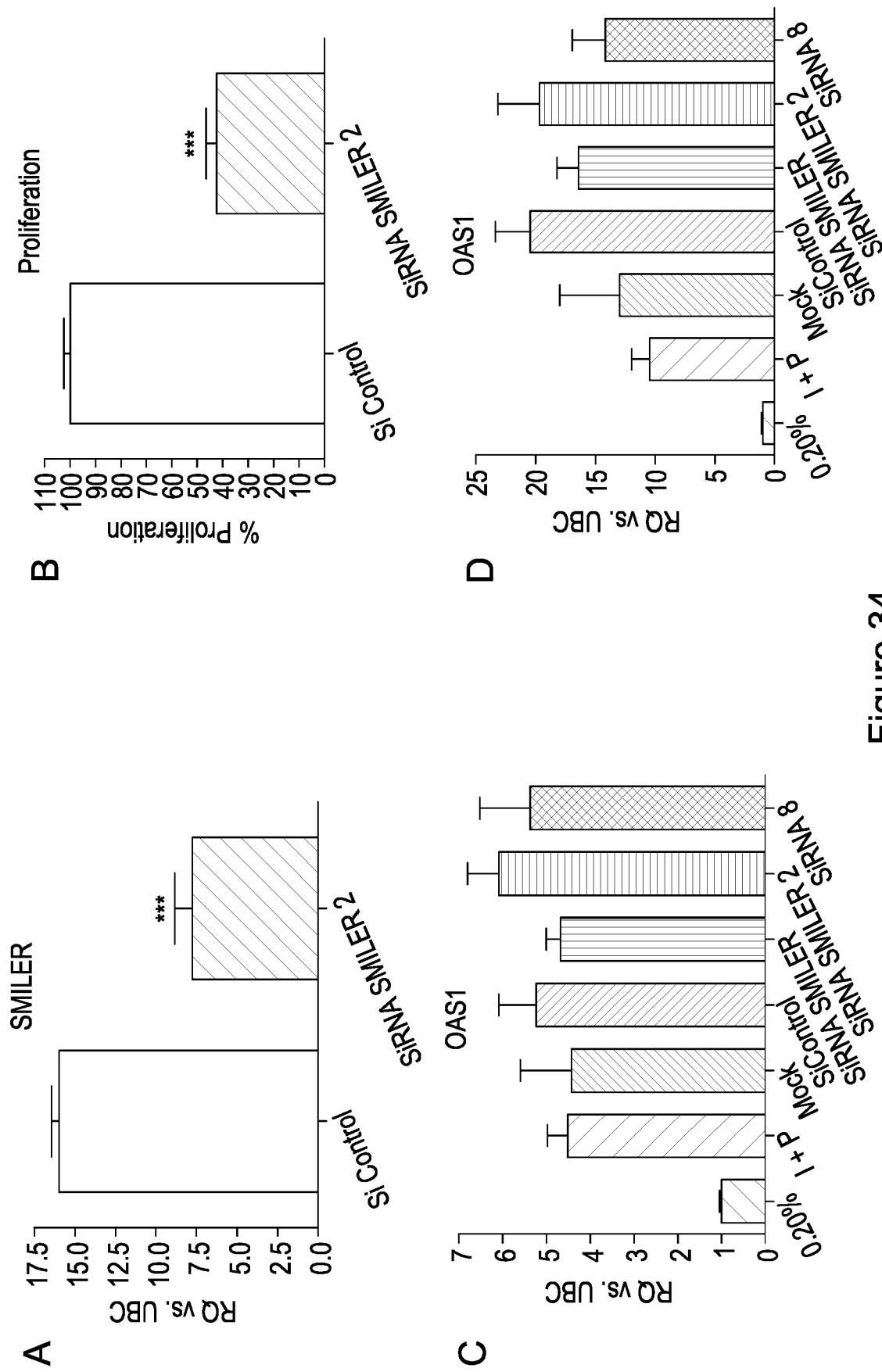
Figure 34:
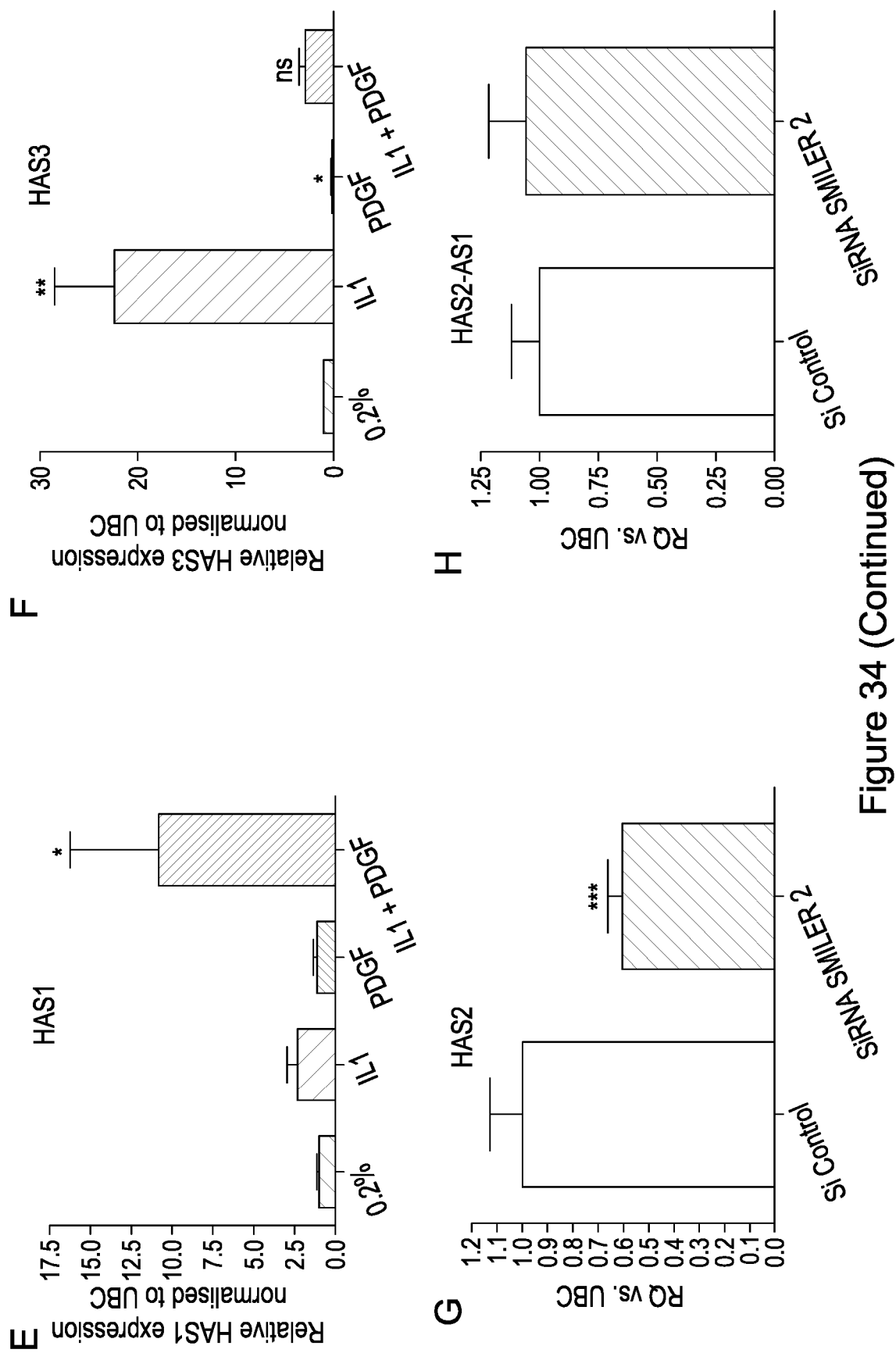
Figure 34:
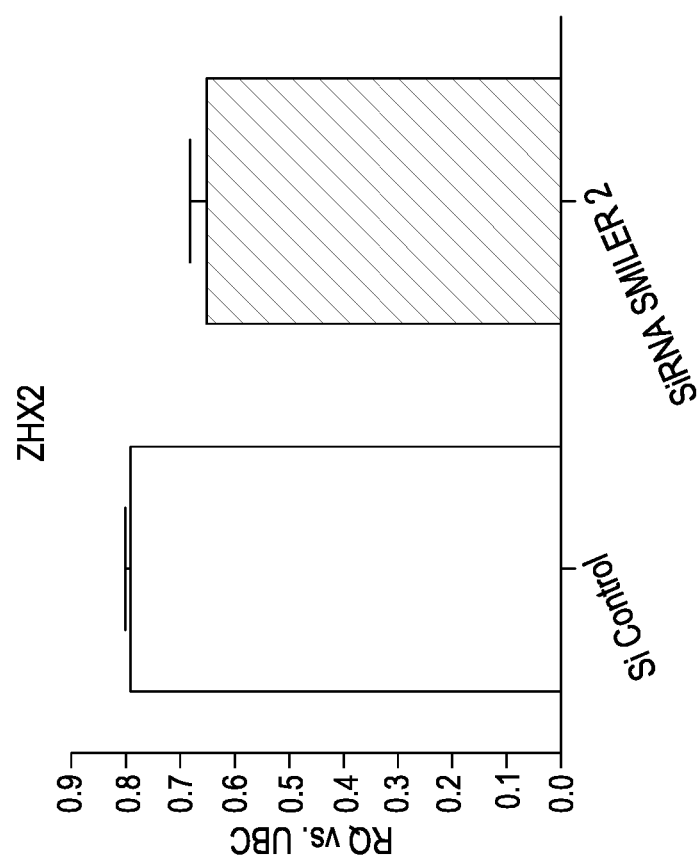

FIG. 34. (A): Confirmation of siRNA mediated down regulation of SMILR using second siRNA targeting a separate sequence of SMILR. (B): Confirmation of knockdown of SMILR using second siRNA. Analysed by students t-test ***$P<0.001$ vs SiControl. (C-D):qRT-PCR analysis of interferon gamma associated mRNA OAS1 and IRF7. (E-F): qRT-PCR validation of HAS1 and HAS3 regulation by IL1α and PDGF. One way ANOVA *$P<0.05$. (G-I): Validation of siSMILR using second siRNA targeting different section of the lncRNA.

Figure 35:
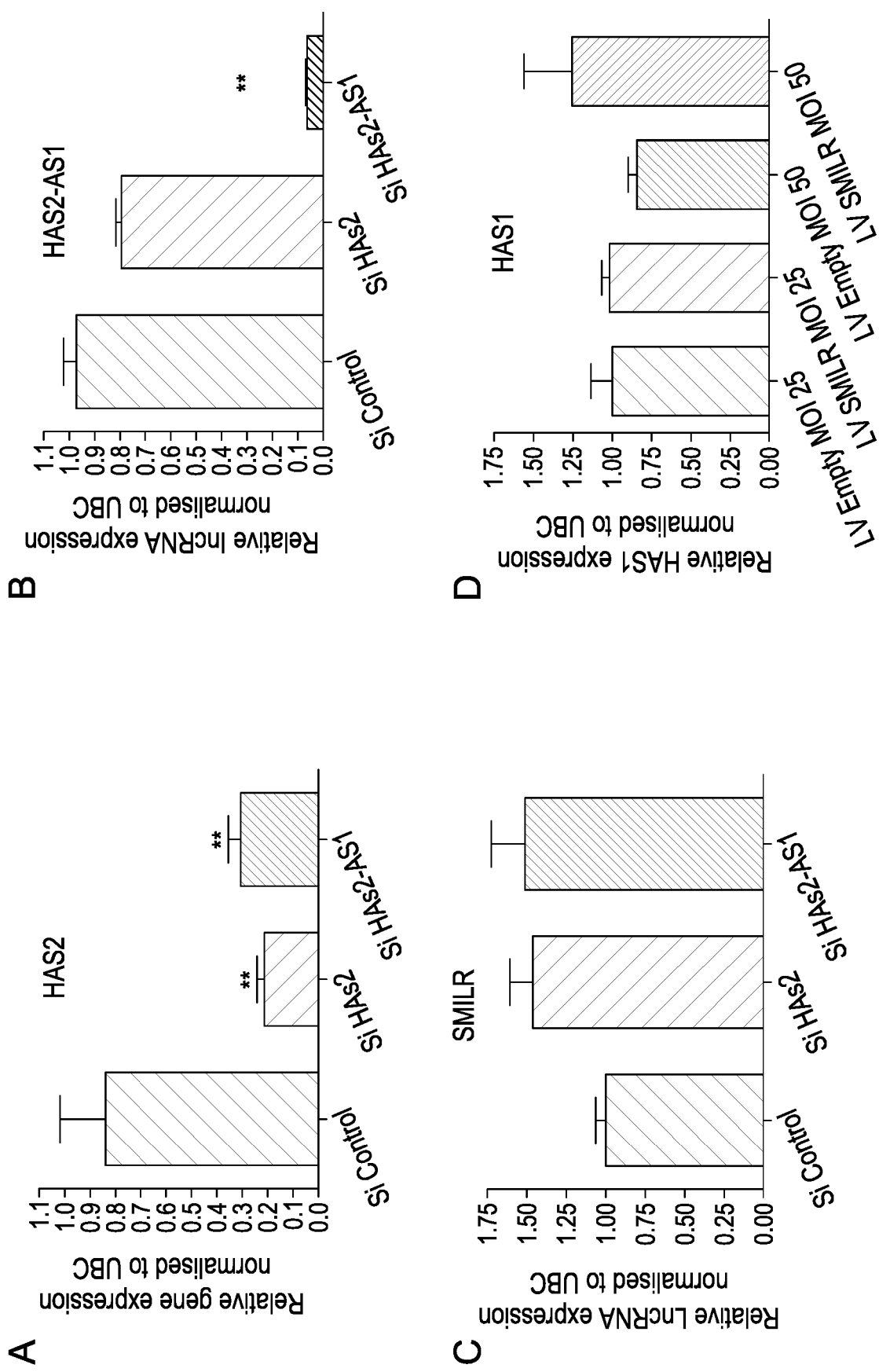
Figure 35:
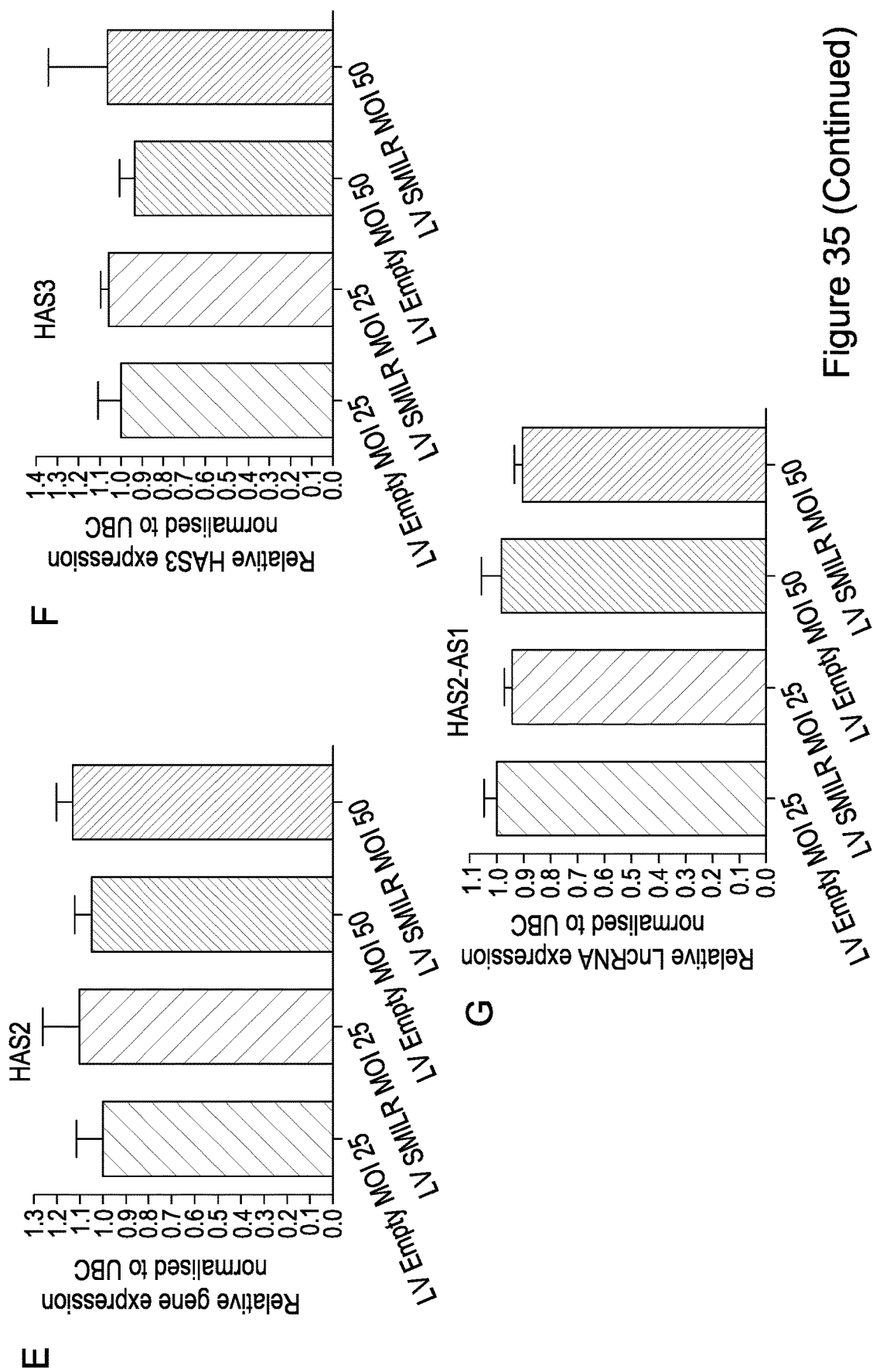

FIG. 35. Effect of HAS2 and HAS2-AS1 knockdown on SMILR expression. (A): Knockdown of HAS2 or HAS2-AS1 both reduced HAS2 expression. (B): Knockdown of neither HAS2 nor HAS2-AS1 affected SMILR expression levels. (C): Knockdown of HAS2-AS but not HAS2 significantly reduced HAS2-AS1levels. (D-F): Overexpression of SMILR did not affect HAS1-HAS3 nor HAS1-AS1 expression levels.

Figure 36:
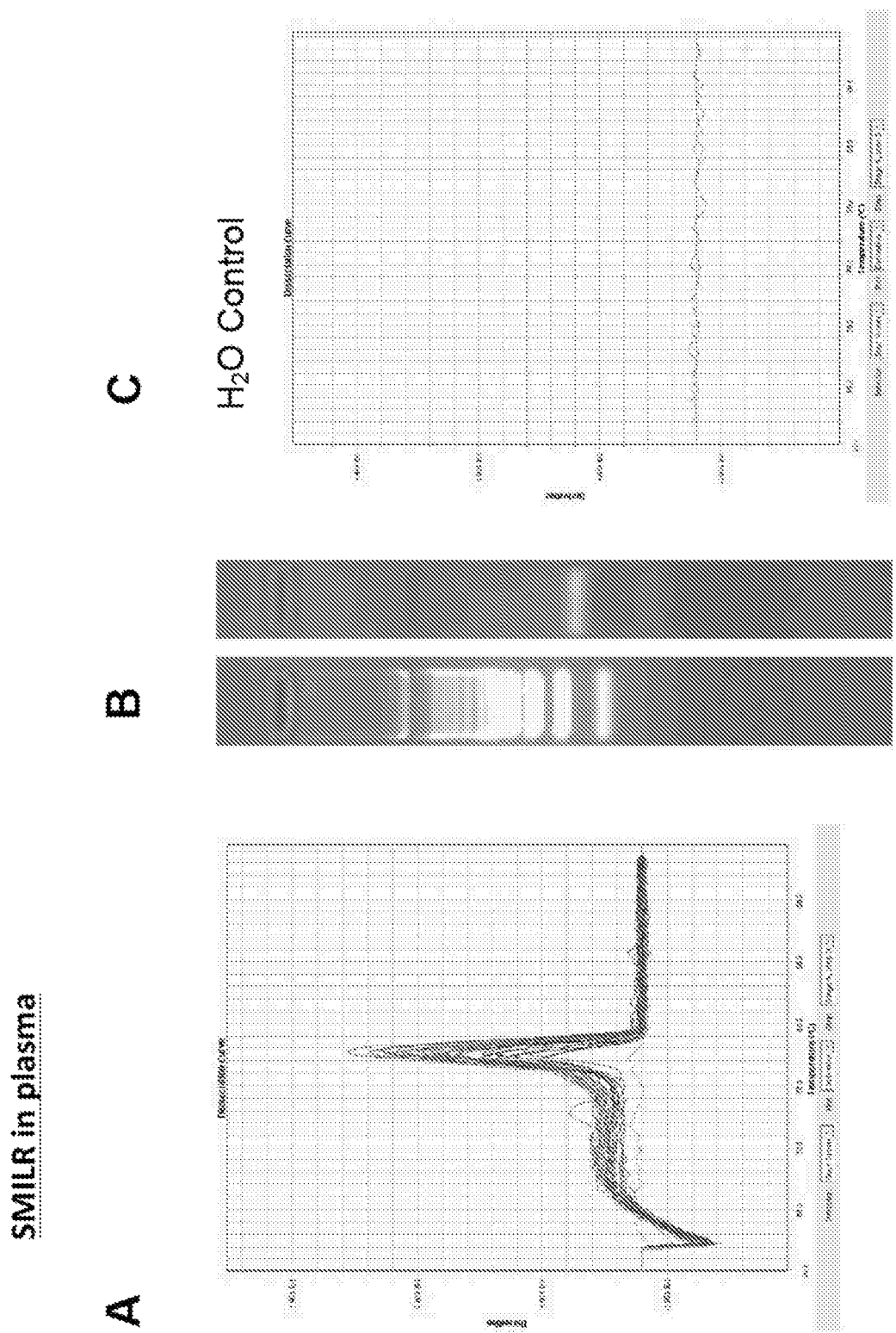

FIG. 36. Primer validation and quality control in plasma samples. (A): Melting curve for SMILR in plasma. (B): Agarose gel of qPCR product. (C): Water melting curve.

FIG. 37. Statistical analysis of SMILR vs. CRP correlation. (A): Pearson correlation of SMILR vs. CRP utilising all data points. R=0.5719, $r^2$=0.327 and $P<0.001$. (B): Pearson correlation of SMILR vs. CRP omitting the 2 highest outlying points. R=0.389, $r^2$=0.151, p=0.014.

FIG. 38. A: LncRNA 7 validation of RNA-seq data. (n=4). B: LncRNA 7 is upregulated in both endothelial (n=3) and smooth muscle cells (n=4). Assessed via qRT-PCR at 72 h post stimulation. C: RNA fluorescent in sutu hybridisation (RNA-FISH). LncRNA 7 located in the nucleus. DAPI used as a nuclear marker while UBC was used to mark cell borders. D: Tissue panel expression of lncRNA 7. Tissue panel consists of a set of 10 healthy tissues. E: Overview of IL1 signalling pathways and routes via which lncRNA 7 may be expressed. F: Inhibition of MEKK1 (shown as a cross in FIG. 38E) does not affect lncRNA 7 expression. Assessed via qRT-PCR (n=3). G: Expression of lncRNA7 in stable and unstable carotid plaques (n=5). H: LncRNA 7 expression in human coronary artery smooth muscle cells (HCASMC) following IL1 and PDGF treatment n=2.

FIG. 39. cDNA and RNA sequences of lncRNA 2, 4, 5, 6, 7 and 8. cDNA sequences for lncRNA 4-8 were obtained from Ensembl. LncRNA 2 cDNA was obtained from Ensembl and additional sequence derived from 5'3' RNA RACE. RNA sequence is the complement sequence to the cDNA sequence.

DETAILED DESCRIPTION

Phenotypic switching of vascular smooth muscle cells (VSMCs) from a contractile to a synthetic state is implicated in diverse vascular pathologies including atherogenesis, plaque stabilisation, and neointimal hyperplasia. However, very little is known as to the role of long non coding RNA (lncRNA) during this process. The inventors have investigated a role for long non-coding (lnc)RNAs in VSMC biology and pathology.

Vessel wall remodelling is an integral pathological process central to cardiovascular diseases including atherogenesis, plaque rupture and neointimal hyperplasia associated vein graft failure and in-stent restenosis [1, 2]. Resident vascular smooth muscle cells (VSMC) are typically quiescent and contractile in the normal physiological state. However, following pathological or iatrogenic vascular injury, the release of cytokines and growth factors from VSMC, aggregated platelets and inflammatory cells on the damaged intimal surface, leads to "phenotypic switching" of VSMC and the adoption of a more synthetic, pro-proliferative and pro-migratory state [3]. In the setting of the pathological injury of atherosclerosis, VSMCs not only contribute to the atherogenic process itself but can also engender plaque stabilisation through the generation of a thick-capped fibroatheroma. For acute iatrogenic vascular injury, over exuberant proliferation of VSMC subpopulations promotes neointimal hyperplasia leading to luminal narrowing such as seen in vein graft failure or in-stent restenosis [4]. Phenotypic switching of VSMCs and release of cytokines and growth factors are therefore critical in vascular disease and understanding the mechanisms involved is critical to gain insights into pathology and identify new opportunities for therapies.

The highly conserved IL1α and PDGF pathways play prominent roles in VSMC-associated pathologies [1, 5]. IL1α is a central mediator in the cytokine cascade and a potent activator of vascular cytokine production. Furthermore, previous studies have demonstrated that ligation injury result in reduced neointimal formation in IL-1 receptor knockout mice [6]. Downstream mediators include the signalling molecules MEKK1, p38 and the transcription factor NF-KB that activate mediators of inflammation and cellular migration[7]. PDGF is a potent mitogen and chemoattractant and expression is increased following vascular injury [8]. Conversely a reduction in PDGF expression reduces intimal thickening and cellular content of the neointima [9]. Activation of both IL1α and PDGF signalling pathways simultaneously can activate common downstream targets leading to additive or synergistic effects. This includes activation of NFκB leading to the up-regulation of MMP 3 and 9 [10]: genes critical in the development of vasculoproliferative pathologies.

Over the past decade, there has been substantial interest in determining the complex interactions between hierarchical levels of gene regulation. Up to 90% of the human genome is transcribed at different developmental stages and only approximately 2% of RNA molecules are translated into protein [11]. The functional complexity of organisms therefore appears to be reliant upon non-coding RNA molecules. Non-coding RNAs are subdivided into several classes, including microRNA (miRNA) and long non-coding RNA (lncRNA). MiRNAs are abundantly expressed in vascular tissues and play an important role in vascular pathology. Interestingly, recent studies have demonstrated that miRNAs are capable of being released into the blood from injured cells. These miRNAs are relatively stable and have been reported as biomarkers for several disease states including myocardial infarction [12] and heart failure [13]. While the role of miRNAs is reasonably established in the setting of cardiovascular pathology, relatively little is known about the role of lncRNAs. LncRNAs are capable of regulating target DNA, RNA and protein at the pre and post-transcriptional level. It is becoming clear that lncRNAs play a pivotal role in cellular physiology and pathology via localisation in sub populations of cells and through highly controlled temporal expression [14]. However, detailed insights into their regulation and biological roles are only beginning to emerge. In the vascular setting, SENCR and MALAT1 have been implicated in the control of vascular cell migration and endothelial cell sprouting, respectively [15, 16]. Interestingly, SENCR is implicated in phenotypic switching of VSMCs to a more pro-migratory phenotype as knockdown of this lncRNA downregulates contractile genes [16]. A greater understanding of lncRNAs in quiescent and proliferative VSMCs may provide valuable insight into the specific roles of lncRNAs in response to pathological processes.

Methods

Tissue and Cell Culture

Segments of saphenous vein tissue, excess to CABG surgery, were obtained with informed consent from patients undergoing CABG and all procedures had local ethical approval (Research Ethical Committee number: 06/S0703/110 and 12/NW/0036). Carotid Carotid plaques were obtained from patients undergoing endarterectomy following an acute and symptomatic neurovascular event. Human plasma samples were utilised from a previously published study: Carotid Ultrasound and Risk of Vascular disease in Europeans and South Asians (CURVES). All patients gave their written, informed consent. All procedures had local ethical approval (06/S0703/110, 12/VVS/0227, 09/S0703/118 and 12/NW/0036). All studies were approved by East and West Scotland Research Ethics Committees and all experiments were conducted according to the principles expressed in the Declaration of Helsinki.

All cells were propagated at 37° C. in a humidified atmosphere containing 5% (v/v) $CO_2$. Primary human saphenous vein smooth muscle cells (HSVSMC) were isolated by explants technique (Southgate and Newby 1990). Cells were utilised at passage 3-5 and cultured in Smooth Muscle Cell Growth Medium 2 (PromoCell, Heidelberg, Germany) supplemented with 15% foetal bovine serum (PAA laboratories, UK), 2 mM L-Glutamine (Invitrogen, Paisley, UK) 50 µg/ml penicillin (Invitrogen) and 50 µg/ml streptomycin (Invitrogen).

Primary human saphenous vein derived endothelial cells (HSVECs) were isolated by collagenase digestion and cultured in large vessel endothelial cell media (TCS Cellworks, Buckingham, UK) supplemented with 20% foetal bovine serum (PAA laboratories, UK), 2 mM L-Glutamine (Invitrogen, Paisley, UK) 50 µg/ml penicillin (Invitrogen) and 50 µg/ml streptomycin (Invitrogen).

Tissue panel samples were obtained from Ambion, lifetechnologies (UK).

Human coronary artery VSMC were purchased from Lonza (Basel, Switzerland) and maintained in VSMC media as above.

All cells were used between passages 3-5.

RNA-Seq Library Construction and Analysis

HSVSMC were plated at $1 \times 10^5$ cells per well in 6 well plates, quiesced in medium containing 0.2% fetal calf serum for 48 hour before the stimulation and stimulated with 10 ng/ml IL1α, 20 ng/ml PDGF (R&D systems)or a combination of both for 72 hours. Total RNA was processed through miRNeasy kit (Qiagen,Hilden, Germany) following the manufacturer's instructions, treated with DNAse 1 (amplification grade; Sigma, St. Louis, Mo., USA) in order to eliminate genomic DNA contamination and quantified using a NanoDrop ND-1000 Spectrophotometer (Nano-Drop Technologies, Wilmington, Del., USA). Following bioanalyzer quality control for RNA integrity number (RIN) values >8, RNA-seq was performed on ribosomal-depleted RNA using an Illumina Hiseq platform by Beckman Coulter Genomics. RNA-seq reads were aligned to the human genome (h19) and edgeR software used to calculated differential expression of transcripts. Specifically, Paired-end sequencing was carried out with a read depth of 70 million (n=4/group). RNA-seq reads were processed and trimmed to ensure quality and remove adapter sequences using Flexbar [19] and mapped to the Ensembl annotation of GRCh37.75 using the TopHat2 version 2.0.9 [20]. The transcriptome was assembled from the aligned reads and quantified using Cufflinks version 2.2.1 [21]. The differential expression levels between the groups was assessed using Cuffdiff version 2.2.1 [22]. The data set are deposited in the GEO repository, study number GSE69637. The biotype of each transcript was annotated according to the Ensembl database. Normalisation and statistical analysis of differentially expressed transcripts were carried out using edgeR and data filtered to find transcripts that were differentially expressed (p<0.01) between 0.2% media and each treatment group. Those transcripts that were differentially expressed (p<0.01, FDR<0.01, logFC>2) between 0.2% media and IL1/PDGF treatment were then filtered according to transcript abundance (FPKM>1 in at least one group). Data outputs such as pie charts and heatmaps were generated using R. IPA analysis was carried out using protein coding genes differentially expressed (FDR<0.01) from Edge R analysis. Exon-spanning transcript specific primers were designed for Sybr green.

Gene Expression Quantitative RealTime-PCR (qRT-PCR)

For gene expression analysis, cDNA for mRNA analysis was obtained from total RNA using the Multiscribe Reverse Transcriptase (Life technologies, UK). qRT-PCR was performed using Power SYBR green (life technologies, UK) with custom PCR primers (Eurofins, MWG, Ebersberg, Germany) the specificity of these primers was confirmed by performing a melting curve and running their PCR produce on a gel (Table 1—primer sequences). Ubiquitin C (UBC) was selected as housekeeping gene due to its stability across all groups studied. Fold-changes were calculated using the $2^{-\Delta\Delta Ct}$ method (Livak and Schmittgen 2001—http://www.ncbi.nlm.nih.gov/pubmed/11846609; analysis of relative gene expression data using real-time quantitative PCR and the 2(-Delta Delta C(T)) method. Methods 2001;25;402-8).

HSVSMC BrdU Incorporation Assay

HSVSMC proliferation was quantified using a DNA bromodeoxyuride (BrdU) incorporation assay (Millipore, Watford, UK), or EdU according to the manufacturer's instructions. The amount of incorporated BrdU is a measurement of DNA synthesis of the cells and thus an indirect measurement of proliferation. Briefly, cells were seeded into 96 well plates at a density of $1 \times 10^4$ cells per well. Cells were quiesced in 0.2% FCS media for 48 hours prior to stimulation. Cells were stimulated with either 10 ng/ml IL1α, 20 ng/ml PDGF or a combination of both for 72 hours (or the appropriate times stated elsewhere). For BrdU experiments, 5 to 6 hours after stimulation cells were incubated with BrdU for the remaining time to allow cell proliferation. For EdU experiments, EdU was added at the point of stimulation for the remaining time to allow cell proliferation. For BrdU: After removing the culture medium, the cells were fixed followed by incubation with anti-BrdU antibody which binds the incorporated DNA. After adding the substrate solution, the immune complexes were detected using a plate reader set at dual wavelength of 450/550 nm, Victor (Perkin elmer). For EdU: following stimulation, cellular RNA was extracted as described earlier or fixed in 70% ethanol for EdU FACs analysis. EdU incorporation was quantified using Click-it EdU Proliferation assay with an Alexa Fluor 594 antibody according to the manufacturer's protocol (Life Technologies).

5'3' RACE

5'3' Rapid amplification of cDNA ends (RACE) (see ref 23) was performed to determine the full length transcript of LncRNA 2 using the SMARTer RACE 5'/3' Kit (Clontech) according to manufacturer's instructions. Nested PCR was used to ensure only specific 5' and 3' products were detected (PCR Primer sequence—Table 1: SEQ ID NO: 3 to 8 (forward primers) and SEQ ID NO: 9 to 14 (reverse primers)).

TABLE 1

Sybr green primer sequences. Exon spanning lncRNA primers were designed to each lncRNA to ensure no genomic DNA was assessed during qRT-PCR.

| LncRNA Name | Chromosomal Location | Ensemble ID | Forward primer Sequence | Reverse Primer Sequence |
|---|---|---|---|---|
| SMILER | chr8:123426571-123440790 | RP11-94A24.1 | ACCTTGGAGGTCTTGGGAGT | TTGCAGACACCTTCCAAACA |
| LncRNA 4 | chr15:68591128-68593343 | RP11-709B3.2 | AAAAACTGCCACCTGTGACC | TTGGTGTAGGTCTGGGGAAG |
| LncRNA 6 | chr8:121066919-121068440 | RP11-760H22.2 | CTGCATTGGAGAGACAGGAAT | AAAGCTGAAACCCTAAAGTCATTG |
| LncRNA 7 | chr3:177534653-177617012 | RP11-91K9.1 | TGGCTAGGAGGGGGTCTATC | CACGGTGGCTCACACTTTTA |
| LncRNA 8 | Chr7:35756084-35774497 | AC018647.3 | CCAAGGTGATGAGCACAAAA | AAAGGTGGCAGAGTCCTTGA |
| SMILER RACE | | | GATTACGCCAAGCTTTGCAAACATTGGGATCAGCCGTGA | GATTACGCCAAGCTTTCTCACAGCCATGCTCTGGCCATT |

Following Cloning into Supplied Cloning Vector, Products were Sequenced.

Fluorescent In Situ Hybridisation

Custom RNA-FISH tiled probe sets were generated to all exons of LncRNA2. RNA FISH utilises "branch tree" technology. Briefly, a target specific probe set, containing 40 oligo probes, hybridises to the target mRNA as 20 oligo pairs. Each oligo pair forms a required platform for assembly of the signal amplification structure (tree) through a series of sequential hybridisation steps. Each fully assembled structure, covers a space of 40-50 nt of the target RNA, and has the capacity for 400-fold signal amplification. Therefore, a typical RNA probe set (containing 20 oligo pairs) has the capacity to generate 8,000-fold signal amplification. Due to this technology the company confirms single-molecule RNA sensitivity, thus each fluorescent signal corresponds to an individual lncRNA molecule.

Control SNORD3 and UBC were used as housekeepers to determine spatial location of LncRNA2 (Panomics, Affymetrix). RNA-FISH was performed according to manufacturer's instructions (ViewRNA™ cell FISH) with minor modifications for both cell and tissue experiments. For cellular analysis HSVSMC±IL1α/PDGF were grown on 16mm coverslips to 80% confluency, washed in PBS and fixed in 4% paraformaldehyde supplemented with 1% glacial acetic acid. Following detergent QS permeablisation and 1:6000 protease digest coverslips were incubated with a combination of UBC and LncRNA 2 probe sets or UBC. Probe set buffer was used as a negative control and SNORD3 as confirmation of nuclear permeabilisation. Following probe hybridisation, cover slips were incubated with branched tree technology pre amplifier for 1 hour and amplifier for 30 minutes. Cover slips were finally incubated with fluorescent probes, mounted onto glass slides using Prolong gold antifade with Dapi mounting medium (lifetechnologies) and sealed with nail polish.

For tissue RNA-FISH, serial 5 μm paraffin sections of failed human vein grafts were dewaxed and rehydrated. Sections were unmasked with sodium citrate (pH6) followed by proteinase K treatment (Sigma Aldrich, Suffolk, UK). Slides were then fixed in paraformaldehyde containing 1% glacial acetic acid and hybridised overnight at 40° C. with probe sets as described above. Pre-amlifier, amplifier and fluorescent probe hybridisation times were as above.

Assessment of RNA Secretion from HSVSMC

RNA extraction on conditioned HSVSMC media was performed using a standard volume (2 mL). The conditioned media was first centrifuged (10 min; 2000 g; 4° C.) to remove all cells and debris. After addition of 1.4 mL of QIAzol (Qiagen), 3 μL of c. elegans total RNA at 25 ng/μL was added to each sample. Following 5-min incubation at RT, 140 μL of chloroform was added and samples centrifuged (15 min; 15000 g; 4° C.). The clear upper aqueous phase was used to isolate RNA using miRNEasy mini kit (Qiagen) as previously described with alteration of the final wash step (75% ethanol in DEPC water). Different quantities of total RNA were spiked and a dose response effect was observed (FIG. 23A). The quality of the amplicon was assessed via analysis of melting curves (FIG. 23B) and subsequent visualisation on agarose gel (FIG. 23C). This showed a unique amplification product corresponding to the cDNA fragment of ama-1. Due to the correlation observed between quantity of spike-in and ama-1 expression (FIG. 23D), the inventors utilised 75 ng in all subsequent extractions. This amount allowed reproducibility of the method, with the Ct values of ama-1 being 29.4±0.3 across 5 separate extractions in non-conditioned media (FIG. 23E).

Image Acquisition

Images acquired on a zeiss 510 confocal system. At least 5 images, and typically greater than 10 images were taken per condition. Parameters for acquisition and post analysis are identical for all conditions. Images were Z stacked to confirm nuclear or perinuclear localisation.

MEKK1 and P38 Inhibitor Studies

For inhibitor studies, HSVSMC were plated at $1 \times 10^5$ cells in 6 well plates and quiesced for 48 h. 1 hour prior to stimulation, cells were incubated with either 10, 15 or 20 uM AZD6244 (MEKK1 inhibitor, Selleckchem) or 5, 10 or 20 uM P38 (SB 203580). Cells were then stimulated with either 0.2% media or a combination of IL1α and PDGF for 24 hours for RNA quantification or western blot analysis.

Dicer Substrate siRNA (dsiRNA) Mediated Transfection and EdU lncorporation

Double stranded dicer substrate siRNA targeting LncRNA 2 and Si-control were synthesised (Integrated DNA technologies). The Si-control does not target any sequence in the human, mouse, or rat transcriptomes. Transient transfection was performed with Lipofectamine 2000 (life technologies). $1 \times 10^5$ HSVSM cells were seeded in 12-well plates and transfected with either 25 nM Si-LncRNA2 or Si-Control. 6 hours post transfection cells were quiesced for 48 h and stimulated for a further 48 h with 0.2% media containing IL1α/PDGF with or without 10 uM EdU (EdU analysis or RNA analysis respectively). Following the 48 stimulation cells were RNA extracted as described earlier or fixed in 70% ethanol for EdU FACs analysis. EdU incorporation was visualized using Click-iT Alexa Fluor 594 according to the manufacturers protocol (Invitrogen).

Lentiviral Mediated Infection

Lentiviral vectors were produced by triple transient transfection of HEK293T cells with a packaging plasmid (pCMVΔ8.74), a plasmid encoding the envelope of vesicular stomatitis virus (VSVg) (pMDG) (Plasmid Factory, Bielefeld, Germany) and pLNT/SFFV-MCS plasmid employing polyethylenimine (PEI; Sigma-Aldrich, St Louis, USA) as previously described. Lentiviral titres were ascertained by TaqMan quantitative real-time FOR (qRT-PCR) using the following primer/probe sequences: forward, (SEQ ID NO: 15) 5'-TGTGTGCCCGTCTGTTGTGT-3'; reverse, (SEQ ID NO: 16) 5-GAGTCCTGCGTCGAGAGAGC-3'; probe, (SEQ ID NO:17) 5'-(FAM)-CAGTGGCGC-CCGAACAGGGA-(TAMRA)-3. SMILR was cloned into the pLNT/SFFV-MCS (kind gift from Adrian J. Thrasher, London, UK) plasmid using Platinum taq polymerase, according to manufacturer's instructions, to create pLNT/SFFV-MCS-SMILR. A confluent monolayer of smooth muscle cells were plated and infected with a multiplicity of infection of either 25 or 50, neither of which induced any form of toxicity in the cells. Following 24 h infection, media was changed to 0.2% for a further 48 h. Cells were then stimulated and EdU incorporation or SMILR expression investigated as above.

Detection of LncRNA in Exosomes Secreted from HSVSMC

SMILR expression in conditioned media utilising both ultracentrifugation and exosome isolation kits. RNA extraction of exosome free HSVSMC media was performed using a standard volume (15 mL). The conditioned media was centrifuged at 2000 g at 4° C. for 10 min and then at 12000 g for 45 min to remove all cell debris. The supernatant was filtered (0.22 μm) followed by ultracentrifugation at 110 000 g, 4° C. for 90 min (Optima L-80 XP ultracentrifuge Beckman coulter) to obtain microvesicles (MV) and exosomes and exosome free media compartments. Additional experiments were performed utilising the Total exosome isolation kit (Life technologies) following the manufacturer's instructions. The presence of microvesicles and exosomes was verified using the Nanosight technology For exosomes and microvesicles, 700 µL of Qiazol (Qiagen) was added and 3 µL of *c. elegans* total RNA at 25 ng/µL and the RNA was extracted using miRN Easy mini kit (Qiagen) as previously described. For the exosome free media compartment, RNA was extracted from 2 mL and following the same protocol as describe in the manuscript. SMILR relative expression was determined in theses 2 compartments by qRT-PCR.

In Vivo Studies Atherosclerosis Studies: Patients, Imaging and Sampling

Carotid Cohort

Patients with symptomatic carotid artery stenosis (≥50% by NASCET criteria [58]) scheduled to undergo carotid endarterectomy were recruited from neurovascular clinics at the Royal Infirmary of Edinburgh between January 2013 and April 2014. Exclusion criteria included a modified Rankin score of 3, insulin-dependent diabetes mellitus, women of child-bearing age not receiving contraception, severe chronic kidney disease (eGFR <30 mL/min/1.73 m$^2$), known iodine-based contrast media allergy, prior ipsilateral carotid intervention, prior neck irradiation, and inability to provide informed consent. Patients underwent a standard baseline clinical assessment including blood sampling (for standard clinical haematological and biochemical indices, including C reactive protein, and plasma RNA analysis) before undergoing separate [18F]-fluoride and [18F]-fluorodeoxyglucose ([18F]-FDG) positron emission tomography [59] combined with computed tomography (CT) scans with the use of a hybrid scanner (Biograph mCT, Siemens Medical Systems, Erlangen, Germany). Both of these tracers have been used by the inventors group and others for plaque imaging and highlight high-risk actively calcifying [60] and inflamed or hypoxic atherosclerotic plaques.

For [18F]-fluoride imaging, a target dose of 250 MBq was administered intravenously. Scanning took place after a 60-min delay. Following an attenuation-correction CT scan (non-enhanced, low dose 120 kV, 50 mAs) PET imaging was performed in static mode covering 2 bed positions (15 min each) with the superior bed centered over the carotid bifurcation. Following PET acquisition, a CT carotid angiogram was performed without moving the patient (Care Dose 4 D, 120 kV, 145 mA, rotation time 0.5 s, pitch 0.8).

[18F]-FDG PET/CT was performed on a separate day. A target dose of 125 MBq was administered intravenously and scanning commenced after a 90-min delay. PET/CT acquisition was identical to [18F]-Fluoride save for a longer bed time of 20-min and a pre-scan fast of 6 h. Static images were reconstructed using the Siemens Ultra-HD algorithm (time of flight+True X) with corrections applied for attenuation, dead time, scatter, and random coincidences.

PET tracer uptake was quantified using an OsiriX workstation (OsiriX version 3.5.1 64-bit; OsiriX Imaging Software, Geneva, Switzerland). PET/CT image data were reviewed for evidence of tracer uptake, image quality and registration. The CT angiogram was examined to establish plaque presence, location and characteristics. Regions of interest [61] were then drawn on three adjacent 3-mm PET slices to incorporate the internal carotid artery plaque. Three ROI were then drawn around adjacent healthy portions of carotid artery and the lumen of the SVC to derive control values for "normal" arterial uptake and the blood pool respectively. Arterial standardized uptake values (SUV) were recorded and also indexed to blood pool activity thus giving a target-to-background-ratio (TBR).

At the time of surgery, plaques were collected immediately following excision and photographed. Two-millimeter diameter core biopsy specimens for RNA analysis were taken from regions of focally high uptake on PET and from normal tissue at the periphery of the endarterectomy specimen. These, along with the main specimen, were immediately frozen and placed in an −80° C. fridge for subsequent batch analysis. Patient characteristic found in Table. 5.

Assessment of lncRNA in Human Plasma

A standard volume of each plasma sample (300 µL) was used to extract RNA. Five volumes of QIAzol lysis reagent (Qiagen) was added per extraction and supplemented with spike-in RNA controls: 3.5 µL of miRNeasy Serum/Plasma Spike-In Control at 1.6×108 copies/µL (*C. elegans* miR-39 miRNA mimic; Qiagen) and 3 µL of *c. elegans* total RNA at 25 ng/µL. Following 5-min incubation at RT, chloroform was added at equal volumes to the starting sample. Following centrifugation (15 min; 8000 g; 4° C.) the clear upper aqueous phase was used to isolate RNA as above.

Statistical Analysis

Statistical analysis was performed according to the figure legends. Data in graphs are expressed as mean±SEM. All samples were assessed for equal variance using Levene's test on minitab version 17 prior to statistical analysis. Comparisons between 2 groups were analysed using 2-tailed unpaired Student's t test. 1-way ANOVA with Tukey's post hoc or one way ANOVA multiple comparison test for pooled samples, via Graph Pad Prism version 5.0, was used for comparisons among 3 or more groups. Statistical significance is denoted by a P value of less than 0.05.

Results

Identification of Differentially Expressed LncRNA in HSVSMC Treated with IL1α and PDGF.

To identify NFκB dependent LncRNA, the inventors performed RNA-seq in human saphenous vein smooth muscle cells (HSVSMC) treated with 10 ng/ml IL1α or 20 ng/ml PDGF for 72 hours. RNA had previously been assessed for RNA integrity via bioanalyzer analysis. Proliferation and NFκB synergistic effects were confirmed via BrdU (thymidine analogue) incorporation and analysis of the inflammation-associated miRNA miR146α (FIG. 2). The inventors obtained raw sequencing reads per sample. Of these reads, a percentage were aligned to hg19 genome reference files. The majority of reads corresponded to mRNA. Quantification of transcript and gene expression levels was performed using Cufflinks according to hg19 RefSeq annotation files. Differential expression between groups was assessed by the EdgeR bioinformatics program.

Treatment with IL1α and PDGF Significantly altered lncRNA Expression Profiles and Nearby Transcript Expression.

Differential expression analysis confirmed differences in LncRNA expression patterns between 0.2% FCS cells and cells stimulated with IL1α/PDGF. Using the criteria of false discovery rate (FDR) ≤0.01, $\log_2$ fold change (FC) ≥2 to declare significance and fragments per kilobase of exon per million fragments mapped (FPKM) >1, to confirm expression, the inventors identified 96 differentially expressed LncRNA. From this data set they focused on 6 of the most differently expressed lncRNA, 4 of which were down regulated greater than 20 fold (denoted LncRNA 4,5,6 and 8) and two which were up-regulated greater than 40 fold (denoted LncRNA 2 and 7). 5 out of the 6 of these LncRNA were intergenic, with LncRNA 5 overlapping IL16. In order to validate and further quantify the expression levels of these LncRNA the inventors profiled their expression in 4 independent set of HSVSMCs stimulated with IL1/PDGF. qRT-PCR confirmed the 20.8+5.7 fold up regulation of LncRNAs 2 and 7 and the 43.7+11.7 fold down regulation of LncRNAs 4,5,6 and 8. Since the functional relationship between genomic location and expression is unknown, the expression of the closest protein coding genes to each LncRNA were analysed from RNA-seq data. In 4 out of 6 cases the expression of at least one protein coding gene corresponded to the expression of each lncRNA in smooth muscle cells, possibly implying that these transcripts share a common transcriptional regulatory mechanism. See FIG. 4 A and B.

LncRNA Show Specific Expression in Tissues.

After identifying lncRNAs expressed in our HSVSM cells, the inventors explored how these LncRNAs were expressed across different types of tissue. Using SYBR green gene assays it was found that all LncRNAs with the exception of LncRNA 6 and 8 showed highest expression in HSVSMC (FIG. 5A), possibly indicating a greater role in modulating SMC physiology and/or pathology.

Figure 5A:
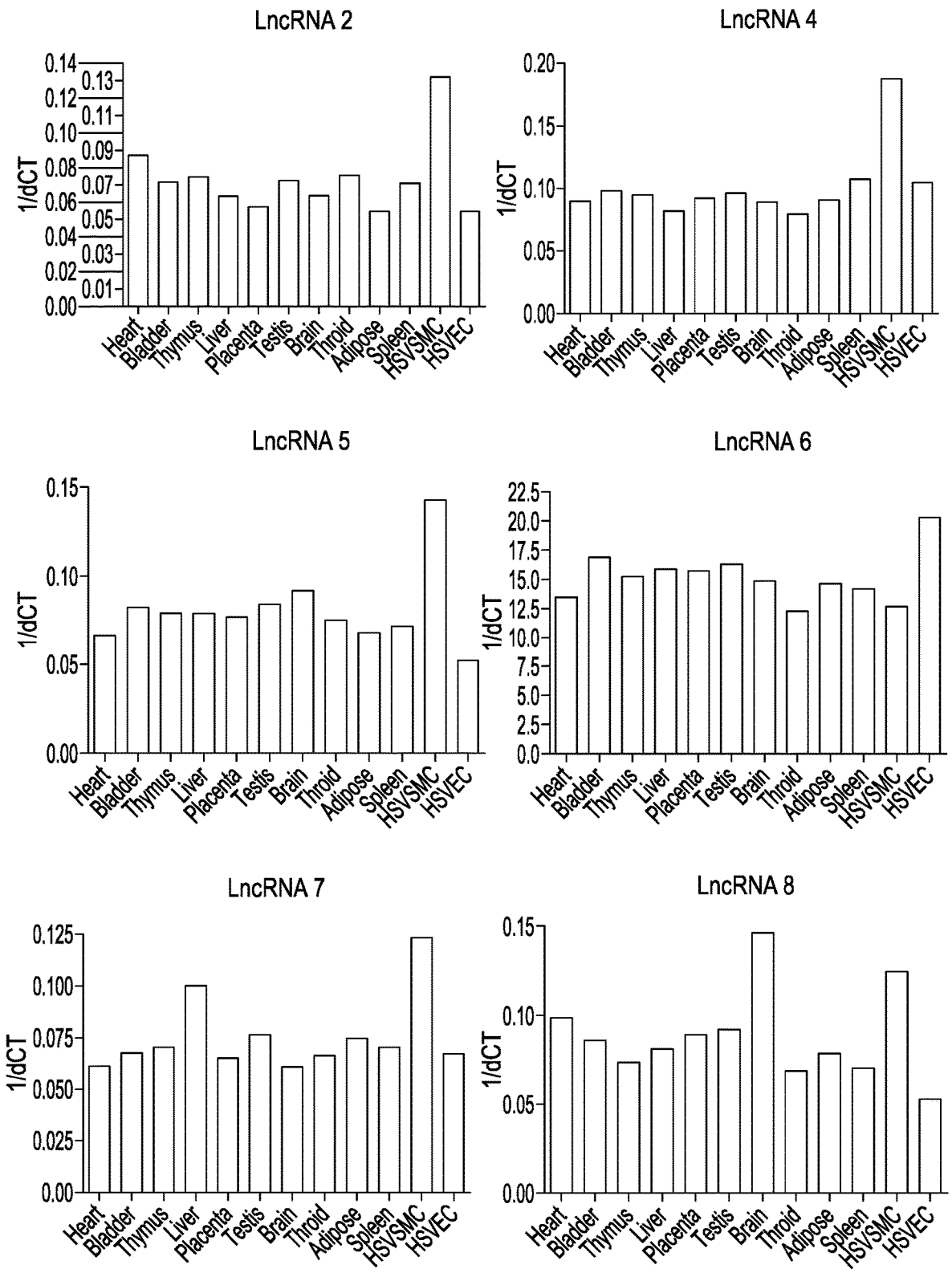
Figure 5B:
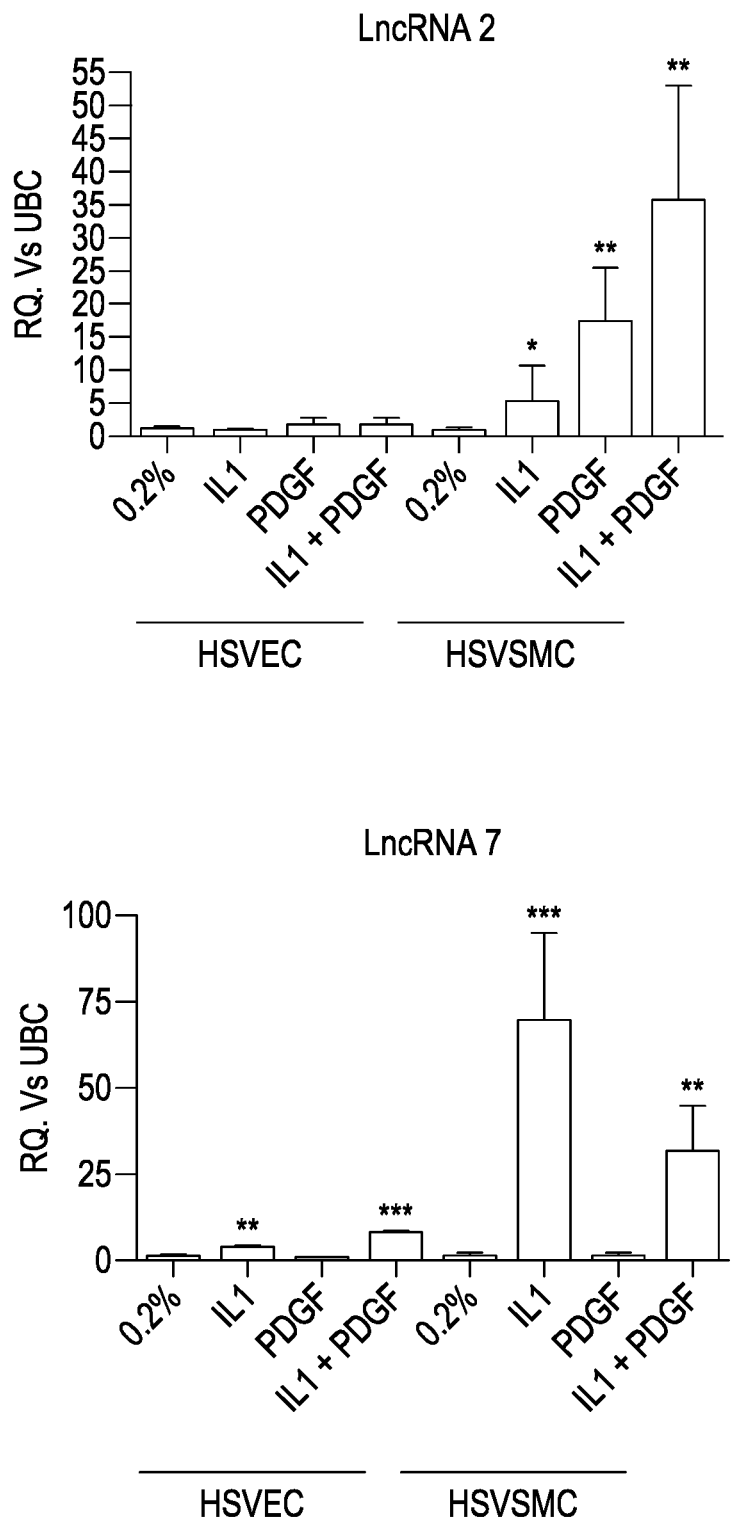

In the treatment of neointimal formation it would be beneficial to target SMC proliferation/migration whilst having no effect upon vessel re-endothelialisation. Therefore, the inventors assessed if HSV endothelial cells stimulation with IL1α/PDGF could evoke the up regulation of LncRNAs 2 and 7, similar to that seen in SMCs. Stimulation of HSVEC produced a significant 3.4±0.32 and 6.0±1.49 fold up regulation of LncRNA 7 following IL1 and IL1/PDGF treatment respectively, however had no effect upon lncRNA 2 expression (FIG. 5B). Due to its SMC specificity, LncRNA 2 was taken forward for further characterisation.

5'3' RACE Identified Additional 3' Sequence to LncRNA 2.

In order to further identify the 5' and 3' termini of the LncRNA 2 transcript, 5'3' RACE was employed. 5' RACE did not identify any additional sequence, however 3' RACE identified a band of approximately 800 bp corresponding to an additional 337 bp sequence at the end of lncRNA2, confirmed via sequencing analysis (FIG. 7).

IL1/PDGF Treatment Induces the Expression of LncRNA2 in a Time Dependent Manner.

To investigate the temporal regulation of LncRNA 2, the inventors stimulated SMC with IL1/PDGF for varying time points (1.5 h, 4 h, 24 h, 48 h and 72 h—See FIG. 2). From as early as 4 hours post stimulation, LncRNA induction could be observed. LncRNA expression increased gradually from 4-72 hours post stimulation.

Identifying Upstream Mediators of LncRNA 2 Expression in Smooth Muscle Cells.

It has been previously reported IL1 can induce the activation of NF-κB and the MAP kinases, ERK-1/2, JNK-1/2 and p38 MAP kinase in SMC. These pathways can be inhibited in the presence of the selective pharmacological inhibitors AZD6244 (MEKK1) and SB 203580 (p38) (FIG. 9C). Biologically active concentrations of these inhibitors were used to examine the role of the MAP kinase and p38 pathways during LncRNA2 expression. Following 60 minute pre-treatment with inhibitors, SMC were stimulated with IL1/PDGF and the generation of LncRNA 2 was determined at 24 h. Exposure to 10, 15 and 20 μM AZD6244 (MEKK1 inhibition) and subsequently 5, 10 and 20 uM SB 203580 (p38 inhibition) completely inhibited LncRNA 2 expression in the presence of IL1 and PDGF (FIG. 9B and 9C respectively).

Localisation of LncRNA 2 within Cells and Human Disease Tissue.

In order to ascertain the localisation of LncRNA 2 within cells and diseased tissue, the inventors performed RNA Fluorescent in situ hybridization (RNA-FISH). Although qRT-PCR serves as a great indicator of cellular abundance; LncRNA FISH provides visiospatial information as to the location of LncRNAs within cells. In the absence of stimulation SMC typically exhibited between 0 and 3 dots corresponding to individual LncRNA2 molecules (FIG. 8). However, IL1/PDGF treatment saw a marked increase in positive signals within the nucleus and cytoplasm of SM cells. Approximately >30 individual LncRNA molecules were observed within the nucleus or cytoplasm (FIG. 8). Negative coverslips were absent of any fluorescent signal while SNORD3 fluorescent activity confirmed the nuclear permeabilisation of cells. UBC and DAPI served as markers of cellular borders to assist in the determination of LncRNA localisation.

Additionally, the localisation of LncRNA 2 was determined in sections from failed human grafts. Serial H&E sections confirm the existence of a neointima in these samples. Additionally, as smooth muscle cells are integral to the formation of neointima, serial sections were also stained for aSMA, showing the localisation of LncRNA within SMC of the neointima and hinting at a pathological role for this LncRNA.

Effect of Dicer Substrate siRNA Mediated Knockdown on HSVSMC Proliferation.

In order to assess if the elevated levels of LncRNA 2 during IL1/PDGF treatment play a role in HSVSMC proliferation, the inventors performed dicer substrate siRNA (dsiRNA) mediated knockdown of LncRNA 2 followed by the assessment of EdU (thymidine analogue) incorporation into the DNA of dividing cells. DsiRNA mediated knockdown inhibited SMC proliferation following stimulation with IL1/PDGF (FIG. 11A). Significant knockdown of LncRNA was also established via qRT-PCR. DsiRNA2 mediated transfection caused a significant decrease in LncRNA 2 (FIG. 11B).

LncRNA 7 (also known as RP11-91k9.1 herein)

Data generated by the inventors show that:

LncRNA7 is a lncRNA consisting of 2 splice variants that is upregulated with IL1 treatment alone (FIG. 38A). PDGF has no effect.

LncRNA7 expression can be induced in endothelial cells (EC) but to a lesser extent than that in smooth muscle cells (SMC). (FIG. 38B)

LncRNA 7 expression appears to be upregulated through the NfKB IL1 signalling pathway but not the MEKK1 pathway possibly hinting at a role in vascular smooth muscle cell proliferation.(FIGS. 38E and 38F)

LncRNA 7 is a nuclear lncRNA as evidenced by fluorescent RNA FISH.(FIG. 38C). It is most highly expressed in the liver (FIG. 38D).

It has been shown that lncRNA 7 can bind HuR (also known as ELAVL1). Hur is a nuclear binding protein known to play a role in SMC proliferation.

LncRNA7 is upregulated in atherosclerotic plaques and appears also to be secreted from SMC (data not shown).

LncRNA7 is upregulated with IL1 treatment in human coronary artery smooth muscle cells (HCASMC).(Figure 38H)

Further Details of Experiments Undertaken

Induction of Inflammatory and Cell Cycle Pathways by IL1α and PDGF

The inventors sought to identify lncRNAs that are regulated during the induction of proliferative and inflammatory pathways in HSVSMC. RNAs were identified using RNA-seq of HSVSMC treated for 72 h (FIG. 3). Activation of the IL1α and PDGF signalling pathways was confirmed by presence of the inflammatory microRNA miR-146α (FIG. 2B) and induction of VSMC proliferation (FIG. 2A). The RNA-sequencing obtained an average of 70 million reads per sample; with 93.5% aligning to the GRCh37 genome reference files. The majority of reads, under all conditions, corresponded to mRNA (49.6±0.48%; FIG. 16A and FIG. 24A). To identify the biological function, networks, and canonical pathways that were affected by VSMC stimulation, the inventors performed Ingenuity Pathway Analysis (IPA) after RNA-seq analysis. IPA confirmed the mRNAs with altered expression following IL1α treatment were significantly enriched in pathways related to cellular movement and inflammatory disease (Table 2), while PDGF stimulation led to the marked enrichment in cell cycle pathways (Table 3).

TABLE 2

IL1α stimulation Ingenuity Pathway analysis. Top 10 disease and functional pathways predicted to be altered by IPA in HSVSM cells stimulated with IL1α. 0.2% vs IL1a

| Categories | Disease or Function Annotation | p-value |
| --- | --- | --- |
| Cellular Movement | cellular movement | $1.3 \times 10^{-36}$ |
| Cell Death and Survival | necrosis | $1.6 \times 10^{-33}$ |
| Cellular Growth and Proliferation | proliferation of cells | $2.4 \times 10^{-28}$ |
| Organismal Development | angiogenisis | $2.3 \times 10^{-26}$ |
| Cancer | growth of tumour | $6.7 \times 10^{-25}$ |
| Connective Tissue Disorder | arthropathy | $8.1 \times 10^{-24}$ |
| Inflammatory Disease | chronic inflammatory disorder | $1.4 \times 10^{-22}$ |
| Cellular Movement | leukocyte migration | $1.9 \times 10^{-23}$ |
| Inflammatory Response | Inflammatory response | $4.3 \times 10^{-23}$ |
| Gastrointestinal Response | Digestive system cancer | $6.9 \times 10^{-23}$ |

TABLE 3

PDGF stimulation Ingenuity Pathway analysis. Top 10 disease and functional pathways predicted to be altered by IPA in HSVSM cells stimulated with PDGF. 0.2% VS PDGF

| Categories | Disease or Function Annotation | p-value |
| --- | --- | --- |
| Cellular Growth and Proliferation | proliferation of cells | $2.5 \times 10^{-29}$ |
| Cell Death and Survival | apoptosis | $3.3 \times 10^{-25}$ |
| Cellular Movement | migration of cells | $5.3 \times 10^{-23}$ |
| Cardiovascular System Development | development of cardiovascular system | $2.3 \times 10^{-26}$ |
| Organismal Development | angiogenesis | $7.1 \times 10^{-21}$ |
| Cellular Development | proliferation of tumour cell lines | $8.5 \times 10^{-21}$ |
| Cancer | cancer | $1.5 \times 10^{-20}$ |
| Cell Cycle | mitosis | $1.7 \times 10^{-17}$ |
| Cell Morphology | morphology of cells | $5.3 \times 10^{-16}$ |
| Tissue Development | growth of connective tissue | $6.7 \times 10^{-16}$ |

Interestingly, co-stimulation led to enrichment in cell cycle and cardiovascular development pathways (Table 4).

TABLE 4

IL1α + PDGF stimulation Ingenuity Pathway analysis. Top 10 disease and functional pathways predicted to be altered by IPA in HSVSM cells stimulated with IL1α and PDGF. 0.2% VS IL1α + PDGF

| Categories | Disease or Function Annotation | p-value |
| --- | --- | --- |
| Cell Growth and Proliferation | proliferation of cells | $1.0 \times 10^{-45}$ |
| Cell Death and Survival | apoptosis | $7.2 \times 10^{-44}$ |
| Cancer | cancer | $1.2 \times 10^{-37}$ |
| Cellular Movement | migration of cells | $2.3 \times 10^{-34}$ |
| Gastrointestinal Response | digestive system cancer | $7.0 \times 10^{-30}$ |
| Cellular Development | proliferation of tumour cell lines | $8.5 \times 10^{-28}$ |
| Reproductive System Disease | Tumour | $4.8 \times 10^{-27}$ |
| Cell Cycle | Cell cycle progression | $6.2 \times 10^{-26}$ |
| Cardiovascular System Development | morphology of cells | $2.2 \times 10^{-24}$ |
| Cardiovascular System development | angiogenisis | $4.8 \times 10^{-24}$ |

Further analysis of differentially expressed mRNAs with a stringent cut off of FDR<0.01 identified 518 protein coding genes altered following IL1α treatment and 540 following PDGF treatment. Notably, dual stimulation altered 1133 known protein-coding genes with 480 uniquely associated with dual stimulation and not affected by IL1α or PDGF treatment alone (FIG. 16B and FIG. 24B).

Figure 17B:
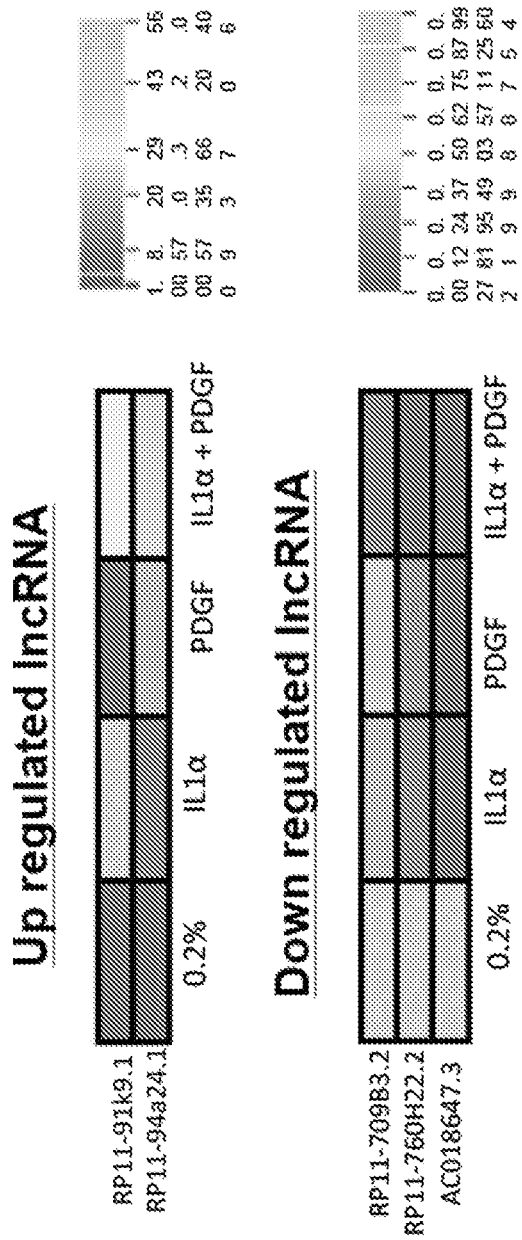

Identification of differentially expressed LncRNAs in HSVSMC treated with IL1α and PDGF. The inventors next assessed whether lncRNAs were dynamically regulated by growth factor and cytokine stimulation. Approximately 33% of reads in each condition aligned to known or predicted lncRNAs (FIG. 25A). Differential expression analysis confirmed substantial differences in lncRNA expression between control and stimulated cells. Using the stringent criteria FDR ≤1.01 and log2 fold change (FC) ≥2, to declare significance and fragments per kilobase of exon per million fragments mapped (FPKM) >1, to confirm quantifiable expression the inventors identified 224, 215 and 369 differentially expressed lncRNAs following IL1α, PDGF or dual stimulation respectively (FIG. 25A). Since lncRNAs can typically contain multiple splice variants, the numbers quoted refer to a single consensus gene model and therefore do not reflect the multiple transcripts of each lncRNA. To determine if specific biotypes of lncRNA were enriched following HSVSMC stimulation, those differentially expressed were further subdivided according to biotype in the Ensembl database. These are based upon their relative orientation to protein coding genes; intervening lncRNA (lincRNA), antisense, overlapping and processed transcripts. Utilising control and dual stimulation as an example, the distribution of different lncRNA biotypes was: intervening (45.5%), antisense (45.3%), overlapping (1.4%) and processed transcripts (7.9%) (FIG. 25B). Focusing on lincRNA, the candidates (control vs IL1α and PDGF, FDR<0.01, LogFC<2, FPKM>1) were ranked according to their FPKM and level of up/down-regulation (FIG. 17A; FIG. 24 for heat map of all conditions). A subset of the most differentially expressed transcripts was identified and validated by qRT-PCR (RP11-91k9.1, RP11-94a24.1, RP11-709B3.2, RP11-760H22.2 and AC018647.3; FIG. 17B, chromosomal locations in Table. 1). This was consistent with the RNA-seq results, showing RP11-94a24.1 and RP11-91k9.1 upregulated 20.2±30 and 45±26.4 fold, respectively following co-stimulation and lncRNAs RP11-709B3.2, RP11-760H22.2 and AC018647.3 being down regulated 16, 28 and 1209 fold, respectively (FIG. 4A) (RQ=0.06±0.04, 0.035±0.01 and 0.0008±0.001 respectively). The dissociation curves and gel products of each primer set are shown in FIG. 27.

Vascular enriched expression of RP11-94a24.1. The expression of each lncRNA was quantified in a range of 10 normal human tissues including specimens derived from brain, gastrointestinal, reproductive, and endocrine systems. In general, lncRNAs were expressed at relatively low levels across the tissue panel. However, the inventors observed that RP11-91k9.1 was expressed highest in the heart, while RP11-91K9.1 and AC018647.3 showed preferential expression within the liver and brain respectively. RP11-709B3.2 and RP11-760H22.2 displayed highest expression in spleen and thyroid respectively (FIG. 5A). The inventors next examined the expression of each lncRNA in primary HSVEC, HSVSMC and human coronary artery SMC (HCASMC). All lncRNAs had higher expression in VSMCs of either venous or arterial lineage compared to endothelial cells, suggesting VSMC enrichment (FIG. 5A). The inventors also assessed whether the expression of these lncRNAs could be modulated by IL1α and PDGF in HSVEC as had been found in the HSVSMCs. Notably, subsequent down regulation of RP11-709B3.2, RP11-760H22.2 and AC018647.3 was not observed in HSVECs as was the case in HSVSMC (data not shown). Stimulation of HSVECs produced a significant 3.8±0.7 and 8.7±2.1 fold up regulation of RP11-91K9.1 following IL1α and IL1α/PDGF treatment respectively (FIG. 5B). However, stimulation had no effect upon RP11-94a24.1 expression (FIG. 5B), indicating selective regulation in HSVSMC. Due to the expression of RP11-94a24.1 in HSVSMC and its cell specific induction in response to pathological mediators of vascular injury, the inventors focused further studies on RP11-94a24.1. They termed this lncRNA, smooth muscle induced lncRNA enhances replication (SMILR). SMILR expression was assessed through the utilisation of 3 independent primer sets targeting differential exons of the LncRNA. qRT-PCR revealed similar Ct and fold changes amongst the 3 sets, further confirming their previous data (FIG. 28). The longest open reading frame within SMILR is 57 amino acids. Analysis of this open reading frame using the Coding Potential Calculator (http://cpc.cbi.pku.edu.cn) did not reveal any similarity to known protein coding sequences suggesting that this RNA has no protein coding potential (data not shown).

IL1α/PDGF treatment induces the expression of SMILR in a time dependent manner. To investigate the longitudinal regulation of SMILR, the inventors stimulated HSVSMC with PDGF, IL1α or a combination of both (1.5 h, 4 h, 24 h, 48 h and 72 h). They found significant up regulation of SMILR in response to PDGF as early as 4 h post stimulation. By 24 h SMILR expression was increased by treatment with PDGF or IL1α as well as both together (FIG. 29). The combination of PDGF and IL1a induced a synergistic increase in SMILR expression at 72 h.

Cellular Localisation of SMILR in HSVSM Cells

Rapid amplification of cDNA ends [23], was utilised to design specific RNA FISH probes. RNA-FISH highlighted a SMILR isoform, consisting of an additional 6 bp at the 5' end and 316 bp at the 3' end (FIG. 30A and B). RACE data is supported by the raw RNA-seq files (FIG. 31 A-C).

The inventors performed RNA-FISH to provide visuospatial information as to the location of SMILR within HSVMSC. Negative control samples showed no fluorescent signal while SNORD3 fluorescent activity confirmed the nuclear permeabilisation of cells (FIG. 18A). In the absence of growth factor and cytokine stimulation, HSVSMC typically exhibited between 0 and 3 positive fluorescent signals corresponding to SMILR localisation (FIG. 18A). IL1α/PDGF treatment induced a marked increase in fluorescent signal within the nucleus and cytoplasm of HSVSMC. Further specificity of the FISH probes was confirmed through the utilisation of cells treated with either lentivirus containing SMILR or siRNA targeting SMILR. In each case an increase and decrease in SMILR transcripts was observed (FIG. 18A). Quantification of FISH samples is provided in FIG. 18B. In the absence of stimulation 2±3.6 SMILR molecules were observed. Following stimulation, 25±5 individual SMILR molecules were observed within the nucleus and cytoplasm (FIG. 18B).

Identifying upstream mediators of SMILR expression in HSVSMC. It is well established that IL1α and PDGF work through distinct pathways leading to vascular cell activation. To assess the functional consequences of inhibition of these pathways on SMILR expression, selective pharmacological inhibitors AZD6244 (MEKK1) and SB 203580 (p38) were utilised (FIG. 9A). Following 60 min pre-treatment with inhibitors, VSMC were stimulated with IL1α/PDGF and the expression of SMILR was determined at 24 h. Pre-treatment with AZD6244 (5, 10 or 15 µM) prevented the induction of SMILR in response to PDGF and IL1α (FIG. 9B), while inhibition of p38 with SB203580 induced a dose-dependent reduction in SMILR expression in response to PDGF and IL1α (FIG. 9C).

IL1α/PDGF treatment induces the release of SMILR into conditioned media. MicroRNAs have been reported to be secreted from cells as a means of cell to cell communication [24]. To investigate whether HSVSMCs release SMILR as an indication of expression, the inventors modified a method commonly utilised to evaluate miRNA expression [25]. As no endogenous control was stably expressed across all conditions in this study, an exogenous control was added in order to monitor extraction efficiency and to normalise data. Consequently, total RNA from C. elegans was used as a spike-in and ama-1 encoding polymerase II was chosen as a control for its high constitutive expression (see methods). Interestingly, SMILR was detected at low levels in media from quiesced VSMCs and those stimulated by either PDGF or IL1α, while conditioned media obtained from VSMC stimulated by combination contained significantly higher levels of SMILR (4.8±4.5 fold) (FIG. 19A), consistent with the increased intracellular expression of SMILR following co-stimulation of VSMC. Thus, treatment with PDGF and IL1α increased intracellular and released levels of SMILR.

Additionally the inventors sought to identify if SMILR was encapsulated within exosomes or microvesicles (MV). They utilised both ultracentrifugation, to remove cell debris, and an exosome isolation kit. FIG. 32A and B confirms the presence of microvesicles and exosomes using Nanosight technology and the expression of the previously described miR-143 within the exosomes/MV [26]. Our data highlights the expression of SMILR restricted to exosome free media (FIG. 32C) and inability to detect SMILR expression in the exosomes/MV compartment using both techniques of isolation. This observation has been confirmed by agarose gel electrophoresis (FIG. 32D). Primer melting curves are also shown in FIG. 32E. Our data confirm that SMILR is secreted into the media and located in a non-exosome/MV fraction. This could possibly be through interaction with specific membrane channels but requires additional experimentation.

Additionally, the inventors examined the release of SMILR following lentiviral overexpression in IL1 and PDGF treated cells. Lentiviral overexpression resulted in a 10-fold increase in SMILR RNA intracellularly. However, only a marginal (not significant) increase was observed within conditioned media analysed from infected cells (FIG. 32F). When this media was transferred onto additional quiesced cells, no change in proliferation was detected (FIG. 32G). This may suggest that the release of SMILR is under stringent control mechanism and simply increasing SMILR expression via lentiviral approach is not sufficient to induce the additional release of this lncRNA from the cells. In addition, these cells were stimulated with IL1 and PDGF, which strongly enhances SMILR expression in VSMC. The secretory machinery may have been saturated with the high levels of LncRNA within the cytoplasm. This has previously been demonstrated with microRNA where high levels of miR, via overexpression with microRNA mimics, saturated the exportin-5 pathway of endogenous miRNAs with fatal consequences[27,28].

Effect of dicer substrate siRNA mediated knockdown of SMILR on HSVSMC proliferation. The inventors investigated the function of SMILR using dicer substrate siRNA (dsiRNA)-mediated knockdown and EdU incorporation. Forty-eight hours post stimulation, IL1 and PDGF treatment induced a 34±15% increase in VSMC proliferation compared to control (FIG. 33). DsiRNA SMILR caused 75±24% decrease in SMILR expression when compared to dsiControl (FIG. 19B). Following SMILR knock down with dsiRNA, VSMC proliferation was reduced by 56±15% (FIG. 19C). Results were confirmed through the use of a second dsiRNA targeting an alternative region of SMILR (FIG. 34A and 8). No effect on the interferon pathway was observed upon assessment of the response genes OAS1 and IRF7, which have previously been linked to disRNA off target effects [29] (FIG. 34C and D).

Additionally the effect of SMILR overexpression on SMC proliferation was investigated. SMC were infected with SMILR lentivirus or empty control for 24 hours prior to stimulation. Infection at a multiplicity of infection of 25 and 50 produced a 5.5±3.5 and 11.4±4.7 fold increase in SMILR expression compared to the empty control, with no apparent toxicity effects (FIG. 19D). Overexpression produced a dose dependent increase of 1.3±0.3 fold and 1.66±0.5 fold in SMC proliferation respectively (FIG. 19E), confirming the knock down data.

SMILR Expression Correlates with other Proximal Genes

The expression of lincRNAs can correlate with the expression of adjacent genes and other RNAs within the genomic locale [30]. The inventors therefore assessed the expression of genes and non-coding RNAs within 5 million base pairs of SMILR, from COL14A1 on the forward strand to FERIL6-AS1 on the reverse strand (FIG. 20A), using the RNA-seq data set (FIG. 20B). Up-regulation of SMILR was not associated with a widespread increase in transcriptional activity within the region (FIG. 20B). However, similar changes in expression in response to VSMC stimulation were observed in two proximal transcripts (HAS2 and HAS2-AS1). SMILR is located ~750 kbp downstream of HAS2 on the same (reverse) strand and ~350 kbp from ZHX2 and ~750 kbp from HAS2-AS1 on the opposite strand of chromosome 8 (FIG. 20C). The upregulation of HAS2 was accompanied by an increase in HAS1 but not HAS3 following dual stimulation (FIG. 20D-F). Interestingly, IL1 and PDGF in combination had no effect on HAS3 expression as IL1 and PDGF have opposing effects on HAS3 expression (Full graph with single stimulation FIG. 34 E and F). In addition to SMILR, up-regulation of HAS2-AS1 was evident following IL1α and PDGF treatment, but not ZHX1 in the RNA-seq data (Data not shown). This observation was validated by qRT-PCR (FIG. 20 G,H and I).

It has been previously shown that lncRNA can modulate the expression of nearby protein coding genes. Thus, the expression of proximal genes HAS2, ZHX2 and HAS2-AS1 were determined following SMILR knockdown. RNAi-mediated knockdown of SMILR significantly altered levels of HAS2 mRNA. However, no change in the HAS2-AS1 lncRNA or the ZHX2 gene was observed via qRT-PCR (FIG. 20 J-L). Results were confirmed using a second siRNA targeting SMILR (FIG. 34 G-I). Additionally, no effect on HAS1 or HAS3 expression was observed while utilising SMILR siRNA indicating that the effect of SMILR knockdown is specific to HAS2 and not all isoforms of HAS (FIG. 20 M and N).

Additionally, knockdown of HAS2-AS1 greatly reduced HAS2 expression with no effect on SMILR expression (FIGS. 35 A and 35B). However, the reverse experiment utilising HAS2 knockdown, did not affect the expression of HAS2-AS1 nor SMILR (FIG. 35C). Finally, lentiviral mediated overexpression did not affect HAS1, 2,3 or HAS2-AS1 expression (FIG. 35 D-G).

SMILR expression is dysregulated in unstable human carotid plaques. To investigate the importance of SMILR in human vascular pathologies, the inventors assessed levels of SMILR in unstable atherosclerotic plaques. They used two established inflammatory ([18F]-fluorodeoxyglucose (FDG) and calcification ([18F]-fluoride) PET radiotracers to define prospectively portions of high-risk plaque [31][32][33] for RNA extraction. Plaque and relatively 'healthy' adjacent sections of vessel were assessed from within individual patients (Table 5 for patient characteristics).

TABLE 5

Baseline Patient Characteristics - Carotid Cohorts.

|  | Carotid (n = 7) |
|---|---|
| Age in years, mean (SD) | 63 (13.8) |
| Men, n (%) | 4 (57) |
| BMI (kg/m$^2$), mean (SD) | 26.3 (5.8) |
| Systolic blood pressure (mmHg), mean (SD) | 141.1 (22.5) |
| Diastolic blood pressure (mmHg), mean (SD) | 88.4 (16.6) |
| Presenting syndrome, n (%) | |
| Stroke | 2 (29) |
| TIA/Amaurosis fugax | 5 (71) |
| Cardiovascular History, n (%) | |
| Ischemic heart disease | 3 (43) |
| Myocardial infarction | 1 (14) |
| Risk Factors, n (%) | |
| Hypertension | 5 (71) |
| Diabetes | 1 (14) |
| Hypercholesterolemia | 7 (100) |
| Current smoker | 3 (43) |
| Medication, n (%) | |
| Aspirin | 2 (29) |
| Clopidogrel | 5 (71) |
| Anti-coagulant | 1 (14) |
| Statin | 7 (100) |
| ACEi/ARB | 3 (43) |
| B-blocker | 2 (29) |
| Hematology, mean (SD) | |
| Hemoglobin | 137.0 (23.1) |
| White cell count | 8.1 (1.8) |
| Platelet count | 284 (66) |
| Serum Biochemistry, mean (SD) | |
| Creatinine (mmol/L) | 90 (21.1) |
| Total cholesterol (mmol/L) | 4.7 (1.3) |

This is of key importance as it permits the assessment of non-coding RNA expression from within each micro environment (plaque vs. non plaque) from within the one vessel. Compared to quiescent adjacent tissue, portions of high-risk plaque showed higher uptake of both [18F]-FDG (maximum tissue-to-background ratio (TBR$_{max}$) 1.81±0.21 versus 1.31±1.6) and [18F]-fluoride (TBR$_{max}$ 2.32±0.52 versus 1.31±0.43) indicating that plaques subjected to RNA analysis had enhanced rates of inflammation (FIG. 21A-G for image examples and FIG. 21 H-K for graphs of tracer uptake). Since non-coding RNAs have not been assessed in a similar sample set before, the inventors first confirmed whether expression of a panel of miRNAs associated with atherosclerosis processes were dysregulated [34]. As expected, inflammation-associated miRNAs 146a-and 146b were significantly upregulated in unstable plaques compared to adjacent quiescent tissue, while miR-29 and miR-204, which are inversely associated with osteoblastogenesis and arterial calcification, were down regulated in mineralised regions of the atherosclerotic plaque [35, 36]. In addition the inventors also found a downregulation of the miR-143/145 cluster, which is associated with SMC differentiation and aortic aneurysm formation [37], an event which has previously been linked to osteogenic differentiation of SMC (FIG. 21L). Thus expression of small non-coding RNAs (miRs) was associated with PET/CT defined high-risk plaques. Therefore, the inventors used the same cohort of samples to assess SMILR, HAS2 and HAS2-AS1 levels. A 3.9±2.3 fold increase in SMILR expression was observed in high-risk plaques compared to adjacent stable regions of the carotid artery (FIG. 21M). Intriguingly, they also observed an increased in HAS2 (FIG. 21N) but not HAS2-AS1 (FIG. 21O).

SMILR is Detectable in Human Plasma and Correlates with Inflammatory CRP

Due to the release of SMILR into conditioned media from VSMC following stimulation with inflammatory mediators, the inventors evaluated whether SMILR was detectable in stored samples from a cohort of men with varying metabolic dysfunction. These samples were ranked in order of the serologic parameter CRP levels into 3 groups: CRP <2, CRP 2-5 and CRP >5 mg/L representing broad tertiles of CRP. SMILR showed no difference in patients with CRP levels below 2 mg versus 2-5 mg/L. However, a 3.3±5.7 fold increase in SMILR was observed when CRP concentrations were greater than 5 mg/L (FIG. 22A). Furthermore, a significant positive correlation was seen between SMILR and CRP ($R^2$=0.33, P<0.0001) (FIG. 22B). There was no correlation between SMILR and additional risk factors including age (P=0.66), blood pressure (P=0.12), BMI (P=0.14) or social deprivation status (P=0.11) (Table 6).

TABLE 6

Baseline Patient Characteristics - CRP matched plasma samples. Values are represented in mean ± SEM with p values calculated by one-way ANOVA or by Fisher's exact test for categorical variables.

|  | Group 1: crp < 2 (n = 13) | Group 2: 2 < crp < 5 (n = 13) | Group 3: crp > 5 (n = 15) | p values |
|---|---|---|---|---|
| Age (years) | 48.5 ± 1.8 | 48.5 ± 1.9 | 50.7 ± 2.1 | 0.66 |
| CRP (mg/L) | 1.24 ± 0.15 | 3.56 ± 0.28 | 7.09 ± 0.48 | p < 0.0001 |
| Systolic BP (mmHg) | 123 ± 2.9 | 131.2 ± 6.5 | 137.5 ± 4.6 | 0.12 |
| Diastolic BP (mmHg) | 77.5 ± 1.9 | 76.2 ± 2.0 | 79.0 ± 2.7 | 0.68 |
| BMI (kg/m2) | 26.0 ± 0.5 | 28.7 ± 1.3 | 29.6 ± 1.7 | 0.14 |
| WHR | 0.96 ± 0.02 | 1.00 ± 0.02 | 0.99 ± 0.02 | 0.23 |
| cIMT (mm) | 0.64 ± 0.03 | 0.59 ± 0.03 | 0.64 ± 0.04 | 0.47 |
| Smoking status, n (%) |  |  |  | 0.015 |
| Never smoker | 61.5 | 61.5 | 60.0 |  |
| Ex-smoker | 15.4 | 38.5 | 0.0 |  |
| Current | 23.1 | 0.0 | 40.0 |  |
| SMID quintile, n (%) |  |  |  | 0.111 |
| 1 | 30.8 | 0.0 | 0.0 |  |
| 2 | 23.1 | 7.7 | 6.7 |  |
| 3 | 7.7 | 23.1 | 40 |  |
| 4 | 7.7 | 15.4 | 13.3 |  |
| 5 | 30.8 | 53.8 | 40 |  |

Melting curves and gel products of SMILR primers in plasma are shown in FIG. 36. Further information regarding the statistical analysis of SMILR CRP correlation can be found in FIG. 37.

General Discussion

We have shown that stimulation of HSVSMCs with PDGF and IL1α increases expression of SMILR. This novel lincRNA increases cell proliferation which may be linked to its ability to regulate the proximal gene HAS2. In a clinical setting, the inventors found increased expression of SMILR in unstable atherosclerotic plaques suggesting an association with fundamentally important vascular pathologies linked to inflammation and VSMC proliferation. The inventors also discovered that SMILR can be released from cells and is detectable in plasma from patients with enhanced inflammation and thus susceptibility to atherosclerosis. These findings support the growing body of evidence that non-coding RNAs can act as mediators to modulate disease pathways.

Recent advances in RNA-sequencing have demonstrated that previously thought "genome deserts" are in fact pervasively transcribed and are populated by lncRNAs. Utilising paired end-sequencing allowed accurate alignment of reads to the human genome (GRCh37), the 93% alignment rate met quality standards for the RNA-seq technique [38] and ensured that our RNA-seq provided a high quality profile of the HSVSMC transcriptome during quiescent and stimulated conditions. Notably, compared to control cells, protein-coding genes accounted for 3-4 fold greater abundance than lncRNAs. The RNA-seq depth of 70 million reads was sufficient to identify lncRNAs within VSMC, however, it should be noted that greater read depths and use of refined capture-seq technique would be beneficial in order to offer greater annotation of specific areas within the genome.

Analysis of the RNA-seq data pinpointed SMILR as an IL1α/PDGF responsive lincRNA located on chromosome 8, 750 kbp from the closest protein-coding gene, on the same strand. This gene, HAS2, encodes an enzyme which synthesises hyaluronic acid (HA), a critical component of the extracellular matrix that accumulates in human restenotic and atherosclerotic lesions [39, 40]. The results show knockdown of SMILR reduces HAS2 expression and VSMC proliferation. This mechanism of action is supported by a number of studies demonstrating HA can enhance VSMC proliferation and migration [41]. Recent studies using transgenic mice with VSMC specific over-expression of HA have found increased susceptibility to atherosclerosis [42] and enhanced neointima formation in response to cuff injury [43]. The ability of SMILR to specifically target HAS2 with no effect on HAS1 or HAS3 allows a means of specifically altering HAS2 expression, the main HAS isoform expressed and functioning in SMC pathology [44].

LncRNAs can regulate other RNAs via a number of mechanisms [45], including changes in chromatin signatures within their locus. For example, the HOTAIR lncRNA is capable of repressing transcription in trans across 40 kbp of the HOXD locus [46]. Thus SMILR may act as an enhancer or scaffold via interaction with the promoter region, and potentially other transcription factors of HAS2, to regulate expression following inflammatory cytokine stimulation. However, further detailed co-immunoprecipitation or site directed mutagenesis studies would be required to demonstrate whether SMILR participates in transcription factor complexes with NF-κβ. or other transcription factors. Previous work has found HAS2 is regulated by an additional lncRNA, HAS2-AS1 [47]. Interestingly, the RNA-seq data herein show HAS2-AS1 expression was also upregulated by PDGF treatment alone and in combination with IL1α. However, knockdown of SMILR did not alter HAS2-AS1 expression. LncRNA HAS2-AS1 modulates chromatin structures around the gene in order to allow more efficient binding of the RNA polymerase 2, and enhance HAS2 gene expression [47]. This suggests both SMILR and HAS2-AS1 can regulate HAS2 by independent mechanisms. Interestingly, knockdown of HAS2 did not affect either SMILR nor HAS2-AS1 expression indicating that the expression of these lncRNA are not directly linked to HAS2 expression.

The composition of ECM assists in the determination of the stability of the atherosclerotic plaques, the phenotype of cells within it and the volume of neointima. During the progression of atherosclerosis, VSMC are exposed to a plethora of signalling molecules, including inflammatory cytokines. Using the clinical gold-standard methods of 18F-FDG and 18F-fluoride PET/CT imaging to identify inflamed, necrotic and mineralising atherosclerotic plaque [31, 32], our results indicate miRs 29, 143, 145, 146 and 204 are differentially expressed in unstable regions of atherosclerotic plaques. These miRs have previously been linked to VSMC differentiation, inflammatory cell signalling [48] and VSMC calcification [49]. The strong association and co-localisation of SMILR with this classical miRNA profile and focal 18F-FDG and 18F-fluoride uptake within atherosclerotic plaque suggests that SMILR may play a role in atherosclerosis through inflammatory and proliferative pathways. In keeping with the results showing HAS2 regulation by SMILR, HA content has been shown to reflect the progression of atherosclerotic disease and promotes vessel wall thickening [50]. Indeed, HA has been implicated in the recruitment of inflammatory cells, known to play a prominent role in the initiation and progression of atherosclerotic lesion to an unstable plaque phenotype.

Our results demonstrate SMILR is up-regulated by a combination of PDGF and IL1α in VSMCs but not ECs, suggesting modulation of SMILR could specifically alter VSMC proliferation without detrimental effects on vessel re-endothelialisation. If this is the case, it would provide a suitable candidate to improve current anti-proliferative therapies since current pharmacological agents target cell proliferation in a non-cell specific manner, events which can lead to late stent thrombosis [51].

The ability to identify confidently a plaque, or patient, at particular risk of a major adverse cardiovascular event (i.e plaque rupture) remains an important goal of cardiovascular research. Long RNA, both mRNA and non-coding RNA, have been previously shown to be stable in vivo for up to 3 weeks [52]. As such the search for prognostic biomarkers has greatly increased in recent years. SMILR was expressed in both the nucleus and cytoplasm of cells following stimulation and was released into the media. It will be important to determine whether the cytoplasmic copies induce functional effects, such as regulation of gene expression through post-translational mechanisms or if they are simply being processed for release. Dual transcriptional functions of lncRNAs have been shown previously[53], but to date no reports of a single lncRNA affecting both transcription and translation have been published. The release of SMILR could affect function in neighbouring cells, particularly in a vascular injury setting where phenotypic switching of VSMCs occurs in distinct areas of the vessel wall. In support of this theory, it has been shown that miR 143/145 can be transferred from VSMC into EC[54]. This transfer produced physiological effects within EC including modulation of angiogenesis. The inventors also found that SMILR could be detected in the plasma of patients with higher CRP levels indicative of chronic low grade inflammation. In light of their studies, they propose this release could be due to the increased levels of SMILR in the diseased vasculature, although delineating whether plasma SMILR is simply a by-product of increased intracellular levels or is functionally active in disease pathology is difficult to definitely demonstrate. However, circulating levels of miR 143 and 145 are associated with in-stent restenosis and as such have been proposed as biomarkers[55]. The correlation of SMILR and high CRP further supports its expression in low grade chronic inflammatory settings as well as proliferative settings. Further large clinical cohorts will be required to ascertain if SMILR has prognostic potential in inflammatory vascular disease, and if so, whether it provides enhanced prognostic value over current biomarkers.

Vessel re-narrowing after surgical intervention and atherosclerosis remain significant clinical problems and HA/HAS2/SMILR have emerged as key components of these pathological processes. Administration of an siRNA targeting SMILR could be used to prevent re-narrowing after surgical intervention for acute coronary syndrome. Using siRNAs has been proven to be effective in phase I clinical trials. Davis et al. recently showed a dose-dependent increase of siRNA delivered via nanoparticles and observed a reduction in the specific mRNA target[56].

REFERENCES

A: Li, C., Y. Hu, G. Sturm, G. Wick and Q. Xu (2000). "Ras/Rac-Dependent activation of p38 mitogen-activated protein kinases in smooth muscle cells stimulated by cyclic strain stress." *Arterioscler Thromb Vasc Biol* 20(3): E1-9.

B: Gabay, C., C. Lamacchia and G. Palmer (2010). IL-1 pathways in inflammation and human diseases. Nat Rev Rheumatol, Nature Publishing Group. 6.

C: Caglayan, E., M. Vantler, O. Leppänen, F. Gerhardt, L. Mustafov, H. Ten Freyhaus, K. Kappert, M. Odenthal, W. H. Zimmermann, M. D. Tallquist and S. Rosenkranz (2011). "Disruption of platelet-derived growth factor-dependent phosphatidylinositol 3-kinase and phospholipase Cγ 1 activity abolishes vascular smooth muscle cell proliferation and migration and attenuates neointima formation in vivo." *J Am Coll Cardiol* 57(25): 2527-2538.

D: Bond M, Fabunmi R P, Baker A H, Newby A C (1998). "Synergistic upregulation of metalloproteinase-9 by growth factors and inflammatory cytokines: an absolute requirement for transcription factor NF-kappa B." FEBS Lett, 29-34.

1. Marx S O, Totary-Jain H and Marks A R. Vascular smooth muscle cell proliferation in restenosis. Circulation Cardiovascular interventions. 2011;4:104-11.

2. Ghouri N, Purves D, McConnachie A, Wilson J, Gill J M and Sattar N. Lower cardiorespiratory fitness contributes to increased insulin resistance and fasting glycaemia in middle-aged South Asian compared with European men living in the UK. *Diabetologia*. 2013;56:2238-49.

3. Gomez D and Owens G K. Smooth muscle cell phenotypic switching in atherosclerosis. *Cardiovascular research*. 2012;95:156-64.

4. Alexander M R and Owens G K. Epigenetic control of smooth muscle cell differentiation and phenotypic switching in vascular development and disease. *Annual review of physiology*. 2012;74:13-40.

5. Schermuly R T, Dony E, Ghofrani H A, Pullamsetti S, Savai R, Roth M, Sydykov A, Lai Y J, Weissmann N, Seeger W and Grimminger F. Reversal of experimental pulmonary hypertension by PDGF inhibition. *The Journal of clinical investigation*. 2005;115:2811-21.

6. Rectenwald J E, Moldawer L L, Huber T S, Seeger J M and Ozaki C K. Direct evidence for cytokine involvement in neointimal hyperplasia. *Circulation*. 2000;102:1697-702.

7. Dardik A, Yamashita A, Aziz F, Asada H and Sumpio B E. Shear stress-stimulated endothelial cells induce smooth muscle cell chemotaxis via platelet-derived growth factor-BB and i nterleu kin-1alpha. *Journal of vascular surgery*. 2005;41:321-31.

8. Ferns G A, Raines E W, Sprugel K H, Motani A S, Reidy M A and Ross R. Inhibition of neointimal smooth muscle accumulation after angioplasty by an antibody to PDGF. *Science*. 1991;253:1129-32.

9. Guan S, Tang Q, Liu W, Zhu R and Li B. Nobiletin Inhibits PDGF-BB-induced vascular smooth muscle cell proliferation and migration and attenuates neointimal hyperplasia in a rat carotid artery injury model. *Drug development research*. 2014;75:489-96.

10. Johnson J L, Dwivedi A, Somerville M, George S J and Newby A C. Matrix metalloproteinase (MMP)-3 activates MMP-9 mediated vascular smooth muscle cell migration and neointima formation in mice. *Arteriosclerosis, thrombosis, and vascular biology*. 2011;31:e35-44.

11. Elgar G and Vavouri T. Tuning in to the signals: noncoding sequence conservation in vertebrate genomes. *Trends in genetics: TIG*. 2008;24:344-52.

12. Salic K and De Windt L J. MicroRNAs as biomarkers for myocardial infarction. *Current atherosclerosis reports*. 2012;14:193-200.

13. Jiang Y, Wang H Y, Li Y, Guo S H, Zhang L and Cai J H. Peripheral blood miRNAs as a biomarker for chronic cardiovascular diseases. *Scientific reports*. 2014;4:5026.

14. Kaushik K, Leonard V E, Kv S, Lalwani M K, Jalali S, Patoway A, Joshi A, Scaria V and Sivasubbu S. Dynamic expression of long non-coding RNAs (lncRNAs) in adult zebrafish. *PloS one*. 2013;8:e83616.

15. Liu J Y, Yao J, Li X M, Song Y C, Wang X Q, Li Y J, Yan B and Jiang Q. Pathogenic role of lncRNA-MALAT1 in endothelial cell dysfunction in diabetes mellitus. *Cell death & disease*. 2014;5:e1506.

16. Bell R D, Long X, Lin M, Bergmann J H, Nanda V, Cowan S L, Zhou Q, Han Y, Spector D L, Zheng D and Miano J M. Identification and initial functional characterization of a human vascular cell-enriched long noncoding RNA. *Arteriosclerosis, thrombosis, and vascular biology*. 2014;34:1249-59.

17. Jaffe E A, Nachman R L, Becker C G and Minick C R. Culture of human endothelial cells derived from umbilical veins. Identification by morphologic and immunologic criteria. *The Journal of clinical investigation*. 1973;52:2745-56.

18. Southgate K M, Davies M, Booth R F and Newby A C. Involvement of extracellular-matrix-degrading metalloproteinases in rabbit aortic smooth-muscle cell proliferation. *The Biochemical journal*. 1992;288 (Pt 1):93-9.

19. Dodt M, Roehr J T, Ahmed R and Dieterich C. FLEXBAR-Flexible Barcode and Adapter Processing for Next-Generation Sequencing Platforms. *Biology*. 2012;1: 895-905.

20. Kim D, Pertea G, Trapnell C, Pimentel H, Kelley R and Salzberg S L. TopHat2: accurate alignment of transcriptomes in the presence of insertions, deletions and gene fusions. *Genome biology*. 2013; 14:R36.

21. Trapnell C, Williams B A, Pertea G, Mortazavi A, Kwan G, van Baren M J, Salzberg S L, Wold B J and Pachter L. Transcript assembly and quantification by RNA-Seq reveals unannotated transcripts and isoform switching during cell differentiation. *Nature biotechnology.* 2010;28:511-5.

22. Trapnell C, Hendrickson, D. G., Sauvageau, M., Goff, L., Rinn, J. L., & Pachter, L. Differential analysis of gene regulation at transcript resolution with RNA-seq. *Nature biotechnology.* 2012;1:46-53.

23. Billings FTt, Balaguer J M, C Y, Wright P, Petracek M R, Byrne J G, Brown N J and Pretorius M. Comparative effects of angiotensin receptor blockade and ACE inhibition on the fibrinolytic and inflammatory responses to cardiopulmonary bypass. *Clinical pharmacology and therapeutics.* 2012;91:1065-73.

24. Glynn C L, Khan S, Kerin M J and Dwyer R M. Isolation of secreted microRNAs (miR-NAs) from cell-conditioned media. *MicroRNA.* 2013;2:14-9.

25. Morley-Smith A C, Mills A, Jacobs S, Meyns B, Rega F, Simon A R, Pepper J R, Lyon A R and Thum T. Circulating microRNAs for predicting and monitoring response to mechanical circulatory support from a left ventricular assist device. *European journal of heart failure.* 2014;16:871-9.

26. Deng L, Blanco F J, Stevens H, Lu R, Caudrillier A, McBride M, McClure J D, Grant J, Thomas M, Frid M, Stenmark K, White K, Seto A G, Morrell N W, Bradshaw A C, MacLean M R and Baker A H. MicroRNA-143 Activation Regulates Smooth Muscle and Endothelial Cell Crosstalk in Pulmonary Arterial Hypertension. *Circulation research.* 2015;117:870-83.

27. Soifer H S, Rossi J J and Saetrom P. MicroRNAs in disease and potential therapeutic applications. *Mol Ther.* 2007;15:2070-9.

28. Grimm D, Streetz K L, Jopling C L, Storm T A, Pandey K, Davis C R, Marion P, Salazar F and Kay M A. Fatality in mice due to oversaturation of cellular microRNA/short hairpin RNA pathways. *Nature.* 2006;441:537-41.

29. Karpala A J, Doran T J and Bean A G. Immune responses to dsRNA: implications for gene silencing technologies. *Immunology and cell biology.* 2005;83:211-6.

30. Wang K C and Chang H Y. Molecular mechanisms of long noncoding RNAs. *Molecular cell.* 2011;43:904-14.

31. Rudd J H, Warburton E A, Fryer T D, Jones H A, Clark J C, Antoun N, Johnstrom P, Davenport A P, Kirkpatrick P J, Arch B N, Pickard J D and Weissberg P L. Imaging atherosclerotic plaque inflammation with [18F]-fluorodeoxyglucose positron emission tomography. *Circulation.* 2002;105:2708-11.

32. Joshi N V, Vesey A T, Williams M C, Shah A S, Calvert P A, Craighead F H, Yeoh S E, Wallace W, Salter D, Fletcher A M, van Beek E J, Flapan A D, Uren N G, Behan M W, Cruden N L, Mills N L, Fox K A, Rudd J H, Dweck M R and Newby D E. 18F-fluoride positron emission tomography for identification of ruptured and high-risk coronary atherosclerotic plaques: a prospective clinical trial. *Lancet.* 2014;383:705-13.

33. Vesey A T, lrkle A, Lewis D Y, Skepper J N, Bird J L E, Dweck M R, Joshi F R, Gallagher F A, Warburton E A, Bennett M R, Brindle K M, Newby D E, Rudd J H and Davenport A P. YY Identifying Active Vascular Microcalcification By F-18-Sodium Fluoride Positron Emission Tomography. *Brit J Surg.* 2015;102:5-5.

34. Raitoharju E, Lyytikainen L P, Levula M, Oksala N, Mennander A, Tarkka M, Klopp N, Illig T, Kahonen M, Karhunen P J, Laaksonen R and Lehtimaki T. miR-21, miR-210, miR-34a, and miR-146a/b are up-regulated in human atherosclerotic plaques in the Tampere Vascular Study. *Atherosclerosis.* 2011;219:211-7.

35. Du Y, Gao C, Liu Z, Wang L, Liu B, He F, Zhang T, Wang Y, Wang X, Xu M, Luo G Z, Zhu Y, Xu Q, Wang X and Kong W. Upregulation of a disintegrin and metalloproteinase with thrombospondin motifs-7 by miR-29 repression mediates vascular smooth muscle calcification. *Arteriosclerosis, thrombosis, and vascular biology.* 2012;32:2580-8.

36. Cui R R, Li S J, Liu L J, Yi L, Liang Q H, Zhu X, Liu G Y, Liu Y, Wu S S, Liao X B, Yuan L Q, Mao D A and Liao E Y. MicroRNA-204 regulates vascular smooth muscle cell calcification in vitro and in vivo. *Cardiovascular research.* 2012;96:320-9.

37. Elia L, Quintavalle M, Zhang J, Contu R, Cossu L, Latronico M V, Peterson K L, Indolfi C, Catalucci D, Chen J, Courtneidge S A and Condorelli G. The knockout of miR-143 and -145 alters smooth muscle cell maintenance and vascular homeostasis in mice: correlates with human disease. *Cell death and differentiation.* 2009;16:1590-8.

38. Mortazavi A, Williams B A, McCue K, Schaeffer L and Wold B. Mapping and quantifying mammalian transcriptomes by RNA-Seq. *Nature methods.* 2008;5:621-8.

39. Papakonstantinou E, Roth M, Block L H, Mirtsou-Fidani V, Argiriadis P and Karakiulakis G. The differential distribution of hyaluronic acid in the layers of human atheromatic aortas is associated with vascular smooth muscle cell proliferation and migration. *Atherosclerosis.* 1998;138:79-89.

40. Riessen R, Wight T N, Pastore C, Henley C and Isner J M. Distribution of hyaluronan during extracellular matrix remodeling in human restenotic arteries and balloon-injured rat carotid arteries. *Circulation.* 1996;93:1141-7.

41. Papakonstantinou E, Karakiulakis G, Roth M and Block L H. Platelet-derived growth factor stimulates the secretion of hyaluronic acid by proliferating human vascular smooth muscle cells. *Proceedings of the National Academy of Sciences of the United States of America.* 1995;92:9881-5.

42. Chai S, Chai Q, Danielsen C C, Hjorth P, Nyengaard J R, Ledet T, Yamaguchi Y, Rasmussen L M and Wogensen L. Overexpression of hyaluronan in the tunica media promotes the development of atherosclerosis. *Circulation research.* 2005;96:583-91.

43. Kashima Y, Takahashi M, Shiba Y, Itano N, Izawa A, Koyama J, Nakayama J, Taniguchi S, Kimata K and Ikeda U. Crucial role of hyaluronan in neointimal formation after vascular injury. *PloS one.* 2013;8:e58760.

44. van den Boom M, Sarbia M, von Wnuck Lipinski K, Mann P, Meyer-Kirchrath J, Rauch B H, Grabitz K, Levkau B, Schror K and Fischer J W. Differential regulation of hyaluronic acid synthase isoforms in human saphenous vein smooth muscle cells: possible implications for vein graft stenosis. Circulation research. 2006;98:36-44.

45. Geisler S and Coller J. RNA in unexpected places: long non-coding RNA functions in diverse cellular contexts. *Nature reviews Molecular cell biology.* 2013;14:699-712.

46. Rinn J L, Kertesz M, Wang J K, Squazzo S L, Xu X, Brugmann S A, Goodnough L H, Helms J A, Farnham P J, Segal E and Chang H Y. Functional demarcation of active and silent chromatin domains in human HOX loci by noncoding RNAs. *Cell.* 2007;129:1311-23.

47. Vigetti D, Deleonibus S, Moretto P, Bowen T, Fischer J W, Grandoch M, Oberhuber A, Love D C, Hanover J A, Cinquetti R, Karousou E, Viola M, D'Angelo M L, Hascall V C, De Luca G and Passi A. Natural antisense transcript for hyaluronan synthase 2 (HAS2-AS1) induces transcription of HAS2 via protein O-GIcNAcylation. *The Journal of biological chemistry.* 2014;289:28816-26.

48. Taganov K D, Boldin M P, Chang K J and Baltimore D. NF-kappaB-dependent induction of microRNA miR-146, an inhibitor targeted to signaling proteins of innate immune responses. *Proceedings of the National Academy of Sciences of the United States of America.* 2006;103:12481-6.

49. Du Y, Gao C, Liu Z, Wang L, Liu B, He F, Zhang T, Wang Y, Wang X, Xu M, Luo G Z, Zhu Y, Xu Q and Kong W. Upregulation of a disintegrin and metalloproteinase with thrombospondin motifs-7 by miR-29 repression mediates vascular smooth muscle calcification. *Arteriosclerosis, thrombosis, and vascular biology.* 2012;32:2580-8.

50. Johnson J L. Matrix metalloproteinases: influence on smooth muscle cells and atherosclerotic plaque stability. *Expert review of cardiovascular therapy.* 2007;5:265-82.

51. Lemesle G, Maluenda G, Collins S D and Waksman R. Drug-eluting stents: issues of late stent thrombosis. *Cardiology clinics.* 2010;28:97-105.

52. Pinel K, Lacoste J, Plane G, Ventura M and Couillaud F. Long-term in vivo imaging of translated RNAs for gene therapy. *Gene therapy.* 2014;21:434-9.

53. Vance K W, Sansom S N, Lee S, Chalei V, Kong L, Cooper S E, Oliver P L and Ponting C P. The long non-coding RNA Paupar regulates the expression of both local and distal genes. *The EMBO journal.* 2014;33:296-311.

54. Climent M, Quintavalle M, Miragoli M, Chen J, Condorelli G and Elia L. TGFbeta Triggers miR-143/145 Transfer From Smooth Muscle Cells to Endothelial Cells, Thereby Modulating Vessel Stabilization. *Circulation research.* 2015;116:1753-64.

55. He M, Gong Y, Shi J, Pan Z, Zou H, Sun D, Tu X, Tan X, Li J, Li W, Liu B, Xue J, Sheng L, Xiu C, Yang N, Xue H, Ding X, Yu C and Li Y. Plasma microRNAs as potential noninvasive biomarkers for in-stent restenosis. *PloS one.* 2014;9:e112043.

56. Davis M E, Zuckerman J E, Choi C H, Seligson D, Tolcher A, Alabi C A, Yen Y, Heide! J D and Ribas A. Evidence of RNAi in humans from systemically administered siRNA via targeted nanoparticles. *Nature.* 2010;464: 1067-70.

57. Hess C N, Lopes R D, Gibson C M, Hager R, Wojdyla D M, Englum B R, Mack M J, Califf R M, Kouchoukos N T, Peterson E D and Alexander J H. Saphenous vein graft failure after coronary artery bypass surgery: insights from PREVENT IV. *Circulation.* 2014;130:1445-51.

58. Hathout G M, Fink J R, E l-Saden S M and Grant E G. Sonographic NASCET index: a new doppler parameter for assessment of internal carotid artery stenosis. *AJNR American journal of neuroradiology.* 2005; 26:68-75.

59. Upadhyay S, Ganguly K, Stoeger T, Semmler-Bhenke M, Takenaka S, Kreyling W G, Pitz M, Reitmeir P, Peters A, Eickelberg O, Wichmann H E and Schulz H. Cardiovascular and inflammatory effects of intratracheally instilled ambient dust from Augsburg, Germany, in spontaneously hypertensive rats (SHRs). *Particle and fibre toxicology.* 2010;7:27.

60. lrkle A, Vesey A T, Lewis D Y, Skepper J N, Bird J L, Dweck M R, Joshi F R, Gallagher FA, Warburton E A, Bennett M R, Brindle K M, Newby D E, Rudd J H and Davenport A P. Identifying active vascular microcalcification by (18)F-sodium fluoride positron emission tomography. *Nat Commun.* 2015;6:7495.

61. Armand-Labit V, Meyer N, Casanova A, Bonnabau H, Platzer V, Tournier E, Sansas B, Verdun S, Thouvenot B, Hilselberger B, Doncescu A, Lamant L, Lacroix-Triki M, Favre G and Pradines A. Identification of a Circulating MicroRNA Profile as a Biomarker of Metastatic Cutaneous Melanoma. Acta dermato-venereologica 2015.

The invention claimed is:

1. A method of treating a vascular condition within a subject in need thereof comprising administering to said subject a therapeutic agent that downregulates the amount and/or level of activity of a long non-coding RNA (lncRNA) comprising SEQ ID NO:29, or an RNA sequence corresponding to SEQ ID NO:28 or SEQ ID NO:27.

2. The method of claim 1, wherein the lncRNA comprises SEQ ID NO:29.

3. The method of claim 1, wherein the vascular condition is a vascular disease or a condition arising from injury or trauma of the vascular tissue.

4. The method of claim 3, wherein the vascular disease is selected from the group consisting of cardiovascular disease, atherosclerosis, ischemia, stroke, aneurysm, Buerger's disease, peripheral venous disease, peripheral artery disease (PAD) and carotid artery disease.

5. The method of claim 1, wherein the therapeutic agent is a complementary targeting oligonucleotide selected from the group consisting of a single stranded oligonucleotide, an antisense oligonucleotide, siRNA, shRNA, miRNA, and an anti-microRNA antisense oligonucleotide.

6. The method of claim 1, further comprising before the administering step:
   (i) determining the level of the lncRNA in a sample isolated from the subject; and
   (ii) comparing the level of the lncRNA in the subject sample with the level of the lncRNA in a control sample or with a predetermined reference level of the lncRNA, wherein an increased level of the lncRNA in the subject sample compared to the control sample or compared to the predetermined reference level identifies the subject as having or being susceptible to having a vascular condition.

7. The method according to claim 6, wherein the vascular condition is a vascular disease or a condition arising from injury or trauma of the vascular tissue, cardiovascular disease, atherosclerosis, ischemia, stroke, aneurysm, Buerger's disease, peripheral venous disease, peripheral artery disease (PAD) and carotid artery disease.

8. The method of claim 6, wherein the lncRNA has the RNA sequence of SEQ ID NO:29.

* * * * *